United States Patent
Regula et al.

(10) Patent No.: US 12,264,196 B2
(45) Date of Patent: *Apr. 1, 2025

(54) Fc-RECEPTOR BINDING MODIFIED ASYMMETRIC ANTIBODIES AND METHODS OF USE

(71) Applicant: Hoffmann-La Roche Inc., Little Falls, NJ (US)

(72) Inventors: Joerg Thomas Regula, Munich (DE); Wolfgang Schaefer, Mannheim (DE); Tilman Schlothauer, Penzberg (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 335 days.

This patent is subject to a terminal disclaimer.

(21) Appl. No.: 16/590,938

(22) Filed: Oct. 2, 2019

(65) Prior Publication Data

US 2020/0095310 A1 Mar. 26, 2020

Related U.S. Application Data

(63) Continuation of application No. 14/927,022, filed on Oct. 29, 2015, now abandoned, which is a continuation of application No. PCT/EP2014/058416, filed on Apr. 25, 2014.

(30) Foreign Application Priority Data

Apr. 29, 2013 (EP) ..................................... 13165725
Jan. 15, 2014 (EP) ..................................... 14151314

(51) Int. Cl.
| C07K 16/00 | (2006.01) |
| C07K 16/22 | (2006.01) |
| C07K 16/28 | (2006.01) |
| C07K 16/46 | (2006.01) |
| C12P 21/08 | (2006.01) |
| A61K 39/00 | (2006.01) |

(52) U.S. Cl.
CPC .............. *C07K 16/22* (2013.01); *C07K 16/00* (2013.01); *C07K 16/2863* (2013.01); *C07K 16/468* (2013.01); *A61K 2039/505* (2013.01); *A61K 2039/54* (2013.01); *C07K 2317/31* (2013.01); *C07K 2317/33* (2013.01); *C07K 2317/35* (2013.01); *C07K 2317/41* (2013.01); *C07K 2317/52* (2013.01); *C07K 2317/56* (2013.01); *C07K 2317/565* (2013.01); *C07K 2317/71* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| 6,277,375 | B1 * | 8/2001 | Ward ...................... C07K 16/06 |
| | | | 530/387.3 |
| 6,737,056 | B1 | 5/2004 | Presta |
| 7,695,936 | B2 * | 4/2010 | Carter ................ C07K 16/2809 |
| | | | 435/71.1 |
| 7,923,538 | B2 | 4/2011 | Shitara et al. |
| 8,227,577 | B2 | 7/2012 | Klein et al. |
| 9,217,880 | B2 | 12/2015 | Pugh et al. |
| 9,695,233 | B2 * | 7/2017 | Duerr ...................... A61P 27/02 |
| 10,195,262 | B2 | 2/2019 | Wacker et al. |
| 10,316,092 | B2 | 6/2019 | Yao et al. |
| 11,091,541 | B2 * | 8/2021 | Hartmann ............... A61P 27/02 |
| 2005/0249723 | A1 | 11/2005 | Lazar |
| 2006/0067930 | A1 | 3/2006 | Adams et al. |
| 2007/0219133 | A1 | 9/2007 | Lazar et al. |
| 2009/0136936 | A1 | 5/2009 | Georgiou et al. |
| 2009/0162360 | A1 | 6/2009 | Klein et al. |
| 2010/0093979 | A1 | 4/2010 | Lazar |
| 2010/0111967 | A1 * | 5/2010 | Baehner .................. A61P 27/02 |
| | | | 424/158.1 |
| 2010/0184959 | A1 | 7/2010 | Guler-Gane et al. |
| 2010/0203046 | A1 | 8/2010 | van Vlijmen et al. |
| 2011/0288276 | A1 | 11/2011 | Oganesyan et al. |
| 2012/0134984 | A1 | 5/2012 | Lubman et al. |
| 2012/0251531 | A1 | 10/2012 | Baehner et al. |
| 2012/0282280 | A1 | 11/2012 | Bramlage et al. |
| 2013/0039913 | A1 | 2/2013 | Labrijn et al. |
| 2013/0131319 | A1 | 5/2013 | Igawa et al. |
| 2013/0247234 | A1 | 9/2013 | McWhirter et al. |
| 2014/0017244 | A1 * | 1/2014 | Duerr ...................... C07K 16/22 |
| | | | 435/69.6 |
| 2015/0175707 | A1 | 6/2015 | De Jong et al. |
| 2016/0231320 | A1 | 8/2016 | Young et al. |

FOREIGN PATENT DOCUMENTS

| BR | 102016022721 A2 | 5/2018 |
| CA | 3159061 A1 | 8/2013 |
| EP | 1601697 B1 | 5/2007 |

(Continued)

OTHER PUBLICATIONS

Chamow et al. The Journal of Immunology. 1994; 153:4268-4280. (Year: 1994).*
Chamow et al. The Journal of Immunology. 1994; 153:4268-4280. (Year: 1994) (Year: 1994).*
Adams et al., "Structure and function of the type 1 insulin-like growth factor receptor." Cell Mol Life Sci 57(7):1050-93. (Jul. 2000).
Avdeeva Z.I., et al., "Preparations of next generation monoclonal antibodies (issues and prospects)," BIOpreparations. Prevention, Diagnosis, Treatment. 2015;(1):21-35. (In Russ.) English abstract included.

(Continued)

*Primary Examiner* — Chun W Dahle

(57) ABSTRACT

The present invention relates to antibodies and Fc-region fusion polypeptides which are asymmetrically modified with respect to their Fc-receptor, especially their FcRn, and methods of using the same.

14 Claims, 23 Drawing Sheets

Specification includes a Sequence Listing.

(56) References Cited

FOREIGN PATENT DOCUMENTS

| WO | 9734631 | A1 | 9/1997 | | |
| WO | 9845331 | A2 | 10/1998 | | |
| WO | 2004035752 | A2 | 4/2004 | | |
| WO | 2005005635 | A2 | 1/2005 | | |
| WO | 2005016967 | A2 | 2/2005 | | |
| WO | 2005035752 | A2 | 4/2005 | | |
| WO | 2005058967 | A2 | 6/2005 | | |
| WO | 2005061541 | A2 | 7/2005 | | |
| WO | 2005077981 | A2 | 8/2005 | | |
| WO | 2006039137 | A2 | 4/2006 | | |
| WO | 2006053301 | A2 | 5/2006 | | |
| WO | 2006/072620 | A1 | 7/2006 | | |
| WO | 2007110339 | A1 | 10/2007 | | |
| WO | 2009045389 | A2 | 4/2009 | | |
| WO | 2009058492 | A2 | 5/2009 | | |
| WO | 2010066868 | A2 | 6/2010 | | |
| WO | 2010099137 | A2 | 9/2010 | | |
| WO | WO 2011008517 | A2 | 1/2011 | | |
| WO | 2011117330 | A1 | 9/2011 | | |
| WO | 2012058768 | A1 | 5/2012 | | |
| WO | 2012069557 | A1 | 5/2012 | | |
| WO | 2012083370 | A1 | 6/2012 | | |
| WO | 2012093125 | A1 | 7/2012 | | |
| WO | 2013056233 | A1 | 4/2013 | | |
| WO | 2013063702 | A1 | 5/2013 | | |
| WO | WO-2013060867 | A2 | * 5/2013 | .......... | C07K 1/1133 |
| WO | 2013166594 | A1 | 11/2013 | | |
| WO | 2014036385 | A1 | 3/2014 | | |
| WO | 2014177459 | A2 | 11/2014 | | |
| WO | WO-2014177460 | A1 | * 11/2014 | .......... | A61K 39/395 |
| WO | 2015057668 | A1 | 4/2015 | | |

OTHER PUBLICATIONS

Chiu et al., "Associations between Genetic Polymorphisms of Insulin-like Growth Factor Axis Genes and Risk for Age-Related Macular Degeneration," Invest Ophthalmol Vis Sci., 52(12): 9099-9107, Nov. 24, 2011.

Diamond B., Scharff M.D. "Somatic mutation of the T15 heavy chain gives rise to an antibody with autoantibody specificity", Proc. Natl. Acad. Sci. USA, 1984, vol. 81, abstract.

Folkman and Shing, "Angiogenesis" J Biol Chem 267(16):10931-10934 (Jun. 5, 1992).

Garner, A. Pathobiology of Ocular Disease. A Dynamic Approach "Vascular Diseases" Garner, A., Klintworth GK Eds., 2nd edition, NY:Marcel Dekker,:1625-1710 ( 1994).

Ghetie and Ward, "FcRn: the MHC class I-related receptor that is more than an IgG transporter" Immunol Today 18 (12):592-598 (Dec. 1997).

Hezareh et al., "Effector Function Activities of a Panel of Mutants of a Broadly Neutralizing Antibody Against Human Immunodeficiency Virus Type 1," J Virol, Dec. 2001;75(24):12161-8.

Jaeger L. "Kliničeskaâ immunologiâ i allergologiâ", 2nd edition, translation from German, M.: Medicina, 1990, in 3 volumes, vol. 2, pp. 484-485.

JArilin A.A., "Osnovy immunologii" ["Basics of Immunology"], M.: Medicina, 1999, pp. 170-171, figure 41.

Kenanova et al., "Tailoring the Pharmacokinetics and Positron Emission Tomography Imaging Properties of Anti-Carcinoembryonic Antigen Single-Chain Fv-Fc Antibody Fragments," Cancer Res 65(2): 622-630 (Year: 2005).

Klagsbrun and D'Amore, "Regulators of angiogenesis" Ann Rev Physiol 53:217-239, ( 1991).

LeRoith et al., "Molecular and cellular aspects of the insulin-like growth factor I receptor" Endocr Rev 16(2):143-63 (Apr. 1995).

Ohno et al., "Antigen-binding specificities of antibodies are primarily Determined by seven residues of VH," Proc Natl Acad Sci USA_82_1985, pp. 2945-2949.

Roitt, A et al, Immunology, Moscow, "Mir", 2000, p. 98_EN Translation.

Roitt, A. et al., Immunology, Moscow, "Mir" (2000) pp. 110-111 (copy and English translation attached).

Chinese Office Action, mailed on Mar. 22, 2019, in the related Chinese Patent Application No. 201580003626.0.

Chinese Office Action, mailed on Jun. 4, 2020, in the related Chinese Patent Application No. 201480023252.4.

Israeli Office Action, mailed on Sep. 17, 2020, in the related Israeli Patent Application No. 274398.

Japanese Office Action, mailed on Jul. 5, 2018, in the related Japanese Patent Application No. 2016-511014.

Japanese Office Action, mailed on Nov. 20, 2018, in the related Japanese Patent Application No. 2016-546942.

Japanese Office Action, mailed on Dec. 4, 2018, in the related Japanese Patent Application No. 2016-546941.

Japanese Office Action, mailed on Apr. 28, 2020, in the related Japanese Patent Application No. 2016-546941.

Japanese Office Action, mailed on Jun. 2, 2020, in the related Japanese Patent Application No. 2019-097631.

Korean Office Action, mailed on Aug. 31, 2020 , in the related Korean Appl. No. 2015-7031019.

Korean Office Action, mailed on Sep. 21, 2020, in the related Korean Patent Application No. 10-2015-7033963.

New Zealand Office Action, mailed on Oct. 30, 2020, in the related New Zealand Appl. No. 751585.

Russian Office Action, mailed on Jun. 22, 2018, in the related Russian Patent Application No. 2016133346.

Russian Office Action, mailed on Aug. 8, 2018, in the related Russian Patent Application No. 2016133347.

Russian Office Action, mailed on Mar. 13, 2019, in the related Russian Patent Application No. 2016133347.

Russian Office Action, mailed on Oct. 31, 2018, in the related Russian Patent Application No. 2016133345.

Russian Office Action, mailed on Sept. 6, 2018, in the related Russian Patent Application No. 2015145719.

Russian Office Action, mailed on Oct. 18, 2018, in the related Russian Patent Application No. 2015145719.

Russian Office Action, mailed on Apr. 27, 2020, in the related Russian Patent Application No. 2016133345.

Russian Office Action, mailed on May 27, 2020, in the related Russian Patent Application No. 2016 133 346.

Taiwanese Office Action, mailed on May 26, 2020, in the related Taiwanese Appl. No. 108105062. (Translation).

The European Search Report and Opinion, mailed on Sep. 24, 2013,in the related European Appl. No 14721806.9.

The European Search Report and Opinion, mailed on Mar. 27, 2018, in the related European Appl. No 17205688.9.

The European Search Report and Opinion, mailed on Feb. 24, 2020,in the related European Appl. No 19183116.3.

US Office Action, mailed on Sep. 5, 2018, in the related U.S. Appl. No. 14/785,900.

US Office Actions, mailed on Aug. 10, 2020 and Nov. 17, 2020, in the related U.S. Appl. No. 15/947,377.

US Office Action, mailed on Aug. 24, 2020, in the related U.S. Appl. No. 15/947,424.

US Office Actions, mailed on Aug. 28, 2018, Mar. 14, 2019, Jan. 2, 2020, Aug. 31, 2020 and Dec. 14, 2020, in the related U.S. Appl. No. 14/926,982.

US Office Actions, mailed on Jun. 7, 2019 and Feb. 13, 2020, in the related U.S. Appl. No. 14/926,844.

US Office Actions, mailed on Nov. 6, 2019, Dec. 20, 2019, Jul. 30, 2020 and Nov. 13, 2020, in the related U.S. Appl. No. 16/244,378.

The English translation of the Decision to Grant a Patent, mailed on Nov. 8, 2019, in the related Japanese Appl. No. 2016-511014.

The English translation of the Brazilian Office Action, mailed on Oct. 7, 2019, in the related Brazilian Appl. No. BR112016014969-6.

The extended European Search Report, mailed on May 14, 2021, in the related European Appl. No. 20214926.6.

The Canadian Office Action, mailed on Feb. 23, 2021, in the related Canadian Patent Appl. No. 2,932,364.

The US Office Action, mailed on May 20, 2021, in the related U.S. Appl. No. 15/947,377.

The Notice of Allowance, mailed on May 26, 2021, in the related U.S. Appl. No. 14/926,844.

(56) References Cited

OTHER PUBLICATIONS

The US Office Action, mailed on Jul. 6, 2021, in the related U.S. Appl. No. 15/947,424.
The US Office Action, mailed on Nov. 30, 2021, in the related U.S. Appl. No. 16/422,147.
The English translation of the Korean Office Action, mailed on Jul. 30, 2021, in the related Korean Patent Application No. 10-2016-7018968.
The US Office Action, mailed on Aug. 4, 2021, in the related U.S. Appl. No. 16/422,147.
The Canadian Office Action, mailed on Feb. 2, 2021, in the related Canadian Patent Appl. No. 2,931,986.
Yang et al., "Assessment of naturally occurring covalent and total dimer levels in human IgG1 and IgG2" Molecular Immunology 58:108-115 ( 2014).
McAuley et al., "Contributions of a disulfide bond to the structure, stability, and dimerization of human IgG1 antibody CH3 domain," Protein Sci. Jan. 2008; 17(1): 95-106.
US Office Action, mailed on Mar. 17, 2021, in the related U.S. Appl. No. 14/926,982.
US Office Actions, mailed on Feb. 9, 2021 and Apr. 20, 2021, in the related U.S. Appl. No. 14/926,844.
The English translation of the Decision to Grant dated Jul. 26, 2022, in the related Russian Patent Application No. 2020122367/10(038452).
The English translation of the Japanese Office Action, mailed on May 16, 2022, in the related Japanese Patent Application No. 2021-092002.
The US Office Action, mailed on Aug. 31, 2021, in the related U.S. Appl. No. 15/947,377.
The US Office Action, mailed on Feb. 24, 2022, in the related U.S. Appl. No. 15/947,424.
Spiekerrnann et al., "Receptor-mediated Immunoglobulin G Transport Across Mucosal Barriers in Adult Life: Functional Expression of FcRn in the Mammalian Lung," J Exp Med (2002) 196 (3): 303-310.
The Canadian Office Action, mailed on Feb. 17, 2022, in the related Canadian Patent Appl. No. 2,904,805.
The Chinese Office Action, mailed on Feb. 27, 2023, in the related Chinese Patent Appl. No. 201911344011.0.
The English translation of the Japanese Office Action, mailed on Aug. 29, 2023, in the related Japanese Patent Appl. No. 2022-010878.
The English translation of the Chinese Office Action, mailed on Aug. 28, 2023, in the related Chinese Patent Appl. No. 202110445639.0.
The US Office Action, mailed on Sep. 22, 2023, in the related U.S. Appl. No. 15/947,424.
The Third Party Observations, posted on Dec. 1, 2023, in the related European Patent Appl. No. 15700545.5.
Hinton et al., "An engineered human IgG1 antibody with longer serum half-life" J Immunol 176(1):346-56 ( 2006).
Jansson et al., "All individual domains of staphylococcal protein A show Fab binding," FEMS Immunology and Medical Microbiology 20 (1998) 69-78.
Tustian et al., "Development of purification processes for fully human bispecific antibodies based upon modification of protein A binding avidity," MAbs May-Jun. 2016;8(4):828-38.
The Chinese Office Action, mailed on Jul. 8, 2023, in the related Chinese Patent Appl. No. 201480024044.6.
The English translation of the Chinese Office Action, mailed on Nov. 25, 2022, in the related Chinese Patent Appl. No. 201911266804.5.
Columbian Office Action, mailed on Jul. 25, 2019, in the related Columbian Patent Application No. 15260305.
Taiwanese Search Report, mailed on Jun. 28, 2019, in the related Taiwanese Patent Application No. 103115072.
The European Communication, mailed on Oct. 19, 2017, in the related European Appl. No 15700545.5.
The US office actions, mailed on Dec. 13, 2017, Mar. 16, 2018 and Sep. 6, 2018, in the related U.S. Appl. No. 14/927,022.
The US office action, mailed on Jan. 12, 2023, in the related U.S. Appl. No. 15/947,377.
The US office action, mailed on Sep. 23, 2024, in the related U.S. Appl. No. 15/947,424.
The US office action, mailed on Oct. 8, 2021, in the related U.S. Appl. No. 16/244,378.
The US office action, mailed on Oct. 23, 2024, in the related U.S. Appl. No. 18/079,307.
The US office actions, mailed on Aug. 31, 2023 and Mar. 13, 2024, in the related U.S. Appl. No. 17/373,062.
The English translation of the Chinese Office Action, mailed on Jul. 8, 2023, in the related Chinese Patent Appl. No. 201480024044.6.
The US Office Action, mailed on Aug. 31, 2023, in the related U.S. Appl. No. 17/373,062.
DeLano et al., "Convergent Solutions to Binding at a Protein-Protein Interface," Science, 287:1279-1283, Feb. 18, 2000.
The English translation (Google Translate) of the Argentina Office Action, mailed on Dec. 22, 2023, in related Argentina Application No. 20140101718.
The English translation of the Chinese Office Action, mailed on Jan. 24, 2024, in the related Chinese Patent Appl. No. 202110445639.0.

* cited by examiner

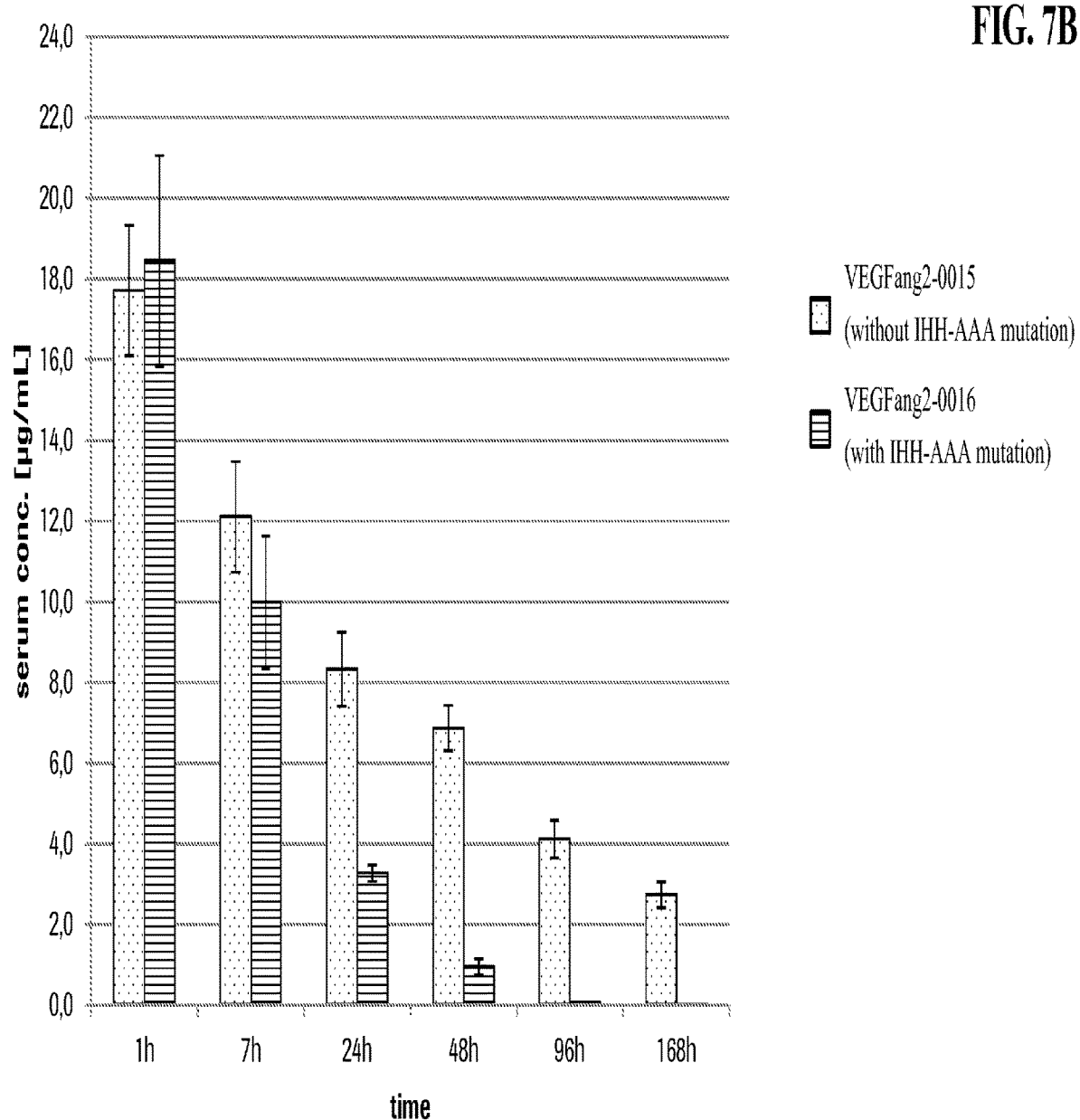

| Knob | | | Hole | | | |
|------|------|------|------|------|------|------|
| Pos 1 | Pos 2 | Pos 3 | Pos 1 | Pos 2 | Pos 3 | |
| I253A | H310A | H435A | I253A | H310A | H435A | No binding |
| --- | --- | --- | I253A | H310A | H435A | Binding |
| I253A | H310A | H435A | --- | H310A | --- | No binding |
| I253A | H310A | H435A | --- | --- | H435A | No binding |

Fc-RECEPTOR BINDING MODIFIED ASYMMETRIC ANTIBODIES AND METHODS OF USE

CROSS-REFERENCE TO RELATED APPLICATIONS

This application is a Continuation of U.S. patent application Ser. No. 14/927,022, filed Oct. 29, 2015, which in turn is a National Stage Application of PCT/EP2014/058416 filed Apr. 25, 2014, which claims priority from European Patent Application No. 13165725.6, filed on Apr. 29, 2013 and European Patent Application No. 14151314.3, filed on Jan. 15, 2014. The priority of said PCT, European Patent, and US Applications are claimed. Each of prior mentioned applications is hereby incorporated by reference herein in its entirety.

SEQUENCE LISTING

This application hereby incorporates by reference the material of the electronic Sequence Listing filed concurrently herewith. The material in the electronic Sequence Listing is submitted as a text (.txt) file entitled "P31559US Sequence_listing.txt" created on Feb. 21, 2014 which has a file size of 246 KB, and is herein incorporated by reference in its entirety.

FIELD OF THE INVENTION

The present invention relates to antibodies and Fc-region fusion polypeptides which are asymmetrically modified with respect to their Fc-receptor, especially their FcRn, interaction and methods of using the same.

BACKGROUND

Almost all Fc-receptors bind to the symmetrical Fc-region of antibodies asymmetrically.

For example, the human Fcγ-receptor IIIA interacts with different amino acids residues on the two Fc-region polypeptide chains. Thus, asymmetrically introduced mutations (e.g. in the lower hinge region at residues 233 to 238) have to be used to either increase or decrease the interaction of the antibody with the human Fcγ receptor IIIA.

But, the interaction between the human neonatal Fc-receptor FcRn is symmetrical: two FcRn molecules can bind to a single IgG with a 2:1 stoichiometry (see. e.g. Huber, A. W., et al., J. Mol. Biol. 230 (1993) 1077-1083). Thus, asymmetrically introduced mutations reduce the binding to/by one FcRn but not to/by both.

Examples of asymmetric IgG-like molecules include but are not limited to those obtained with the following technologies or using the following formats: Triomab/Quadroma, Knobs-into-Holes, CrossMabs, electrostatically-matched antibodies, LUZ-Y, Strand Exchange Engineered Domain body, Biclonic and DuoBody.

In WO 2012/125850 Fc-containing proteins comprising asymmetric substitutions in their Fc-regions and having increased binding to human Fcγ-receptor IIIA and enhanced ADCC activity are reported.

In WO 2012/58768 isolated heteromultimers comprising a heterodimer Fc-region, wherein the heterodimer Fc-region comprises a variant CH3 domain comprising amino acid mutations to promote heterodimer formation with increased stability, wherein the heterodimer Fc-region further comprises a variant CH2 domain comprising asymmetric amino acid modifications to promote selective binding of an Fcgamma receptor are reported.

In WO 2011/131746 it is reported that by introducing asymmetrical mutations in the CH3 regions of the two monospecific starting proteins, the Fab-arm exchange reaction can be forced to become directional and thereby yield highly stable heterodimeric proteins.

Kim et al. (Kim, H., et al., Invest. Ophthalmol. Vis. Sci. 49 (2008) 2025-2029) report that, except for the retinal pigment epithelial and choroid tissue, ocular tissues, including the ciliary body and iris, retina, conjunctiva, cornea, lens, and optic nerve bundle, showed the presence of FcRn transcript at the predicted size. The blood-ocular barrier showed FcRn receptor expression, indicating that IgG transport from ocular tissues to the blood system may use this receptor. Since the inner ocular tissues such as the retina are separated from the blood system by the blood-ocular barrier, one would not expect to detect a full-length antibody in the blood system only a short time after intravitreous injection. However, recent pharmacokinetic data from monkey and humans all indicate that intravitreous bevacizumab appears in the blood within hours after intravitreous injection. Therefore, it may be that the function of the FcRn receptor in the conjunctival lymphatic vessels is to act as an efflux receptor for the efficient elimination of antigen-antibody IgG complexes from the conjunctival space. Despite similar molecular weights, IgG (150 kDa) was detected in the aqueous humor, however, IgA (160 kDa) was not. The discrepancy between IgG and IgA penetration from the serum into the aqueous humor may be explained by the presence of the FcRn receptors, which are selective for IgGs.

Kim et al. further report (Kim, H., et al., Mol. Vis. 15 (2009) 2803-2812) that direct intravitreal injection has become a common approach for delivering therapeutic antibodies to the posterior segment of the eye for retina disorders. Both intravitreally administered bevacizumab (IgG) and chicken IgY overcame the inner limiting membrane barrier and diffused into the deeper retinal structures. After diffusing through the retina bevacizumab crossed the blood-retina barrier and leaked into the systemic circulation. The intraretinal chicken IgY was only localized along the abluminal side of the blood-retina barrier. Furthermore, the choroidal blood vessels were negative for the presence of chicken IgY. Physiologically relevant serum levels of bevacizumab after intravitreal administration, representing up to 30% of the injected dose, were found. This suggests greater risk for systemic side effects than previously recognized. The blood-ocular barrier manifests a specific mechanism for transporting and clearing full-length IgGs into the systemic circulation. Kim's current study confirms the hypothesis that this mechanism is the neonatal Fc-receptor.

In US 2011/054151 compositions and methods for simultaneous bivalent and monovalent co-engagement of antigens is reported.

In US 2011/236388 bispecific, bivalent anti-VEGF/anti-ANG-2 antibodies are reported.

In WO 2010/121766 antibody fusion proteins with modified FcRn binding sites are reported.

Kim, J. K., et al. report the mapping of the site on human IgG for binding of the MHC class I-related receptor, FcRn (Eur. J. Immunol. 29 (1999) 2819-2825).

Qiao, S.-W., et al. report the dependence of antibody-mediated presentation of antigen on FcRn (Proc. Natl. Acad. Sci. USA 105 (2008) 9337-9342).

Kuo, T. T., et al. report about the neonatal Fc receptor: from immunity to therapeutics (J. Clin. Immunol. 30 (2010) 777-789).

Firan, M., et al. report that the MHC class I-related receptor, FcRn, plays an essential role in the maternofetal transfer of gamma-globulin in humans (Int. Immunol. 13 (2001) 993-1002).

Vidarsson, G., et al. report that FcRn is an IgG receptor on phagocytes with a novel role in phagocytosis (Blood 108 (2006) 3573-3579).

Gillies, S. D., et al. report the improving of the efficacy of antibody-interleukin 2 fusion proteins by reducing their interaction with Fc-receptors (Cancer Res. 59 (1999) 2159-2166).

In WO 2013/060867 the production of heterodimeric proteins is reported.

SUMMARY

It has been found that the FcRn-binding of an antibody or Fc-region fusion polypeptide can be modified by altering amino acid residues at non-corresponding positions in the individual Fc-region polypeptides as these alterations act together in the modification of the FcRn-binding. Antibodies and Fc-region fusion polypeptides as reported herein are useful, e.g., for the treatment of diseases in which tailor-made systemic retention times are required.

One aspect as reported herein is a variant (human) IgG class Fc-region comprising a first Fc-region polypeptide and a second Fc-region polypeptide,
wherein
  a) the first Fc-region polypeptide and the second Fc-region polypeptide are derived from the same parent (human) IgG class Fc-region polypeptide, and
  b) the first Fc-region polypeptide has an amino acid sequence that differs from the second Fc-region polypeptide amino acid sequence at least at one corresponding position according to the Kabat EU index numbering system,
  whereby the variant (human) IgG class Fc-region has a different affinity to a human Fc-receptor compared to a (human) IgG class Fc-region that has the same amino acid residues (as the (parent) human Fc-region polypeptide of a)) at corresponding positions according to the Kabat EU index numbering system in the first Fc-region polypeptide and the second Fc-region polypeptide.

One aspect as reported herein is a variant (human) IgG class Fc-region comprising a first Fc-region polypeptide and a second Fc-region polypeptide,
wherein
  a) the first Fc-region polypeptide has an amino acid sequence that differs from the second Fc-region polypeptide amino acid sequence at least at one corresponding position according to the Kabat EU index numbering system,
  whereby the variant (human) IgG class Fc-region has a different affinity to a human Fc-receptor compared to an IgG class Fc-region that has the same amino acid residue (as in a corresponding human Fc-region) in the first and the second Fc-region polypeptide at the corresponding position.

One aspect as reported herein is a variant (human) IgG class Fc-region comprising a first Fc-region polypeptide and a second Fc-region polypeptide,
wherein
  a) the amino acid sequence of the first Fc-region polypeptide differs from the amino acid sequence of a first parent IgG class Fc-region polypeptide in one or more amino acid residues, and
  the amino acid sequence of the second Fc-region polypeptide differs from the amino acid sequence of a second parent IgG class Fc-region polypeptide in one or more amino acid residues, and
  b) the first Fc-region polypeptide has an amino acid sequence that differs from the second Fc-region polypeptide amino acid sequence at least at one corresponding position according to the Kabat EU index numbering system,
  whereby the variant (human) IgG class Fc-region has a different affinity to a human Fc-receptor compared to a parent IgG class Fc-region comprising the first and the second parent IgG class Fc-region polypeptide of a).

One aspect as reported herein is a variant (human) IgG class Fc-region comprising a first Fc-region polypeptide and a second Fc-region polypeptide,
wherein
  a) the amino acid sequence of the first Fc-region polypeptide is derived from a first parent IgG class Fc-region polypeptide and the amino acid sequence of the second Fc-region polypeptide is derived from a second parent IgG class Fc-region polypeptide, and
  b) in the first Fc-region polypeptide and/or in the second Fc-region polypeptide one or more mutations are introduced so that the first Fc-region polypeptide has an amino acid sequence that differs from the second Fc-region polypeptide amino acid sequence at least at one corresponding position according to the Kabat EU index numbering system,
  whereby the variant (human) IgG class Fc-region has a different affinity to a human Fc-receptor compared to an IgG class Fc-region comprising the first and the second parent IgG class Fc-region polypeptide of a).

In one embodiment of all aspects the variant (human) IgG class Fc-region is a variant (human) IgG class heterodimeric Fc-region.

In one embodiment of all aspects the first parent IgG class Fc-region polypeptide and the second parent IgG class Fc-region polypeptide are non-human IgG class Fc-region polypeptides.

In one embodiment of all aspects the first parent IgG class Fc-region polypeptide and the second parent IgG class Fc-region polypeptide are the same IgG class Fc-region polypeptide.

In one embodiment of all aspects the pairing of the first Fc-region polypeptide and the second Fc-region polypeptide to form a dimeric (functional) Fc-region results in the formation of a heterodimer.

In one embodiment of all aspects the first and the second Fc-region polypeptide differ independently of each other in at least one amino acid residue from the respective parent IgG class Fc-region polypeptide.

In one embodiment of all aspects the IgG class is selected from the subclasses IgG1, IgG2, IgG3 and IgG4.

In one embodiment of all aspects the human Fc-receptor is selected from the human neonatal Fc-receptor and the human Fcγ receptor.

In one embodiment of all aspects the first Fc-region polypeptide differs in 1 or 2 or 3 or 4 or 5 or 6 or 7 or 8 or 9 or 10 or 11 or 12 amino acid residues at corresponding position according to the Kabat EU index numbering system from the second Fc-region polypeptide.

In one embodiment the variant (human) IgG class Fc-region has reduced binding to *Staphylococcus* protein A as the corresponding parent human IgG class Fc-region.

In one embodiment the variant (human) IgG class Fc-region has the same binding to *Staphylococcus* protein A as the corresponding parent human IgG class Fc-region.

In one embodiment of all aspects the variant (human) IgG class Fc-region comprises a first and a second Fc-region polypeptide both of human IgG1 or human IgG4 subclass (derived from human origin) which comprise one or two of the mutations selected from i) the group I253A, H310A and H435A, or ii) the group H310A, H433A and Y436A, or iii) the group L251D, L314D and L432D, or iv) the group L251S, L314S and L432S (numbering according to Kabat EU index numbering system) in the first Fc-region polypeptide and one or two of the mutations selected from the group comprising the mutations L251D, L251S, I253A, H310A, L314D, L314S, L432D, L432S, H433A, H435A and Y436A (numbering according to Kabat EU index numbering system) in the second Fc-region polypeptide so that all of the mutations i) I253A, H310A and H435A, or ii) H310A, H433A and Y436A, or iii) L251D, L314D and L432D, or iv) L251S, L314S and L432S are comprised in the variant (human) IgG class Fc-region.

In one embodiment of all aspects the variant (human) IgG class Fc-region comprises a first and a second Fc-region polypeptide both of human IgG1 or human IgG4 subclass (derived from human origin), which comprise the mutations I253A/H310A/H435A or H310A/H433A/Y436A or L251D/L314D/L432D or L251S/L314S/L432S or combinations thereof in the Fc-region (numbering according to Kabat EU index numbering system), whereby i) all mutations are in the first or the second Fc-region polypeptide, or ii) one or two mutations are in the first Fc-region polypeptide and one or two mutations are in the second Fc-region polypeptide so that all of the mutations i) I253A, H310A and H435A, or ii) H310A, H433A and Y436A, or iii) L251D, L314D and L432D, or iv) L251S, L314S and L432S are comprised in the Fc-region.

In one embodiment of all aspects the variant (human) IgG class Fc-region comprises a first and a second Fc-region polypeptide of human IgG1 subclass wherein
a) the first and the second Fc-region polypeptide both further comprise the mutations L234A and L235A (numbering according to Kabat EU index numbering system), or
b) the first and the second Fc-region polypeptide both further comprise the mutation P329G (numbering according to Kabat EU index numbering system), or
c) the first and the second Fc-region polypeptide both further comprise the mutations L234A and L235A and P329G (numbering according to Kabat EU index numbering system), or
d) the first and the second Fc-region polypeptide both further comprise the mutations L234A and L235A (numbering according to Kabat EU index numbering system) and the first Fc-region polypeptide further comprises the mutation Y349C or S354C and the mutation T366W and the second Fc-region polypeptide further comprises the mutation Y349C or S354C and the mutations T366S, L368A and Y407V, or
e) the first and the second Fc-region polypeptide both further comprise the mutations L234A and L235A and P329G (numbering according to Kabat EU index numbering system) and the first Fc-region polypeptide further comprises the mutation Y349C or S354C and the mutation T366W and the second Fc-region polypeptide further comprises the mutation Y349C or S354C and the mutations T366S, L368A and Y407V.

In one embodiment the variant (human) IgG class Fc-region comprises a first and a second Fc-region polypeptide of human IgG4 subclass wherein
a) the first and the second Fc-region polypeptide both further comprise the mutations S228P and L235E (numbering according to Kabat EU index numbering system), or
b) the first and the second Fc-region polypeptide both further comprise the mutation P329G (numbering according to Kabat EU index numbering system), or
c) the first and the second Fc-region polypeptide both further comprise the mutations S228P and L235E and P329G (numbering according to Kabat EU index numbering system), or
d) the first and the second Fc-region polypeptide both further comprise the mutations S228P and L235E (numbering according to Kabat EU index numbering system) and the first Fc-region polypeptide further comprises the mutation Y349C or S354C and the mutation T366W and the second Fc-region polypeptide further comprises the mutation Y349C or S354C and the mutations T366S, L368A and Y407V,
e) the first and the second Fc-region polypeptide both further comprise the mutations S228P and L235E and P329G (numbering according to Kabat EU index numbering system) and the first Fc-region polypeptide further comprises the mutation Y349C or S354C and the mutation T366W and the second Fc-region polypeptide further comprises the mutation Y349C or S354C and the mutations T366S, L368A and Y407V.

One aspect as reported herein is an antibody or Fc-region fusion polypeptide comprising the variant (human) IgG class Fc-region as reported herein.

In one embodiment the antibody is a monoclonal antibody.

In one embodiment the antibody is a human, humanized, or chimeric antibody.

One aspect as reported herein is a nucleic acid encoding the variant (human) IgG class Fc-region as reported herein.

One aspect as reported herein is a nucleic acid encoding the antibody as reported herein.

One aspect as reported herein is a nucleic acid encoding the Fc-region fusion polypeptide as reported herein.

One aspect as reported herein is a host cell comprising the nucleic acid as reported herein.

One aspect as reported herein is a method of producing the variant (human) IgG class Fc-region as reported herein comprising culturing the host cell as reported herein so that the variant (human) IgG class Fc-region is produced.

One aspect as reported herein is a method of producing the antibody as reported herein comprising culturing the host cell as reported herein so that the antibody is produced.

One aspect as reported herein is a method of producing the Fc-region fusion polypeptide as reported herein comprising culturing the host cell as reported herein so that the Fc-region fusion polypeptide is produced.

One aspect as reported herein is a pharmaceutical formulation comprising the variant (human) IgG class Fc-region as reported herein or the antibody as reported herein or the Fc-region fusion polypeptide as reported herein.

One aspect as reported herein is the variant (human) IgG class Fc-region as reported herein or the antibody as reported herein or the Fc-region fusion polypeptide as reported herein for use as a medicament.

One aspect as reported herein is the use of the variant (human) IgG class Fc-region as reported herein or the antibody as reported herein or the Fc-region fusion polypeptide as reported herein in the manufacture of a medicament.

The antibodies as reported herein can be used as e.g. T-cell recruiters, as Fc gamma receptor binder with high biological activity (potency) and fast clearance from the blood circulation (blood serum), as antibody-drug-conjugates with fast clearance in order to reduce systemic side effects, or as pre-targeting antibodies.

BRIEF DESCRIPTION OF THE FIGURES

FIG. 7B Serum concentration after intravenous (i.v.) application: comparison of VEGFang2-0015 without IHH-AAA mutation and VEGFang2-0016 with IHH-AAA mutation.

DETAILED DESCRIPTION OF EMBODIMENTS OF THE INVENTION

I. Definitions

Figure 1:
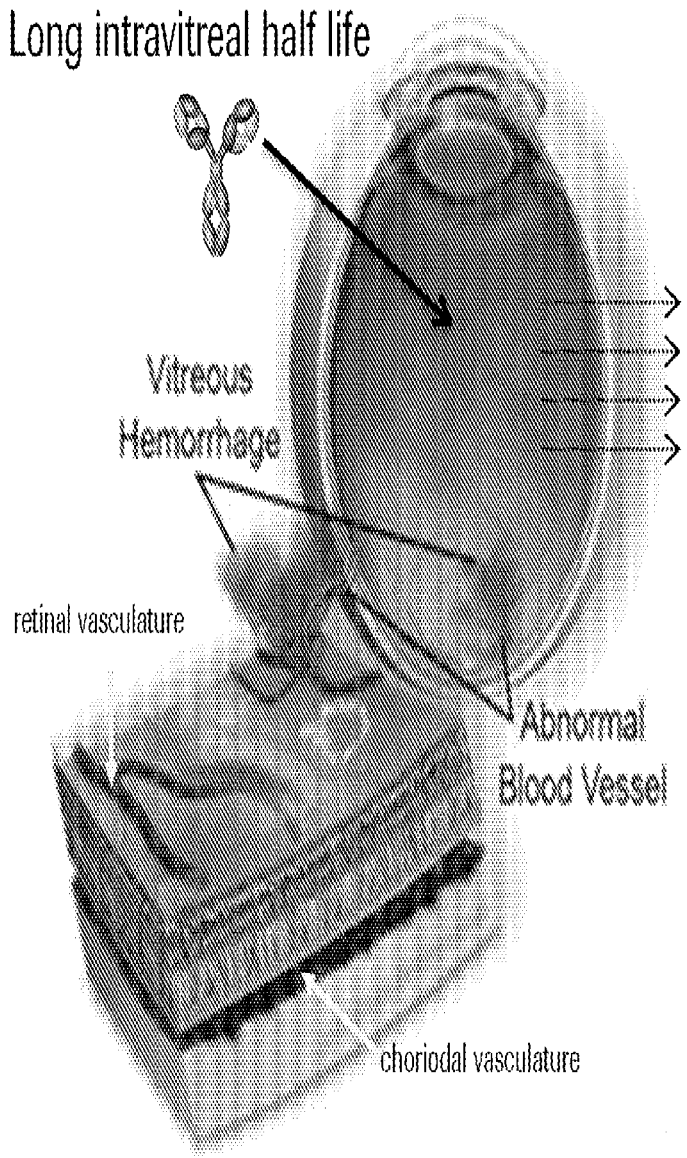
FIG. 1 Scheme of concept and advantages of <VEGF-ANG-2> IgG1 or IgG4 antibodies with IHH-AAA mutation (=combination of mutations I253A, H310A and H435A (numbering according to EU Index of Kabat)).

The term "about" denotes a range of +/−20% of the thereafter following numerical value. In one embodiment the term about denotes a range of +/−10% of the thereafter following numerical value. In one embodiment the term about denotes a range of +/−5% of the thereafter following numerical value.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence alterations. In some embodiments, the number of amino acid alterations are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

The term "alteration" denotes the mutation (substitution), insertion (addition), or deletion of one or more amino acid residues in a parent antibody or fusion polypeptide, e.g. a fusion polypeptide comprising at least an FcRn binding portion of an Fc-region, to obtain a modified antibody or fusion polypeptide. The term "mutation" denotes that the specified amino acid residue is substituted for a different amino acid residue. For example the mutation L234A denotes that the amino acid residue lysine at position 234 in an antibody Fc-region (polypeptide) is substituted by the amino acid residue alanine (substitution of lysine with alanine) (numbering according to the EU index).

The term "amino acid mutation" denotes the substitution of at least one existing amino acid residue with another different amino acid residue (=replacing amino acid residue). The replacing amino acid residue may be a "naturally occurring amino acid residues" and selected from the group consisting of alanine (three letter code: ala, one letter code: A), arginine (arg, R), asparagine (asn, N), aspartic acid (asp, D), cysteine (cys, C), glutamine (gln, Q), glutamic acid (glu, E), glycine (gly, G), histidine (his, H), isoleucine (ile, I), leucine (leu, L), lysine (lys, K), methionine (met, M), phenylalanine (phe, F), proline (pro, P), serine (ser, S), threonine (thr, T), tryptophan (trp, W), tyrosine (tyr, Y), and valine (val, V). The replacing amino acid residue may be a "non-naturally occurring amino acid residue". See e.g. U.S. Pat. No. 6,586,207, WO 98/48032, WO 03/073238, US 2004/0214988, WO 2005/35727, WO 2005/74524, Chin, J. W., et al., J. Am. Chem. Soc. 124 (2002) 9026-9027; Chin, J. W. and Schultz, P. G., ChemBioChem 11 (2002) 1135-1137; Chin, J. W., et al., PICAS United States of America 99 (2002) 11020-11024; and, Wang, L. and Schultz, P. G., Chem. (2002) 1-10 (all entirely incorporated by reference herein).

The term "amino acid insertion" denotes the (additional) incorporation of at least one amino acid residue at a predetermined position in an amino acid sequence. In one embodiment the insertion will be the insertion of one or two amino acid residues. The inserted amino acid residue(s) can be any naturally occurring or non-naturally occurring amino acid residue.

The term "amino acid deletion" denotes the removal of at least one amino acid residue at a predetermined position in an amino acid sequence.

The term "ANG-2" as used herein refers to human angiopoietin-2 (ANG-2) (alternatively abbreviated with ANGPT2 or ANG2) (SEQ ID NO: 31) which is described e.g. in Maisonpierre, P. C., et al, Science 277 (1997) 55-60 and Cheung, A. H., et al., Genomics 48 (1998) 389-91. The angiopoietins-1 (SEQ ID NO: 32) and –2 were discovered as ligands for the Ties, a family of tyrosine kinases that is selectively expressed within the vascular endothelium (Yancopoulos, G. D., et al., Nature 407 (2000) 242-248). There are now four definitive members of the angiopoietin family. Angiopoietin-3 and –4 (ANG-3 and ANG-4) may represent widely diverged counterparts of the same gene locus in mouse and man (Kim, I., et al., FEBS Let, 443 (1999) 353-356; Kim, I., et al., J. Biol. Chem. 274 (1999) 26523-26528). ANG-1 and ANG-2 were originally identified in tissue culture experiments as agonist and antagonist, respectively (see for ANG-1: Davis, S., et al., Cell 87 (1996) 1161-1169; and for ANG-2: Maisonpierre, P. C., et al., Science 277 (1997) 55-60). All of the known angiopoietins bind primarily to Tie2 (SEQ ID NO: 33), and both ANG-1 and –2 bind to Tie2 with an affinity of 3 nM (Kd) (Maisonpierre, P. C., et al., Science 277 (1997) 55-60).

The term "antibody" herein is used in the broadest sense and encompasses various antibody structures, including but not limited to monoclonal antibodies, multispecific antibodies (e.g. bispecific antibodies, trispecific antibodies), and antibody fragments so long as they exhibit the desired antigen- and/or protein A and/or FcRn-binding activity.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein.

The term "asymmetric Fc-region" denotes a pair of Fc-region polypeptides that have different amino acid residues at corresponding positions according to the Kabat EU index numbering system.

The term "asymmetric Fc-region with respect to FcRn binding" denotes an Fc-region that consists of two polypeptide chains that have different amino acid residues at corresponding positions, whereby the positions are determined according to the Kabat EU index numbering system, whereby the different positions affect the binding of the Fc-region to the human neonatal Fc-receptor (FcRn). For the purpose herein the differences between the two polypeptide chains of the Fc-region in an "asymmetric Fc-region with respect to FcRn binding" do not include differences that have been introduced to facilitate the formation of heterodimeric Fc-regions, e.g. for the production of bispecific antibodies. These differences can also be asymmetric, i.e. the two chains have differences at non corresponding amino acid residues according to the Kabat EU index numbering system. These differences facilitate heterodimerization and reduce homodimerization. Examples of such differences are the so-called "knobs into holes" substitutions (see, e.g., U.S. Pat. No. 7,695,936 and US 2003/0078385). The following knobs and holes substitutions in the individual polypeptide chains of an Fc-region of an IgG antibody of subclass IgG1 have been found to increase heterodimer formation: 1) Y407T in one chain and T366Y in the other chain; 2) Y407A in one chain and T366W in the other chain; 3) F405A in one chain and T394W in the other chain; 4) F405W in one chain and T394S in the other chain; 5) Y407T in one chain and T366Y in the other chain; 6) T366Y and F405A in one chain and T394W and Y407T in the other chain; 7) T366W and F405W in one chain and T394S and Y407A in the other chain; 8) F405W and Y407A in one chain and T366W and T394S in the other chain; and 9) T366W in one chain and T366S, L368A, and Y407V in the other chain, whereby the last listed is especially suited. In addition, changes creating new disulfide bridges between the two Fc-region polypeptide chains facilitate heterodimer formation (see, e.g., US 2003/0078385). The following substitutions resulting in appropriately spaced apart cysteine residues for the formation of new intra-chain disulfide bonds in the individual polypeptide chains of an Fc-region of an IgG antibody of subclass IgG1 have been found to increase heterodimer formation: Y349C in one chain and S354C in the other; Y349C in one chain and E356C in the other; Y349C in one chain and E357C in the other; L351C in one chain and S354C in the other; T394C in one chain and E397C in the other; or D399C in one chain and K392C in the other. Further examples of heterodimerization facilitating amino acid changes are the so-called "charge pair substitutions" (see, e.g., WO 2009/089004). The following charge pair substitutions in the individual polypeptide chains of an Fc-region of an IgG antibody of subclass IgG1 have been found to increase heterodimer formation: 1) K409D or K409E in one chain and D399K or D399R in the other chain; 2) K392D or K392E in one chain and D399K or D399R in the other chain; 3) K439D or K439E in one chain and E356K or E356R in the other chain; 4) K370D or K370E in one chain and E357K or E357R in the other chain; 5) K409D and K360D in one chain plus D399K and E356K in the other chain; 6) K409D and K370D in one chain plus D399K and E357K in the other chain; 7) K409D and K392D in one chain plus D399K, E356K, and E357K in the other chain; 8) K409D and K392D in one chain and D399K in the other chain; 9) K409D and K392D in one chain and D399K and E356K in the other chain; 10) K409D and K392D in one chain and D399K and D357K in the other chain; 11) K409D and K370D in one chain and D399K and D357K in the other chain; 12) D399K in one chain and K409D and K360D in the other chain; and 13) K409D and K439D in one chain and D399K and E356K on the other.

The term "binding (to an antigen)" denotes the binding of an antibody to its antigen in an in vitro assay, in one embodiment in a binding assay in which the antibody is bound to a surface and binding of the antigen to the antibody is measured by Surface Plasmon Resonance (SPR). Binding means a binding affinity ($K_D$) of $10^{-8}$ M or less, in some embodiments of $10^{-13}$ to $10^{-8}$ M, in some embodiments of $10^{-13}$ to $10^{-9}$ M.

Binding can be investigated by a BIAcore assay (GE Healthcare Biosensor AB, Uppsala, Sweden). The affinity of the binding is defined by the terms $k_a$ (rate constant for the association of the antibody from the antibody/antigen complex), $k_d$ (dissociation constant), and $K_D$ ($k_d/k_a$).

The term "chimeric" antibody refers to an antibody in which a portion of the heavy and/or light chain is derived from a particular source or species, while the remainder of the heavy and/or light chain is derived from a different source or species.

The term "CH2-domain" denotes the part of an antibody heavy chain polypeptide that extends approximately from EU position 231 to EU position 340 (EU numbering system according to Kabat). In one embodiment a CH2 domain has the amino acid sequence of SEQ ID NO: 09: APELLGG PSVFLFPPKP KDTLMISRTP EVTCVWDVS HEDPE-VKFNW YVDGVEVHNA KTKPREEQ E STYRWSVLT VLHQDWLNGK EYKCKVSNKA LPAPIEKTIS KAK.

The term "CH3-domain" denotes the part of an antibody heavy chain polypeptide that extends approximately from EU position 341 to EU position 446. In one embodiment the CH3 domain has the amino acid sequence of SEQ ID NO: 10: GQPREPQ VYTLPPSRDE LTKNQVSLTC LVKGFYPSDI AVEWESNGQP ENNYKTTPPV LDSDGSFFLY SKLTVDKSRW QQGNVFSCSV MHEALHNHYT QKSLSLSPG.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called α, δ, ε, γ, and μ, respectively.

The term "comparable length" denotes that two polypeptides comprise the identical number of amino acid residues or can be different in length by one or more and up to 10 amino acid residues at most. In one embodiment the Fc-region polypeptides comprise the identical number of amino acid residues or differ by a number of from 1 to 10 amino acid residues. In one embodiment the Fc-region polypeptides comprise the identical number of amino acid residues or differ by a number of from 1 to 5 amino acid residues. In one embodiment the Fc-region polypeptides comprise the identical number of amino acid residues or differ by a number of from 1 to 3 amino acid residues.

The term "derived from" denotes that an amino acid sequence is derived from a parent amino acid sequence by introducing alterations at least one position. Thus a derived amino acid sequence differs from the corresponding parent amino acid sequence at least one corresponding position (numbering according to Kabat EU index numbering system for antibody Fc-regions). In one embodiment an amino acid sequence derived from a parent amino acid sequence differs by one to fifteen amino acid residues at corresponding positions. In one embodiment an amino acid sequence derived from a parent amino acid sequence differs by one to ten amino acid residues at corresponding positions. In one embodiment an amino acid sequence derived from a parent amino acid sequence differs by one to six amino acid residues at corresponding positions. Likewise a derived amino acid sequence has a high amino acid sequence identity to its parent amino acid sequence. In one embodiment an amino acid sequence derived from a parent amino acid sequence has 80% or more amino acid sequence identity. In one embodiment an amino acid sequence derived from a parent amino acid sequence has 90% or more amino acid sequence identity. In one embodiment an amino acid sequence derived from a parent amino acid sequence has 95% or more amino acid sequence identity.

"Effector functions" refer to those biological activities attributable to the Fc-region of an antibody, which vary with the antibody class. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B-cell receptor); and B-cell activation.

An "effective amount" of an agent, e.g., a pharmaceutical formulation, refers to an amount effective, at dosages and for periods of time necessary, to achieve the desired therapeutic or prophylactic result.

The term "Fc-fusion polypeptide" denotes a fusion of a binding domain (e.g. an antigen binding domain such as a single chain antibody, or a polypeptide such as a ligand of a receptor) with an antibody Fc-region that exhibits the desired target- and/or protein A and/or FcRn-binding activity.

The term "Fc-region of human origin" denotes the C-terminal region of an immunoglobulin heavy chain of human origin that contains at least a part of the hinge region, the CH2 domain and the CH3 domain. In one embodiment, a human IgG heavy chain Fc-region extends from Cys226, or from Pro230, to the carboxyl-terminus of the heavy chain. In one embodiment the Fc-region has the amino acid sequence of SEQ ID NO: 60. However, the C-terminal lysine (Lys447) of the Fc-region may or may not be present. Unless otherwise specified herein, numbering of amino acid residues in the Fc-region or constant region is according to the EU numbering system, also called the EU index, as described in Kabat, E. A., et al., Sequences of Proteins of Immunological Interest, 5th ed., Public Health Service, National Institutes of Health, Bethesda, MD (1991), NIH Publication 91 3242. The Fc-region is composed of two heavy chain Fc-region polypeptides, which can be covalently linked to each other via the hinge region cysteine residues forming inter-polypeptide disulfide bonds.

The term "FcRn" denotes the human neonatal Fc-receptor. FcRn functions to salvage IgG from the lysosomal degradation pathway, resulting in reduced clearance and increased half-life. The FcRn is a heterodimeric protein consisting of two polypeptides: a 50 kDa class I major histocompatibility complex-like protein ($\alpha$-FcRn) and a 15 kDa $\beta$2-microglobulin ($\beta$2m). FcRn binds with high affinity to the CH2-CH3 portion of the Fc-region of IgG. The interaction between IgG and FcRn is strictly pH dependent and occurs in a 1:2 stoichiometry, with one IgG binding to two FcRn molecules via its two heavy chains (Huber, A. H., et al., J. Mol. Biol. 230 (1993) 1077-1083). FcRn binding occurs in the endosome at acidic pH (pH<6.5) and IgG is released at the neutral cell surface (pH of about 7.4). The pH-sensitive nature of the interaction facilitates the FcRn-mediated protection of IgGs pinocytosed into cells from intracellular degradation by binding to the receptor within the acidic environment of endosomes. FcRn then facilitates the recycling of IgG to the cell surface and subsequent release into the blood stream upon exposure of the FcRn-IgG complex to the neutral pH environment outside the cell.

The term "FcRn binding portion of an Fc-region" denotes the part of an antibody heavy chain polypeptide that extends approximately from EU position 243 to EU position 261 and approximately from EU position 275 to EU position 293 and approximately from EU position 302 to EU position 319 and approximately from EU position 336 to EU position 348 and approximately from EU position 367 to EU position 393 and EU position 408 and approximately from EU position 424 to EU position 440. In one embodiment one or more of the following amino acid residues according to the EU numbering of Kabat are altered F243, P244, P245P, K246, P247, K248, D249, T250, L251, M252, I253, S254, R255, T256, P257, E258, V259, T260, C261, F275, N276, W277, Y278, V279, D280, V282, E283, V284, H285, N286, A287, K288, T289, K290, P291, R292, E293, V302, V303, S304, V305, L306, T307, V308, L309, H310, Q311, D312, W313, L314, N315, G316, K317, E318, Y319, I336, S337, K338, A339, K340, G341, Q342, P343, R344, E345, P346, Q347, V348, C367, V369, F372, Y373, P374, S375, D376, I377, A378, V379, E380, W381, E382, S383, N384, G385, Q386, P387, E388, N389, Y391, T393, S408, S424, C425, S426, V427, M428, H429, E430, A431, L432, H433, N434, H435, Y436, T437, Q438, K439, and S440 (EU numbering).

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The term "full length antibody" denotes an antibody having a structure substantially similar to a native antibody structure or having heavy chains that contain an Fc-region as defined herein. A full length antibody may comprise further domains, such as e.g. a scFv or a scFab conjugated to one or more of the chains of the full length antibody. These conjugates are also encompassed by the term full length antibody.

The terms "heterodimer" or "heterodimeric" denote a molecule that comprises two polypeptide chains (e.g. of comparable length), wherein the two polypeptide chains have an amino acid sequence that have at least one different amino acid residue in a corresponding position, whereby corresponding position is determined according to the EU index of Kabat.

The terms "homodimer" and "homodimeric" denote a molecule that comprises two polypeptide chains of comparable length, wherein the two polypeptide chains have an amino acid sequence that is identical in corresponding positions, whereby corresponding positions are determined according to the EU index of Kabat.

An antibody or Fc-region fusion polypeptide as reported herein can be homodimeric or heterodimeric with respect to its Fc-region which is determined with respect to mutations or properties in focus. For example, with respect to FcRn and/or protein A binding (i.e. the focused on properties) an Fc-region (antibody) is homodimeric (i.e. both heavy chain Fc-region polypeptides comprise these mutations) with respect to the mutations H310A, H433A and Y436A (these mutations are in focus with respect to FcRn and/or protein A binding property of the Fc-region fusion polypeptide or antibody) but at the same time heterodimeric with respect to the mutations Y349C, T366S, L368A and Y407V (these mutations are not in focus as these mutations are directed to the heterodimerization of the heavy chains and not to the FcRn/protein A binding properties) as well as the mutations S354C and T366W, respectively (the first set is comprised only in the first Fc-region polypeptide whereas the second set is comprised only in the second Fc-region polypeptide). Further for example, an Fc-region fusion polypeptide or an antibody as reported herein can be heterodimeric with respect to the mutations I253A, H310A, H433A, H435A and Y436A (i.e. these mutations are directed all to the FcRn and/or protein A binding properties of the dimeric polypeptide), i.e. one Fc-region polypeptide comprises the mutations I253A, H310A and H435A, whereas the other Fc-region polypeptide comprises the mutations H310A, H433A and Y436A.

The terms "host cell", "host cell line", and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat, E. A. et al., Sequences of Proteins of Immunological Interest, 5th ed., Bethesda MD (1991), NIH Publication 91-3242, Vols. 1-3. In one embodiment, for the VL, the subgroup is subgroup kappa I as in Kabat et al., supra. In one embodiment, for the VH, the subgroup is subgroup III as in Kabat et al., supra.

The term "human Fc-region polypeptide" denotes an amino acid sequence which is identical to a "native" or "wild-type" human Fc-region polypeptide. The term "variant (human) Fc-region polypeptide" denotes an amino acid sequence which derived from a "native" or "wild-type" human Fc-region polypeptide by virtue of at least one "amino acid alteration". A "human Fc-region" is consisting of two human Fc-region polypeptides. A "variant (human) Fc-region" is consisting of two Fc-region polypeptides, whereby both can be variant (human) Fc-region polypeptides or one is a human Fc-region polypeptide and the other is a variant (human) Fc-region polypeptide.

In one embodiment the human Fc-region polypeptide has the amino acid sequence of a human IgG1 Fc-region polypeptide of SEQ ID NO: 60, or of a human IgG2 Fc-region polypeptide of SEQ ID NO: 61, or of a human IgG3 Fc-region polypeptide of SEQ ID NO: 62, or of a human IgG4 Fc-region polypeptide of SEQ ID NO: 63. In one embodiment the variant (human) Fc-region polypeptide is derived from an Fc-region polypeptide of SEQ ID NO: 60, or 61, or 62, or 63 and has at least one amino acid mutation compared to the human Fc-region polypeptide of SEQ ID NO: 60, or 61, or 62, or 63. In one embodiment the variant (human) Fc-region polypeptide comprises/has from about one to about twelve amino acid mutations, and in one embodiment from about one to about eight amino acid mutations. In one embodiment the variant (human) Fc-region polypeptide has at least about 80% homology with a human Fc-region polypeptide of SEQ ID NO: 60, or 61, or 62, or 63. In one embodiment the variant (human) Fc-region polypeptide has least about 90% homology with a human Fc-region polypeptide of SEQ ID NO: 60, or 61, or 62, or 63. In one embodiment the variant (human) Fc-region polypeptide has at least about 95% homology with a human Fc-region polypeptide of SEQ ID NO: 60, or 61, or 62, or 63.

The variant (human) Fc-region polypeptide derived from a human Fc-region polypeptide of SEQ ID NO: 60, or 61, or 62, or 63 is defined by the amino acid alterations that are contained. Thus, for example, the term P329G denotes a variant (human) Fc-region polypeptide derived human Fc-region polypeptide with the mutation of proline to glycine at amino acid position 329 relative to the human Fc-region polypeptide of SEQ ID NO: 60, or 61, or 62, or 63.

As used herein, the amino acid positions of all constant regions and domains of the heavy and light chain are numbered according to the Kabat numbering system described in Kabat, et al., Sequences of Proteins of Immunological Interest, 5th ed., Public Health Service, National Institutes of Health, Bethesda, MD (1991) and is referred to as "numbering according to Kabat" herein. Specifically the Kabat numbering system (see pages 647-660) of Kabat, et al., Sequences of Proteins of Immunological Interest, 5th ed., Public Health Service, National Institutes of Health, Bethesda, MD (1991) is used for the light chain constant domain CL of kappa and lambda isotype and the Kabat EU index numbering system (see pages 661-723) is used for the constant heavy chain domains (CH1, Hinge, CH2 and CH3).

A human IgG1 Fc-region polypeptide has the following amino acid sequence:

```
                                              (SEQ ID NO: 60)
DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPSRDELTKNQVSLTCLVK

GFYPSDIAVEWESNGQPENNYKTTPPVLDSDGSFFLYSKLTVDKSRWQQG

NVFSCSVMHEALHNHYTQKSLSLSPGK.
```

A human IgG1 Fc-region derived Fc-region polypeptide with the mutations L234A, L235A has the following amino acid sequence:

```
                                              (SEQ ID NO: 64)
DKTHTCPPCPAPEAAGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPSRDELTKNQVSLTCLVK

GFYPSDIAVEWESNGQPENNYKTTPPVLDSDGSFFLYSKLTVDKSRWQQG

NVFSCSVMHEALHNHYTQKSLSLSPGK.
```

A human IgG1 Fc-region derived Fc-region polypeptide with Y349C, T366S, L368A and Y407V mutations has the following amino acid sequence:

```
                                              (SEQ ID NO: 65)
DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVCTLPPSRDELTKNQVSLSCAVK

GFYPSDIAVEWESNGQPENNYKTTPPVLDSDGSFFLVSKLTVDKSRWQQG

NVFSCSVMHEALHNHYTQKSLSLSPGK.
```

A human IgG1 Fc-region derived Fc-region polypeptide with S354C, T366W mutations has the following amino acid sequence:

```
                                              (SEQ ID NO: 66)
DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPCRDELTKNQVSLWCLVK

GFYPSDIAVEWESNGQPENNYKTTPPVLDSDGSFFLYSKLTVDKSRWQQG

NVFSCSVMHEALHNHYTQKSLSLSPGK.
```

A human IgG1 Fc-region derived Fc-region polypeptide with L234A, L235A mutations and Y349C, T366S, L368A, Y407V mutations has the following amino acid sequence:

```
                                              (SEQ ID NO: 67)
DKTHTCPPCPAPEAAGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVCTLPPSRDELTKNQVSLSCAVK

GFYPSDIAVEWESNGQPENNYKTTPPVLDSDGSFFLVSKLTVDKSRWQQG

NVFSCSVMHEALHNHYTQKSLSLSPGK.
```

A human IgG1 Fc-region derived Fc-region polypeptide with a L234A, L235A and S354C, T366W mutations has the following amino acid sequence:

```
                                          (SEQ ID NO: 68)
DKTHTCPPCPAPEAAGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPCRDELTKNQVSLWCLVK

GFYPSDIAVEWESNGQPENNYKTTPPVLDSDGSFFLYSKLTVDKSRWQQG

NVFSCSVMHEALHNHYTQKSLSLSPGK.
```

A human IgG1 Fc-region derived Fc-region polypeptide with a P329G mutation has the following amino acid sequence:

```
                                          (SEQ ID NO: 69)
DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALGAPIEKTISKAKGQPREPQVYTLPPSRDELTKNQVSLTCLVK

GFYPSDIAVEWESNGQPENNYKTTPPVLDSDGSFFLYSKLTVDKSRWQQG

NVFSCSVMHEALHNHYTQKSLSLSPGK.
```

A human IgG1 Fc-region derived Fc-region polypeptide with L234A, L235A mutations and P329G mutation has the following amino acid sequence:

```
                                          (SEQ ID NO: 70)
DKTHTCPPCPAPEAAGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALGAPIEKTISKAKGQPREPQVYTLPPSRDELTKNQVSLTCLVK

GFYPSDIAVEWESNGQPENNYKTTPPVLDSDGSFFLYSKLTVDKSRWQQG

NVFSCSVMHEALHNHYTQKSLSLSPGK.
```

A human IgG1 Fc-region derived Fc-region polypeptide with a P239G mutation and Y349C, T366S, L368A, Y407V mutations has the following amino acid sequence:

```
                                          (SEQ ID NO: 71)
DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALGAPIEKTISKAKGQPREPQVCTLPPSRDELTKNQVSLSCAVK

GFYPSDIAVEWESNGQPENNYKTTPPVLDSDGSFFLVSKLTVDKSRWQQG

NVFSCSVMHEALHNHYTQKSLSLSPGK.
```

A human IgG1 Fc-region derived Fc-region polypeptide with a P329G mutation and S354C, T366W mutation has the following amino acid sequence:

```
                                          (SEQ ID NO: 72)
DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALGAPIEKTISKAKGQPREPQVYTLPPCRDELTKNQVSLWCLVK

GFYPSDIAVEWESNGQPENNYKTTPPVLDSDGSFFLYSKLTVDKSRWQQG

NVFSCSVMHEALHNHYTQKSLSLSPGK.
```

A human IgG1 Fc-region derived Fc-region polypeptide with L234A, L235A, P329G and Y349C, T366S, L368A, Y407V mutations has the following amino acid sequence:

```
                                          (SEQ ID NO: 73)
DKTHTCPPCPAPEAAGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALGAPIEKTISKAKGQPREPQVCTLPPSRDELTKNQVSLSCAVK

GFYPSDIAVEWESNGQPENNYKTTPPVLDSDGSFFLVSKLTVDKSRWQQG

NVFSCSVMHEALHNHYTQKSLSLSPGK.
```

A human IgG1 Fc-region derived Fc-region polypeptide with L234A, L235A, P329G mutations and S354C, T366W mutations has the following amino acid sequence:

```
                                          (SEQ ID NO: 74)
DKTHTCPPCPAPEAAGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALGAPIEKTISKAKGQPREPQVYTLPPCRDELTKNQVSLWCLVK

GFYPSDIAVEWESNGQPENNYKTTPPVLDSDGSFFLYSKLTVDKSRWQQG

NVFSCSVMHEALHNHYTQKSLSLSPGK.
```

A human IgG4 Fc-region polypeptide has the following amino acid sequence:

```
                                          (SEQ ID NO: 63)
ESKYGPPCPSCPAPEFLGGPSVFLFPPKPKDTLMISRTPEVTCVVVDVSQ

EDPEVQFNWYVDGVEVHNAKTKPREEQFNSTYRVVSVLTVLHQDWLNGKE

YKCKVSNKGLPSSIEKTISKAKGQPREPQVYTLPPSQEEMTKNQVSLTCL

VKGFYPSDIAVEWESNGQPENNYKTTPPVLDSDGSFFLYSRLTVDKSRWQ

EGNVFSCSVMHEALHNHYTQKSLSLSLGK.
```

A human IgG4 Fc-region derived Fc-region polypeptide with S228P and L235E mutations has the following amino acid sequence:

```
                                          (SEQ ID NO: 75)
ESKYGPPCPPCPAPEFEGGPSVFLFPPKPKDTLMISRTPEVTCVVVDVSQ

EDPEVQFNWYVDGVEVHNAKTKPREEQFNSTYRVVSVLTVLHQDWLNGKE

YKCKVSNKGLPSSIEKTISKAKGQPREPQVYTLPPSQEEMTKNQVSLTCL

VKGFYPSDIAVEWESNGQPENNYKTTPPVLDSDGSFFLYSRLTVDKSRWQ

EGNVFSCSVMHEALHNHYTQKSLSLSLGK.
```

A human IgG4 Fc-region derived Fc-region polypeptide with S228P, L235E mutations and P329G mutation has the following amino acid sequence:

```
                                          (SEQ ID NO: 76)
ESKYGPPCPPCPAPEFEGGPSVFLFPPKPKDTLMISRTPEVTCVVVDVSQ

EDPEVQFNWYVDGVEVHNAKTKPREEQFNSTYRVVSVLTVLHQDWLNGKE

YKCKVSNKGLGSSIEKTISKAKGQPREPQVYTLPPSQEEMTKNQVSLTCL

VKGFYPSDIAVEWESNGQPENNYKTTPPVLDSDGSFFLYSRLTVDKSRWQ

EGNVFSCSVMHEALHNHYTQKSLSLSLGK.
```

A human IgG4 Fc-region derived Fc-region polypeptide with S354C, T366W mutations has the following amino acid sequence:

(SEQ ID NO: 77)
ESKYGPPCPSCPAPEFLGGPSVFLFPPKPKDTLMISRTPEVTCVVVDVSQ

EDPEVQFNWYVDGVEVHNAKTKPREEQFNSTYRVVSVLTVLHQDWLNGKE

YKCKVSNKGLPSSIEKTISKAKGQPREPQVYTLPPCQEEMTKNQVSLWCL

VKGFYPSDIAVEWESNGQPENNYKTTPPVLDSDGSFFLYSRLTVDKSRWQ

EGNVFSCSVMHEALHNHYTQKSLSLSLGK.

A human IgG4 Fc-region derived Fc-region polypeptide with Y349C, T366S, L368A Y407V mutations has the following amino acid sequence:

(SEQ ID NO: 78)
ESKYGPPCPSCPAPEFLGGPSVFLFPPKPKDTLMISRTPEVTCVVVDVSQ

EDPEVQFNWYVDGVEVHNAKTKPREEQFNSTYRVVSVLTVLHQDWLNGKE

YKCKVSNKGLPSSIEKTISKAKGQPREPQVCTLPPSQEEMTKNQVSLSCA

VKGFYPSDIAVEWESNGQPENNYKTTPPVLDSDGSFFLVSRLTVDKSRWQ

EGNVFSCSVMHEALHNHYTQKSLSLSLGK.

A human IgG4 Fc-region derived Fc-region polypeptide with a S228P, L235E and S354C, T366W mutations has the following amino acid sequence:

(SEQ ID NO: 79)
ESKYGPPCPPCPAPEFEGGPSVFLFPPKPKDTLMISRTPEVTCVVVDVSQ

EDPEVQFNWYVDGVEVHNAKTKPREEQFNSTYRVVSVLTVLHQDWLNGKE

YKCKVSNKGLPSSIEKTISKAKGQPREPQVYTLPPCQEEMTKNQVSLWCL

VKGFYPSDIAVEWESNGQPENNYKTTPPVLDSDGSFFLYSRLTVDKSRWQ

EGNVFSCSVMHEALHNHYTQKSLSLSLGK.

A human IgG4 Fc-region derived Fc-region polypeptide with a S228P, L235E and Y349C, T366S, L368A, Y407V mutations has the following amino acid sequence:

(SEQ ID NO: 80)
ESKYGPPCPPCPAPEFEGGPSVFLFPPKPKDTLMISRTPEVTCVVVDVSQ

EDPEVQFNWYVDGVEVHNAKTKPREEQFNSTYRVVSVLTVLHQDWLNGKE

YKCKVSNKGLPSSIEKTISKAKGQPREPQVCTLPPSQEEMTKNQVSLSCA

VKGFYPSDIAVEWESNGQPENNYKTTPPVLDSDGSFFLVSRLTVDKSRWQ

EGNVFSCSVMHEALHNHYTQKSLSLSLGK.

A human IgG4 Fc-region derived Fc-region polypeptide with a P329G mutation has the following amino acid sequence:

(SEQ ID NO: 81)
ESKYGPPCPSCPAPEFLGGPSVFLFPPKPKDTLMISRTPEVTCVVVDVSQ

EDPEVQFNWYVDGVEVHNAKTKPREEQFNSTYRVVSVLTVLHQDWLNGKE

YKCKVSNKGLGSSIEKTISKAKGQPREPQVYTLPPSQEEMTKNQVSLTCL

VKGFYPSDIAVEWESNGQPENNYKTTPPVLDSDGSFFLYSRLTVDKSRWQ

EGNVFSCSVMHEALHNHYTQKSLSLSLGK.

A human IgG4 Fc-region derived Fc-region polypeptide with a P239G and Y349C, T366S, L368A, Y407V mutations has the following amino acid sequence:

(SEQ ID NO: 82)
ESKYGPPCPSCPAPEFLGGPSVFLFPPKPKDTLMISRTPEVTCVVVDVSQ

EDPEVQFNWYVDGVEVHNAKTKPREEQFNSTYRVVSVLTVLHQDWLNGKE

YKCKVSNKGLGSSIEKTISKAKGQPREPQVCTLPPSQEEMTKNQVSLSCA

VKGFYPSDIAVEWESNGQPENNYKTTPPVLDSDGSFFLVSRLTVDKSRWQ

EGNVFSCSVMHEALHNHYTQKSLSLSLGK.

A human IgG4 Fc-region derived Fc-region polypeptide with a P329G and S354C, T366W mutations has the following amino acid sequence:

(SEQ ID NO: 83)
ESKYGPPCPSCPAPEFLGGPSVFLFPPKPKDTLMISRTPEVTCVVVDVSQ

EDPEVQFNWYVDGVEVHNAKTKPREEQFNSTYRVVSVLTVLHQDWLNGKE

YKCKVSNKGLGSSIEKTISKAKGQPREPQVYTLPPCQEEMTKNQVSLWCL

VKGFYPSDIAVEWESNGQPENNYKTTPPVLDSDGSFFLVSRLTVDKSRWQ

EGNVFSCSVMHEALHNHYTQKSLSLSLGK.

A human IgG4 Fc-region derived Fc-region polypeptide with a S228P, L235E, P329G and Y349C, T366S, L368A, Y407V mutations has the following amino acid sequence:

(SEQ ID NO: 84)
ESKYGPPCPPCPAPEFEGGPSVFLFPPKPKDTLMISRTPEVTCVVVDVSQ

EDPEVQFNWYVDGVEVHNAKTKPREEQFNSTYRVVSVLTVLHQDWLNGKE

YKCKVSNKGLGSSIEKTISKAKGQPREPQVCTLPPSQEEMTKNQVSLSCA

VKGFYPSDIAVEWESNGQPENNYKTTPPVLDSDGSFFLVSRLTVDKSRWQ

EGNVFSCSVMHEALHNHYTQKSLSLSLGK.

A human IgG4 Fc-region derived Fc-region polypeptide with a S228P, L235E, P329G and S354C, T366W mutations has the following amino acid sequence:

(SEQ ID NO: 85)
ESKYGPPCPPCPAPEFEGGPSVFLFPPKPKDTLMISRTPEVTCVVVDVSQ

EDPEVQFNWYVDGVEVHNAKTKPREEQFNSTYRVVSVLTVLHQDWLNGKE

YKCKVSNKGLGSSIEKTISKAKGQPREPQVYTLPPCQEEMTKNQVSLWCL

VKGFYPSDIAVEWESNGQPENNYKTTPPVLDSDGSFFLVSRLTVDKSRWQ

EGNVFSCSVMHEALHNHYTQKSLSLSLGK.

An alignment of different human Fc-regions is shown below (EU numbering):

```
                          2             2
                          3             5
                          0             0
IGG1    DKTHTCPPCP   APELLGGPSV    FLFPPKPKDT    LMISRTPEVT    CVVVDVSHED
IGG2    ...VECPPCP   APP.VAGPSV    FLFPPKPKDT    LMISRTPEVT    CVVVDVSHED
IGG3    DTPPPCPRCP   APELLGGPSV    FLFPPKPKDT    LMISRTPEVT    CVVVDVSHED
IGG4    ...PPCPSCP   APEFLGGPSV    FLFPPKPKDT    LMISRTPEVT    CVVVDVSQED
        -- HINGE -|-- CH2 ------------------------------------

3
                                         0
                                         0
IGG1    PEVKFNWYVD   GVEVHNAKTK    PREEQYNSTY    RVVSVLTVLH    QDWLNGKEYK
IGG2    PEVQFNWYVD   GVEVHNAKTK    PREEQFNSTF    RVVSVLTVVH    QDWLNGKEYK
IGG3    PEVQFKWYVD   GVEVHNAKTK    PREEQYNSTF    RVVSVLTVLH    QDWLNGKEYK
IGG4    PEVQFNWYVD   GVEVHNAKTK    PREEQFNSTY    RVVSVLTVLH    QDWLNGKEYK
        -- CH2 --------------------------------------

3
                                         5
                                         0
IGG1    CKVSNKALPA   PIEKTISKAK    GQPREPQVYT    LPPSRDELTK    NQVSLTCLVK
IGG2    CKVSNKGLPA   PIEKTISKTK    GQPREPQVYT    LPPSREEMTK    NQVSLTCLVK
IGG3    CKVSNKALPA   PIEKTISKTK    GQPREPQVYT    LPPSREEMTK    NQVSLTCLVK
IGG4    CKVSNKGLPS   SIEKTISKAK    GQPREPQVYT    LPPSQEEMTK    NQVSLTCLVK
        -- CH2 ------- CH2 --|-- CH3 ------------------------

4
                                   0
                                   0
IGG1    GFYPSDIAVE   WESNGQPENN    YKTTPPVLDS    DGSFFLYSKL    TVDKSRWQQG
IGG2    GFYPSDISVE   WESNGQPENN    YKTTPPMLDS    DGSFFLYSKL    TVDKSRWQQG
IGG3    GFYPSDIAVE   WESSGQPENN    YNTTPPMLDS    DGSFFLYSKL    TVDKSRWQQG
IGG4    GFYPSDIAVE   WESNGQPENN    YKTTPPVLDS    DGSFFLYSRL    TVDKSRWQEG
        -- CH3 --------------------------------------

4
                              4
                              7
IGG1    NVFSCSVMHE   ALHNHYTQKS    LSLSPGK
IGG2    NVFSCSVMHE   ALHNHYTQKS    LSLSPGK
IGG3    NIFSCSVMHE   ALHNRFTQKS    LSLSPGK
IGG4    NVFSCSVMHE   ALHNHYTQKS    LSLSLGK
        -- CH3 ---------------------|
```

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., the CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR", as used herein, refers to each of the regions of an antibody variable domain which are hypervariable in sequence ("complementarity determining regions" or "CDRs") and form structurally defined loops ("hypervariable loops"), and/or contain the antigen-contacting residues ("antigen contacts"). Generally, antibodies comprise six HVRs; three in the VH (H1, H2, H3), and three in the VL (L1, L2, L3). HVRs as denoted herein include (a) hypervariable loops occurring at amino acid residues 26-32 (L1), 50-52 (L2), 91-96 (L3), 26-32 (H1), 53-55 (H2), and 96-101 (H3) (Chothia, C. and Lesk, A. M., J. Mol. Biol. 196 (1987) 901-917);

(b) CDRs occurring at amino acid residues 24-34 (L), 50-56 (L2), 89-97 (L3), 31-35b (H1), 50-65 (H2), and 95-102 (H3) (Kabat, E. A. et al., Sequences of Proteins of Immunological Interest, 5th ed. Public Health Service, National Institutes of Health, Bethesda, MD (1991), NIH Publication 91-3242);

(c) antigen contacts occurring at amino acid residues 27c-36 (L1), 46-55 (L2), 89-96 (L3), 30-35b (H1), 47-58 (H2), and 93-101 (H3) (MacCallum et al. J. Mol. Biol. 262: 732-745 (1996)); and (d) combinations of (a), (b), and/or (c), including HVR amino acid residues 46-56 (L2), 47-56 (L2), 48-56 (L2), 49-56 (L2), 26-35 (H1), 26-35b (H1), 49-65 (H2), 93-102 (H3), and 94-102 (H3).

In one embodiment, HVR residues comprise those identified elsewhere in the specification.

Unless otherwise indicated, HVR residues and other residues in the variable domain (e.g., FR residues) are numbered herein according to the Kabat EU index numbering system (Kabat et al., supra).

The term "IGF-1R" as used herein, refers to any native IGF-1R from any vertebrate source, including mammals such as primates (e.g. humans) and rodents (e.g., mice and rats), unless otherwise indicated. The term encompasses "full-length", unprocessed IGF-1R as well as any form of IGF-1R that results from processing in the cell. The term also encompasses naturally occurring variants of IGF-1R, e.g., splice variants or allelic variants. The amino acid sequence of human IGF-1R is shown in SEQ ID NO: 11.

An "individual" or "subject" is a mammal. Mammals include, but are not limited to, domesticated animals (e.g. cows, sheep, cats, dogs, and horses), primates (e.g., humans and non-human primates such as monkeys), rabbits, and rodents (e.g., mice and rats). In certain embodiments, the individual or subject is a human.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., size-exclusion chromatography or ion exchange or reverse phase HPLC). For review of methods for assessment of antibody purity, see, e.g., Flatman, S. et al., J. Chrom. B 848 (2007) 79-87.

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-IGF-1R antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

The term "package insert" is used to refer to instructions customarily included in commercial packages of therapeutic products, that contain information about the indications, usage, dosage, administration, combination therapy, contraindications and/or warnings concerning the use of such therapeutic products.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington DC, 20559, where it is registered under U.S. Copyright Registration No. TXU510087. The ALIGN-2 program is publicly available from Genentech, Inc., South San Francisco, CA, or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

$$100 \text{ times the fraction } X/Y$$

where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

The term "peptidic linker" as used herein denotes a peptide with amino acid sequences, which is in one embodiment of synthetic origin. The peptidic linker is in one embodiment a peptide with an amino acid sequence with a length of at least 30 amino acids, in one embodiment with a length of 32 to 50 amino acids. In one embodiment the peptidic linker is a peptide with an amino acid sequence with a length of 32 to 40 amino acids. In one embodiment the peptidic linker is (G×S)n with G=glycine, S=serine, (x=3, n=8, 9 or 10) or (x=4 and n=6, 7 or 8), in one embodiment with x=4, n=6 or 7, in one embodiment with x=4, n=7. In one embodiment the peptidic linker is $(G_4S)_6G_2$.

The term "recombinant antibody" denotes all antibodies (chimeric, humanized and human) that are prepared, expressed, created or isolated by recombinant means. This includes antibodies isolated from a host cell such as a NS0 or CHO cell or from an animal (e.g. a mouse) that is transgenic for human immunoglobulin genes or antibodies expressed using a recombinant expression vector transfected into a host cell. Such recombinant antibodies have variable and constant regions in a rearranged form. The recombinant antibodies as reported herein can be subjected to in vivo somatic hypermutation. Thus, the amino acid sequences of the VH and VL regions of the recombinant antibodies are sequences that, while derived from and related to human germ line VH and VL sequences, may not naturally exist within the human antibody germ line repertoire in vivo.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies or Fc-region fusion polypeptides as reported herein are used to delay development of a disease or to slow the progression of a disease.

The term "valent" as used within the current application denotes the presence of a specified number of binding sites in a (antibody) molecule. As such, the terms "bivalent", "tetravalent", and "hexavalent" denote the presence of two binding site, four binding sites, and six binding sites, respectively, in a (antibody) molecule. The bispecific antibodies as reported herein are in one preferred embodiment "bivalent".

The term "variable region" or "variable domain" refer to the domain of an antibody heavy or light chain that is involved in binding of the antibody to its antigen. The variable domains of the heavy chain and light chain (VH and VL, respectively) of an antibody generally have similar structures, with each domain comprising four framework regions (FRs) and three hypervariable regions (HVRs) (see, e.g., Kindt, T. J. et al. Kuby Immunology, 6th ed., W. H. Freeman and Co., NY (2007), page 91). A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano, S. et al., J. Immunol. 150 (1993) 880-887; Clackson, T. et al., Nature 352 (1991) 624-628).

The term "ocular vascular disease" includes, but is not limited to intraocular neovascular syndromes such as diabetic retinopathy, diabetic macular edema, retinopathy of prematurity, neovascular glaucoma, retinal vein occlusions, central retinal vein occlusions, macular degeneration, age-related macular degeneration, retinitis pigmentosa, retinal angiomatous proliferation, macular telangectasia, ischemic retinopathy, iris neovascularization, intraocular neovascularization, corneal neovascularization, retinal neovascularization, choroidal neovascularization, and retinal degeneration (see e.g. Garner, A., Vascular diseases, In: Pathobiology of ocular disease, A dynamic approach, Garner, A., and Klintworth, G. K., (eds.), 2nd edition, Marcel Dekker, New York (1994), pp. 1625-1710).

The term "vector", as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors".

The term "VEGF" as used herein refers to human vascular endothelial growth factor (VEGF/VEGF-A) the 165-amino acid human vascular endothelial cell growth factor (amino acid 27-191 of precursor sequence of human VEGF165: SEQ ID NO: 30; amino acids 1-26 represent the signal peptide), and related 121, 189, and 206 vascular endothelial cell growth factor isoforms, as described by Leung, D. W., et al., Science 246 (1989) 1306-1309; Houck et al., Mol. Endocrin. 5 (1991) 1806-1814; Keck, P. J., et al., Science 246 (1989) 1309-1312 and Connolly, D. T., et al., J. Biol. Chem. 264 (1989) 20017-20024; together with the naturally occurring allelic and processed forms of those growth factors. VEGF is involved in the regulation of normal and abnormal angiogenesis and neovascularization associated with tumors and intraocular disorders (Ferrara, N., et al., Endocrin. Rev. 18 (1997) 4-25; Berkman, R. A., et al., J. Clin. Invest. 91 (1993) 153-159; Brown, L. F., et al., Human Pathol. 26 (1995) 86-91; Brown, L. F., et al., Cancer Res. 53 (1993) 4727-4735; Mattern, J., et al., Brit. J. Cancer. 73 (1996) 931-934; and Dvorak, H. F., et al., Am. J. Pathol. 146 (1995) 1029-1039). VEGF is a homodimeric glycoprotein that has been isolated from several sources and includes several isoforms. VEGF shows highly specific mitogenic activity for endothelial cells.

The term "with (the) mutation IHH-AAA" as used herein refers to the combination of the mutations I253A (Ile253Ala), H310A (His310Ala), and H435A (His435Ala) and the term "with (the) mutation HHY-AAA" as used herein refers to the combination of the mutations H310A (His310Ala), H433A (His433Ala), and Y436A (Tyr436Ala) and the term "with (the) mutation YTE" as used herein refers to the combination of mutations M252Y (Met252Tyr), S254T (Ser254Thr), and T256E (Thr256Glu) in the constant heavy chain region of IgG1 or IgG4 subclass, wherein the numbering is according to the EU Index of Kabat.

The term "with (the) mutations P329G LALA" as used herein refers to the combination of the mutations L234A (Leu234Ala), L235A (Leu235Ala) and P329G (Pro329Gly) in the constant heavy chain region of IgG1 subclass, wherein the numbering is according to the EU Index of Kabat. The term "with (the) mutation SPLE" as used herein refers to the combination of the mutations S228P (Ser228Pro) and L235E (Leu235Glu) in the constant heavy chain region of IgG4 subclass, wherein the numbering is according to the EU Index of Kabat. The term "with (the) mutation SPLE and P239G" as used herein refers to the combination of the mutations S228P (Ser228Pro), L235E (Leu235Glu) and P329G (Pro329Gly) in the constant heavy chain region of IgG4 subclass, wherein the numbering is according to the EU Index of Kabat.

II. The Current Invention

The invention is based, at least in part, on the finding that the FcRn-binding of an antibody or Fc-region fusion polypeptide can be modified by altering amino acid residues at non-corresponding positions in the individual Fc-region polypeptides because these alterations act together in the modification of the FcRn-binding. Antibodies and Fc-region fusion polypeptides as reported herein are useful, e.g., for the treatment of diseases in which tailor-made systemic retention times are required.

A. The Neonatal Fc-Receptor (FcRn)

The neonatal Fc-receptor (FcRn) is important for the metabolic fate of antibodies of the IgG class in vivo. The FcRn functions to salvage wild-type IgG from the lysosomal degradation pathway, resulting in reduced clearance and increased half-life. It is a heterodimeric protein consisting of two polypeptides: a 50 kDa class I major histocompatibility complex-like protein (α-FcRn) and a 15 kDa β2-microglobulin (β2m). FcRn binds with high affinity to the CH2-CH3 portion of the Fc-region of an antibody of the class IgG. The interaction between an antibody of the class IgG and the FcRn is pH dependent and occurs in a 1:2 stoichiometry, i.e. one IgG antibody molecule can interact with two FcRn molecules via its two heavy chain Fc-region polypeptides (see e.g. Huber, A. H., et al., J. Mol. Biol. 230 (1993) 1077-1083).

Thus, an IgGs in vitro FcRn binding properties/characteristics are indicative of its in vivo pharmacokinetic properties in the blood circulation.

In the interaction between the FcRn and the Fc-region of an antibody of the IgG class different amino acid residues of the heavy chain CH2- and CH3-domain are participating. The amino acid residues interacting with the FcRn are located approximately between EU position 243 and EU position 261, approximately between EU position 275 and EU position 293, approximately between EU position 302 and EU position 319, approximately between EU position 336 and EU position 348, approximately between EU position 367 and EU position 393, at EU position 408, and approximately between EU position 424 and EU position 440. More specifically the following amino acid residues according to the EU numbering of Kabat are involved in the interaction between the Fc-region and the FcRn: F243, P244, P245P, K246, P247, K248, D249, T250, L251, M252, I253, S254, R255, T256, P257, E258, V259, T260, C261, F275, N276, W277, Y278, V279, D280, V282, E283, V284, H285, N286, A287, K288, T289, K290, P291, R292, E293, V302, V303, S304, V305, L306, T307, V308, L309, H310, Q311, D312, W313, L314, N315, G316, K317, E318, Y319, I336, S337, K338, A339, K340, G341, Q342, P343, R344, E345, P346, Q347, V348, C367, V369, F372, Y373, P374, S375, D376, I377, A378, V379, E380, W381, E382, S383, N384, G385, Q386, P387, E388, N389, Y391, T393, S408, S424, C425, S426, V427, M428, H429, E430, A431, L432, H433, N434, H435, Y436, T437, Q438, K439, and S440.

Site-directed mutagenesis studies have proven that the critical binding sites in the Fc-region of IgGs for FcRn are Histidine 310, Histidine 435, and Isoleucine 253 and to a lesser extent Histidine 433 and Tyrosine 436 (see e.g. Kim, J. K., et al., Eur. J. Immunol. 29 (1999) 2819-2825; Raghavan, M., et al., Biochem. 34 (1995) 14649-14657; Medesan, C., et al., J. Immunol. 158 (1997) 2211-2217).

Methods to increase IgG binding to FcRn have been performed by mutating IgG at various amino acid residues: Threonine 250, Methionine 252, Serine 254, Threonine 256, Threonine 307, Glutamic acid 380, Methionine 428, Histidine 433, and Asparagine 434 (see Kuo, T. T., et al., J. Clin. Immunol. 30 (2010) 777-789).

In some cases antibodies with reduced half-life in the blood circulation are desired. For example, drugs for intravitreal application should have a long half-live in the eye and a short half-life in the circulation of the patient. Such antibodies also have the advantage of increased exposure to a disease site, e.g. in the eye.

Different mutations that influence the FcRn binding and therewith the half-live in the blood circulation are known. Fc-region residues critical to the mouse Fc-mouse FcRn interaction have been identified by site-directed mutagenesis (see e.g. Dall'Acqua, W. F., et al. J. Immunol 169 (2002) 5171-5180). Residues I253, H310, H433, N434, and H435 (EU numbering according to Kabat) are involved in the interaction (Medesan, C., et al., Eur. J. Immunol. 26 (1996) 2533-2536; Firan, M., et al., Int. Immunol. 13 (2001) 993-1002; Kim, J. K., et al., Eur. J. Immunol. 24 (1994) 542-548). Residues I253, H310, and H435 were found to be critical for the interaction of human Fc with murine FcRn (Kim, J. K., et al., Eur. J. Immunol. 29 (1999) 2819-2825). Residues M252Y, S254T, T256E have been described by Dall'Acqua et al. to improve FcRn binding by protein-protein interaction studies (Dall'Acqua, W. F., et al. J. Biol. Chem. 281 (2006) 23514-23524). Studies of the human Fc-human FcRn complex have shown that residues I253, S254, H435, and Y436 are crucial for the interaction (Firan, M., et al., Int. Immunol. 13 (2001) 993-1002; Shields, R. L., et al., J. Biol. Chem. 276 (2001) 6591-6604). In Yeung, Y. A., et al. (J. Immunol. 182 (2009) 7667-7671) various mutants of residues 248 to 259 and 301 to 317 and 376 to 382 and 424 to 437 have been reported and examined. Exemplary mutations and their effect on FcRn binding are listed in the following Table.

TABLE

| mutation | effect on FcRn binding | half-live in the circulation | reference |
|---|---|---|---|
| H285 H310Q/H433N (murine IgG1) | reduced (murine) | reduced (in mouse) | Kim, J. K., Scand. J. Immunol. 40 (1994) 457-465 |

TABLE-continued

| mutation | effect on FcRn binding | half-live in the circulation | reference |
|---|---|---|---|
| I253A<br>H310A<br>H435A<br>H436A<br>(murine IgG1) | reduced<br>(murine) | reduced<br>(in mouse) | Ghetie, V.<br>and Ward, E. S.,<br>Immunol.<br>Today 18<br>(1997) 592-598 |
| T252L/T254S/T256F<br>T252A/T254S/T256A<br>(murine IgG1) | increased<br>(murine) | increased<br>(in mouse) | Ghetie, V.<br>and Ward, E. S.,<br>Immunol.<br>Today 18<br>(1997) 592-598 |
| I253A<br>H310A<br>H435A<br>H436A<br>H433A/N434Q<br>(murine IgG1) | reduced<br>(murine) | reduced<br>(in mouse) | Medesan, C.,<br>et al., J.<br>Immunol.<br>158 (1997)<br>2211-2217 |
| I253A<br>H310A<br>H435A<br>H435R<br>(human IgG1) | reduced<br>H310A: <0.1<br>rel. binding to<br>muFcRn<br>(murine) | reduced<br>(in mouse) | Kim, J. K.,<br>Eur. J.<br>Immunol.<br>29 (1999)<br>2819-2825 |
| H433A<br>(human IgG1) | 1.1 rel. binding<br>to muFcRn,<br>0.4 rel. binding<br>hu FcRn<br>(murine) | | Kim, J. K.,<br>Eur. J.<br>Immunol.<br>29 (1999)<br>2819-2825 |
| I253A<br>S254A<br>H435A<br>Y436A<br>(human IgG1) | reduced<br><0.1 relative<br>binding to<br>huFcRn | reduced | Shields, R. L.,<br>et al.,<br>J. Biol.<br>Chem. 276<br>(2001)<br>6591-6604 |
| R255A<br>K288A<br>L309A<br>S415A<br>H433A<br>(human IgG1) | reduced<br>(human) | reduced | Shields, R. L.,<br>et al.,<br>J. Biol.<br>Chem. 276<br>(2001)<br>6591-6604 |
| P238A<br>T256A<br>E272A<br>V305A<br>T307A<br>Q311A<br>D312A<br>K317A<br>D376A<br>A378Q<br>E380A<br>E382A<br>S424A<br>N434A<br>K288A/N434A<br>E380A/N434A<br>T307A/E380A/N434A<br>(human IgG1) | increased<br>(human) | increased | Shields, R. L.,<br>et al.,<br>J. Biol.<br>Chem. 276<br>(2001)<br>6591-6604 |
| H435A<br>(humanized IgG1) | reduced<br><0.1 rel.<br>binding to<br>huFcRn | reduced | Firan, M.,<br>et al., Int.<br>Immunol.<br>13 (2001)<br>993-1002 |
| I253A (no binding)<br>M252W<br>M252Y<br>M252Y/T256Q<br>M252F/T256D<br>N434F/Y436H<br>M252Y/S254T/T256E<br>G385A/Q386P/N389S<br>H433K/N434F/Y436H<br>H433R/N434Y/Y436H | increased<br>(murine and<br>human) | reduced<br>(in mouse) | Dall'Acqua,<br>J.<br>Immunol.<br>169 (2002)<br>5171-5180 |

TABLE-continued

| mutation | effect on FcRn binding | half-live in the circulation | reference |
|---|---|---|---|
| G385R/Q386T/P387R/N389P M252Y/S254T/T256E/H433K/ N434F/Y436H M252Y/S254T/T256E/G385R/ Q386T/P387R/N389P (human IgG1) | | | |
| M428L T250Q/M428L (human IgG2) | increased (human) | increased (in monkey) | Hinton, P. R., et al., J. Biol. Chem. 279 (2004) 6213-6216 |
| M252Y/S254T/T256E + H433K/N434F (human IgG) | increased (human) | increased (in mouse) | Vaccaro, C., et al., Nat. Biotechnol. 23 (2005) 1283-1288 |
| T307A/E380A/N434A (chimeric IgG1) | increased | increased in transgenic mouse | Pop, L. M., et al., Int. Immunopharmacol. 5 (2005) 1279-1290 |
| T250Q E380A M428L N434A K288A/N434A E380A/N434A T307A/E380A/N434A (human IgG1) | increased (human) | increased in transgenic mouse | Petkova, S. B., et al., Int. Immunol 18 (2006) 1759-1769 |
| I253A (human IgG1) | reduced (human) | reduced in transgenic mouse | Petkova, S. B., et al., Int. Immunol 18 (2006) 1759-1769 |
| S239D/A330L/I332E M252Y/S254T/T256E (humanized) | increased (human and Cynomolgus) | increased in Cynomolgus | Dall'Acqua, W. F., et al., J. Biol. Chem. 281 (2006) 23514-23524 |
| T250Q M428L T250Q/M428L (human IgG1) | increased (human) | increased in Rhesus apes | Hinton, P. R., et al., J. Immunol. 176 (2006) 346-356 |
| T250Q/M428L P257I/Q311I (humanized IgG1) | increased (mouse and Cynomolgus) | no change in Cynomolgus increased in mouse | Datta-Mannan, A., et al., J. Biol. Chem. 282 (2007) 1709-1717 |
| P257I/Q311I P257I/N434H D376V/N434H (humanized IgG1) | increased at pH 6 (human, Cynomolgus, mouse) | reduced in mice P257I/N434H reduced in Cynomolgus | Datta-Mannan, A., et al., Drug Metab. Dispos. 35 (2007) 86-94 |
| abrogate FcRn binding: I253 H310 H433 H435 reduce FcRn binding: Y436 increased FcRn binding: T250 N252 S254 T256 T307 M428 N434 | increased and reduced | reducing the binding ability of IgG for FcRn reduces its serum persistence; a higher-affinity FcRn-IgG interaction prolongs the half-lives of IgG and Fc-coupled drugs in the serum | Ropeenian, D. C. and Akilesh, S., Nat. Rev. Immunol. 7 (2007) 715-725 |

TABLE-continued

| mutation | effect on FcRn binding | half-live in the circulation | reference |
|---|---|---|---|
| N434A | increased (Cynomolgus monkey) | increased in Cynomolgus monkey | Yeung, Y. A., et al., Cancer Res. 70 (2010) 3269-3277 |
| T307Q/N434A | | | |
| T307Q/N434S | | | |
| V308P/N434A | | | |
| T307Q/E380A/N434A (human IgG1) | | | |
| 256P | increased at neutral pH | | WO 2011/122011 |
| 280K | | | |
| 339T | | | |
| 385H | | | |
| 428L | | | |
| 434W/Y/F/A/H (human IgG) | | | |

It has been found that one mutation one-sided in one Fc-region polypeptide is sufficient to weaken the binding to an Fc receptor significantly. The more mutations are introduced into the Fc-region the weaker the binding to the FcRn becomes. But one-sided asymmetric mutations are not sufficient to completely inhibit FcRn binding. M TABLE-continued

| FcRn affecting mutation | retention time on FcRn affinity column |
|---|---|
| one chain with H310A/H433A/Y436A | 46.7 min. |
| one chain with I253A/H310A/H435A | 46.6 min. |
| one chain with L251D/L314D/L432D | 46.3 min. |
| first chain with I253A/H310A/H435A and second chain with H310A or H435A or I253A/H310A/H435A | no binding |

The asymmetric IHH-AAA- and LLL-DDD-mutations (LLL-DDD-mutation=L251D, L314D and L432D) show weaker binding than the corresponding parent or wild-type antibody.

The symmetric HHY-AAA mutation (=combination of the mutations H310A, H433A and Y436A) results in an Fc-region that does no longer bind to the human FcRn whereas the binding to protein A is maintained (see FIGS. 11, 12, 13 and 14).

The effect of the introduction of asymmetric FcRn-binding affecting mutations in the Fc-region has further been exemplified with a bispecific anti-VEGF/ANG2 antibody (VEGF/ANG2), a monospecific anti-IGF-1R antibody (IGF-1R), and a full length antibody with fusions to the C-terminus of both heavy chains (fusion) assembled using the knobs-into-holes technology in order to allow the introduction of asymmetric mutations (see e.g. U.S. Pat. No. 7,695,936, US 2003/0078385; "knob chain" mutations: S354C/T366W, "hole chain" mutations: Y349C/T366S/L368A/Y407V). The effect of the asymmetrically introduced mutations on FcRn-binding and protein A binding can easily be determined using an FcRn affinity chromatography method, a protein A affinity chromatography method and SPR-based methods (see the following Table).

| antibody | further mutation in knob chain | further mutation in hole chain | FcR binding affecting mutations | FcRn binding (SPR) | FcRn binding (column) | protein A binding (SPR) | protein A binding (column) |
|---|---|---|---|---|---|---|---|
| VEGF/ANG2 0096 | none | none | L234A L235A P329G | yes | yes | stable binding | yes |
| VEGF/ANG2 0097 | none | I253A H310A H435A | L234A L235A P329G | yes | yes | fast off-rate | yes |
| VEGF/ANG2 0098 | none | H310A H433A Y436A | L234A L235A P329G | yes | yes | stable binding | yes |
| VEGF/ANG2 0099 | none | L251D L314D L432D | L234A L235A P329G | reduced | reduced | fast off-rate | yes |
| VEGF/ANG2 0100 | none | M252Y S254T T256E | L234A L235A P329G | increased | increased | increased | yes |
| VEGFang2-0016 | I253A H310A H435A | I253A H310A H435A | L234A L235A P329G | no | no | n.d. | no |
| VEGF/ANG2-0121 | H310A H433A Y436A | H310A H433A Y436A | L234A L235A P329G | no. | n.d. | yes | yes |
| fusion 0008 | none | none | L234A L235A P329G | yes | yes | n.d. | n.d. |
| fusion 0019 | I253A | I253A | L234A L235A P329G | no. | no | n.d. | n.d. |
| fusion 0020 | H310A | H310A | L234A L235A P329G | no | no | n.d. | n.d. |
| fusion 0021 | H435A | H435A | L234A L235A P329G | no | no | n.d. | n.d. |
| fusion 0038 | Y436A | Y436A | L234A L235A P329G | reduced | reduced | yes | n.d. |
| fusion 0022 | I253A H310A | I253A H310A | L234A L235A P329G | no | no | n.d. | n.d. |
| fusion 0023 | I253A H435A | I253A H435A | L234A L235A P329G | no | no | n.d. | n.d. |
| fusion 0036 | H310A H435A | H310A H435A | L234A L235A P329G | no | no | n.d. | n.d. |
| fusion 0037 | H310A Y436A | H310A Y436A | L234A L235A P329G | no | no | n.d. | n.d. |

-continued

| antibody | further mutation in knob chain | further mutation in hole chain | FcR binding affecting mutations | FcRn binding (SPR) | FcRn binding (column) | protein A binding (SPR) | protein A binding (column) |
|---|---|---|---|---|---|---|---|
| fusion 0018 | I253A H310A H435A | I253A H310A H435A | L234A L235A P329G | no | no | n.d. | n.d. |
| fusion 0039 | H310A H433A Y436A | H310A H433A Y436A | L234A L235A P329G | no | no | yes | n.d. |

The combination of mutations I253A, H310A, H435A, or L251D, L314D, L432D, or L251S, L314S, L432S result in a loss of the binding to protein A, whereas the combination of mutations I253A, H310A, H435A, or H310A, H433A, Y436A, or L251D, L314D, L432D result in a loss of the binding to the human neonatal Fc receptor.

One aspect as reported herein is an antibody or Fc-region fusion polypeptide comprising the variant human IgG class Fc-region as reported herein.

The Fc-region in the Fc-region fusion polypeptide confers the above described characteristics to its fusion partner. The fusion partner can be any molecules having a biological activity whose in vivo half-live shall be reduced or increased, i.e. whose in vivo half-live shall be clearly defined and tailor-made for its intended application.

Fc-region fusion polypeptides may comprise e.g. a variant (human) IgG class Fc-region as reported herein and a receptor protein that binds to a target including a ligand, such as, for example, TNFR-Fc-region fusion polypeptide (TNFR=human tumor necrosis factor receptor), or IL-1R-Fc-region fusion polypeptide (IL-1R=human interleukin-1 receptor), or VEGFR-Fc-region fusion polypeptides (VEGFR=human vascular endothelial growth factor receptor), or ANG2R-Fc-region fusion polypeptides (ANG2R=human angiopoietin 2 receptor).

Fc-region fusion polypeptides may comprise e.g. a variant (human) IgG class Fc-region as reported herein and an antibody fragment that binds to a target including, such as, for example, an antibody Fab fragment, scFvs (see e.g. Nat. Biotechnol. 23 (2005) 1126-1136), or domain antibodies (dAbs) (see e.g. WO 2004/058821, WO 2003/002609).

Fc-region fusion polypeptides may comprise e.g. a variant (human) IgG class Fc-region as reported herein and a receptor ligand (either naturally occurring or artificial).

B. Exemplary Antibodies

In one aspect, the invention provides isolated antibodies that have modified FcRn-binding, i.e. these antibodies bind to human FcRn with an affinity higher or lower than an antibody having no mutations affecting the FcRn-binding.

In one embodiment the antibody comprises an Fc-region comprising a first Fc-region polypeptide and a second Fc-region polypeptide,
wherein
  a) the first Fc-region polypeptide and the second Fc-region polypeptide are derived from the same human Fc-region polypeptide, and
  b) the first Fc-region polypeptide has been modified in that its amino acid sequence differs from the second Fc-region polypeptide amino acid sequence at least at one corresponding position according to the Kabat EU index numbering system, and the second Fc-region polypeptide has been modified in that its amino acid sequence differs from the first Fc-region polypeptide amino acid sequence at least at one corresponding position according to the Kabat EU index numbering system, whereby the modified position in the first Fc-region polypeptide and the modified position in the second Fc-region polypeptide are different, and
  c) the Fc-region has a different affinity to a human Fc-receptor compared to an Fc-region that comprises as first and second Fc-region polypeptide the human Fc-region polypeptide of a) (i.e. that has the same amino acid residues as the human Fc-region polypeptide of a) at corresponding positions according to the Kabat EU index numbering system).

One exemplary antibody as reported herein and also one aspect of the current invention is a bispecific, bivalent antibody with abolished FcRn binding comprising a first antigen-binding site that specifically binds to human VEGF and a second antigen-binding site that specifically binds to human ANG-2,
wherein
  i) the first antigen-binding site specifically binding to VEGF comprises in the heavy chain variable domain a CDR3H region of SEQ ID NO: 14, a CDR2H region of SEQ ID NO: 15, and a CDR1H region of SEQ ID NO: 16, and in the light chain variable domain a CDR3L region of SEQ ID NO: 17, a CDR2L region of SEQ ID NO: 18, and a CDR1L region of SEQ ID NO: 19, and
  ii) the second antigen-binding site specifically binding to ANG-2 comprises in the heavy chain variable domain a CDR3H region of SEQ ID NO: 22, a CDR2H region of, SEQ ID NO: 23, and a CDR1H region of SEQ ID NO: 24, and in the light chain variable domain a CDR3L region of SEQ ID NO: 25, a CDR2L region of SEQ ID NO: 26, and a CDR1L region of SEQ ID NO: 27, and
  iii) the bispecific antibody comprises an Fc-region comprising a first Fc-region polypeptide and a second Fc-region polypeptide,
  wherein
    a) the first Fc-region polypeptide and the second Fc-region polypeptide are derived from the same human Fc-region polypeptide, and
    b) the first Fc-region polypeptide has been modified in that its amino acid sequence differs from the second Fc-region polypeptide amino acid sequence at least at one corresponding position according to the Kabat EU index numbering system, and the second Fc-region polypeptide has been modified in that its amino acid sequence differs from the first Fc-region polypeptide amino acid sequence at least at one corresponding position according to the Kabat EU index numbering system, whereby the modified position in the first Fc-region polypeptide and the modified position in the second Fc-region polypeptide are different, and c) the Fc-region has a different affinity to a human Fc-receptor compared to an Fc-region that comprises as first and second Fc-region polypeptide the human Fc-region polypeptide of a) (i.e. that has the same amino acid residues as the human Fc-region polypeptide of a) at corresponding positions according to the Kabat EU index numbering system).

In one embodiment of all aspects the Fc-region is a variant (human) IgG class Fc-region. In one embodiment the variant (human) IgG class Fc-region is an IgG class heterodimeric Fc-region.

In one embodiment of all aspects the pairing of the first Fc-region polypeptide and the second Fc-region polypeptide to form a (functional) Fc-region results in the formation of a heterodimer.

In one embodiment the human Fc-region polypeptide is a human Fc-region polypeptide of the IgG1 subclass or of the IgG4 subclass.

In one embodiment the human Fc-region polypeptide is a human Fc-region polypeptide of the IgG1 subclass which further comprises the mutations L234A, L235A and P329G.

In one embodiment the human Fc-region polypeptide is a human Fc-region polypeptide of the IgG4 subclass which further comprises the mutations S228P and L235E.

In one embodiment the first Fc-region polypeptide further comprises the mutations S354C and T366W and the second Fc-region polypeptide further comprises the mutations Y349C, T366S, L368A and Y407V.

In one embodiment the bispecific antibody is characterized in that
   i) the first antigen-binding site specifically binding to VEGF comprises as heavy chain variable domain VH an amino acid sequence of SEQ ID NO: 20, and as light chain variable domain VL an amino acid sequence of SEQ ID NO: 21, and
   ii) the second antigen-binding site specifically binding to ANG-2 comprises as heavy chain variable domain VH an amino acid sequence of SEQ ID NO: 28, and as light chain variable domain VL an amino acid sequence of SEQ ID NO: 29.

In one embodiment the bispecific antibody is characterized in that the Fc-region of iii) is of human IgG1 subclass. In one embodiment the bispecific antibody is characterized in that the Fc-region of human IgG1 subclass further comprises the mutations L234A, L235A and P329G (numbering according to EU Index of Kabat).

In one embodiment the bispecific antibody is characterized in that the Fc-region of iii) is of human IgG4 subclass. In one embodiment the bispecific antibody is characterized in that the Fc-region of human IgG4 subclass further comprises the mutations S228P and L235E (numbering according to EU Index of Kabat). In one embodiment the bispecific antibody is characterized in that the Fc-region of human IgG4 subclass further comprises the mutations S228P, L235E and P329G (numbering according to EU Index of Kabat).

In one embodiment the bispecific antibody comprises an Fc-region comprising a first and a second Fc-region polypeptide both of human IgG1 or human IgG4 subclass (i.e. derived from human origin), which comprise one or two of the mutations selected from i) the group I253A, H310A, H435A, or ii) the group H310A, H433A, Y436A, or iii) the group L251D, L314D, L432D, or iv) the group L251S, L314S, L432S (numbering according to Kabat EU index numbering system) in the first Fc-region polypeptide and one or two of the mutations selected from the group comprising the mutations L251D, L251S, I253A, H310A, L314D, L314S, L432D, L432S, H433A, H435A, and Y436A (numbering according to Kabat EU index numbering system) in the second Fc-region polypeptide so that all of the mutations i) I253A, H310A, H435A, or ii) H310A, H433A, Y436A, or iii) L251D, L314D, L432D, or iv) L251S, L314S, L432S are comprised in the Fc-region.

In one embodiment the bispecific antibody comprises an Fc-region comprising a first and a second Fc-region polypeptide both of human IgG1 or human IgG4 subclass (i.e. derived from human origin), which comprise the mutations I253A/H310A/H435A or H310A/H433A/Y436A or L251D/L314D/L432D or L251S/L314S/L432S or combinations thereof in the Fc-region (numbering according to Kabat EU index numbering system), whereby either all mutations are in the first or the second Fc-region polypeptide or one or two mutations are in the first Fc-region polypeptide and one or two mutations are in the second Fc-region polypeptide so that all of the mutations i) I253A, H310A, H435A, or ii) H310A, H433A, Y436A, or iii) L251D, L314D, L432D, or iv) L251S, L314S, L432S are comprised in the Fc-region.

Still further aspects as reported herein are a pharmaceutical formulation comprising the bispecific antibody, the pharmaceutical formulation for use in the treatment of ocular vascular diseases, the use of the bispecific antibody for the manufacture of a medicament for the treatment of ocular vascular diseases, a method of treatment of patient suffering from ocular vascular diseases by administering the bispecific antibody to a patient in the need of such treatment. In one embodiment the bispecific antibody or the pharmaceutical formulation comprising the bispecific antibody is administered via intravitreal application.

A further aspect according to the current invention is a nucleic acid molecule encoding a heavy and/or light chain of a bispecific antibody as reported herein.

The invention further provides expression vectors containing the nucleic acid as reported herein capable of expressing the nucleic acid in a prokaryotic or eukaryotic host cell, and host cells containing such vectors for the recombinant production of a bispecific antibody as reported herein.

The invention further comprises a prokaryotic or eukaryotic host cell comprising a vector as reported herein.

The invention further comprises a method for the production of a bispecific antibody as reported herein, characterized by expressing a nucleic acid as reported herein in a prokaryotic or eukaryotic host cell and recovering the bispecific antibody from the cell or the cell culture supernatant. One embodiment is a method for the preparation of a bispecific antibody as reported herein comprising the steps of
   a) transforming a host cell with vectors comprising nucleic acid molecules encoding the antibody;
   b) culturing the host cell under conditions that allow synthesis of the antibody; and
   c) recovering the antibody from the culture.

The invention further comprises the antibody obtained by such method for the production of a bispecific antibody.

The antibodies as reported herein have highly valuable properties due to their specific modifications in the Fc-region causing a benefit for a patient suffering from ocular vascular diseases. They show high stability in the intravitreal environment and slow diffusion from the eye (compared to smaller antibody fragments without a constant heavy chain region), where the actual disease is located and treated (so treatment schedule may potentially be improved compared to non-IgG like antibodies like e.g. Fab and (Fab)2 fragments). The antibodies as reported herein are cleared on the other hand quite rapidly from serum (which is highly desired to reduce potential side effects arising from systemic exposure). Surprisingly they also show lower viscosity (see FIG. 2) (compared to versions without the combination of the mutations I253A, H310A and H435A in the constant region) and are therefore especially useful for intravitreal application through thin needles during the treatment of eye diseases (for such application typically thin needles are used and high viscosity makes an appropriate application rather difficult). The lower viscosity also allows higher concentration formulations.

Figure 4:
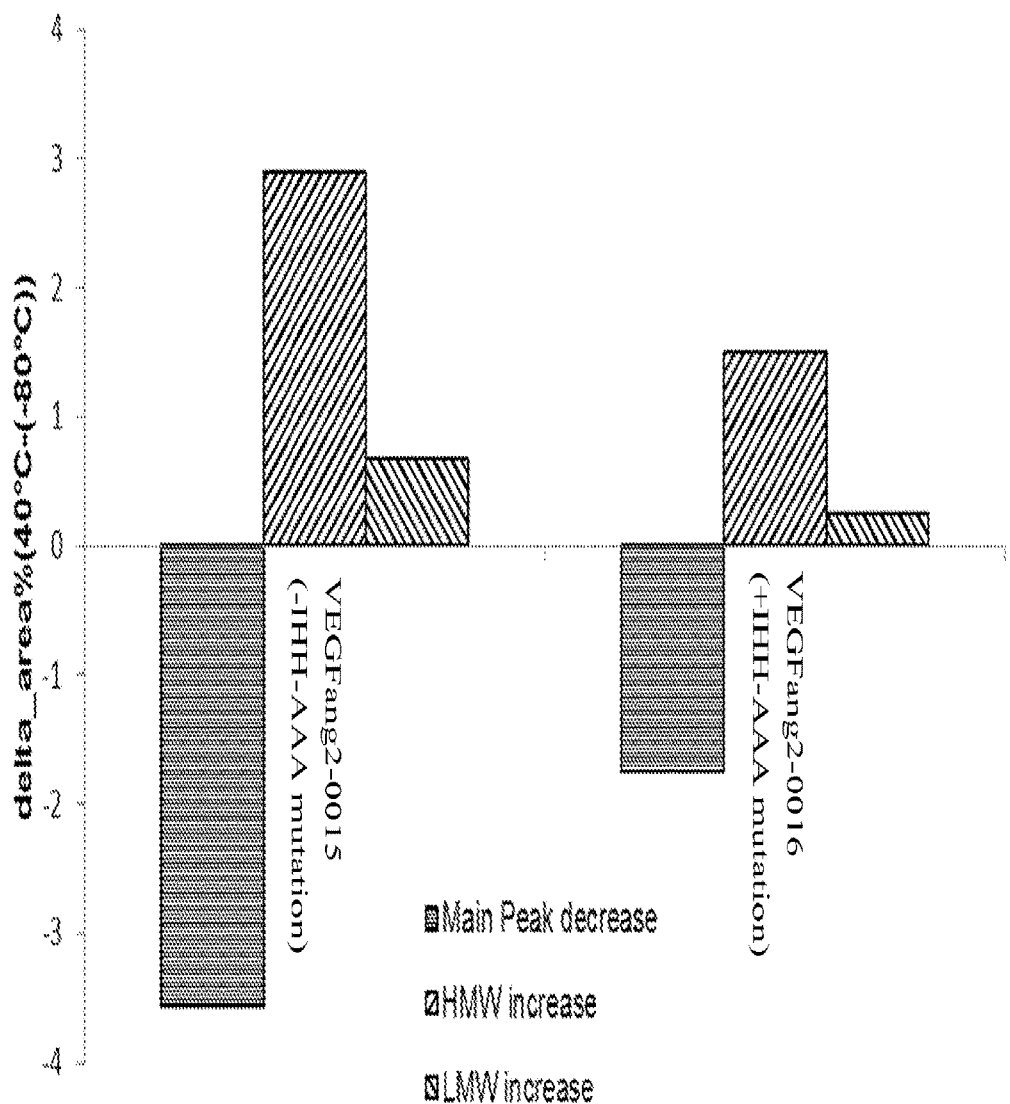
FIG. 4 Seven day storage at 40° C. at 100 mg/mL (decrease of Main Peak and High Molecular Weight (HMW) increase) (comparison of <VEGF-ANG-2> antibodies as reported herein VEGFang2-0016 (with IHH-AAA mutation) which showed a lower aggregation with a reference antibody VEGFang2-0015 (without such IHH-AAA mutation)).

Also surprisingly the antibodies as reported herein show a lower aggregation tendency (see FIG. 4) during storage (compared to versions without the combination of the mutations I253A, H310A and H435A in the Fc-region) which is critical for intravitreal application in the eye (as an aggregation in the eye can lead to complications during such treatment).

The bispecific antibodies as reported herein show good efficacy in inhibition of vascular diseases.

In certain embodiments, the bispecific antibodies as reported herein due to their specific modifications in the constant region (e.g. P329G LALA) show valuable properties like no binding to/of Fcgamma receptors which reduces the risk of side effects like thrombosis and/or unwanted cell death (due to e.g. ADCC).

In one embodiment as reported herein the bispecific antibody as reported herein is bivalent.

In one aspect according to the current invention the bispecific, bivalent antibody as reported herein is characterized in comprising
  a) the heavy chain and the light chain of a first full length antibody that specifically binds to VEGF, and
  b) the modified heavy chain and modified light chain of a second full length antibody that specifically binds to ANG-2, wherein the constant domains CL and CH1 are replaced by each other.

This bispecific, bivalent antibody format for the bispecific antibody specifically binding to human vascular endothelial growth factor (VEGF) and human angiopoietin-2 (ANG-2) is described in WO 2009/080253 (including knobs-into-holes modified CH3 domains). The antibodies based on this bispecific, bivalent antibody format are named CrossMabs.

In one embodiment such bispecific, bivalent antibody is characterized in comprising
  a) as heavy chain of the first full length antibody the amino acid sequence of SEQ ID NO: 38 and as light chain of the first full length antibody the amino acid sequence of SEQ ID NO: 40, and
  b) as modified heavy chain of the second full length antibody the amino acid sequence of SEQ ID NO: 39 and as modified light chain of the second full length antibody the amino acid sequence of SEQ ID NO: 41.

In one embodiment such bispecific, bivalent antibody is characterized in comprising
  a) as heavy chain of the first full length antibody the amino acid sequence of SEQ ID NO: 34 and as light chain of the first full length antibody the amino acid sequence of SEQ ID NO: 36, and
  b) as modified heavy chain of the second full length antibody the amino acid sequence of SEQ ID NO: 35 and as modified light chain of the second full length antibody the amino acid sequence of SEQ ID NO: 37.

In one embodiment such bispecific, bivalent antibody is characterized in comprising
  a) as heavy chain of the first full length antibody the amino acid sequence of SEQ ID NO: 42 and as light chain of the first full length antibody the amino acid sequence of SEQ ID NO: 44, and
  b) as modified heavy chain of the second full length antibody the amino acid sequence of SEQ ID NO: 43 and as modified light chain of the second full length antibody the amino acid sequence of SEQ ID NO: 45.

In one embodiment such bispecific, bivalent antibody is characterized in comprising
  a) as heavy chain of the first full length antibody the amino acid sequence of SEQ ID NO: 90 and as light chain of the first full length antibody the amino acid sequence of SEQ ID NO: 40, and
  b) as modified heavy chain of the second full length antibody the amino acid sequence of SEQ ID NO: 91 and as modified light chain of the second full length antibody the amino acid sequence of SEQ ID NO: 41.

In one embodiment such bispecific, bivalent antibody is characterized in comprising
  a) as heavy chain of the first full length antibody the amino acid sequence of SEQ ID NO: 88 and as light chain of the first full length antibody the amino acid sequence of SEQ ID NO: 36, and
  b) as modified heavy chain of the second full length antibody the amino acid sequence of SEQ ID NO: 89 and as modified light chain of the second full length antibody the amino acid sequence of SEQ ID NO: 37.

In one embodiment such bispecific, bivalent antibody is characterized in comprising
  a) as heavy chain of the first full length antibody the amino acid sequence of SEQ ID NO: 92 and as light chain of the first full length antibody the amino acid sequence of SEQ ID NO: 44, and
  b) as modified heavy chain of the second full length antibody the amino acid sequence of SEQ ID NO: 93 and as modified light chain of the second full length antibody the amino acid sequence of SEQ ID NO: 45.

Accordingly one aspect as reported herein is a bispecific, bivalent antibody comprising a first antigen-binding site that specifically binds to human VEGF and a second antigen-binding site that specifically binds to human ANG-2, characterized in comprising the amino acid sequences of SEQ ID NO: 38, of SEQ ID NO: 39, of SEQ ID NO: 40, and of SEQ ID NO: 41.

Accordingly one aspect as reported herein is a bispecific, bivalent antibody comprising a first antigen-binding site that specifically binds to human VEGF and a second antigen-binding site that specifically binds to human ANG-2, characterized in comprising the amino acid sequences of SEQ ID NO: 34, of SEQ ID NO: 35, of SEQ ID NO: 36, and of SEQ ID NO: 37.

Accordingly one aspect as reported herein is a bispecific, bivalent antibody comprising a first antigen-binding site that specifically binds to human VEGF and a second antigen-binding site that specifically binds to human ANG-2, characterized in comprising the amino acid sequences of SEQ ID NO: 42, of SEQ ID NO: 43, of SEQ ID NO: 44, and of SEQ ID NO: 45.

Accordingly one aspect as reported herein is a bispecific, bivalent antibody comprising a first antigen-binding site that specifically binds to human VEGF and a second antigen-binding site that specifically binds to human ANG-2, characterized in comprising the amino acid sequences of SEQ ID NO: 90, of SEQ ID NO: 91, of SEQ ID NO: 40, and of SEQ ID NO: 41.

Accordingly one aspect as reported herein is a bispecific, bivalent antibody comprising a first antigen-binding site that specifically binds to human VEGF and a second antigen-binding site that specifically binds to human ANG-2, characterized in comprising the amino acid sequences of SEQ ID NO: 88, of SEQ ID NO: 89, of SEQ ID NO: 36, and of SEQ ID NO: 37.

Accordingly one aspect as reported herein is a bispecific, bivalent antibody comprising a first antigen-binding site that specifically binds to human VEGF and a second antigen-binding site that specifically binds to human ANG-2, characterized in comprising the amino acid sequences of SEQ ID NO: 92, of SEQ ID NO: 93, of SEQ ID NO: 44, and of SEQ ID NO: 45.

In another aspect as reported herein the bispecific antibody as reported herein is characterized in comprising
a) the heavy chain and the light chain of a first full length antibody that specifically binds to VEGF, and
b) the heavy chain and the light chain of a second full length antibody that specifically binds to ANG-2, wherein the N-terminus of the heavy chain is connected to the C-terminus of the light chain via a peptidic linker.

This bispecific, bivalent antibody format for this bispecific antibody specifically binding to human vascular endothelial growth factor (VEGF) and human angiopoietin-2 (ANG-2) is described in WO 2011/117330 (including knobs-into-holes modified CH3 domains). The antibodies based on this bispecific, bivalent antibody format are named one-armed single chain Fabs (OAscFabs).

In one embodiment such bispecific, bivalent antibody is characterized in comprising
a) as heavy chain of the first full length antibody the amino acid sequence of SEQ ID NO: 46 and as light chain of the first full length antibody the amino acid sequence of SEQ ID NO: 48, and
b) as heavy chain of the second full length antibody connected to the light chain of the second full length antibody via a peptidic linker the amino acid sequence of SEQ ID NO: 47.

In one embodiment such bispecific, bivalent antibody is characterized in comprising
a) as heavy chain of the first full length antibody the amino acid sequence of SEQ ID NO: 49 and as light chain of the first full length antibody the amino acid sequence of SEQ ID NO: 51, and
b) as heavy chain of the second full length antibody connected to the light chain of the second full length antibody via a peptidic linker the amino acid sequence of SEQ ID NO: 50.

In one embodiment such bispecific, bivalent antibody is characterized in comprising
a) as heavy chain of the first full length antibody the amino acid sequence of SEQ ID NO: 94 and as light chain of the first full length antibody the amino acid sequence of SEQ ID NO: 48, and
b) as heavy chain of the second full length antibody connected to the light chain of the second full length antibody via a peptidic linker the amino acid sequence of SEQ ID NO: 95.

In one embodiment such bispecific, bivalent antibody is characterized in comprising
a) as heavy chain of the first full length antibody the amino acid sequence of SEQ ID NO: 96 and as light chain of the first full length antibody the amino acid sequence of SEQ ID NO: 51, and
b) as heavy chain of the second full length antibody connected to the light chain of the second full length antibody via a peptidic linker the amino acid sequence of SEQ ID NO: 97.

In one embodiment the antibody heavy chain variable domain (VH) and the antibody light chain variable domain (VL) of the heavy and light chain of the second full length antibody are further stabilized by the introduction of a disulfide bond between the following positions: heavy chain variable domain position 44 and light chain variable domain position 100 (numbering according to Kabat (Kabat, E. A., et al., Sequences of Proteins of Immunological Interest, 5th ed., Public Health Service, National Institutes of Health, Bethesda, MD (1991)). Techniques to introduce disulfide bridges for stabilization are described e.g. in WO 94/029350, Rajagopal, V., et al, Prot. Eng. 10 (1997) 1453-1459, Kobayashi et al., Nuclear Medicine & Biology 25 (1998) 387-393, and Schmidt, M., et al., Oncogene 18 (1999) 1711-1721.

Accordingly one aspect as reported herein is a bispecific, bivalent antibody comprising a first antigen-binding site that specifically binds to human VEGF and a second antigen-binding site that specifically binds to human ANG-2, characterized in comprising the amino acid sequences of SEQ ID NO: 46, of SEQ ID NO: 47, and of SEQ ID NO: 48.

Accordingly one aspect as reported herein is a bispecific, bivalent antibody comprising a first antigen-binding site that specifically binds to human VEGF and a second antigen-binding site that specifically binds to human ANG-2, characterized in comprising the amino acid sequences of SEQ ID NO: 49, of SEQ ID NO: 50, and of SEQ ID NO: 51.

Accordingly one aspect as reported herein is a bispecific, bivalent antibody comprising a first antigen-binding site that specifically binds to human VEGF and a second antigen-binding site that specifically binds to human ANG-2, characterized in comprising the amino acid sequences of SEQ ID NO: 94, of SEQ ID NO: 95, and of SEQ ID NO: 48.

Accordingly one aspect as reported herein is a bispecific, bivalent antibody comprising a first antigen-binding site that specifically binds to human VEGF and a second antigen-binding site that specifically binds to human ANG-2, characterized in comprising the amino acid sequences of SEQ ID NO: 96, of SEQ ID NO: 97, and of SEQ ID NO: 51.

In one embodiment the CH3 domains of the bispecific, bivalent antibody as reported herein are altered by the "knob-into-holes" technology which is described in detail with several examples e.g. in WO 96/027011, Ridgway J. B., et al., Protein Eng. 9 (1996) 617-621, and Merchant, A. M., et al., Nat. Biotechnol. 16 (1998) 677-681. In this method the interaction surfaces of the two CH3 domains are altered to increase the heterodimerization of both heavy chains containing these two CH3 domains. Each of the two CH3 domains (of the two heavy chains) can be the "knob" while the other is the "hole". The introduction of a disulfide bridge further stabilizes the heterodimers (Merchant, A. M, et al., Nature Biotech. 16 (1998) 677-681, Atwell, S., et al. J. Mol. Biol. 270 (1997) 26-35) and increases the yield.

In one preferred embodiment of all aspects as reported herein the bispecific antibodies is characterized in that
the CH3 domain of one heavy chain and the CH3 domain of the other heavy chain each meet at an interface which comprises an original interface between the antibody CH3 domains,
wherein the interface is altered to promote the formation of the bispecific antibody, wherein the alteration is characterized in that:
a) the CH3 domain of one heavy chain is altered,
so that within the original interface the CH3 domain of one heavy chain that meets the original interface of the CH3 domain of the other heavy chain within the bispecific antibody an amino acid residue is replaced with an amino acid residue having a larger side chain volume, thereby generating a protuberance within the interface of the CH3 domain of one heavy chain which is positionable in a cavity within the interface of the CH3 domain of the other heavy chain, and b) the CH3 domain of the other heavy chain is altered,
so that within the original interface of the second CH3 domain that meets the original interface of the first CH3 domain within the bispecific antibody
an amino acid residue is replaced with an amino acid residue having a smaller side chain volume, thereby generating a cavity within the interface of the second CH3 domain within which a protuberance within the interface of the first CH3 domain is positionable.

Thus, the antibody according to invention is in one preferred embodiment characterized in that
the CH3 domain of the heavy chain of the full length antibody of a) and the CH3 domain of the heavy chain of the full length antibody of b) each meet at an interface which comprises an alteration in the original interface between the antibody's CH3 domains,
wherein
i) in the CH3 domain of one heavy chain
an amino acid residue is replaced with an amino acid residue having a larger side chain volume, thereby generating a protuberance within the interface of the CH3 domain of one heavy chain which is positionable in a cavity within the interface of the CH3 domain of the other heavy chain,
and wherein
ii) in the CH3 domain of the other heavy chain
an amino acid residue is replaced with an amino acid residue having a smaller side chain volume, thereby generating a cavity within the interface of the second CH3 domain within which a protuberance within the interface of the first CH3 domain is positionable.

In one preferred embodiment the amino acid residue having a larger side chain volume is selected from the group consisting of arginine (R), phenylalanine (F), tyrosine (Y), tryptophan (W).

In one preferred embodiment the amino acid residue having a smaller side chain volume is selected from the group consisting of alanine (A), serine (S), threonine (T), valine (V).

In one embodiment both CH3 domains are further altered by the introduction of a cysteine residue (C) in the corresponding positions of each CH3 domain such that a disulfide bridge between both CH3 domains can be formed.

In one embodiment, the bispecific antibody comprises a T366W mutation in the CH3 domain of the "knobs chain" and the T366S, L368A and Y407V mutations in the CH3 domain of the "hole chain". An additional interchain disulfide bridge between the CH3 domains can also be used (Merchant, A. M, et al., Nature Biotech 16 (1998) 677-681) e.g. by introducing a Y349C or S354C mutation into the CH3 domain of the "knobs chain" and a Y439C or E356C or S354C mutation into the CH3 domain of the "hole chain".

In one embodiment the bispecific antibody as reported herein comprises the mutation Y349C or S354C and the mutation T366W in one of the two CH3 domains and the mutations S354C or E356C or Y349C and the mutations T366S, L368A and Y407V in the other of the two CH3 domains. In one preferred embodiment the bispecific antibody comprises the Y349C, T366W mutations in one of the two CH3 domains and the S354C, T366S, L368A, Y407V mutations in the other of the two CH3 domains (the additional Y349C mutation in one CH3 domain and the additional S354C mutation in the other CH3 domain forming a interchain disulfide bridge) (numbering according to EU index of Kabat (Kabat, E. A., et al., Sequences of Proteins of Immunological Interest, 5th ed., Public Health Service, National Institutes of Health, Bethesda, MD (1991)). In one preferred embodiment the bispecific antibody comprises the S354C, T366W mutations in one of the two CH3 domains and the Y349C, T366S, L368A, Y407V mutations in the other of the two CH3 domains (the additional Y349C mutation in one CH3 domain and the additional S354C mutation in the other CH3 domain forming a interchain disulfide bridge) (numbering according to EU index of Kabat (Kabat, E. A., et al., Sequences of Proteins of Immunological Interest, 5th ed., Public Health Service, National Institutes of Health, Bethesda, MD (1991)).

But also other knobs-in-holes technologies as described by EP 1 870 459 A1, can be used alternatively or additionally. Thus another example for the bispecific antibody are the R409D and K370E mutations in the CH3 domain of the "knobs chain" and the D399K and E357K mutations in the CH3 domain of the "hole chain" (numbering according to EU index of Kabat (Kabat, E. A., et al., Sequences of Proteins of Immunological Interest, 5th ed., Public Health Service, National Institutes of Health, Bethesda, MD (1991)).

In another embodiment the bispecific antibody comprises a T366W mutation in the CH3 domain of the "knobs chain" and the T366S, L368A and Y407V mutations in the CH3 domain of the "hole chain" and additionally the R409D, K370E mutations in the CH3 domain of the "knobs chain" and the D399K, E357K mutations in the CH3 domain of the "hole chain".

In one embodiment the bispecific antibody comprises the Y349C, T366W mutations in one of the two CH3 domains and the S354C, T366S, L368A and Y407V mutations in the other of the two CH3 domains, or the bispecific antibody comprises the Y349C, T366W mutations in one of the two CH3 domains and the S354C, T366S, L368A and Y407V mutations in the other of the two CH3 domains and additionally the R409D, K370E mutations in the CH3 domain of the "knobs chain" and the D399K, E357K mutations in the CH3 domain of the "hole chain".

In one embodiment the bispecific antibody comprises the S354C, T366W mutations in one of the two CH3 domains and the Y349C, T366S, L368A, Y407V mutations in the other of the two CH3 domains, or the bispecific antibody comprises the S354C, T366W mutations in one of the two CH3 domains and the Y349C, T366S, L368A, Y407V mutations in the other of the two CH3 domains and additionally the R409D, K370E mutations in the CH3 domain of the "knobs chain" and the D399K, E357K mutations in the CH3 domain of the "hole chain".

In one embodiment the bispecific antibody as reported herein is characterized in having one or more of the following properties:
shows a lower serum concentration compared to a corresponding bispecific antibody without the mutations described under iii) (96 hours after intravitreal application in mice, which are mouse FcRn deficient, but hemizygous transgenic for human FcRn) (determined in an assays as described in Example 6),
shows a similar (factor 0.8 to 1.2) concentration in whole right eye lysates compared to a corresponding bispecific antibody without the mutations described under iii) (in mice, which are mouse FcRn deficient, but hemizygous transgenic for human FcRn, 96 hours after intravitreal application in the right eye) (determined in an assays as described in Example 6),
shows no binding to the human neonatal Fc receptor.

In one embodiment the bispecific, bivalent antibody is characterized in comprising a first Fc-region polypeptide and a second Fc-region polypeptide wherein
- a) the first and the second Fc-region polypeptide comprise the mutation Y436A, or
- b) the first and the second Fc-region polypeptide comprise the mutations I253A, H310A and H435A, or
- c) the first and the second Fc-region polypeptide comprise the mutations H310A, H433A and Y436A, or
- d) the first and the second Fc-region polypeptide comprise the mutations L251D, L314D and L432D, or
- e) the first and the second Fc-region polypeptide comprise the mutations L251S, L314S and L432S, or
- f) the first Fc-region polypeptide comprises the mutation Y436A and the second Fc-region polypeptide comprises
  the mutations I253A, H310A and H435A, or
  the mutations H310A, H433A and Y436A, or
  the mutations L251D, L314D and L432D, or
  the mutations L251S, L314S and L432S,
  or
- g) the first Fc-region polypeptide comprises the mutations I253A, H310A and H435A and the second Fc-region polypeptide comprises
  the mutations H310A, H433A and Y436A, or
  the mutations L251D, L314D and L432D, or
  the mutations L251S, L314S and L432S,
  or
- h) the first Fc-region polypeptide comprises the mutations H310A, H433A and Y436A and the second Fc-region polypeptide comprises
  a) the mutations L251D, L314D and L432D, or
  b) the mutations L251S, L314S and L432S,
  or
- i) the first Fc-region polypeptide comprises the mutations L251D, L314D and L432D and the second Fc-region polypeptide comprises
  a) the mutations L251S, L314S and L432S.

In one embodiment the bispecific antibody comprises an Fc-region comprising a first and a second Fc-region polypeptide both of human IgG1 or human IgG4 subclass (i.e. derived from human origin), which comprise one or two of the mutations selected from i) the group I253A, H310A, H435A, or ii) the group H310A, H433A, Y436A, or iii) the group L251D, L314D, L432D, or iv) the group L251S, L314S, L432S (numbering according to Kabat EU index numbering system) in the first Fc-region polypeptide and one or two of the mutations selected from the group comprising the mutations L251D, L251S, I253A, H310A, L314D, L314S, L432D, L432S, H433A, H435A and Y436A (numbering according to Kabat EU index numbering system) in the second Fc-region polypeptide so that all of the mutations in the first and the second Fc-region polypeptide when taken together result in that the mutations i) I253A, H310A and H435A, or ii) H310A, H433A and Y436A, or iii) L251D, L314D and L432D, or iv) L251S, L314S and L432S are comprised in the Fc-region.

In one embodiment the bispecific antibody comprises an Fc-region comprising a first and a second Fc-region polypeptide both of human IgG1 or human IgG4 subclass (i.e. derived from human origin), which comprise the mutations I253A/H310A/H435A or H310A/H433A/Y436A or L251D/L314D/L432D or L251S/L314S/L432S or combinations thereof in the Fc-region (numbering according to Kabat EU index numbering system), whereby either all mutations are in the first or the second Fc-region polypeptide, or one or two mutations are in the first Fc-region polypeptide and one or two mutations are in the second Fc-region polypeptide so that all of the mutations in the first and the second Fc-region polypeptide when taken together result in that the mutations i) I253A, H310A and H435A, or ii) H310A, H433A and Y436A, or iii) L251D, L314D and L432D, or iv) L251S, L314S and L432S are comprised in the Fc-region.

In one embodiment the bispecific, bivalent antibody is characterized in comprising
a first antigen-binding site that specifically binds to human VEGF and a second antigen-binding site that specifically binds to human ANG-2, characterized in that
- i) the first antigen-binding site comprises as heavy chain variable domain (VH) the amino acid sequence of SEQ ID NO: 20, and as light chain variable domain (VL) the amino acid sequence of SEQ ID NO: 21, and
- ii) the second antigen-binding site comprises as heavy chain variable domain (VH) the amino acid sequence of SEQ ID NO: 28, and as light chain variable domain (VL) the amino acid sequence of SEQ ID NO: 29, and
- iii) the bispecific antibody comprises an Fc-region comprising a first and a second Fc-region polypeptide both of human IgG1 or human IgG4 subclass (i.e. derived from human origin), which comprise one or two of the mutations selected from i) the group I253A, H310A, H435A, or ii) the group H310A, H433A, Y436A, or iii) the group L251D, L314D, L432D, or iv) the group L251S, L314S, L432S (numbering according to Kabat EU index numbering system) in the first Fc-region polypeptide and one or two of the mutations selected from the group comprising the mutations L251D, L251S, I253A, H310A, L314D, L314S, L432D, L432S, H433A, H435A and Y436A (numbering according to Kabat EU index numbering system) in the second Fc-region polypeptide so that all of the mutations in the first and the second Fc-region polypeptide when taken together result in that the mutations i) I253A, H310A and H435A, or ii) H310A, H433A and Y436A, or iii) L251D, L314D and L432D, or iv) L251S, L314S and L432S are comprised in the Fc-region,
and having one or more of the following properties
shows a lower serum concentration compared to a corresponding bispecific antibody without the mutations described under iii) (96 hours after intravitreal application in mice, which are mouse FcRn deficient, but hemizygous transgenic for human FcRn) (determined in assays as described in Example 6),
shows a similar (factor 0.8 to 1.2) concentration in whole right eye lysates compared to a corresponding bispecific antibody without the mutations described under iii) (in mice, which are mouse FcRn deficient, but hemizygous transgenic for human FcRn, 96 hours after intravitreal application in the right eye) (determined in assays as described in Example 6),
shows no binding to the human neonatal Fc receptor.

In one embodiment the bispecific, bivalent antibody is characterized in comprising a first antigen-binding site that specifically binds to human VEGF and a second antigen-binding site that specifically binds to human ANG-2, characterized in that
   i) the first antigen-binding site comprises as heavy chain variable domain (VH) the amino acid sequence of SEQ ID NO: 20, and as light chain variable domain (VL) the amino acid sequence of SEQ ID NO: 21, and
   ii) the second antigen-binding site comprises as heavy chain variable domain (VH) the amino acid sequence of SEQ ID NO: 28, and as light chain variable domain (VL) the amino acid sequence of SEQ ID NO: 29, and
   iii) the bispecific antibody comprises a first Fc-region polypeptide and a second Fc-region polypeptide wherein
      a) the first and the second Fc-region polypeptide comprise the mutation Y436A, or
      b) the first and the second Fc-region polypeptide comprise the mutations I253A, H310A and H435A, or
      c) the first and the second Fc-region polypeptide comprise the mutations H310A, H433A and Y436A, or
      d) the first and the second Fc-region polypeptide comprise the mutations L251D, L314D and L432D, or
      e) the first and the second Fc-region polypeptide comprise the mutations L251S, L314S and L432S, or
      f) the first Fc-region polypeptide comprises the mutation Y436A and the second Fc-region polypeptide comprises
         the mutations I253A, H310A and H435A, or
         the mutations H310A, H433A and Y436A, or
         the mutations L251D, L314D and L432D, or
         the mutations L251S, L314S and L432S,
      or
      g) the first Fc-region polypeptide comprises the mutations I253A, H310A and H435A and the second Fc-region polypeptide comprises
         the mutations H310A, H433A and Y436A, or
         the mutations L251D, L314D and L432D, or
         the mutations L251S, L314S and L432S,
      or
      h) the first Fc-region polypeptide comprises the mutations H310A, H433A and Y436A and the second Fc-region polypeptide comprises
         a) the mutations L251D, L314D and L432D, or
         b) the mutations L251S, L314S and L432S,
      or
      i) the first Fc-region polypeptide comprises the mutations L251D, L314D and L432D and the second Fc-region polypeptide comprises
         a) the mutations L251S, L314S and L432S,
and having one or more of the following properties
shows a lower serum concentration compared to a corresponding bispecific antibody without the mutations described under iii) (96 hours after intravitreal application in mice, which are mouse FcRn deficient, but hemizygous transgenic for human FcRn) (determined in assays as described in Example 6),
shows a similar (factor 0.8 to 1.2) concentration in whole right eye lysates compared to a corresponding bispecific antibody without the mutations described under iii) (in mice, which are mouse FcRn deficient, but hemizygous transgenic for human FcRn, 96 hours after intravitreal application in the right eye) (determined in assays as described in Example 6),
shows no binding to the human neonatal Fc receptor.

In one embodiment the bispecific antibody is characterized in comprising a first antigen-binding site that specifically binds to human VEGF and a second antigen-binding site that specifically binds to human ANG-2, characterized in that
   i) the first antigen-binding site comprises as heavy chain variable domain (VH) the amino acid sequence of SEQ ID NO: 20 with 1, 2 or 3 amino acid substitutions, and as light chain variable domain (VL) the amino acid sequence of SEQ ID NO: 21 with 1, 2 or 3 amino acid substitutions, and
   ii) the second antigen-binding site comprises as heavy chain variable domain (VH) the amino acid sequence of SEQ ID NO: 28 with 1, 2 or 3 amino acid substitutions, and as light chain variable domain (VL) the amino acid sequence of SEQ ID NO: 29 with 1, 2 or 3 amino acid substitutions, and
   iii) the bispecific antibody comprises an Fc-region comprising a first and a second Fc-region polypeptide both of human IgG1 or human IgG4 subclass (i.e. derived from human origin), which comprise one or two of the mutations selected from i) the group I253A, H310A, H435A, or ii) the group H310A, H433A, Y436A, or iii) the group L251D, L314D, L432D, or iv) the group L251S, L314S, L432S (numbering according to Kabat EU index numbering system) in the first Fc-region polypeptide and one or two of the mutations selected from the group comprising the mutations L251D, L251S, I253A, H310A, L314D, L314S, L432D, L432S, H433A, H435A, and Y436A (numbering according to Kabat EU index numbering system) in the second Fc-region polypeptide so that all of the mutations in the first and the second Fc-region polypeptide when taken together result in that the mutations i) I253A, H310A and H435A, or ii) H310A, H433A and Y436A, or iii) L251D, L314D and L432D, or iv) L251S, L314S and L432S are comprised in the Fc-region,
and having one or more of the following properties
shows a lower serum concentration compared to a corresponding bispecific antibody without the mutations described under iii) (96 hours after intravitreal application in mice, which are mouse FcRn deficient, but hemizygous transgenic for human FcRn) (determined in assays as described in Example 6),
shows a similar (factor 0.8 to 1.2) concentration in whole right eye lysates compared to a corresponding bispecific antibody without the mutations described under iii) (in mice, which are mouse FcRn deficient, but hemizygous transgenic for human FcRn, 96 hours after intravitreal application in the right eye) (determined in assays as described in Example 6),
shows no binding to the human neonatal Fc receptor.

In one embodiment the bispecific antibody is characterized in comprising a first antigen-binding site that specifically binds to human VEGF and a second antigen-binding site that specifically binds to human ANG-2, characterized in that
   i) the first antigen-binding site comprises as heavy chain variable domain (VH) the amino acid sequence of SEQ ID NO: 20 with 1, 2 or 3 amino acid substitutions, and as light chain variable domain (VL) the amino acid sequence of SEQ ID NO: 21 with 1, 2 or 3 amino acid substitutions, and ii) the second antigen-binding site comprises as heavy chain variable domain (VH) the amino acid sequence of SEQ ID NO: 28 with 1, 2 or 3 amino acid substitutions, and as light chain variable domain (VL) the amino acid sequence of SEQ ID NO: 29 with 1, 2 or 3 amino acid substitutions, and iii) the bispecific antibody comprises a first Fc-region polypeptide and a second Fc-region polypeptide wherein
  a) the first and the second Fc-region polypeptide comprise the mutation Y436A, or
  b) the first and the second Fc-region polypeptide comprise the mutations I253A, H310A and H435A, or
  c) the first and the second Fc-region polypeptide comprise the mutations H310A, H433A and Y436A, or
  d) the first and the second Fc-region polypeptide comprise the mutations L251D, L314D and L432D, or
  e) the first and the second Fc-region polypeptide comprise the mutations L251S, L314S and L432S, or
  f) the first Fc-region polypeptide comprises the mutation Y436A and the second Fc-region polypeptide comprises
    the mutations I253A, H310A and H435A, or
    the mutations H310A, H433A and Y436A, or
    the mutations L251D, L314D and L432D, or
    the mutations L251S, L314S and L432S,
    or
  g) the first Fc-region polypeptide comprises the mutations I253A, H310A and H435A and the second Fc-region polypeptide comprises
    the mutations H310A, H433A and Y436A, or
    the mutations L251D, L314D and L432D, or
    the mutations L251S, L314S and L432S,
    or
  h) the first Fc-region polypeptide comprises the mutations H310A, H433A and Y436A and the second Fc-region polypeptide comprises
    a) the mutations L251D, L314D and L432D, or
    b) the mutations L251S, L314S and L432S,
    or
  i) the first Fc-region polypeptide comprises the mutations L251D, L314D and L432D and the second Fc-region polypeptide comprises
    a) the mutations L251S, L314S and L432S, and having one or more of the following properties
shows a lower serum concentration compared to corresponding bispecific antibody without the mutations described under iii) (96 hours after intravitreal application in mice, which are mouse FcRn deficient, but hemizygous transgenic for human FcRn) (determined in assays as described in Example 6),
shows a similar (factor 0.8 to 1.2) concentration in whole right eye lysates compared to a corresponding bispecific antibody without the mutations described under iii) (in mice, which are mouse FcRn deficient, but hemizygous transgenic for human FcRn, 96 hours after intravitreal application in the right eye) (determined in assays as described in Example 6),
shows no binding to the human neonatal Fc receptor.

An antigen-binding site of the bispecific antibody as reported herein contains six complementarity determining regions (CDRs) which contribute in varying degrees to the affinity of the binding site for its antigen. There are three heavy chain variable domain CDRs (CDRH1, CDRH2 and CDRH3) and three light chain variable domain CDRs (CDRL1, CDRL2 and CDRL3). The extent of CDR and framework regions (FRs) is determined by comparison to a compiled database of amino acid sequences in which those regions have been defined according to variability among the sequences.

In one embodiment of all aspects the antibody does not specifically bind to the human FcRn. In one embodiment of all aspects the antibody in addition does specifically bind to Staphylococcal protein A.

In one embodiment of all aspects the antibody does not specifically bind to the human FcRn. In one embodiment of all aspects the antibody in addition does not specifically bind to Staphylococcal protein A In one embodiment of all aspects the first polypeptide further comprises the mutations Y349C, T366S, L368A and Y407V ("hole") and the second polypeptide comprises the mutations S354C and T366W ("knob").

In one embodiment of all aspects the first polypeptide further comprises the mutations S354C, T366S, L368A and Y407V ("hole") and the second polypeptide comprises the mutations Y349C and T366W ("knob").

In one embodiment of all aspects the Fc-region polypeptides are of the human IgG1 subclass. In one embodiment the first Fc-region polypeptide and the second Fc-region polypeptide further comprise the mutations L234A and L235A. In one embodiment the first Fc-region polypeptide and the second Fc-region polypeptide further comprise the mutation P329G.

In one embodiment of all aspects the Fc-region polypeptides are of the human IgG4 subclass. In one embodiment the first Fc-region polypeptide and the second Fc-region polypeptide further comprise the mutations S228P and L235E. In one embodiment the first Fc-region polypeptide and the second Fc-region polypeptide further comprise the mutation P329G.

The antibody as reported herein is produced by recombinant means. Thus, one aspect as reported herein is a nucleic acid encoding the antibody as reported herein and a further aspect is a cell comprising the nucleic acid encoding an antibody as reported herein. Methods for recombinant production are widely known in the state of the art and comprise protein expression in prokaryotic and eukaryotic cells with subsequent isolation of the antibody and usually purification to a pharmaceutically acceptable purity. For the expression of the antibodies as aforementioned in a host cell, nucleic acids encoding the respective (modified) light and heavy chains are inserted into expression vectors by standard methods. Expression is performed in appropriate prokaryotic or eukaryotic host cells like CHO cells, NS0 cells, SP2/0 cells, HEK293 cells, COS cells, PER.C6 cells, yeast, or E. coli cells, and the antibody is recovered from the cells (cultivation supernatant or cells after lysis). General methods for recombinant production of antibodies are well-known in the state of the art and described, for example, in the review articles of Makrides, S. C., Protein Expr. Purif. 17 (1999) 183-202, Geisse, S., et al., Protein Expr. Purif. 8 (1996) 271-282, Kaufman, R. J., Mol. Biotechnol. 16 (2000) 151-160, and Werner, R. G., Drug Res. 48 (1998) 870-880.

Accordingly one aspect as reported herein is a method for the preparation of a bispecific antibody as reported herein, comprising the steps of
  a) transforming a host cell with vectors comprising nucleic acid molecules encoding the antibody,
  b) culturing the host cell under conditions that allow synthesis of the antibody, and
  c) recovering the antibody from the culture.

In one embodiment the recovering step under c) includes the use of a light chain constant domain specific capture reagent (which e.g. specific for the kappa or the lambda constant light chain, depending on whether a kappa or a lambda light chain is contained in the bispecific antibody). In one embodiment this light chain specific capture reagent is used in in a bind-and-elute-mode. Examples of such light chain constant domain specific capture reagents are e.g. KappaSelect™ and LambdaFabSelect™ (available from GE Healthcare/BAC), which are based on a highly rigid agarose base matrix that allows high flow rates and low back pressure at large scale. These materials contain a ligand that binds to the constant region of the kappa or the lambda light chain, respectively (i.e. fragments lacking the constant region of the light chain will not bind; FIG. 1). Both are therefore capable of binding other target molecules containing the constant region of the light chain, for example, IgG, IgA and IgM. The ligands are attached to the matrix via a long hydrophilic spacer arm to make them easily available for binding to the target molecule. They are based on a single-chain antibody fragment that is screened for either human Ig kappa or lambda.

In one embodiment the recovering step under c) includes the use of an Fc-region specific capture reagent. In one embodiment the Fc-region specific capture reagent is used in a bind-and-elute-mode. Examples of such Fc-region specific capture reagents are e.g. *Staphylococcus* protein A-based affinity chromatography materials.

The bispecific antibodies are suitably separated from the culture medium by conventional immunoglobulin purification procedures such as, for example, affinity chromatography (protein A-Sepharose, or KappaSelect™, LambdaFabSelect™), hydroxylapatite chromatography, gel electrophoresis, or dialysis.

DNA and RNA encoding the monoclonal antibodies is readily isolated and sequenced using conventional procedures. B-cells or hybridoma cells can serve as a source of such DNA and RNA. Once isolated, the DNA may be inserted into expression vectors, which are then transfected into host cells such as HEK 293 cells, CHO cells, or myeloma cells that do not otherwise produce immunoglobulin protein, to obtain the synthesis of recombinant monoclonal antibodies in the host cells.

Some of the molecules as reported herein provide ease of isolation/purification by comprising Fc-regions that are differentially modified, wherein at least one of the modifications results in i) a differential affinity of the molecule for (Staphylococcal) protein A and ii) a differential affinity of the molecule for the human FcRn, and the molecule is isolable from a disrupted cell, from medium, or from a mixture of molecules based on its affinity for protein A.

Purification of antibodies is performed in order to eliminate cellular components or other contaminants, e.g. other cellular nucleic acids or proteins, by standard techniques, including alkaline/SDS treatment, CsCl banding, column chromatography, agarose gel electrophoresis, and others well known in the art (see e.g. Ausubel, F., et al., ed. Current Protocols in Molecular Biology, Greene Publishing and Wiley Interscience, New York (1987)). Different methods are well established and widespread used for protein purification, such as affinity chromatography with microbial proteins (e.g. protein A or protein G affinity chromatography), ion exchange chromatography (e.g. cation exchange (carboxymethyl resins), anion exchange (amino ethyl resins) and mixed-mode exchange), thiophilic adsorption (e.g. with beta-mercaptoethanol and other SH ligands), hydrophobic interaction or aromatic adsorption chromatography (e.g. with phenyl-sepharose, aza-arenophilic resins, or m-aminophenylboronic acid), metal chelate affinity chromatography (e.g. with Ni(II)- and Cu(II)-affinity material), size exclusion chromatography, and electrophoretical methods (such as gel electrophoresis, capillary electrophoresis) (Vijayalakshmi, M. A., Appl. Biochem. Biotech. 75 (1998) 93-102).

The bivalent bispecific antibody against human VEGF and human ANG-2 as reported herein may have a valuable efficacy/safety profile and may provide benefits for a patient in the need of an anti-VEGF and anti-ANG-2 therapy.

One aspect as reported herein is a pharmaceutical formulation comprising an antibody as reported herein. Another aspect as reported herein is the use of an antibody as reported herein for the manufacture of a pharmaceutical formulation. A further aspect as reported herein is a method for the manufacture of a pharmaceutical formulation comprising an antibody as reported herein. In another aspect, a formulation is provided, e.g. a pharmaceutical formulation, containing an antibody as reported herein, formulated together with a pharmaceutical carrier.

A formulation of the present invention can be administered by a variety of methods known in the art. As will be appreciated by the skilled artisan, the route and/or mode of administration will vary depending upon the desired results. To administer a compound as reported herein by certain routes of administration, it may be necessary to coat the compound with, or co-administer the compound with a material to prevent its inactivation. For example, the compound may be administered to a subject in an appropriate carrier, for example, liposomes, or a diluent. Pharmaceutically acceptable diluents include saline and aqueous buffer solutions. Pharmaceutical carriers include sterile aqueous solutions or dispersions and sterile powders for the extemporaneous preparation of sterile injectable solutions or dispersion. The use of such media and agents for pharmaceutically active substances is known in the art.

Many possible modes of delivery can be used, including, but not limited to intraocular application or topical application. In one embodiment the application is intraocular and includes, but it's not limited to, subconjunctival injection, intracanieral injection, injection into the anterior chamber via the termporai limbus, intrastromal injection, intracomeal injection, subretinal injection, aqueous humor injection, subtenon injection or sustained delivery device, intravitreal injection (e.g., front, mid or back vitreal injection). In one embodiment the application is topical and includes, but it's not limited to eye drops to the cornea.

In one embodiment the bispecific antibody or pharmaceutical formulation as reported herein is administered via intravitreal application, e.g. via intravitreal injection. This can be performed in accordance with standard procedures known in the art (see, e.g., Ritter et al., J. Clin. Invest. 116 (2006) 3266-3276, Russelakis-Carneiro et al., Neuropathol. Appl. Neurobiol. 25 (1999) 196-206, and Wray et al., Arch. Neurol. 33 (1976) 183-185).

In some embodiments, therapeutic kits as reported herein can contain one or more doses of a (bispecific) antibody present in a pharmaceutical formulation described herein, a suitable device for intravitreal injection of the pharmaceutical formulation, and an instruction detailing suitable subjects and protocols for carrying out the injection. In these embodiments, the formulations are typically administered to the subject in need of treatment via intravitreal injection. This can be performed in accordance with standard procedures known in the art (see, e.g., Ritter et al., J. Clin. Invest. 116 (2006) 3266-3276, Russelakis-Carneiro et al., Neuropathol. Appl. Neurobiol. 25 (1999) 196-206, and Wray et al., Arch. Neurol. 33 (1976) 183-185).

The formulations may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol, sorbic acid, and the like. It may also be desirable to include isotonic agents, such as sugars, sodium chloride, and the like into the formulations. In addition, prolonged absorption of the injectable pharmaceutical form may be brought about by the inclusion of agents which delay absorption such as aluminum monostearate and gelatin.

Regardless of the route of administration selected, the compounds as reported herein, which may be used in a suitable hydrated form, and/or the pharmaceutical formulations as reported herein, are formulated into pharmaceutically acceptable dosage forms by conventional methods known to those of skill in the art.

Actual dosage levels of the active ingredients in the pharmaceutical formulations as reported herein may be varied so as to obtain an amount of the active ingredient which is effective to achieve the desired therapeutic response for a particular patient, formulation, and mode of administration, without being toxic to the patient. The selected dosage level will depend upon a variety of pharmacokinetic factors including the activity of the particular formulations employed, the route of administration, the time of administration, the rate of excretion of the particular compound being employed, the duration of the treatment, other drugs, compounds and/or materials used in combination with the particular formulations employed, the age, sex, weight, condition, general health and prior medical history of the patient being treated, and like factors well known in the medical arts.

The formulation must be sterile and fluid to the extent that the formulation is deliverable by syringe. In addition to water, the carrier preferably is an isotonic buffered saline solution.

Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the formulation.

The formulation can comprise an ophthalmic depot formulation comprising an active agent for subconjunctival administration. The ophthalmic depot formulation comprises microparticles of essentially pure active agent, e.g., the bispecific antibody as reported herein. The microparticles comprising the bispecific antibody as reported herein can be embedded in a biocompatible pharmaceutically acceptable polymer or a lipid encapsulating agent. The depot formulations may be adapted to release all of substantially all the active material over an extended period of time. The polymer or lipid matrix, if present, may be adapted to degrade sufficiently to be transported from the site of administration after release of all or substantially all the active agent. The depot formulation can be liquid formulation, comprising a pharmaceutical acceptable polymer and a dissolved or dispersed active agent. Upon injection, the polymer forms a depot at the injections site, e.g. by gelifying or precipitating.

Another aspect as reported herein is the bispecific antibody as reported herein for use in the treatment of ocular vascular diseases.

Another aspect as reported herein is the pharmaceutical formulation as reported herein for use in the treatment of ocular vascular diseases.

Another aspect as reported herein is the use of an antibody as reported herein for the manufacture of a medicament for the treatment of ocular vascular disease.

Another aspect as reported herein is method of treatment of patient suffering from ocular vascular diseases by administering an antibody as reported herein to a patient in the need of such treatment.

It is herewith expressly stated that the term "comprising" as used herein comprises the term "consisting of". Thus, all aspects and embodiments that contain the term "comprising" are likewise disclosed with the term "consisting of".

Modifications

In a further aspect, an antibody according to any of the above embodiments may incorporate any of the features, singly or in combination, as described in Sections 1-6 below:

1. Antibody Affinity

In certain embodiments, an antibody provided herein has a dissociation constant (Kd) of ≤100 nM, ≤10 nM (e.g. $10^{-7}$ M or less, e.g. from $10^{-7}$ M to $10^{-13}$ M, e.g., from $10^{-8}$M to $10^{-13}$ M).

In one embodiment, Kd is measured using a BIACORE® surface plasmon resonance assay. For example, an assay using a BIACORE®-2000 or a BIACORE®-3000 (GE Healthcare Inc., Piscataway, NJ) is performed at 25° C. with immobilized antigen CM5 chips at ~10 response units (RU). In one embodiment, carboxymethylated dextran biosensor chips (CM5, GE Healthcare Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 μg/mL (~0.2 μM) before injection at a flow rate of 5 μL/minute to achieve approximately 10 response units (RU) of coupled protein. Following the injection of antigen, 1 M ethanolamine is injected to block non-reacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 μL/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$ (see, e.g., Chen, Y. et al., J. Mol. Biol. 293 (1999) 865-881). If the on-rate exceeds $10^6$ $M^{-1}$ $s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-AMINCO™ spectrophotometer (ThermoSpectronic) with a stirred cuvette.

2. Chimeric and Humanized Antibodies

In certain embodiments, an antibody provided herein is a chimeric antibody. Certain chimeric antibodies are described, e.g., in U.S. Pat. No. 4,816,567; and Morrison, S. L., et al., Proc. Natl. Acad. Sci. USA 81 (1984) 6851-6855). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro, J. C. and Fransson, J., Front. Biosci. 13 (2008) 1619-1633, and are further described, e.g., in Riechmann, I., et al., Nature 332 (1988) 323-329; Queen, C., et al., Proc. Natl. Acad. Sci. USA 86 (1989) 10029-10033; U.S. Pat. Nos. 5,821,337, 7,527,791, 6,982,321, and 7,087,409; Kashmiri, S. V., et al., Methods 36 (2005) 25-34 (describing specificity determining region (SDR) grafting); Padlan, E. A., Mol. Immunol. 28 (1991) 489-498 (describing "resurfacing"); Dall'Acqua, W. F. et al., Methods 36 (2005) 43-60 (describing "FR shuffling"); Osbourn, J. et al., Methods 36 (2005) 61-68; and Klimka, A. et al., Br. J. Cancer 83 (2000) 252-260 (describing the "guided selection" approach to FR shuffling).

Human framework regions that may be used for humanization include but are not limited to: framework regions selected using the "best-fit" method (see, e.g., Sims, M. J., et al., J. Immunol. 151 (1993) 2296-2308; framework regions derived from the consensus sequence of human antibodies of a particular subgroup of light or heavy chain variable regions (see, e.g., Carter, P., et al., Proc. Natl. Acad. Sci. USA 89 (1992) 4285-4289; and Presta, L. G., et al., J. Immunol. 151 (1993) 2623-2632); human mature (somatically mutated) framework regions or human germline framework regions (see, e.g., Almagro, J. C. and Fransson, J., Front. Biosci. 13 (2008) 1619-1633); and framework regions derived from screening FR libraries (see, e.g., Baca, M. et al., J. Biol. Chem. 272 (1997) 10678-10684 and Rosok, M. J. et al., J. Biol. Chem. 271 (19969 22611-22618).

3. Human Antibodies

In certain embodiments, an antibody provided herein is a human antibody. Human antibodies can be produced using various techniques known in the art. Human antibodies are described generally in van Dijk, M. A. and van de Winkel, J. G., Curr. Opin. Pharmacol. 5 (2001) 368-374 and Lonberg, N., Curr. Opin. Immunol. 20 (2008) 450-459.

Human antibodies maybe prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, N., Nat. Biotech. 23 (2005) 1117-1125. See also, e.g., U.S. Pat. Nos. 6,075,181 and 6,150,584 describing XENOMOUSE™ technology; U.S. Pat. No. 5,770,429 describing HUMAB® technology; U.S. Pat. No. 7,041,870 describing K-M MOUSE® technology, and US 2007/0061900, describing VELOCIMOUSE® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described (see, e.g., Kozbor, D., J. Immunol. 133 (1984) 3001-3005; Brodeur, B. R., et al., Monoclonal Antibody Production Techniques and Applications, Marcel Dekker, Inc., New York (1987), pp. 51-63; and Boerner, P., et al., J. Immunol. 147 (1991) 86-95). Human antibodies generated via human B-cell hybridoma technology are also described in Li, J. et al., Proc. Natl. Acad. Sci. USA 103 (2006) 3557-3562. Additional methods include those described, for example, in U.S. Pat. No. 7,189,826 (describing production of monoclonal human IgM antibodies from hybridoma cell lines) and Ni, J., Xiandai Mianyixue 26 (2006) 265-268 (describing human-human hybridomas). Human hybridoma technology (Trioma technology) is also described in Vollmers, H. P. and Brandlein, S., Histology and Histopathology 20 (2005) 927-937 and Vollmers, H. P. and Brandlein, S., Methods and Findings in Experimental and Clinical Pharmacology 27 (2005) 185-191.

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

4. Library-Derived Antibodies

Antibodies as reported herein may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom, H. R. et al., Methods in Molecular Biology 178 (2001) 1-37 and further described, e.g., in the McCafferty, J. et al., Nature 348 (1990) 552-554; Clackson, T. et al., Nature 352 (1991) 624-628; Marks, J. D. et al., J. Mol. Biol. 222 (1992) 581-597; Marks, J. D. and Bradbury, A., Methods in Molecular Biology 248 (2003) 161-175; Sidhu, S. S. et al., J. Mol. Biol. 338 (2004) 299-310; Lee, C. V. et al., J. Mol. Biol. 340 (2004) 1073-1093; Fellouse, F. A., Proc. Natl. Acad. Sci. USA 101 (2004) 12467-12472; and Lee, C. V. et al., J. Immunol. Methods 284 (2004) 119-132.

In certain phage display methods, repertoires of VH and VL genes are separately cloned by polymerase chain reaction (PCR) and recombined randomly in phage libraries, which can then be screened for antigen-binding phage as described in Winter, G., et al., Ann. Rev. Immunol. 12 (1994) 433-455.Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self-antigens without any immunization as described by Griffiths, A. D., et al., EMBO J. 12 (1993) 725-734. Finally, naive libraries can also be made synthetically by cloning non-rearranged V-gene segments from stem cells, and using PCR primers containing random sequence to encode the highly variable CDR3 regions and to accomplish rearrangement in vitro, as described by Hoogenboom, H. R. and Winter, G., J. Mol. Biol. 227 (1992) 381-388. Patent publications describing human antibody phage libraries include, for example: U.S. Pat. No. 5,750,373, and US 2005/0079574, US 2005/0119455, US 2005/0266000, US 2007/0117126, US 2007/0160598, US 2007/0237764, US 2007/0292936, and US 2009/0002360.

Antibodies or antibody fragments isolated from human antibody libraries are considered human antibodies or human antibody fragments herein.

5. Multispecific Antibodies

In certain embodiments, an antibody provided herein is a multispecific antibody, e.g. a bispecific antibody. Multispecific antibodies are monoclonal antibodies that have binding specificities for at least two different sites. Bispecific antibodies may also be used to localize cytotoxic agents to cells which express one or more of the target antigens. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein, C. and Cuello, A. C., Nature 305 (1983) 537-540, WO 93/08829, and Traunecker, A., et al., EMBO J. 10 (1991) 3655-3659), and "knob-in-hole" engineering (see, e.g., U.S. Pat. No. 5,731,168). Multispecific antibodies may also be made by engineering electrostatic steering effects for making antibody Fc-heterodimeric molecules (WO 2009/089004); cross-linking two or more antibodies or fragments (see, e.g., U.S. Pat. No. 4,676,980, and Brennan, M. et al., Science 229 (1985) 81-83); using leucine zippers to produce bi-specific antibodies (see, e.g., Kostelny, S. A., et al., J. Immunol. 148 (1992) 1547-1553; using "diabody" technology for making bispecific antibody fragments (see, e.g., Holliger, P. et al., Proc. Natl. Acad. Sci. USA 90 (1993) 6444-6448); and using single-chain Fv (sFv) dimers (see, e.g. Gruber, M et al., J. Immunol. 152 (1994) 5368-5374); and preparing trispecific antibodies as described, e.g., in Tutt, A. et al., J. Immunol. 147 (1991) 60-69).

Engineered antibodies with three or more functional antigen binding sites, including "Octopus antibodies," are also included herein (see, e.g. US 2006/0025576).

The antibody or fragment herein also includes a "Dual Acting Fab" or "DAF" comprising an antigen binding site that binds to a first antigen as well as another, different antigen (see, US 2008/0069820, for example).

The antibody or fragment herein also includes multispecific antibodies described in WO 2009/080251, WO 2009/080252, WO 2009/080253, WO 2009/080254, WO 2010/112193, WO 2010/115589, WO 2010/136172, WO 2010/145792, and WO 2010/145793.

6. Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, and Deletion Variants

In certain embodiments, antibody variants having one or more amino acid substitutions are provided. Sites of interest for substitutional mutagenesis include the HVRs and FRs. Conservative substitutions are shown in the Table below under the heading of "preferred substitutions". More substantial changes are provided in the following Table under the heading of "exemplary substitutions", and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE

| Original Residue | Exemplary Substitutions | Preferred Substitutions |
| --- | --- | --- |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:

(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, P. S., Methods Mol. Biol. 207 (2008) 179-196), and/or residues that contact antigen, with the resulting variant VH or VL being tested for binding affinity. Affinity maturation by constructing and reselecting from secondary libraries has been described, e.g., in Hoogenboom, H. R. et al. in Methods in Molecular Biology 178 (2002) 1-37. In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may, for example, be outside of antigen contacting residues in the HVRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham, B. C. and Wells, J. A., Science 244 (1989) 1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen can be used. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

b) Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc-region, the carbohydrate attached thereto may be altered. Native antibodies produced by mammalian cells typically comprise a branched, biantennary oligosaccharide that is generally attached by an N-linkage to Asn297 of the CH2 domain of the Fc-region. See, e.g., Wright, A. and Morrison, S. L., TIBTECH 15 (1997) 26-32. The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody as reported herein may be made in order to create antibody variants with certain improved properties.

In one embodiment, antibody variants are provided having a carbohydrate structure that lacks fucose attached (directly or indirectly) to an Fc-region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e. g. complex, hybrid and high mannose structures) as measured by MALDI-TOF mass spectrometry, as described in WO 2008/077546, for example. Asn297 refers to the asparagine residue located at about position 297 in the Fc-region (EU numbering of Fc-region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US 2003/0157108; US 2004/0093621. Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO 2005/053742; WO 2002/031140; Okazaki, A. et al., J. Mol. Biol. 336 (2004) 1239-1249; Yamane-Ohnuki, N. et al., Biotech. Bioeng. 87 (2004) 614-622. Examples of cell lines capable of producing defucosylated antibodies include Lec13 CHO cells deficient in protein fucosylation (Ripka, J., et al., Arch. Biochem. Biophys. 249 (1986) 533-545; US 2003/0157108; and WO 2004/056312, especially at Example 11), and knockout cell lines, such as alpha-1,6-fucosyltransferase gene, FUT8, knockout CHO cells (see, e.g., Yamane-Ohnuki, N., et al., Biotech. Bioeng. 87 (2004) 614-622; Kanda, Y. et al., Biotechnol. Bioeng. 94 (2006) 680-688; and WO 2003/085107).

Antibodies variants are further provided with bisected oligosaccharides, e.g., in which a biantennary oligosaccharide attached to the Fc-region of the antibody is bisected by GlcNAc. Such antibody variants may have reduced fucosylation and/or improved ADCC function. Examples of such antibody variants are described, e.g., in WO 2003/011878; U.S. Pat. No. 6,602,684; and US 2005/0123546. Antibody variants with at least one galactose residue in the oligosaccharide attached to the Fc-region are also provided. Such antibody variants may have improved CDC function. Such antibody variants are described, e.g., in WO 1997/30087; WO 1998/58964; and WO 1999/22764.

c) Fc-Region Variants

In certain embodiments, one or more further amino acid modifications may be introduced into the Fc-region of an antibody provided herein, thereby generating an Fc-region variant. The Fc-region variant may comprise a human Fc-region sequence (e.g., a human IgG1, IgG2, IgG3 or IgG4 Fc-region) comprising an amino acid modification (e.g. a substitution/mutation) at one or more amino acid positions.

In certain embodiments, the invention contemplates an antibody variant that possesses some but not all effector functions, which make it a desirable candidate for applications in which the half-life of the antibody in vivo is important yet certain effector functions (such as CDC and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch, J. V. and Kinet, J. P., Annu. Rev. Immunol. 9 (1991) 457-492. Non-limiting examples of in vitro assays to assess ADCC activity of a molecule of interest are described in U.S. Pat. No. 5,500,362 (see, e.g. Hellstrom, I. et al., Proc. Natl. Acad. Sci. USA 83 (1986) 7059-7063; and Hellstrom, I. et al., Proc. Natl. Acad. Sci. USA 82 (1985) 1499-1502); U.S. Pat. No. 5,821,337 (see Bruggemann, M. et al., J. Exp. Med. 166 (1987) 1351-1361). Alternatively, non-radioactive assays methods may be employed (see, for example, ACTI™ non-radioactive cytotoxicity assay for flow cytometry (CellTechnology, Inc. Mountain View, CA; and CytoTox 96® non-radioactive cytotoxicity assay (Promega, Madison, WI). Useful effector cells for such assays include peripheral blood mononuclear cells (PBMC) and Natural Killer (NK) cells.

Alternatively, or additionally, ADCC activity of the molecule of interest may be assessed in vivo, e.g., in an animal model such as that disclosed in Clynes, R. et al., Proc. Natl. Acad. Sci. USA 95 (1998) 652-656. C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro, H. et al., J. Immunol. Methods 202 (1996) 163-171; Cragg, M. S. et al., Blood 101 (2003) 1045-1052; and Cragg, M. S. and M. J. Glennie, Blood 103 (2004) 2738-2743). FcRn binding and in vivo clearance/half-life determinations can also be performed using methods known in the art (see, e.g., Petkova, S. B. et al., Int. Immunol. 18 (2006) 1759-1769).

Antibodies with reduced effector function include those with substitution of one or more of Fc-region residues 238, 265, 269, 270, 297, 327 and 329 (U.S. Pat. No. 6,737,056). Such Fc-region variants include Fc-regions with substitutions at two or more of amino acid positions 265, 269, 270, 297 and 327, including the so-called "DANA" Fc-region mutant with substitution of residues 265 and 297 to alanine (U.S. Pat. No. 7,332,581).

Certain antibody variants with improved or diminished binding to FcRs are described (see, e.g., U.S. Pat. No. 6,737,056; WO 2004/056312, and Shields, R. L. et al., J. Biol. Chem. 276 (2001) 6591-6604).

In certain embodiments, an antibody variant comprises an Fc-region with one or more amino acid substitutions which improve ADCC, e.g., substitutions at positions 298, 333, and/or 334 of the Fc-region (EU numbering of residues).

In some embodiments, alterations are made in the Fc-region that result in altered (i.e., either improved or diminished) C1q binding and/or Complement Dependent Cytotoxicity (CDC), e.g., as described in U.S. Pat. No. 6,194,551, WO 99/51642, and Idusogie, E. E. et al., J. Immunol. 164 (2000) 4178-4184.

Antibodies with increased half-lives and improved binding to the neonatal Fc receptor (FcRn), which is responsible for the transfer of maternal IgGs to the fetus (Guyer, R. L. et al., J. Immunol. 117 (1976) 587-593, and Kim, J. K. et al., J. Immunol. 24 (1994) 2429-2434), are described in US 2005/0014934. Those antibodies comprise an Fc-region with one or more substitutions therein which improve binding of the Fc-region to FcRn. Such Fc-region variants include those with substitutions at one or more of Fc-region residues: 238, 256, 265, 272, 286, 303, 305, 307, 311, 312, 317, 340, 356, 360, 362, 376, 378, 380, 382, 413, 424 or 434, e.g., substitution of Fc-region residue 434 (U.S. Pat. No. 7,371,826).

See also Duncan, A. R. and Winter, G., Nature 322 (1988) 738-740; U.S. Pat. Nos. 5,648,260; 5,624,821; and WO 94/29351 concerning other examples of Fc-region variants.

d) Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc-region. Cysteine engineered antibodies may be generated as described, e.g., in U.S. Pat. No. 7,521,541.

e) Antibody Derivatives

In certain embodiments, an antibody provided herein may be further modified to contain additional non-proteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or non-branched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and non-proteinaceous moiety that may be selectively heated by exposure to radiation are provided. In one embodiment, the non-proteinaceous moiety is a carbon nanotube (Kam, N. W. et al., Proc. Natl. Acad. Sci. USA 102 (2005) 11600-11605). The radiation may be of any wavelength, and includes, but is not limited to, wavelengths that do not harm ordinary cells, but which heat the non-proteinaceous moiety to a temperature at which cells proximal to the antibody-non-proteinaceous moiety are killed.

f) Heterodimerization

There exist several approaches for CH3-modifications to enforce the heterodimerization, which are well described e.g. in WO 96/27011, WO 98/050431, EP 1870459, WO 2007/110205, WO 2007/147901, WO 2009/089004, WO 2010/129304, WO 2011/90754, WO 2011/143545, WO 2012058768, WO 2013157954, WO 2013096291. Typically in all such approaches the first CH3 domain and the second CH3 domains are both engineered in a complementary manner so that each CH3 domain (or the heavy chain comprising it) cannot longer homodimerize with itself but is forced to heterodimerize with the complementary engineered other CH3 domain (so that the first and second CH3 domain heterodimerize and no homodimers between the two first or the two second CH3 domains are formed). These different approaches for improved heavy chain heterodimerization are contemplated as different alternatives in combination with the heavy-light chain modifications (VH and VL exchange/replacement in one binding arm and the introduction of substitutions of charged amino acids with opposite charges in the CH1/CL interface) in the multispecific antibodies according to the invention which reduce light chain mispairing an Bence-Jones type side products.

In one preferred embodiment of the invention (in case the multispecific antibody comprises CH3 domains in the heavy chains) the CH3 domains of said multispecific antibody according to the invention can be altered by the "knob-into-holes" technology which is described in detail with several examples in e.g. WO 96/027011, Ridgway, J. B., et al., Protein Eng. 9 (1996) 617-621; and Merchant, A. M., et al., Nat. Biotechnol. 16 (1998) 677-681; WO 98/050431. In this method the interaction surfaces of the two CH3 domains are altered to increase the heterodimerization of both heavy chains containing these two CH3 domains. Each of the two CH3 domains (of the two heavy chains) can be the "knob", while the other is the "hole". The introduction of a disulfide bridge further stabilizes the heterodimers (Merchant, A. M., et al., Nature Biotech. 16 (1998) 677-681; Atwell, S., et al., J. Mol. Biol. 270 (1997) 26-35) and increases the yield.

Thus in one embodiment of the invention said multispecific antibody (comprises a CH3 domain in each heavy chain and) is further characterized in that the first CH3 domain of the first heavy chain of the antibody under a) and the second CH3 domain of the second heavy chain of the antibody under b) each meet at an interface which comprises an original interface between the antibody CH3 domains.

wherein said interface is altered to promote the formation of the multispecific antibody, wherein the alteration is characterized in that:

i) the CH3 domain of one heavy chain is altered, so that within the original interface of the CH3 domain of one heavy chain that meets the original interface of the CH3 domain of the other heavy chain within the multispecific antibody, an amino acid residue is replaced with an amino acid residue having a larger side chain volume, thereby generating a protuberance within the interface of the CH3 domain of one heavy chain which is positionable in a cavity within the interface of the CH3 domain of the other heavy chain and ii) the CH3 domain of the other heavy chain is altered, so that within the original interface of the second CH3 domain that meets the original interface of the first CH3 domain within the multispecific antibody an amino acid residue is replaced with an amino acid residue having a smaller side chain volume, thereby generating a cavity within the interface of the second CH3 domain within which a protuberance within the interface of the first CH3 domain is positionable.

Preferably said amino acid residue having a larger side chain volume is selected from the group consisting of arginine (R), phenylalanine (F), tyrosine (Y), tryptophan (W).

Preferably said amino acid residue having a smaller side chain volume is selected from the group consisting of alanine (A), serine (S), threonine (T), valine (V).

In one aspect of the invention both CH3 domains are further altered by the introduction of cysteine (C) as amino acid in the corresponding positions of each CH3 domain such that a disulfide bridge between both CH3 domains can be formed.

In one preferred embodiment, said multispecific antibody comprises a amino acid T366W mutation in the first CH3 domain of the "knobs chain" and amino acid T366S, L368A, Y407V mutations in the second CH3 domain of the "hole chain". An additional interchain disulfide bridge between the CH3 domains can also be used (Merchant, A. M., et al., Nature Biotech. 16 (1998) 677-681) e.g. by introducing an amino acid Y349C mutation into the CH3 domain of the "hole chain" and an amino acid E356C mutation or an amino acid S354C mutation into the CH3 domain of the "knobs chain".

In one preferred embodiment, said multispecific antibody (which comprises a CH3 domain in each heavy chain) comprises amino acid S354C, T366W mutations in one of the two CH3 domains and amino acid Y349C, T366S, L368A, Y407V mutations in the other of the two CH3 domains (the additional amino acid S354C mutation in one CH3 domain and the additional amino acid Y349C mutation in the other CH3 domain forming an interchain disulfide bridge) (numbering according to Kabat).

Other techniques for CH3-modifications to enforcing the heterodimerization are contemplated as alternatives of the invention and described e.g. in WO 96/27011, WO 98/050431, EP 1870459, WO 2007/110205, WO 2007/147901, WO 2009/089004, WO 2010/129304, WO 2011/90754, WO 2011/143545, WO 2012/058768, WO 2013/157954, WO 2013/096291.

In one embodiment the heterodimerization approach described in EP 1 870 459A1, can be used alternatively. This approach is based on the by the introduction of substitutions/mutations of charged amino acids with the opposite charge at specific amino acid positions of the in the CH3/CH3 domain interface between both heavy chains. One preferred embodiment for said multispecific antibody are amino acid R409D; K370E mutations in the first CH3 domain of the (of the multispecific antibody) and amino acid D399K; E357K mutations in the seconds CH3 domain of the multispecific antibody (numbering according to Kabat).

In another embodiment said multispecific antibody comprises a amino acid T366W mutation in the CH3 domain of the "knobs chain" and amino acid T366S, L368A, Y407V mutations in the CH3 domain of the "hole chain" and additionally amino acid R409D; K370E mutations in the CH3 domain of the "knobs chain" and amino acid D399K; E357K mutations in the CH3 domain of the "hole chain".

In another embodiment said multispecific antibody comprises amino acid S354C, T366W mutations in one of the two CH3 domains and amino acid Y349C, T366S, L368A, Y407V mutations in the other of the two CH3 domains or said multispecific antibody comprises amino acid Y349C, T366W mutations in one of the two CH3 domains and amino acid S354C, T366S, L368A, Y407V mutations in the other of the two CH3 domains and additionally amino acid R409D; K370E mutations in the CH3 domain of the "knobs chain" and amino acid D399K; E357K mutations in the CH3 domain of the "hole chain".

In one embodiment the heterodimerization approach described in WO2013/157953 can be used alternatively. In one embodiment a first CH3 domain comprises amino acid T366K mutation and a second CH3 domain polypeptide comprises amino acid L351D mutation. In a further embodiment the first CH3 domain comprises further amino acid L351K mutation. In a further embodiment the second CH3 domain comprises further amino acid mutation selected from Y349E, Y349D and L368E (preferably L368E).

In one embodiment the heterodimerization approach described in WO2012/058768 can be used alternatively. In one embodiment a first CH3 domain comprises amino acid L351Y, Y407A mutations and a second CH3 domain comprises amino acid T366A, K409F mutations. In a further embodiment the second CH3 domain comprises a further amino acid mutation at position T411, D399, S400, F405, N390, or K392 e.g. selected from a) T411 N, T411 R, T411Q, T411 K, T411D, T411E, or T411W, b) D399R, D399W, D399Y or D399K, c S400E, S400D, S400R, or S400K F405I, F405M, F405T, F405S, F405V, or F405W, N390R, N390K, or N390D K392V, K392M, K392R, K392L, K392F, or K392E. In a further embodiment a first CH3 domain comprises amino acid L351Y, Y407A mutations and a second CH3 domain comprises amino acid T366V, K409F mutations. In a further embodiment a first CH3 domain comprises amino acid Y407A mutations and a second CH3 domain comprises amino acid T366A, K409F mutations. In a further embodiment the second CH3 domain comprises a further amino acid K392E, T411E, D399R and S400R mutations.

In one embodiment the heterodimerization approach described in WO2011/143545 can be used alternatively e.g. with the amino acid modification at a position selected from the group consisting of 368 and 409.

In one embodiment the heterodimerization approach described in WO2011/090762 which also uses the knobs-into-holes technology described above can be used alternatively. In one embodiment a first CH3 domain comprises amino acid T366W mutations and a second CH3 domain comprises amino acid Y407A mutations. In one embodiment a first CH3 domain comprises amino acid T366Y mutations and a second CH3 domain comprises amino acid Y407T mutations.

In one embodiment the multispecific antibody is of IgG2 isotype and the heterodimerization approach described in WO2010/129304 can be used alternatively.

In one embodiment the heterodimerization approach described in WO2009/089004 can be used alternatively. In one embodiment a first CH3 domain comprises amino acid substitution of K392 or N392 with a negative-charged amino acid (e.g. glutamic acid (E), or aspartic acid (D), preferably K392D or N392D) and a second CH3 domain comprises amino acid substitution of D399, E356, D356, or E357 with a positive-charged amino acid (e.g. Lysine (K) or arginine (R), preferably D399K, E356K, D356K, or E357K and more preferably D399K and E356K. In a further embodiment the first CH3 domain further comprises amino acid substitution of K409 or R409 with a negative-charged amino acid (e.g. glutamic acid (E), or aspartic acid (D), preferably K409D or R409D). In a further embodiment the first CH3 domain further or alternatively comprises amino acid substitution of K439 and/or K370 with a negative-charged amino acid (e.g. glutamic acid (E), or aspartic acid (D)).

In one embodiment the heterodimerization approach described in WO2007/147901 can be used alternatively. In one embodiment a first CH3 domain comprises amino acid K253E, D282K, and K322D mutations and a second CH3 domain comprises amino acid D239K, E240K, and K292D mutations.

In one embodiment the heterodimerization approach described in WO2007/110205 can be used alternatively.

Recombinant Methods and Formulations

Antibodies may be produced using recombinant methods and formulations, e.g., as described in U.S. Pat. No. 4,816,567. In one embodiment, isolated nucleic acid(s) encoding an antibody as described herein is(are) provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell). In one embodiment, a method of making an antibody as reported herein is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an variant Fc-region, nucleic acid encoding the variant Fc-region, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the variant Fc-region polypeptides or heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523 (see also Charlton, K. A., In: Methods in Molecular Biology, Vol. 248, Lo, B. K. C. (ed.), Humana Press, Totowa, NJ (2003), pp. 245-254, describing expression of antibody fragments in *E. coli*).

After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized", resulting in the production of an antibody with a partially or fully human glycosylation pattern. See Gerngross, T. U., Nat. Biotech. 22 (2004) 1409-1414; and Li, H. et al., Nat. Biotech. 24 (2006) 210-215.

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (HEK293 or 293 cells as described, e.g., in Graham, F. L., et al., J. Gen Virol. 36 (1977) 59-74); baby hamster kidney cells (BHK); mouse sertoli cells (TM4 cells as described, e.g., in Mather, J. P., Biol. Reprod. 23 (1980) 243-252); monkey kidney cells (CV1); African green monkey kidney cells (VERO-76); human cervical carcinoma cells (HELA); canine kidney cells (MDCK); buffalo rat liver cells (BRL 3A); human lung cells (W138); human liver cells (Hep G2); mouse mammary tumor (MMT 060562); TRI cells, as described, e.g., in Mather, J. P., et al., Annals NY Acad. Sci. 383 (1982) 44-68; MRC 5 cells; and FS4 cells. Other useful mammalian host cell lines include Chinese hamster ovary (CHO) cells, including DHFR⁻ CHO cells (Urlaub, G., et al., Proc. Natl. Acad. Sci. USA 77 (1980) 4216-4220); and myeloma cell lines such as Y0, NS0 and Sp2/0. For a review of certain mammalian host cell lines suitable for antibody production, see, e.g., Yazaki, P. and Wu, A. M., Methods in Molecular Biology, Vol. 248, Lo, B. K. C. (ed.), Humana Press, Totowa, NJ (2004), pp. 255-268.

Assays

Antibodies provided herein may be identified, screened for, or characterized for their physical/chemical properties and/or biological activities by various assays known in the art.

In one aspect, an antibody as reported herein is tested for its antigen binding activity, e.g., by known methods such as ELISA, Western Blot, etc.

Immunoconjugates

The invention also provides immunoconjugates comprising an antibody as reported herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In one embodiment, an immunoconjugate is an antibody-drug conjugate (ADC) in which an antibody is conjugated to one or more drugs, including but not limited to a maytansinoid (see U.S. Pat. Nos. 5,208,020, 5,416,064 and EP 0 425 235 B1); an auristatin such as monomethyl auristatin drug moieties DE and DF (MMAE and MMAF) (see U.S. Pat. Nos. 5,635,483, 5,780,588, and 7,498,298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman, L. M. et al., Cancer Res. 53 (1993) 3336-3342; and Lode, H. N. et al., Cancer Res. 58 (1998) 2925-2928); an anthracycline such as daunomycin or doxorubicin (see Kratz, F. et al., Curr. Med. Chem. 13 (2006) 477-523; Jeffrey, S. C. et al., Bioorg. Med. Chem. Lett. 16 (2006) 358-362; Torgov, M. Y. et al., Bioconjug. Chem. 16 (2005) 717-721; Nagy, A. et al., Proc. Natl. Acad. Sci. USA 97 (2000) 829-834; Dubowchik, G. M. et al., Bioorg.& Med. Chem. Letters 12 (2002) 1529-1532; King, H. D. et al., J. Med. Chem. 45 (2002) 4336-4343; and U.S. Pat. No. 6,630,579); methotrexate; vindesine; a taxane such as docetaxel, paclitaxel, larotaxel, tesetaxel, and ortataxel; a trichothecene; and CC 1065.

In another embodiment, an immunoconjugate comprises an antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes.

In another embodiment, an immunoconjugate comprises an antibody as described herein conjugated to a radioactive atom to form a radioconjugate. A variety of radioactive isotopes are available for the production of radioconjugates. Examples include $At^{21}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the radioconjugate is used for detection, it may comprise a radioactive atom for scintigraphic studies, for example $TC^{99m}$ or $I^{123}$, or a spin label for nuclear magnetic resonance (NMR) imaging (also known as magnetic resonance imaging, MRI), such as iodine-123, iodine-131, indium-111, fluorine-19, carbon-13, nitrogen-15, oxygen-17, gadolinium, manganese or iron.

Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta, E. S. et al., Science 238 (1987) 1098-1104. Carbon-14-labeled 1-isothiocyanatobenzyl-3-methyldiethylene triamine pentaacetic acid (MX-DTPA) is an exemplary chelating agent for conjugation of radionucleotide to the antibody. See WO 94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari, R. V. et al., Cancer Res. 52 (1992) 127-131; U.S. Pat. No. 5,208,020) may be used.

The immuno-conjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone) benzoate) which are commercially available (e.g., from Pierce Biotechnology, Inc., Rockford, IL., U.S.A).

Methods and Formulations for Diagnostics and Detection

In certain embodiments, any of the antibodies provided herein is useful for detecting the presence of its cognate antigen(s) in a biological sample. The term "detecting" as used herein encompasses quantitative or qualitative detection. In certain embodiments, a biological sample comprises a cell or tissue.

In one embodiment, an antibody as reported herein for use in a method of diagnosis or detection is provided.

In certain embodiments, labeled antibodies as reported herein are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

Pharmaceutical Formulations

Pharmaceutical formulations of an antibody as described herein are prepared by mixing such antibody having the desired degree of purity with one or more optional pharmaceutically acceptable carriers (Remington's Pharmaceutical Sciences, 16th edition, Osol, A. (ed.) (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyl dimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as poly(vinylpyrrolidone); amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include interstitial drug dispersion agents such as soluble neutral-active hyaluronidase glycoproteins (sHASEGP), for example, human soluble PH-20 hyaluronidase glycoproteins, such as rhuPH20 (HYLENEX®, Baxter International, Inc.). Certain exemplary sHASEGPs and methods of use, including rhuPH20, are described in US 2005/0260186 and US 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO 2006/044908, the latter formulations including a histidine-acetate buffer.

The formulation herein may also contain more than one active ingredients as necessary for the particular indication being treated, preferably those with complementary activities that do not adversely affect each other. Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methyl methacrylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences, 16th edition, Osol, A. (ed.) (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules.

The formulations to be used for in vivo administration are generally sterile. Sterility may be readily accomplished, e.g., by filtration through sterile filtration membranes.

Therapeutic Methods and Formulations

Any of the antibodies provided herein may be used in therapeutic methods.

In one aspect, an antibody as reported herein for use as a medicament is provided.

In certain embodiments, an antibody for use in a method of treatment is provided. In one such embodiment, the method further comprises administering to the individual an effective amount of at least one additional therapeutic agent, e.g., as described below.

An "individual" according to any of the above embodiments is in one preferred embodiment a human.

In a further aspect, the invention provides for the use of an antibody in the manufacture or preparation of a medicament. An "individual" according to any of the above embodiments may be a human.

In a further aspect, the invention provides pharmaceutical formulations comprising any of the antibodies provided herein, e.g., for use in any of the above therapeutic methods.

In one embodiment, a pharmaceutical formulation comprises any of the antibodies provided herein and a pharmaceutically acceptable carrier. In another embodiment, a pharmaceutical formulation comprises any of the antibodies provided herein and at least one additional therapeutic agent, e.g., as described below.

Antibodies as reported herein can be used either alone or in combination with other agents in a therapy. For instance, an antibody as reported herein may be co-administered with at least one additional therapeutic agent.

An antibody as reported herein (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein.

Antibodies as reported herein would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody as reported herein (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 µg/kg to 15 mg/kg (e.g. 0.5 mg/kg-10 mg/kg) of antibody can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered. The progress of this therapy is easily monitored by conventional techniques and assays.

It is understood that any of the above formulations or therapeutic methods may be carried out using an immunoconjugate as reported herein in place of or in addition to an antibody as reported herein.

Articles of Manufacture

In another aspect as reported herein, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a formulation which is by itself or combined with another formulation effective for treating, preventing and/or diagnosing the condition and may have a sterile access port (for example the container may be an intravenous solution bag or a vial having a stopper pierceable by a hypodermic injection needle). At least one active agent in the formulation is an antibody as reported herein. The label or package insert indicates that the formulation is used for treating the condition of choice. Moreover, the article of manufacture may comprise (a) a first container with a formulation contained therein, wherein the formulation comprises an antibody as reported herein; and (b) a second container with a formulation contained therein, wherein the formulation comprises a further cytotoxic or otherwise therapeutic agent. The article of manufacture in this embodiment as reported herein may further comprise a package insert indicating that the formulations can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

It is understood that any of the above articles of manufacture may include an immunoconjugate as reported herein in place of or in addition to an antibody as reported herein.

III. Specific Embodiments

1. An IgG class Fc-region comprising a first variant Fc-region polypeptide and a second variant Fc-region polypeptide,
    wherein
    a) the first variant Fc-region polypeptide is derived from a first parent IgG class Fc-region polypeptide and the second variant Fc-region polypeptide is derived from a second parent IgG class Fc-region polypeptide, whereby the first parent IgG class Fc-region polypeptide is identical to or different from the second parent IgG class Fc-region polypeptide, and
    b) the first variant Fc-region polypeptide differs from the second variant Fc-region polypeptide in one or more amino acid residues other than those amino acid residues in which the first parent IgG class Fc-region polypeptide differs from the second parent IgG class Fc-region polypeptide, and
    c) the IgG class Fc-region comprising the first variant Fc-region polypeptide and the second variant Fc-region polypeptide has an affinity to a human Fc-receptor that is different than that of an IgG class Fc-region comprising the first parent IgG class Fc-region polypeptide of a) and the second parent IgG class Fc-region polypeptide of a).

2. The IgG class Fc-region according to embodiment 1, wherein the human Fc-receptor is the human neonatal Fc receptor (FcRn) or the human FcgammaIII receptor (FcγRIII).

3. The IgG class Fc-region according to any one of embodiments 1 to 2, wherein the human Fc-receptor is the human neonatal Fc-receptor.

4. The IgG class Fc-region according to any one of embodiments 1 to 3, wherein the affinity of the IgG class Fc-region comprising the first variant Fc-region polypeptide and the second variant Fc-region polypeptide to a human Fc-receptor is increased or reduced by 10% or more determined by surface plasmon resonance (SPR) compared to that of an IgG class Fc-region comprising the first parent IgG class Fc-region polypeptide of a) and the second parent IgG class Fc-region polypeptide of a).

5. The IgG class Fc-region according to any one of embodiments 1 to 4, wherein at least some of those amino acid residues in which the first parent IgG class Fc-region polypeptide differs from the second parent IgG class Fc-region polypeptide promote the formation of a heterodimeric IgG class Fc-region.

6. The IgG class Fc-region according to any one of embodiments 1 to 5, wherein
  i) the first parent IgG class Fc-region polypeptide is selected from the group comprising
    human IgG1 Fc-region polypeptide,
    human IgG2 Fc-region polypeptide,
    human IgG3 Fc-region polypeptide,
    human IgG4 Fc-region polypeptide,
    human IgG1 Fc-region polypeptide with the mutations L234A, L235A,
    human IgG1 Fc-region polypeptide with the mutations Y349C, T366S, L368A, Y407V,
    human IgG1 Fc-region polypeptide with the mutations S354C, T366S, L368A, Y407V,
    human IgG1 Fc-region polypeptide with the mutations L234A, L235A, Y349C, T366S, L368A, Y407V,
    human IgG1 Fc-region polypeptide with the mutations L234A, L235A, S354C, T366S, L368A, Y407V,
    human IgG1 Fc-region polypeptide with the mutations P329G,
    human IgG1 Fc-region polypeptide with the mutations L234A, L235A, P329G,
    human IgG1 Fc-region polypeptide with the mutations P329G, Y349C, T366S, L368A, Y407V,
    human IgG1 Fc-region polypeptide with the mutations P329G, S354C, T366S, L368A, Y407V,
    human IgG1 Fc-region polypeptide with the mutations L234A, L235A, P329G, Y349C, T366S, L368A, Y407V,
    human IgG1 Fc-region polypeptide with the mutations L234A, L235A, P329G, S354C, T366S, L368A, Y407V,
    human IgG4 Fc-region polypeptide with the mutations S228P, L235E,
    human IgG4 Fc-region polypeptide with the mutations S228P, L235E, P329G,
    human IgG4 Fc-region polypeptide with the mutations Y349C, T366S, L368A, Y407V,
    human IgG4 Fc-region polypeptide with the mutations S354C, T366S, L368A, Y407V,
    human IgG4 Fc-region polypeptide with the mutations S228P, L235E, Y349C, T366S, L368A, Y407V,
    human IgG4 Fc-region polypeptide with the mutations S228P, L235E, S354C, T366S, L368A, Y407V,
    human IgG4 Fc-region polypeptide with the mutations P329G,
    human IgG4 Fc-region polypeptide with the mutations P329G, Y349C, T366S, L368A, Y407V,
    human IgG4 Fc-region polypeptide with the mutations P329G, S354C, T366S, L368A, Y407V,
    human IgG4 Fc-region polypeptide with the mutations S228P, L235E, P329G, Y349C, T366S, L368A, Y407V,
    human IgG4 Fc-region polypeptide with the mutations S228P, L235E, P329G, S354C, T366S, L368A, Y407V,
    human IgG1, IgG2 or IgG4 with the mutation K392D, and
    human IgG3 with the mutation N392D,
  and
  ii) the second parent IgG class Fc-region polypeptide is selected from the group comprising
    human IgG1 Fc-region polypeptide,
    human IgG2 Fc-region polypeptide,
    human IgG3 Fc-region polypeptide,
    human IgG4 Fc-region polypeptide,
    human IgG1 Fc-region polypeptide with the mutations L234A, L235A,
    human IgG1 Fc-region polypeptide with the mutations S354C, T366W,
    human IgG1 Fc-region polypeptide with the mutations Y349C, T366W,
    human IgG1 Fc-region polypeptide with the mutations L234A, L235A, S354C, T366W,
    human IgG1 Fc-region polypeptide with the mutations L234A, L235A, Y349C, T366W,
    human IgG1 Fc-region polypeptide with the mutations P329G,
    human IgG1 Fc-region polypeptide with the mutations L234A, L235A, P329G,
    human IgG1 Fc-region polypeptide with the mutations P329G, S354C, T366W,
    human IgG1 Fc-region polypeptide with the mutations P329G, Y349C, T366W,
    human IgG1 Fc-region polypeptide with the mutations L234A, L235A, P329G, S354C, T366W,
    human IgG1 Fc-region polypeptide with the mutations L234A, L235A, P329G, Y349C, T366W,
    human IgG4 Fc-region polypeptide with the mutations S228P, L235E,
    human IgG4 Fc-region polypeptide with the mutations S228P, L235E, P329G,
    human IgG4 Fc-region polypeptide with the mutations S354C, T366W,
    human IgG4 Fc-region polypeptide with the mutations Y349C, T366W,
    human IgG4 Fc-region polypeptide with the mutations S228P, L235E, S354C, T366W,
    human IgG4 Fc-region polypeptide with the mutations S228P, L235E, Y349C, T366W,
    human IgG4 Fc-region polypeptide with the mutations P329G,
    human IgG4 Fc-region polypeptide with the mutations P329G, S354C, T366W,
    human IgG4 Fc-region polypeptide with the mutations P329G, Y349C, T366W,
    human IgG4 Fc-region polypeptide with the mutations S228P, L235E, P329G, S354C, T366W,
    human IgG4 Fc-region polypeptide with the mutations S228P, L235E, P329G, Y349C, T366W, human IgG1 with the mutations D399K, D356K, and/or E357K, and human IgG2, IgG3 or IgG4 with the mutations D399K, E356K, and/or E357K.

7. The IgG class Fc-region according to any one of embodiments 1 to 6, wherein
   i) the first parent IgG class Fc-region polypeptide has an amino acid sequence selected from the group comprising SEQ ID NO: 60, 61, 62, 63, 64, 65, 67, 69, 70, 71, 73, 75, 76, 78, 80, 81, 82 and 84, and
   ii) the second parent IgG class Fc-region polypeptide has an amino acid sequence selected from the group comprising SEQ ID NO: 60, 61, 62, 63, 64, 66, 68, 69, 70, 72, 74, 75, 76, 77, 79, 81, 83 and 85.

8. The IgG class Fc-region according to any one of embodiments 1 to 7, wherein
   i) the first parent IgG class Fc-region polypeptide is a human IgG1 Fc-region polypeptide and the second parent IgG class Fc-region polypeptide is a human IgG1 Fc-region polypeptide, or
   ii) the first parent IgG class Fc-region polypeptide is a human IgG1 Fc-region polypeptide with the mutations L234A, L235A and the second parent IgG class Fc-region polypeptide is a human IgG1 Fc-region polypeptide with the mutations L234A, L235A, or
   iii) the first parent IgG class Fc-region polypeptide is a human IgG1 Fc-region polypeptide with the mutations L234A, L235A, P329G and the second parent IgG class Fc-region polypeptide is a human IgG1 Fc-region polypeptide with the mutations L234A, L235A, P329G, or
   iv) the first parent IgG class Fc-region polypeptide is a human IgG1 Fc-region polypeptide with the mutations L234A, L235A, S354C, T366W and the second parent IgG class Fc-region polypeptide is a human IgG1 Fc-region polypeptide with the mutations L234A, L235A, Y349C, T366S, L368A, Y407V, or
   v) the first parent IgG class Fc-region polypeptide is a human IgG1 Fc-region polypeptide with the mutations L234A, L235A, P329G, S354C, T366W and the second parent IgG class Fc-region polypeptide is a human IgG1 Fc-region polypeptide with the mutations L234A, L235A, P329G, Y349C, T366S, L368A, Y407V, or
   vi) the first parent IgG class Fc-region polypeptide is a human IgG4 Fc-region polypeptide and the second parent IgG class Fc-region polypeptide is a human IgG4 Fc-region polypeptide, or
   vii) the first parent IgG class Fc-region polypeptide is a human IgG4 Fc-region polypeptide with the mutations S228P, L235E and the second parent IgG class Fc-region polypeptide is a human IgG4 Fc-region polypeptide with the mutations S228P, L235E, or
   viii) the first parent IgG class Fc-region polypeptide is a human IgG4 Fc-region polypeptide with the mutations S228P, L235E, P329G and the second parent IgG class Fc-region polypeptide is a human IgG4 Fc-region polypeptide with the mutations S228P, L235E, P329G, or
   ix) the first parent IgG class Fc-region polypeptide is a human IgG4 Fc-region polypeptide with the mutations S228P, L235E, S354C, T366W and the second parent IgG class Fc-region polypeptide is a human IgG4 Fc-region polypeptide with the mutations S228P, L235E, Y349C, T366S, L368A, Y407V, or
   x) the first parent IgG class Fc-region polypeptide is a human IgG4 Fc-region polypeptide with the mutations S228P, L235E, P329G, S354C, T366W and the second parent IgG class Fc-region polypeptide is a human IgG4 Fc-region polypeptide with the mutations S228P, L235E, P329G, Y349C, T366S, L368A, Y407V.

9. The IgG class Fc-region according to any one of embodiments 1 to 5 and 7, wherein
   i) the first parent IgG class Fc-region polypeptide has the amino acid sequence of SEQ ID NO: 60 and the second parent IgG class Fc-region polypeptide has the amino acid sequence of SEQ ID NO: 60, or
   ii) the first parent IgG class Fc-region polypeptide has the amino acid sequence of SEQ ID NO: 64 and the second parent IgG class Fc-region polypeptide has the amino acid sequence of SEQ ID NO: 64, or
   iii) the first parent IgG class Fc-region polypeptide has the amino acid sequence of SEQ ID NO: 70 and the second parent IgG class Fc-region polypeptide has the amino acid sequence of SEQ ID NO: 70, or
   iv) the first parent IgG class Fc-region polypeptide has the amino acid sequence of SEQ ID NO: 68 and the second parent IgG class Fc-region polypeptide has the amino acid sequence of SEQ ID NO: 67, or
   v) the first parent IgG class Fc-region polypeptide has the amino acid sequence of SEQ ID NO: 74 and the second parent IgG class Fc-region polypeptide has the amino acid sequence of SEQ ID NO: 73, or
   vi) the first parent IgG class Fc-region polypeptide has the amino acid sequence of SEQ ID NO: 63 and the second parent IgG class Fc-region polypeptide has the amino acid sequence of SEQ ID NO: 63, or
   vii) the first parent IgG class Fc-region polypeptide has the amino acid sequence of SEQ ID NO: 75 and the second parent IgG class Fc-region polypeptide has the amino acid sequence of SEQ ID NO: 75, or
   viii) the first parent IgG class Fc-region polypeptide has the amino acid sequence of SEQ ID NO: 76 and the second parent IgG class Fc-region polypeptide has the amino acid sequence of SEQ ID NO: 76, or
   ix) the first parent IgG class Fc-region polypeptide has the amino acid sequence of SEQ ID NO: 79 and the second parent IgG class Fc-region polypeptide has the amino acid sequence of SEQ ID NO: 80, or
   x) the first parent IgG class Fc-region polypeptide has the amino acid sequence of SEQ ID NO: 85 and the second parent IgG class Fc-region polypeptide has the amino acid sequence of SEQ ID NO: 84.

10. The IgG class Fc-region according to any one of embodiments 1 to 9, wherein the first variant Fc-region polypeptide differs from the second variant Fc-region polypeptide in one to eight amino acid residues other than those amino acid residues in which the first parent IgG class Fc-region polypeptide differs from the second parent IgG class Fc-region polypeptide.

11. The IgG class Fc-region according to any one of embodiments 1 to 10, wherein the first variant Fc-region polypeptide differs from the second variant Fc-region polypeptide in one to six amino acid residues other than those amino acid residues in which the first parent IgG class Fc-region polypeptide differs from the second parent IgG class Fc-region polypeptide.

12. The IgG class Fc-region according to any one of embodiments 1 to 11, wherein the first variant Fc-region polypeptide differs from the second variant Fc-region polypeptide in one to three amino acid residues other than those amino acid residues in which the first parent IgG class Fc-region polypeptide differs from the second parent IgG class Fc-region polypeptide.

13. The IgG class Fc-region according to any one of embodiments 1 to 12, wherein the first variant Fc-region polypeptide differs from the second variant Fc-region polypeptide in one or more of the amino acid residues at position 228, 234, 235, 236, 237, 238, 239, 248, 250, 251, 252, 253, 254, 255, 256, 257, 265, 266, 267, 268, 269, 270, 272, 285, 288, 290, 291, 297, 298, 299, 307, 308, 309, 310, 311, 314, 327, 328, 329, 330, 331, 332, 385, 387, 428, 433, 434, 435 and 436 (numbering according to Kabat EU index numbering system).

14. The IgG class Fc-region according to any one of embodiments 1 to 2 and 4 to 13, wherein the first variant Fc-region polypeptide differs from the second variant Fc-region polypeptide in one or more of the amino acid residues at position 228, 234, 235, 236, 237, 238, 239, 253, 254, 265, 266, 267, 268, 269, 270, 288, 297, 298, 299, 307, 311, 327, 328, 329, 330, 331, 332, 434 and 435 (numbering according to Kabat EU index numbering system).

15. The IgG class Fc-region according to any one of embodiments 1 to 2 and 4 to 14, wherein the first variant Fc-region polypeptide differs from the second variant Fc-region polypeptide in one or more of the amino acid residues at position 233, 236, 265, 297, 329 and 331.

16. The IgG class Fc-region according to embodiment 15, wherein the first variant Fc-region polypeptide differs from the second variant Fc-region polypeptide by one or more of the amino acid alterations E233P, AG236, D265A, N297A, N297D, P329A, and P331S.

17. The IgG class Fc-region according to any one of embodiments 1 to 3 and 5 to 13, wherein the first variant Fc-region polypeptide differs from the second variant Fc-region polypeptide in one or more of the amino acid residues at position 248, 250, 251, 252, 253, 254, 255, 256, 257, 272, 285, 288, 290, 291, 308, 309, 310, 311, 314, 385, 386, 387, 428, 432, 433, 434, 435 and 436.

18. The IgG class Fc-region according to any one of embodiments 1 to 3 and 5 to 17, wherein the first variant Fc-region polypeptide differs from the second variant Fc-region polypeptide in one or more of the amino acid residues at position 251, 253, 310, 314, 432, 433, 435 and 436.

19. The IgG class Fc-region according to any one of embodiments 1 to 3 and 5 to 18, wherein the first Fc-region polypeptide differs by one or two of the mutations selected from i) the group I253A, H310A and H435A, or ii) the group H310A, H433A and Y436A, or iii) the group L251D, L314D and L432D, or iv) the group L251S, L314S and L432S (numbering according to Kabat EU index numbering system) from the second Fc-region polypeptide and the second Fc-region polypeptide differs by one or two of the mutations selected from the group comprising the mutations L251D, L251S, I253A, H310A, L314D, L314S, L432D, L432S, H433A, H435A and Y436A (numbering according to Kabat EU index numbering system) from the first Fc-region polypeptide so that all of the mutations in the first and the second Fc-region polypeptide when taken together result in that the mutations i) I253A, H310A and H435A, or ii) H310A, H433A and Y436A, or iii) L251D, L314D and L432D, or iv) L251S, L314S and L432S are comprised in the Fc-region.

20. The IgG class Fc-region according to any one of embodiments 1 to 3 and 5 to 18, wherein the first Fc-region polypeptide differs by one or two of the mutations selected from i) the group I253A, H310A and H435A, or ii) the group H310A, H433A and Y436A (numbering according to Kabat EU index numbering system) from the second Fc-region polypeptide and the second Fc-region polypeptide differs by one or two of the mutations selected from the group comprising the mutations I253A, H310A, H433A, H435A and Y436A (numbering according to Kabat EU index numbering system) from the first Fc-region polypeptide so that all of the mutations in the first and the second Fc-region polypeptide when taken together result in that the mutations i) I253A, H310A and H435A, or ii) H310A, H433A and Y436A are comprised in the Fc-region.

21. The IgG class Fc-region according to any one of embodiments 1 to 3 and 5 to 18, comprising the mutations I253A/H310A/H435A or H310A/H433A/Y436A or L251D/L314D/L432D or L251S/L314S/L432S or combinations thereof in the Fc-region (numbering according to Kabat EU index numbering system), whereby i) all mutations are in the first or the second Fc-region polypeptide, or ii) one or two mutations are in the first Fc-region polypeptide and one or two mutations are in the second Fc-region polypeptide so that all of the mutations in the first and the second Fc-region polypeptide when taken together result in that the mutations i) I253A, H310A and H435A, or ii) H310A, H433A and Y436A, or iii) L251D, L314D and L432D, or iv) L251S, L314S and L432S are comprised in the Fc-region.

22. The IgG class Fc-region according to any one of embodiments 1 to 3 and 5 to 18, comprising the mutations I253A/H310A/H435A or H310A/H433A/Y436A or a combination thereof in the Fc-region (numbering according to Kabat EU index numbering system), whereby i) all mutations are in the first or the second Fc-region polypeptide, or ii) one or two mutations are in the first Fc-region polypeptide and one or two mutations are in the second Fc-region polypeptide so that all of the mutations in the first and the second Fc-region polypeptide when taken together result in that the mutations i) I253A, H310A and H435A, or ii) H310A, H433A and Y436A are comprised in the Fc-region.

23. The IgG class Fc-region according to any one of embodiments 1 to 3 and 5 to 22, wherein the IgG class Fc-region has a reduced binding to Staphylococcus protein A than an IgG class Fc-region comprising the first parent IgG class Fc-region polypeptide of a) and the second parent IgG class Fc-region polypeptide of a).

24. The IgG class Fc-region according to any one of embodiments 1 to 3 and 5 to 17, comprising the mutations M252Y/S254T/T256E in the Fc-region (numbering according to Kabat EU index numbering system), whereby i) all mutations are in the first or the second Fc-region polypeptide, or ii) one or two mutations are in the first Fc-region polypeptide and one or two mutations are in the second Fc-region polypeptide so that all of the mutations in the first and the second Fc-region polypeptide when taken together result in that the mutations M252Y/S254T/T256E are comprised in the IgG class Fc-region.

25. An antibody comprising the IgG class Fc-region according to any one of embodiments 1 to 24.

26. The antibody according to embodiment 25, wherein the antibody is a monoclonal antibody.

27. The antibody according to any one of embodiments 25 to 26, wherein the antibody is a human, humanized, or chimeric antibody.

28. The antibody according to any one of embodiments 25 to 27, wherein the antibody is a bispecific antibody.

29. The antibody according to any one of embodiments 25 to 28, wherein the antibody is a bivalent antibody.

30. The antibody according to any one of embodiments 25 to 29, wherein the antibody is a bispecific, bivalent antibody with abolished FcRn binding comprising a first antigen-binding site that specifically binds to human VEGF and a second antigen-binding site that specifically binds to human ANG-2.

31. A bispecific, bivalent antibody with abolished FcRn binding comprising a first antigen-binding site that specifically binds to human VEGF and a second antigen-binding site that specifically binds to human ANG-2,
wherein
α) the first antigen-binding site specifically binding to VEGF comprises in the heavy chain variable domain a CDR3H region of SEQ ID NO: 14, a CDR2H region of SEQ ID NO: 15, and a CDR1H region of SEQ ID NO: 16, and in the light chain variable domain a CDR3L region of SEQ ID NO: 17, a CDR2L region of SEQ ID NO: 18, and a CDR1L region of SEQ ID NO: 19, and
β) the second antigen-binding site specifically binding to ANG-2 comprises in the heavy chain variable domain a CDR3H region of SEQ ID NO: 22, a CDR2H region of, SEQ ID NO: 23, and a CDR1H region of SEQ ID NO: 24, and in the light chain variable domain a CDR3L region of SEQ ID NO: 25, a CDR2L region of SEQ ID NO: 26, and a CDR1L region of SEQ ID NO: 27,
and
γ) the bispecific antibody comprises an IgG class Fc-region according to any one of embodiments 1 to 24.

32. The bispecific antibody according to embodiment 31, wherein
α) the first antigen-binding site specifically binding to VEGF comprises as heavy chain variable domain VH an amino acid sequence of SEQ ID NO: 20 and as light chain variable domain VL an amino acid sequence of SEQ ID NO: 21, and
β) the second antigen-binding site specifically binding to ANG-2 comprises as heavy chain variable domain VH an amino acid sequence of SEQ ID NO: 28 and as light chain variable domain VL an amino acid sequence of SEQ ID NO: 29, and
γ) the bispecific antibody comprises an IgG class Fc-region according to any one of embodiments 1 to 24.

33. A bispecific, bivalent antibody with abolished FcRn binding comprising a heavy chain and the light chain of a first full length antibody that specifically binds to VEGF and a modified heavy chain and modified light chain of a second full length antibody that specifically binds to ANG-2, in which the constant domains CL and CH1 are replaced by each other, comprising
α) as heavy chain of the first full length antibody the amino acid sequence of SEQ ID NO: 38 and as light chain of the first full length antibody the amino acid sequence of SEQ ID NO: 40, and
β) as modified heavy chain of the second full length antibody the amino acid sequence of SEQ ID NO: 39 and as modified light chain of the second full length antibody the amino acid sequence of SEQ ID NO: 41.

34. A bispecific, bivalent antibody with abolished FcRn binding comprising a heavy chain and the light chain of a first full length antibody that specifically binds to VEGF and a modified heavy chain and modified light chain of a second full length antibody that specifically binds to ANG-2, in which the constant domains CL and CH1 are replaced by each other, comprising
α) as heavy chain of the first full length antibody the amino acid sequence of SEQ ID NO: 34 and as light chain of the first full length antibody the amino acid sequence of SEQ ID NO: 36, and
β) as modified heavy chain of the second full length antibody the amino acid sequence of SEQ ID NO: 35 and as modified light chain of the second full length antibody the amino acid sequence of SEQ ID NO: 37.

35. A bispecific, bivalent antibody with abolished FcRn binding comprising a heavy chain and the light chain of a first full length antibody that specifically binds to VEGF and a modified heavy chain and modified light chain of a second full length antibody that specifically binds to ANG-2, in which the constant domains CL and CH1 are replaced by each other, comprising
α) as heavy chain of the first full length antibody the amino acid sequence of SEQ ID NO: 42 and as light chain of the first full length antibody the amino acid sequence of SEQ ID NO: 44, and
β) as modified heavy chain of the second full length antibody the amino acid sequence of SEQ ID NO: 43 and as modified light chain of the second full length antibody the amino acid sequence of SEQ ID NO: 45.

36. A bispecific, bivalent antibody with abolished FcRn binding comprising a heavy chain and the light chain of a first full length antibody that specifically binds to VEGF and a modified heavy chain and modified light chain of a second full length antibody that specifically binds to ANG-2, in which the constant domains CL and CH1 are replaced by each other, comprising
α) as heavy chain of the first full length antibody the amino acid sequence of SEQ ID NO: 90 and as light chain of the first full length antibody the amino acid sequence of SEQ ID NO: 40, and
β) as modified heavy chain of the second full length antibody the amino acid sequence of SEQ ID NO: 91 and as modified light chain of the second full length antibody the amino acid sequence of SEQ ID NO: 41.

37. A bispecific, bivalent antibody with abolished FcRn binding comprising a heavy chain and the light chain of a first full length antibody that specifically binds to VEGF and a modified heavy chain and modified light chain of a second full length antibody that specifically binds to ANG-2, in which the constant domains CL and CH1 are replaced by each other, comprising
α) as heavy chain of the first full length antibody the amino acid sequence of SEQ ID NO: 88 and as light chain of the first full length antibody the amino acid sequence of SEQ ID NO: 36, and
β) as modified heavy chain of the second full length antibody the amino acid sequence of SEQ ID NO: 89 and as modified light chain of the second full length antibody the amino acid sequence of SEQ ID NO: 37.

38. A bispecific, bivalent antibody with abolished FcRn binding comprising a heavy chain and the light chain of a first full length antibody that specifically binds to VEGF and a modified heavy chain and modified light chain of a second full length antibody that specifically binds to ANG-2, in which the constant domains CL and CH1 are replaced by each other, comprising
α) as heavy chain of the first full length antibody the amino acid sequence of SEQ ID NO: 92 and as light chain of the first full length antibody the amino acid sequence of SEQ ID NO: 44, and
β) as modified heavy chain of the second full length antibody the amino acid sequence of SEQ ID NO: 93 and as modified light chain of the second full length antibody the amino acid sequence of SEQ ID NO: 45.

39. A bispecific antibody with abolished FcRn binding comprising the heavy chain and the light chain of a first full length antibody that specifically binds to VEGF, and the heavy chain and the light chain of a second full length antibody that specifically binds to ANG-2, wherein the N-terminus of the heavy chain is connected to the C-terminus of the light chain via a peptidic linker, comprising
α) as heavy chain of the first full length antibody the amino acid sequence of SEQ ID NO: 46 and as light chain of the first full length antibody the amino acid sequence of SEQ ID NO: 48, and β) as heavy chain of the second full length antibody connected to the light chain of the second full length antibody via a peptidic linker the amino acid sequence of SEQ ID NO: 47.

40. A bispecific antibody with abolished FcRn binding comprising the heavy chain and the light chain of a first full length antibody that specifically binds to VEGF, and the heavy chain and the light chain of a second full length antibody that specifically binds to ANG-2, wherein the N-terminus of the heavy chain is connected to the C-terminus of the light chain via a peptidic linker, comprising α) as heavy chain of the first full length antibody the amino acid sequence of SEQ ID NO: 49 and as light chain of the first full length antibody the amino acid sequence of SEQ ID NO: 51, and β) as heavy chain of the second full length antibody connected to the light chain of the second full length antibody via a peptidic linker the amino acid sequence of SEQ ID NO: 50.

41. A bispecific antibody with abolished FcRn binding comprising the heavy chain and the light chain of a first full length antibody that specifically binds to VEGF, and the heavy chain and the light chain of a second full length antibody that specifically binds to ANG-2, wherein the N-terminus of the heavy chain is connected to the C-terminus of the light chain via a peptidic linker, comprising α) as heavy chain of the first full length antibody the amino acid sequence of SEQ ID NO: 94 and as light chain of the first full length antibody the amino acid sequence of SEQ ID NO: 48, and β) as heavy chain of the second full length antibody connected to the light chain of the second full length antibody via a peptidic linker the amino acid sequence of SEQ ID NO: 95.

42. A bispecific antibody with abolished FcRn binding comprising the heavy chain and the light chain of a first full length antibody that specifically binds to VEGF, and the heavy chain and the light chain of a second full length antibody that specifically binds to ANG-2, wherein the N-terminus of the heavy chain is connected to the C-terminus of the light chain via a peptidic linker, comprising α) as heavy chain of the first full length antibody the amino acid sequence of SEQ ID NO: 96 and as light chain of the first full length antibody the amino acid sequence of SEQ ID NO: 51, and β) as heavy chain of the second full length antibody connected to the light chain of the second full length antibody via a peptidic linker the amino acid sequence of SEQ ID NO: 97.

43. The bispecific antibody according to any one of embodiments 39 to 42, wherein the antibody heavy chain variable domain (VH) and the antibody light chain variable domain (VL) of the heavy and light chain of the second full length antibody are disulfide stabilized by introduction of a disulfide bond between the heavy chain variable domain position 44 and the light chain variable domain position 100 (numbering according to Kabat).

44. The bispecific antibody according to any one of embodiments 33 to 43, wherein the bispecific antibody comprises the mutations S354C, T366W in one of the two CH3 domains and the mutations Y349C, T366S, L368A, Y407V in the other of the two CH3 domains, or wherein the bispecific antibody comprises the mutations Y349C, T366W in one of the two CH3 domains and the mutations S354C, T366S, L368A, Y407V in the other of the two CH3 domains.

45. The bispecific antibody according to any one of embodiments 33 to 43, wherein the bispecific antibody comprises the mutations S354C, T366W in one of the two CH3 domains and the mutations Y349C, T366S, L368A, Y407V in the other of the two CH3 domains and the mutations R409D, K370E in the CH3 domain in addition to the mutations Y349C, T366S, L368A, Y407V and the mutations D399K, E357K in the CH3 domain in addition to the mutations S354C, T366W, or wherein the bispecific antibody comprises the mutations Y349C, T366W in one of the two CH3 domains and the mutations S354C, T366S, L368A, Y407V in the other of the two CH3 domains and the mutations R409D, K370E in the CH3 domain in addition to the mutations S354C, T366S, L368A, Y407V and the mutations D399K, E357K in the CH3 domain in addition to the mutations Y349C, T366W.

46. The bispecific antibody according to any one of embodiments 25 to 45, wherein the antibody has one or more of the following properties:
shows a lower serum concentration compared to a corresponding bispecific antibody without the mutations described under iii) (96 hours after intravitreal application in mice, which are mouse FcRn deficient, but hemizygous transgenic for human FcRn), and/or
shows a similar (factor 0.8 to 1.2) concentration in whole right eye lysates compared to a corresponding bispecific antibody without the mutations described under iii) (in mice, which are mouse FcRn deficient, but hemizygous transgenic for human FcRn, 96 hours after intravitreal application in the right eye), and/or
shows no binding to the human neonatal Fc receptor, and/or
shows no binding to Staphylococcal protein A, and/or
shows binding to Staphylococcal protein A.

47. An Fc-region fusion polypeptide comprising the IgG class Fc-region according to any one of embodiments 1 to 24.

48. A pharmaceutical formulation comprising the antibody according to any one of embodiments 25 to 46 or the Fc-region fusion polypeptide according to embodiment 47.

49. The pharmaceutical formulation according to embodiment 48, wherein the pharmaceutical formulation is for use in the treatment of ocular vascular diseases.

50. The antibody according to any one of embodiments 25 to 46 or the Fc-region fusion polypeptide according to embodiment 47 for use as a medicament.

51. The use according to embodiment 50, wherein the use is for the treatment of ocular vascular diseases.

52. The use of the antibody according to any one of embodiments 25 to 46 or the Fc-region fusion polypeptide according to embodiment 47 in the manufacture of a medicament.

53. The use according to embodiment 52, wherein the use is for the manufacture of a medicament for the treatment of ocular vascular disease.

54. The antibody according to any one of embodiments 25 to 46 or the Fc-region fusion polypeptide according to embodiment 47 for use in the treatment of ocular vascular disease.

55. A method of treatment of patient suffering from ocular vascular diseases by administering the antibody according to any one of embodiments 25 to 46 or the Fc-region fusion polypeptide according to embodiment 47 to a patient in the need of such treatment.

IV. EXAMPLES

The following are examples of methods and formulations as reported herein. It is understood that various other embodiments may be practiced, given the general description provided above.

Although the foregoing invention has been described in some detail by way of illustration and example for purposes of clarity of understanding, the descriptions and examples should not be construed as limiting the scope as reported herein. The disclosures of all patent and scientific literature cited herein are expressly incorporated in their entirety by reference.

Methods

Electrospray Ionization Mass Spectrometry (ESI-MS)

Protein aliquots (50 µg) were deglycosylated by adding 0.5 µL N-Glycanase plus (Roche) and sodium phosphate buffer (0.1 M, pH 7.1) to obtain a final sample volume of 115 µL. The mixture was incubated at 37° C. for 18 h. Afterwards for reduction and denaturing 60 µL 0.5 M TCEP (Pierce) in 4 M guanidine*HCl (Pierce) and 50 µL 8 M guanidine*HCl were added. The mixture was incubated at 37° C. for 30 min. Samples were desalted by size exclusion chromatography (Sepharose G-25, isocratic, 40% acetonitrile with 2% formic acid). ESI mass spectra (+ve) were recorded on a QTOF instrument (maXis, Bruker) equipped with a nano ESI source (TriVersa NanoMate, Advion). MS parameter settings were as follows: Transfer: Funnel RF, 400 Vpp; ISCID Energy, 0 eV; Multipole RF, 400 Vpp; Quadrupole: Ion Energy, 4.0 eV; Low Mass, 600 m/z; Source: Dry Gas, 8 L/min; Dry Gas Temperature, 160° C.; Collision Cell: Collision Energy, 10 eV; Collision RF: 2000 Vpp; Ion Cooler: Ion Cooler RF, 300 Vpp; Transfer Time: 120 µs; Pre Puls Storage, 10 µs; scan range m/z 600 to 2000. For data evaluation in-house developed software (MassAnalyzer) was used.

FcRn Surface Plasmon Resonance (SPR) Analysis

The binding properties of wild-type antibody and the mutants to FcRn were analyzed by surface plasmon resonance (SPR) technology using a BIAcore T100 instrument (BIAcore AB, Uppsala, Sweden). This system is well established for the study of molecular interactions. It allows a continuous real-time monitoring of ligand/analyte bindings and, thus, the determination of kinetic parameters in various assay settings. SPR-technology is based on the measurement of the refractive index close to the surface of a gold coated biosensor chip. Changes in the refractive index indicate mass changes on the surface caused by the interaction of immobilized ligand with analyte injected in solution. If molecules bind to an immobilized ligand on the surface the mass increases, in case of dissociation the mass decreases. In the current assay, the FcRn receptor was immobilized onto a BIAcore CM5-biosensor chip (GE Healthcare Bioscience, Uppsala, Sweden) via amine coupling to a level of 400 Response units (RU). The assay was carried out at room temperature with PBS, 0.05% Tween-20™ pH 6.0 (GE Healthcare Bioscience) as running and dilution buffer. 200 nM of antibody samples were injected at a flow rate of 50 µL/min at room temperature. Association time was 180 seconds, dissociation phase took 360 seconds. Regeneration of the chip surface was reached by a short injection of HBS-P, pH 8.0. Evaluation of SPR-data was performed by comparison of the biological response signal height at 180 seconds after injection and at 300 seconds after injection. The corresponding parameters are the RU max level (180 seconds after injection) and late stability (300 seconds after end of injection).

Protein a Surface Plasmon Resonance (SPR) Analysis

The assay is based on surface plasmon resonance spectroscopy. Protein A is immobilized onto the surface of a SPR biosensor. By injecting the sample into the flow cells of the SPR spectrometer it forms a complex with the immobilized protein A resulting in an increasing mass on the sensor chip surface, and therefore to a higher response (as 1 RU is defined as 1 µg/mm$^2$). Afterwards the sensor chip is regenerated by dissolving the sample-protein A-complex. The gained responses are then evaluated for the signal high in response units (RU) and the dissociation behavior.

Around 3,500 response units (RU) of protein A (20 µg/mL) were coupled onto a CM5 chip (GE Healthcare) at pH 4.0 by using the amine coupling kit of GE Healthcare.

The sample and system buffer was HBS-P+ (0.01 M HEPES, 0.15 M NaCl, 0.005% Surfactant P20 Sterile-filtered, pH 7.4). Flow cell temperature was set to 25° C. and sample compartment temperature to 12° C. The system was primed with running buffer. Then, a 5 nM solutions of the sample constructs were injected for 120 seconds with a flow rate of 30 µL/min, followed by a 300 seconds dissociation phase. Then the sensor chip surface was regenerated by two 30 seconds long injections of Glycine-HCl pH 1.5 at a flow rate of 30 µL/min. Each sample was measured as a triplicate.

Bispecific Antibodies and their Respective Sequences

| Description | Sequences |
| --- | --- |
| <VEGF-ANG-2> CrossMAb IgG1 with IHH-AAA mutations | SEQ ID NO: 34, SEQ ID NO: 35, SEQ ID NO: 36, SEQ ID NO: 37 |
| <VEGF-ANG-2> CrossMAb IgG1 wild type (without IHH-AAA mutations) | SEQ ID NO: 52, SEQ ID NO: 53, SEQ ID NO: 54, SEQ ID NO: 55 |
| <VEGF-ANG-2> CrossMAb IgG1 with IHH-AAA mutations and P329G LALA mutations | SEQ ID NO: 38, SEQ ID NO: 39, SEQ ID NO: 40, SEQ ID NO: 41 |
| <VEGF-ANG-2> CrossMAb IgG1 with P329G LALA mutations only (without IHH-AAA mutations) | SEQ ID NO: 56, SEQ ID NO: 57, SEQ ID NO: 58, SEQ ID NO: 59 |
| <VEGF-ANG-2> CrossMAb IgG4 with IHH-AAA mutations and with SPLE mutations | SEQ ID NO: 42, SEQ ID NO: 43, SEQ ID NO: 44, SEQ ID NO: 45 |
| <VEGF-ANG-2> OAscFab IgG1 with IHH-AAA mutations | SEQ ID NO: 46, SEQ ID NO: 47, SEQ ID NO: 48 |
| <VEGF-ANG-2> OAscFab IgG4 with IHH-AAA mutations and with SPLE mutations | SEQ ID NO: 49, SEQ ID NO: 50, SEQ ID NO: 51 |
| anti-VEGF/ANG2 CrossMab IgG1 with HHY-AAA mutations | SEQ ID NO: 88, SEQ ID NO: 89, SEQ ID NO: 36, SEQ ID NO: 37 |
| anti-VEGF/ANG2 CrossMab IgG1 with HHY-AAA mutations and P329G LALA mutations | SEQ ID NO: 90, SEQ ID NO: 91, SEQ ID NO: 40, SEQ ID NO: 41 |
| anti-VEGF/ANG2 CrossMab IgG4 with HHY-AAA mutations and with SPLE mutations | SEQ ID NO: 92, SEQ ID NO: 93, SEQ ID NO: 44, SEQ ID NO: 45 |
| <VEGF-ANG-2> OAscFab IgG1 with HHY-AAA mutations | SEQ ID NO: 94, SEQ ID NO: 95, SEQ ID NO: 48 |
| <VEGF-ANG-2> OAscFab IgG4 with HHY-AAA mutations and with SPLE mutations | SEQ ID NO: 96, SEQ ID NO: 97, SEQ ID NO: 51 |

The term "with (the) mutation IHH-AAA" as used herein refers to the combination of the mutations I253A (Ile253Ala), H310A (His310Ala), and H435A (His435Ala) in a constant heavy chain region of IgG1 or IgG4 subclass (numbering according to EU Index of Kabat), the term "with (the) mutation HHY-AAA" as used herein refers the combination of the mutations H310A (His310Ala), H433A (His433Ala) and Y436A (Tyr436Ala) in a constant heavy chain region of IgG1 or IgG4 subclass (numbering according to EU Index of Kabat), the term "with (the) mutation P329G LALA" as used herein refers to the combination of the mutations L234A (Leu234Ala), L235A (Leu235Ala) and P329G (Pro329Gly) in a constant heavy chain region of IgG1 subclass (numbering according to EU Index of Kabat), and the term "with (the) mutation SPLE" as used herein refers to the combination of the mutations S228P (Ser228Pro) and L235E (Leu235Glu) a constant heavy chain region of IgG4 subclass (numbering according to EU Index of Kabat).

General

General information regarding the nucleotide sequences of human immunoglobulin light and heavy chains is given in: Kabat, E. A., et al., Sequences of Proteins of Immunological Interest, 5th ed., Public Health Service, National Institutes of Health, Bethesda, MD (1991). Amino acid residues of antibody chains are numbered and referred to according to EU numbering (Edelman, G. M., et al., Proc. Natl. Acad. Sci. USA 63 (1969) 78-85; Kabat, E. A., et al., Sequences of Proteins of Immunological Interest, 5th ed., Public Health Service, National Institutes of Health, Bethesda, MD (1991)).

Recombinant DNA Techniques

Standard methods were used to manipulate DNA as described in Sambrook, J. et al., Molecular Cloning: A laboratory manual; Cold Spring Harbor Laboratory Press, Cold Spring Harbor, NY (1989). The molecular biological reagents were used according to the manufacturer's instructions.

Gene Synthesis

Desired gene segments were ordered according to given specifications at Geneart (Regensburg, Germany).

DNA Sequence Determination

DNA sequences were determined by double strand sequencing performed at MediGenomix GmbH (Martinsried, Germany) or SequiServe GmbH (Vaterstetten, Germany).

DNA and Protein Sequence Analysis and Sequence Data Management

The GCG's (Genetics Computer Group, Madison, WI) software package version 10.2 and Infomax's Vector NT1 Advance suite version 8.0 was used for sequence creation, mapping, analysis, annotation and illustration.

Expression Vectors

For the expression of the described antibodies expression plasmids for transient expression (e.g. in HEK293-F cells) based either on a cDNA organization with or without a CMV-Intron A promoter or on a genomic organization with a CMV promoter were used.

The transcription unit of the antibody gene was composed of the following elements:

unique restriction site(s) at the 5' end, the immediate early enhancer and promoter from the human cytomegalovirus, in the case of the cDNA organization the Intron A sequence, a 5'-untranslated region of a human immunoglobulin gene, a nucleic acid encoding an immunoglobulin heavy chain signal sequence, a nucleic acid encoding the human antibody chain (wild-type or with domain exchange) either as cDNA or in genomic organization with the immunoglobulin exon-intron organization, a 3' non-translated region with a polyadenylation signal sequence, and unique restriction site(s) at the 3' end.

Beside the antibody expression cassette the plasmids contained:

an origin of replication which allows replication of this plasmid in *E. coli,* a ß-lactamase gene which confers ampicillin resistance in *E. coli,* and the dihydrofolate reductase gene from *Mus musculus* as a selectable marker in eukaryotic cells.

The nucleic acids encoding the antibody chains were generated by PCR and/or gene synthesis and assembled by known recombinant methods and techniques by connection of the according nucleic acid segments e.g. using unique restriction sites in the respective vectors. The subcloned nucleic acid sequences were verified by DNA sequencing. For transient transfections larger quantities of the plasmids were prepared by plasmid preparation from transformed *E. coli* cultures (Nucleobond AX, Macherey-Nagel).

Cell Culture Techniques

Standard cell culture techniques were used as described in Current Protocols in Cell Biology (2000), Bonifacino, J. S., Dasso, M., Harford, J. B., Lippincott-Schwartz, J. and Yamada, K. M. (eds.), John Wiley & Sons, Inc.

The bispecific antibodies were expressed by transient co-transfection of the respective expression plasmids in in HEK293-F cells growing in suspension as described below.

Example 1

Expression and Purification

Transient Transfections in HEK293-F System

The monospecific and bispecific antibodies were generated by transient transfection with the respective plasmids (e.g. encoding the heavy and modified heavy chain, as well as the corresponding light and modified light chain) using the HEK293-F system (Invitrogen) according to the manufacturer's instruction. Briefly, HEK293-F cells (Invitrogen) growing in suspension either in a shake flask or in a stirred fermenter in serum-free FreeStyle™ 293 expression medium (Invitrogen) were transfected with a mix of the respective expression plasmids and 293Fectin™ or fectin (Invitrogen). For 2 L shake flask (Corning) HEK293-F cells were seeded at a density of $1*10^6$ cells/mL in 600 mL and incubated at 120 rpm, 8% $CO_2$. The day after the cells were transfected at a cell density of approx. $1.5*10^6$ cells/mL with approx. 42 mL of a mixture of A) 20 mL Opti-MEM (Invitrogen) with 600 µg total plasmid DNA (1 µg/mL) encoding the heavy or modified heavy chain, respectively and the corresponding light chain in an equimolar ratio and B) 20 ml Opti-MEM with 1.2 mL 293 fectin or fectin (2 µL/mL). According to the glucose consumption glucose solution was added during the course of the fermentation. The supernatant containing the secreted antibody was harvested after 5-10 days and antibodies were either directly purified from the supernatant or the supernatant was frozen and stored.

Purification

Bispecific antibodies were purified from cell culture supernatants by affinity chromatography using MabSelect-Sure-Sepharose™ (for non-IHH-AAA mutants) (GE Healthcare, Sweden) or KappaSelect-Agarose (for IHH-AAA mutants) (GE Healthcare, Sweden), hydrophobic interaction chromatography using butyl-Sepharose (GE Healthcare, Sweden) and Superdex 200 size exclusion (GE Healthcare, Sweden) chromatography.

Briefly, sterile filtered cell culture supernatants were captured on a MabSelectSuRe resin equilibrated (non-IHH-AAA mutations and wild-type antibodies) with PBS buffer (10 mM $Na_2HPO_4$, 1 mM $KH_2PO_4$, 137 mM NaCl and 2.7 mM KCl, pH 7.4), washed with equilibration buffer and eluted with 25 mM sodium citrate at pH 3.0. The IHH-AAA mutants were captured on a KappaSelect resin equilibrated with 25 mM Tris, 50 mM NaCl, pH 7.2, washed with equilibration buffer and eluted with 25 mM sodium citrate pH 2.9. The eluted antibody fractions were pooled and neutralized with 2 M Tris, pH 9.0. The antibody pools were prepared for hydrophobic interaction chromatography by adding 1.6 M ammonium sulfate solution to a final concentration of 0.8 M ammonium sulfate and the pH adjusted to pH 5.0 using acetic acid. After equilibration of the butyl-Sepharose resin with 35 mM sodium acetate, 0.8 M ammonium sulfate, pH 5.0, the antibodies were applied to the resin, washed with equilibration buffer and eluted with a linear gradient to 35 mM sodium acetate pH 5.0. The (monospecific or bispecific) antibody containing fractions were pooled and further purified by size exclusion chromatography using a Superdex 200 26/60 GL (GE Healthcare, Sweden) column equilibrated with 20 mM histidine, 140 mM NaCl, pH 6.0. The (monospecific or bispecific) antibody containing fractions were pooled, concentrated to the required concentration using Vivaspin ultrafiltration devices (Sartorius Stedim Biotech S. A., France) and stored at −80° C.

TABLE

Yields of bispecific <VEGF-ANG-2> antibodies

|  | VEGFang2-0015 (without IHH-AAA mutation) | VEGFang2-0016 (with IHH-AAA mutation) | VEGF/ANG2-0121 (with HHY-AAA mutation) |
|---|---|---|---|
| titer supernatant | 64 µg/ml, (2 L = 128 mg) | n.a. (2 L scale) | 60.8 µg/ml (2 L = 121.60 mg) |
| protein A (MabSelectSure) | 118 mg (~70% monomer) | n.a. | 100.5 mg (pool1 + pool2) |
| Kappa Select | n.a. | 117 mg (~83% monomer) | n.a. |
| butyl Sepharose | 60 mg | 57 mg | 49 mg |
| SEC | 35 mg (>95% monomer) | 38 mg (>95% monomer) | 32.4 mg (>95% monomer) |

Purity and antibody integrity were analyzed after each purification step by CE-SDS using microfluidic Labchip technology (Caliper Life Science, USA). Five µL of protein solution was prepared for CE-SDS analysis using the HT Protein Express Reagent Kit according manufacturer's instructions and analyzed on LabChip GXII system using a HT Protein Express Chip. Data were analyzed using LabChip GX Software.

TABLE

Removal of typical side products by different sequential purification steps determined by CE-SDS.

| Purification Step | VEGFang2-0015 % peak area** analysis: CE-SDS (Caliper Labchip GXII) | | | | | | VEGFang2-0016 | | | | | |
|---|---|---|---|---|---|---|---|---|---|---|---|---|
|  | mAb | 3/4Ab | (HC)2 | 1/2Ab | (LC)2 | LC | mAb | 3/4Ab | (HC)2 | 1/2Ab | (LC)2 | LC |
| Mab Select Sure | 55.7 | 19 | 10.6 | 9.8 | 3.5 | 0.9 |  |  | — |  |  |  |
| Kappa Select |  |  | — |  |  |  | 63 | 13.4 | 3.5 | 6.1 | 5.8 | 7.4 |
| butyl-Sepharose | 81.4 | 1.9 | 2.3 | 8.2 | 3.6 | 1.8 | 76.2 | 1.3 | 0.7 | 8.3 | 7.7 | 5.8 |
| Superdex 200_SEC | 92.4 | 1.8 | 2.6 | 1.4 | 0.5 | 0.5 | 99 | 1.1 | n.d. | n.d. | n.d. | n.d. |

The aggregate content of antibody samples was analyzed by high-performance SEC using a Superdex 200 analytical size-exclusion column (GE Healthcare, Sweden) in 2×PBS (20 mM $Na_2HPO_4$, 2 mM $KH_2PO_4$, 274 mM NaCl and 5.4 mM KCl, pH 7.4) running buffer at 25° C. 25 µg protein were injected on the column at a flow rate of 0.75 mL/min and eluted isocratic over 50 minutes.

Analogously the <VEGF-ANG-2> bispecific antibodies VEGFang2-0012 and VEGFang2-0201 were prepared and purified with the following yields:

|  | VEGFang2-0012 (with IHH-AAA mutation) | VEGFang2-0201 (without IHH-AAA mutation) |
|---|---|---|
| titer //amount scale | — 2.1 L | 36 µg/mL/72 mg 2 L |
| protein A (MabSelectSure) | — | 66 mg (~95% monomer) |

-continued

|  | VEGFang2-0012 (with IHH-AAA mutation) | VEGFang2-0201 (without IHH-AAA mutation) |
|---|---|---|
| KappaSelect | 43 mg (~65% monomer) | — |
| butyl Sepharose | — | 45 mg |
| SEC | 14 mg | 21 mg (>98% monomer) |
| yield hydroxylapatite | 8.5 mg (>98% monomer) |  |
| total yield (recovery) | 8.5 mg (20%) | 21 mg (30%) |

Also the <VEGF-ANG-2> bispecific antibodies <VEGF-ANG-2> CrossMAb IgG4 with IHH-AAA mutation and with SPLE mutation (SEQ ID NO: 42, SEQ ID NO: 43, SEQ ID NO: 44, SEQ ID NO: 45), <VEGF-ANG-2> OAscFab IgG1 with IHH-AAA mutation (SEQ ID NO: 46, SEQ ID NO: 47, SEQ ID NO: 48), <VEGF-ANG-2> OAscFab IgG4 with IHH-AAA mutation and with SPLE mutation (SEQ ID NO: 49, SEQ ID NO: 50, SEQ ID NO: 51), <VEGF-ANG-2> CrossMab IgG1 with HHY-AAA mutation and P329G LALA mutation (SEQ ID NO: 90, SEQ ID NO: 91, SEQ ID NO: 40, SEQ ID NO: 41), <VEGF-ANG-2> CrossMab IgG4 with HHY-AAA mutation and SPLE mutation (SEQ ID NO: 92, SEQ ID NO: 93, SEQ ID NO: 44, SEQ ID NO: 45), <VEGF-ANG-2> OAscFab IgG1 with HHY-AAA mutation (SEQ ID NO: 94, SEQ ID NO: 95, SEQ ID NO: 48), and <VEGF-ANG-2> OAscFab IgG4 with HHY-AAA mutation and SPLE mutation (SEQ ID NO: 96, SEQ ID NO: 97, SEQ ID NO: 51) can be prepared and purified analogously.

Example 2

Analytics & Developability
Small-Scale DLS-Based Viscosity Measurement.

Viscosity measurement was essentially performed as described in (He, F. et al., Analytical Biochemistry 399 (2009) 141-143). Briefly, samples were concentrated to various protein concentrations in 200 mM arginine succinate, pH 5.5, before polystyrene latex beads (300 nm diameter) and Polysorbate 20 (0.02% v/v) were added. Samples were transferred into an optical 384-well plate by centrifugation through a 0.4 µm filter plate and covered with paraffin oil. The apparent diameter of the latex beads was determined by dynamic light scattering at 25° C. The viscosity of the solution can be calculated as $\eta=\eta_0(rh/rh,0)$ ($\eta$: viscosity; $\eta_0$: viscosity of water; rh: apparent hydrodynamic radius of the latex beads; rh,0: hydrodynamic radius of the latex beads in water).

To allow comparison of various samples at the same concentration, viscosity-concentration data were fitted with the Mooney equation (Equation 1) (Mooney, M., Colloid. Sci., 6 (1951) 162-170; Monkos, K., Biochem. Biophys. Acta 304 (1997) 1339) and data interpolated accordingly.

$$\eta = \eta_0 \exp\left(\frac{S\Phi}{1 - K\Phi}\right) \quad \text{Equation 1}$$

(S: hydrodynamic interaction parameter of the protein; K: self-crowding factor; $\Phi$: volume fraction of the dissolved protein)

Figure 2:
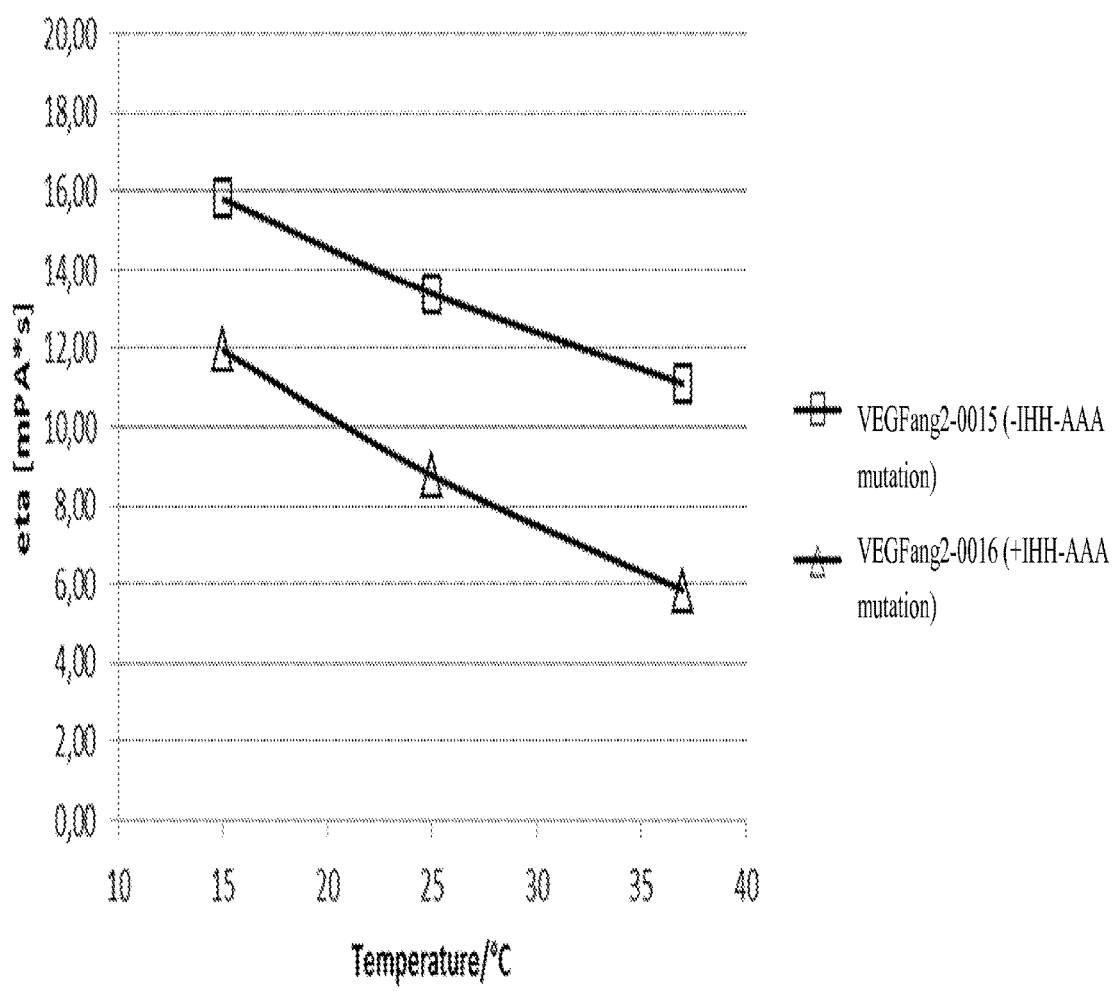
FIG. 2 Small-scale DLS-based viscosity measurement: Extrapolated viscosity at 150 mg/mL in 200 mM arginine/succinate, pH 5.5 (comparison of <VEGF-ANG-2> antibodies VEGFang2-0016 (with IHH-AAA mutation) with a reference antibody VEGFang2-0015 (without such IHH-AAA mutations)).

Results are shown in FIG. 2: VEGFang2-0016 with IHH-AAA mutation in the Fc-region shows a lower viscosity at all measured temperatures compared to VEGFang2-0015 without the IHH-AAA mutation in the Fc-region.

DLS Aggregation Onset Temperature

Figure 3:
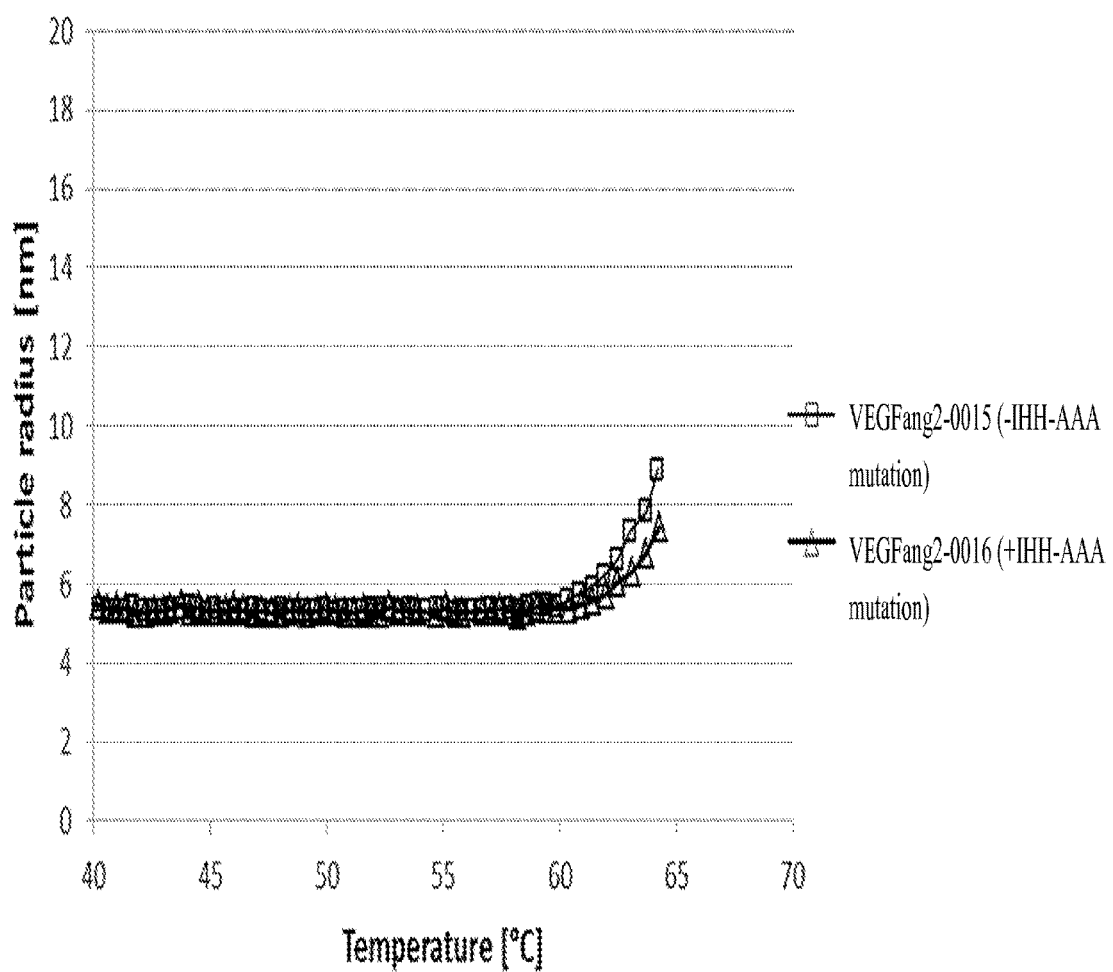
FIG. 3 DLS Aggregation depending on temperature (including DLS aggregation onset temperature) in 20 mM histidine buffer, 140 mM NaCl, pH 6.0 (comparison of <VEGF-ANG-2> antibodies as reported herein VEGFang2-0016 (with IHH-AAA mutation) with a reference antibody VEGFang2-0015 (without such IHH-AAA mutation)).

Samples were prepared at a concentration of 1 mg/mL in 20 mM Histidine/Histidine hydrochloride, 140 mM NaCl, pH 6.0, transferred into an optical 384-well plate by centrifugation through a 0.4 µm filter plate and covered with paraffin oil. The hydrodynamic radius was measured repeatedly by dynamic light scattering while the samples were heated with a rate of 0.05° C./min from 25° C. to 80° C. The aggregation onset temperature is defined as the temperature at which the hydrodynamic radius starts to increase. Results are shown in FIG. 3. In FIG. 3 the aggregation of VEGFang2-0015 without the IHH-AAA mutation versus VEGFang2-0016 with IHH-AAA mutation in the Fc-region is shown. VEGFang2-0016 showed an aggregation onset temperature of 61° C. whereas VEGFang2-0015 without the IHH-AAA mutation showed an onset temperature of 60° C.

DLS Time-Course

Samples were prepared at a concentration of 1 mg/mL in 20 mM Histidine/Histidine hydrochloride, 140 mM NaCl, pH 6.0, transferred into an optical 384-well plate by centrifugation through a 0.4 µm filter plate and covered with paraffin oil. The hydrodynamic radius was measured repeatedly by dynamic light scattering while the samples were kept at a constant temperature of 50° C. for up to 145 hours. In this experiment, aggregation tendencies of the native, unfolded protein at elevated temperature would lead to an increase of the average particle diameter over time. This DLS-based method is very sensitive for aggregates because these contribute over-proportionally to the scattered light intensity. Even after 145 hours at 50° C. (a temperature close to the aggregation-onset temperature, see above), an average particle diameter increase of only less than 0.5 nm was found for both VEGFang2-0015 and VEGFang2-0016.

Seven Day Storage at 40° C. at 100 mg/mL

Samples were concentrated to a final concentration of 100 mg/mL in 200 mM arginine succinate, pH 5.5, sterile filtered and quiescently stored at 40° C. for seven days.

Before and after storage, the content of high and low molecular weight species (HMWs and LMWs, respectively) was determined by size-exclusion chromatography. The difference in HMW and LMW content between the stored sample and a sample measured immediately after preparation is reported as "HMW increase" and "LMW increase", respectively. Results are shown in the Table below and FIG. 4, which show that VEGFang2-0015 (without IHH-AAA mutation) shows a higher reduction of the main peak and a higher HMW increase compared to VEGFang2-0016 (with IHH-AAA mutation). Surprisingly VEGFang2-0016 (with IHH-AAA mutation) showed a lower aggregation tendency compared to VEGFang2-0015 (without IHH-AAA mutation).

TABLE

Delta Main-, HMW and LMW peaks after seven days at 40° C.

|  | delta_area % (40° C.-(-80° C.)) | | |
|---|---|---|---|
|  | main peak | HMW | LMW |
| VEGFang2-0015 (-IHH-AAA mutation) | -3.56 | 2.89 | 0.67 |
| VEGFang2-0016 (+IHH-AAA mutation) | -1.74 | 1.49 | 0.25 |

The functional analysis of <VEGF-ANG-2> bispecific antibodies was assessed by Surface Plasmon Resonance (SPR) using a BIAcore® T100 or T200 instrument (GE Healthcare) at 25° C. The BIAcore® system is well established for the study of molecule interactions. SPR-technology is based on the measurement of the refractive index close to the surface of a gold coated biosensor chip. Changes in the refractive index indicate mass changes on the surface caused by the interaction of immobilized ligand with analyte injected in solution. The mass increases if molecules bind immobilized ligands on the surface, and vice versa, the mass decreases in case of dissociation of the analyte from the immobilized ligand (reflecting complex dissociation). SPR allows a continuous real-time monitoring of ligand/analyte binding and thus the determination of the association rate constant (ka), the dissociation rate constant (kd), and of the equilibrium constant (KD).

Example 3

Figure 5A:
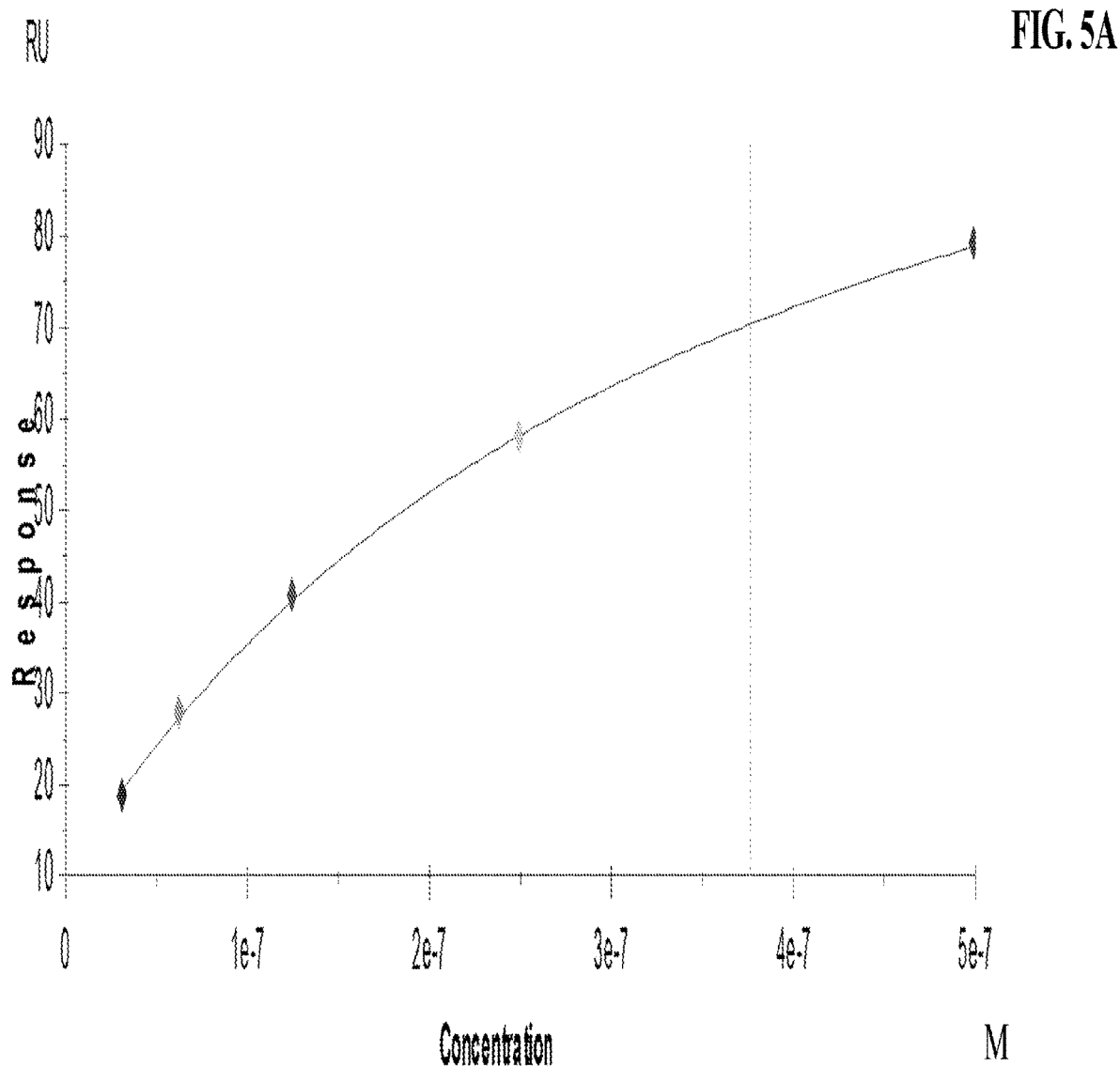
FIGS. 5A and 5B FcRn steady state affinity of A: VEGFang2-0015 (without IHH-AAA mutation) and B: VEGFang2-0016 (with IHH-AAA mutation).
Figure 5B:
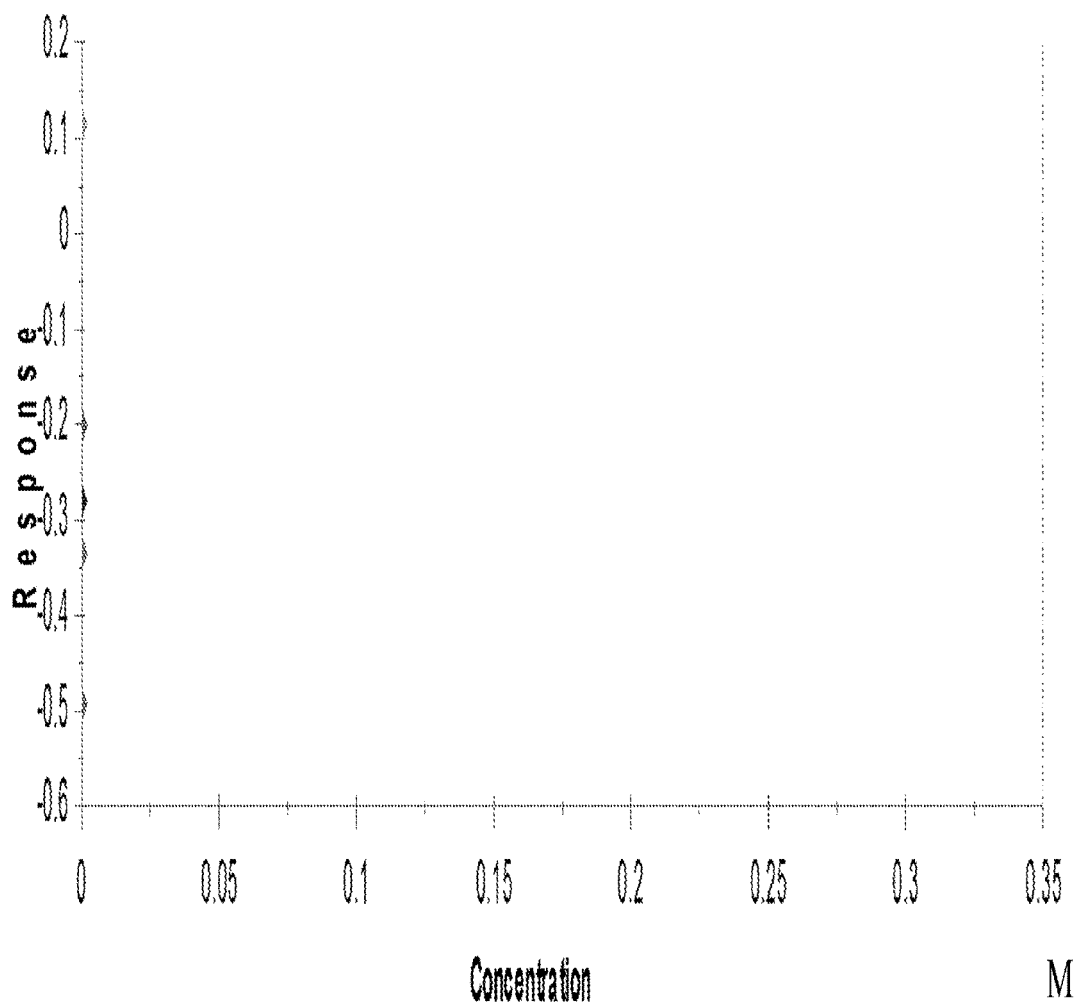
Figure 6:
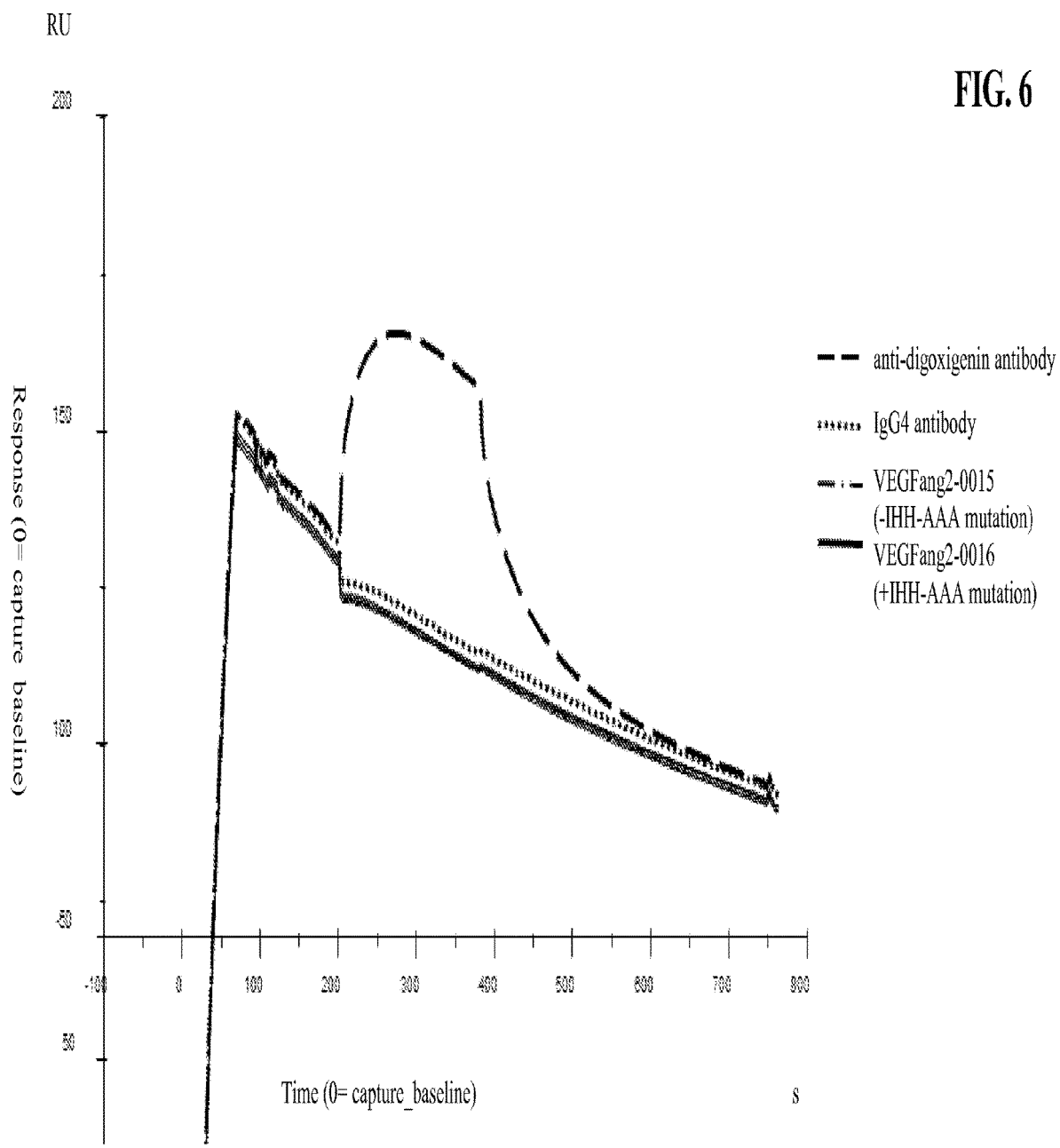
FIG. 6 FcgammaRIIIa interaction measurement of VEGFang2-0015 without IHH-AAA mutation and VEGFang2-0016 with IHH-AAA mutation (both are IgG1 subclass with P329G LALA mutations; as controls an anti-digoxigenin antibody (anti-Dig) of IgG1 subclass and an IgG4 based antibody were used).

Binding to VEGF, ANG-2, FcgammaR and FcRn
VEGF Isoforms Kinetic Affinity Including Assessment of Species-Cross-Reactivity Around 12,000 resonance units (RU) of the capturing system (10 μg/mL goat anti human F(Ab)'$_2$; Order Code: 28958325; GE Healthcare Bio-Sciences AB, Sweden) were coupled on a CM5 chip (GE Healthcare BR-1005-30) at pH 5.0 by using an amine coupling kit supplied by GE Healthcare. The sample and system buffer was PBS-T (10 mM phosphate buffered saline including 0.05% Tween-20™) pH 7.4. The flow cell was set to 25° C.- and the sample block set to 12° C.- and primed with running buffer twice. The bispecific antibody was captured by injecting a 50 nM solution for 30 seconds at a flow of 5 μL/min. Association was measured by injection of human hVEGF121, mouse mVEGF120 or rat rVEGF164 in various concentrations in solution for 300 seconds at a flow of 30 μL/min starting with 300 nM in 1:3 dilutions. The dissociation phase was monitored for up to 1200 seconds and triggered by switching from the sample solution to running buffer. The surface was regenerated by 60 seconds washing with a Glycine pH 2.1 solution at a flow rate of 30 μL/min. Bulk refractive index differences were corrected by subtracting the response obtained from a goat anti human F(Ab')$_2$ surface. Blank injections were also subtracted (=double referencing). For calculation of apparent $K_D$ and other kinetic parameters the Langmuir 1:1 model was used. Results are shown below.
ANG-2 Solution Affinity Including Assessment of Species-Cross-Reactivity Solution affinity measures the affinity of an interaction by determining the concentration of free interaction partners in an equilibrium mixture. The solution affinity assay involves the mixing of an <VEGF-ANG-2> bispecific antibody, kept at a constant concentration, with a ligand (=ANG-2) at varying concentrations. Maximum possible resonance units (e.g. 17,000 resonance units (RU)) of an antibody was immobilized on the CM5 chip (GE Healthcare BR-1005-30) surface at pH 5.0 using an amine coupling kit supplied by GE Healthcare. The sample and system buffer was HBS-P pH 7.4. Flow cell was set to 25° C. and sample block to 12° C. and primed with running buffer twice. To generate a calibration curve increasing concentrations of ANG-2 were injected into a BIAcore flow-cell containing the immobilized <VEGF-ANG-2> bispecific antibody. The amount of bound ANG-2 was determined as resonance units (RU) and plotted against the concentration. Solutions of each ligand (11 concentrations from 0 to 200 nM for the <VEGF-ANG-2> bispecific antibody) were incubated with 10 nM ANG-2 and allowed to reach equilibrium at room temperature. Free ANG-2 concentrations were determined from calibration curve generated before and after measuring the response of solutions with known amounts of ANG-2. A 4-parameter fit was set with XLfit4 (IDBS Software) using Model 201 using free ANG-2 concentration as y-axis and used concentration of antibody for inhibition as x-axis. The affinity was calculated by determining the inflection point of this curve. The surface was regenerated by one time 30 seconds washing with a 0.85% H$_3$PO$_4$ solution at a flow rate of 30 μL/min. Bulk refractive index differences were corrected by subtracting the response obtained from a blank-coupled surface. Results are shown in below.
FcRn Steady State Affinity For FcRn measurement a steady state affinity was used to compare bispecific antibodies against each other. Human FcRn was diluted into coupling buffer (10 μg/mL, Na-Acetate pH 5.0) and immobilized on a C1-Chip (GE Healthcare BR-1005-35) by targeted immobilization procedure using a BIAcore wizard to a final response of 200 RU. Flow cell was set to 25° C. and sample block to 12° C. and primed with running buffer twice. The sample and system buffer was PBS-T (10 mM phosphate buffered saline including 0.05% Tween-20™) pH 6.0. To assess different IgG concentrations for each antibody, a concentration of 62.5 nM, 125 nM 250 nM, and 500 nM was prepared. Flow rate was set to 30 μL/min and the different samples were injected consecutively onto the chip surface choosing 180 seconds association time. The surface was regenerated by injected PBS-T pH 8 for 60 seconds at a flow rate of 30 μL/min. Bulk refractive index differences were corrected by subtracting the response obtained from a blank surface. Buffer injections were also subtracted (=double referencing). For calculation of steady state affinity the method from the BIA-Evaluation software was used. Briefly, the RU values were plotted against the analyzed concentrations, yielding a dose-response curve. Based on a 2-parametric fit, the upper asymptote was calculated, allowing the determination of the half-maximal RU value and hence the affinity. Results are shown in FIG. 5 and the Table below. Analogously the affinity to Cynomolgus, mouse and rabbit FcRn can be determined.
FcgammaRIIIa Measurement For FcgammaRIIIa measurement a direct binding assay was used. Around 3,000 resonance units (RU) of the capturing system (1 μg/mL Penta-His; Qiagen) were coupled on a CM5 chip (GE Healthcare BR-1005-30) at pH 5.0 by using an amine coupling kit supplied by GE Healthcare. The sample and system buffer was HBS-P+ pH 7.4. The flow cell was set to 25° C.- and sample block to 12° C.- and primed with running buffer twice. The FcgammaRIIIa-His-receptor was captured by injecting a 100 nM solution for 60 seconds at a flow of 5 μL/min. Binding was measured by injection of 100 nM of bispecific antibody or monospecific control antibodies (anti-digoxigenin antibody (anti-Dig) for IgG1 subclass and an IgG4 subclass antibody) for 180 seconds at a flow of 30 μL/min. The surface was regenerated by 120 seconds washing with Glycine pH 2.5 solution at a flow rate of 30 μL/min. Because FcgammaRIIIa binding differs from the Langmuir 1:1 model, only binding/no binding was determined with this assay. In a similar manner FcgammaRIa and FcgammaRIIa binding can be determined. Results are shown in FIG. 6, where it follows that by introduction of the mutations P329G LALA no more binding to FcgammaRIIIa could be detected.

Assessment of Independent VEGF- and ANG-2-Binding to the <VEGF-ANG-2> Bispecific Antibodies Around 3,500 resonance units (RU) of the capturing system (10 μg/mL goat anti-human IgG; GE Healthcare Bio-Sciences AB, Sweden) were coupled on a CM4 chip (GE Healthcare BR-1005-34) at pH 5.0 by using an amine coupling kit supplied by GE Healthcare. The sample and system buffer was PBS-T (10 mM phosphate buffered saline including 0.05% Tween-20™) pH 7.4. The temperature of the flow cell was set to 25° C. and of the sample block to 12° C. Before capturing, the flow cell was primed with running buffer twice.

The bispecific antibody was captured by injecting a 10 nM solution for 60 seconds at a flow of 5 μL/min. Independent binding of each ligand to the bispecific antibody was analyzed by determining the active binding capacity for each ligand, either added sequentially or simultaneously (flow of 30 μL/min):

1. Injection of human VEGF with a concentration of 200 nM for 180 seconds (identifies the single binding of the antigen).
2. Injection of human ANG-2 with a concentration of 100 nM for 180 seconds (identifies single binding of the antigen).
3. Injection of human VEGF with a concentration of 200 nM for 180 seconds followed by an additional injection of human ANG-2 with a concentration of 100 nM for 180 seconds (identifies binding of ANG-2 in the presence of VEGF).
4. Injection of human ANG-2 with a concentration of 100 nM for 180 seconds followed by an additional injection of human VEGF with a concentration of 200 nM (identifies binding of VEGF in the presence of ANG-2).
5. Co-injection of human VEGF with a concentration of 200 nM and of human ANG-2 with a concentration of 100 nM for 180 seconds (identifies the binding of VEGF and of ANG-2 at the same time).

The surface was regenerated by 60 seconds washing with a 3 M $MgCl_2$ solution at a flow rate of 30 μL/min. Bulk refractive index differences were corrected by subtracting the response obtained from a goat anti-human IgG surface.

The bispecific antibody was able to bind both antigens mutual independently if the resulting final signal of the approaches 3, 4 & 5 equals or is similar to the sum of the individual final signals of the approaches 1 and 2. Results are shown in the Table below, where both antibodies VEGFang2-0016, VEGFang2-0012 were shown to be able to bind mutual independently to VEGF and ANG-2.

Assessment of Simultaneous VEGF- and ANG-2-Binding to the <VEGF-ANG-2> Bispecific Antibodies First, around 1,600 resonance units (RU) of VEGF (20 μg/mL) were coupled on a CM4 chip (GE Healthcare BR-1005-34) at pH 5.0 by using an amine coupling kit supplied by GE Healthcare. The sample and system buffer was PBS-T (10 mM phosphate buffered saline including 0.05% Tween-20™) pH 7.4. Flow cell was set to 25° C. and sample block to 12° C. and primed with running buffer twice. Second, 50 nM solution of the bispecific antibody was injected for 180 seconds at a flow of 30 μL/min. Third, hANG-2 was injected for 180 seconds at a flow of 30 μL/min. The binding response of hANG-2 depends from the amount of the bispecific antibody bound to VEGF and shows simultaneous binding. The surface was regenerated by 60 seconds washing with a 0.85% $H_3PO_4$ solution at a flow rate of 30 μL/min. Simultaneous binding is shown by an additional specific binding signal of hANG-2 to the previous VEGF bound <VEGF-ANG-2> bispecific antibodies. For both bispecific antibodies VEGFang2-0015 and VEGFang2-0016 simultaneous VEGF- and ANG-2-binding to the <VEGF-ANG-2> bispecific antibodies could be detected (data not shown).

TABLE

Results: Kinetic affinities to VEGF isoforms from different species

|  | VEGFang2-0015-apparent affinity | VEGFang2-0016-apparent affinity | VEGFang2-0012-apparent affinity | VEGFang2-0201-apparent affinity |
| --- | --- | --- | --- | --- |
| human VEGF 121 | ≤1 pM (out of BIAcore specification) | ≤1 pM (out of BIAcore specification) | ≤1 pM (out of BIAcore specification) | ≤1 pM (out of BIAcore specification) |
| mouse VEGF 120 | no binding | no binding | no binding | no binding |
| rat VEGF 164 | 13 nM | 14 nM | 24 nM | 35 nM |

TABLE

Results: Solution affinities to ANG-2

|  | VEGFang2-0015 KD [nM] | VEGFang2-0016 KD [nM] | VEGFang2-0012 KD [nM] | VEGFang2-0201 KD [nM] |
| --- | --- | --- | --- | --- |
| human ANG-2 | 8 | 20 | 20 | tbd |
| Cynomolgus ANG-2 | 5 | 13 | 10 | tbd |
| mouse ANG-2 | 8 | 13 | 8 | tbd |
| rabbit ANG-2 | 4 | 11 | 8 | tbd |

TABLE

Results: Affinity to FcRn of <VEGF-ANG-2> bispecific antibodies

|  | VEGFang2-0015 [affinity] | VEGFang2-0016 [affinity] | VEGFang2-0012 [affinity] | VEGFang2--0201 [affinity] |
| --- | --- | --- | --- | --- |
| human FcRn | 0.8 μM | no binding | no binding | 0.8 μM |
| Cynomolgus FcRn | 0.9 μM | no binding | no binding | 1.0 μM |
| mouse FcRn | 0.2 μM | no binding | no binding | 0.2 μM |

TABLE

Results Binding to FcgammaRI-IIIa

|        | VEGFang2-0015 | VEGFang2-0016 | VEGFang2-0012 | VEGFang2-0201 |
|--------|---------------|---------------|---------------|---------------|
| FcγRIa  | no binding    | no binding    | binding       | binding       |
| FcγRIIa | no binding    | no binding    | no binding    | binding       |
| FcγRIIIa| no binding    | no binding    | no binding    | binding       |

TABLE

Results: Independent binding of VEGF- and ANG-2 to <VEGF-ANG-2> bispecific antibodies

|  | 1) ANG-2 [RUmax] | 2) VEGF [RUmax] | 3) first VEGF then ANG-2 [RUmax] | 4) first ANG-2 then VEGF [RUmax] | 5) Co-injection ANG-2 + VEGF [RUmax] |
|--|---|---|---|---|---|
| VEGFang2-0016 | 174 | 50 | 211 | 211 | 211 |
| VEGFang2-0012 | 143 | 43 | 178 | 177 | 178 |

Example 4

Mass Spectrometry

This section describes the characterization of <VEGF-ANG-2> bispecific antibodies with emphasis on the correct assembly. The expected primary structures were confirmed by electrospray ionization mass spectrometry (ESI-MS) of the deglycosylated, and intact or IdeS-digested (IgG-degrading enzyme of *S. pyogenes*) <VEGF-ANG-2> bispecific antibodies. The IdeS-digestion was performed with 100 µg purified antibody incubated with 2 µg IdeS protease (Fabricator) in 100 mmol/L $NaH_2PO_4/Na_2HPO_4$, pH 7.1 at 37° C. for 5 h. Subsequently, the antibodies were deglycosylated with N-Glycosidase F, Neuraminidase and O-glycosidase (Roche) in 100 mmol/L $NaH_2PO_4/Na_2HPO_4$, pH 7.1 at 37° C. for up to 16 hours at a protein concentration of 1 mg/mL and subsequently desalted via HPLC on a Sephadex G25 column (GE Healthcare). The total mass was determined via ESI-MS on a maXis 4G UHR-QTOF MS system (Bruker Daltonik) equipped with a TriVersa NanoMate source (Advion).

The masses obtained for the IdeS-digested, deglycosylated (Table below), or intact, deglycosylated (Table below) molecules correspond to the predicted masses deduced from the amino acid sequences for the <VEGF-ANG-2> bispecific antibodies consisting of two different light chains $LC_{ANG-2}$ and $LC_{Lucentis}$, and two different heavy chains $HC_{ANG-2}$ and $HC_{Lucentis}$.

TABLE

Masses of the deglycosylated and IdeS-digested bispecific <VEGF/ANG2> antibodies VEGFang2-0201 (without IHH-AAA mutation) and VEGFang2-0012 (with IHH-AAA mutation)

| sample | F(Ab')2 of the <VEGF-ANG-2> bispecific antibody | | Deglycosylated Fc-region of the <VEGF-ANG-2> bispecific antibody | |
|---|---|---|---|---|
|  | predicted average mass [Da] | observed average mass [Da] | predicted average mass [Da] | observed average mass [Da] |
| VEGFang2-0201 | 99360.8 | 99360.7 | 47439.2 | 47430.1 |
| VEGFang2-0012 | 99360.8 | 99361.1 | 47087.7 | 47082.0 |

TABLE

Masses of the deglycosylated <VEGF/ANG2> antibodies VEGFang2-0016 (with IHH-AAA mutation) and VEGFang2-0015 (without IHH-AAA mutation)

| | deglycosylated <VEGF-ANG-2> bispecific antibody | |
|---|---|---|
|  | predicted average mass [Da] | observed average mass [Da] |
| VEGFang2-0016 | 146156.9 | 146161.2 |
| VEGFang2-0015 | 146505.3 | 146509.4 |

Example 5

FcRn Chromatography

Coupling to Streptavidin Sepharose:

One gram streptavidin sepharose (GE Healthcare) was added to the biotinylated and dialyzed receptor and incubated for two hours with shaking. The receptor derivatized sepharose was filled in a 1 mL XK column (GE Healthcare).

Chromatography Using the FcRn Affinity Column:

Conditions:

column dimensions: 50 mm×5 mm bed height: 5 cm loading: 50 µg sample equilibration buffer: 20 mM MES, with 150 mM NaCl, adjusted to pH 5.5 elution buffer: 20 mM Tris/HCl, with 150 mM NaCl, adjusted to pH 8.8 elution: 7.5 CV equilibration buffer, in 30 CV to 100% elution buffer, 10 CV elution buffer Human FcRn Affinity Column Chromatography In the following Table retention times of <VEGF-ANG-2> bispecific antibodies on affinity columns comprising human FcRn are given. Data were obtained using the conditions above.

TABLE

Results: retention times of <VEGF-ANG-2> bispecific antibodies

| antibody | retention time [min] |
|---|---|
| VEGFAng2-0015 (without IHH-AAA mutation) | 78.5 |
| VEGFAng2-0201 (without IHH-AAA mutation) | 78.9 |

TABLE-continued

Results: retention times of <VEGF-ANG-2> bispecific antibodies

| antibody | retention time [min] |
|---|---|
| VEGFAng2-0012 (with IHH-AAA mutation) | 2.7 (Void-peak) |
| VEGFAng2-0016 (with IHH-AAA mutation) | 2.7 (Void-peak) |

Example 6

Pharmacokinetic (PK) Properties of Antibodies with IHH-AAA Mutation
PK Data with FcRn Mice Transgenic for Human FcRn
In Life Phase:

The study included female C57BL/6J mice (background); mouse FcRn deficient, but hemizygous transgenic for human FcRn (huFcRn, line 276-/tg)

Part 1:

All mice were injected once intravitreally into the right eye with 2 µL/animal of the appropriate solution (i.e. 21 µg compound/animal (VEGFAng2-0015 (without IHH-AAA mutation)) or 23.6 µg compound/animal (VEGFAng2-0016 (with IHH-AAA mutation)).

Mice were allocated to 2 groups with 6 animals each. Blood samples were taken from group 1 at 2, 24 and 96 hours and from group 2 at 7, 48 and 168 hours after dosing.

Injection into the vitreous of the right mouse eye was performed by using the NanoFil Microsyringe system for nanoliter injection from World Precision Instruments, Inc., Berlin, Germany. Mice were anesthetized with 2.5% Isoflurane and for visualization of the mouse eye a Leica MZFL 3 microscope with a 40 fold magnification and a ring-light with a Leica KL 2500 LCD lightning was used. Subsequently, 2 µL of the compound were injected using a 35-gauge needle.

Blood was collected via the retrobulbar venous plexus of the contralateral eye from each animal for the determination of the compound levels in serum.

Serum samples of at least 50 µL were obtained from blood after 1 hour at RT by centrifugation (9,300×g) at 4° C. for 3 min. Serum samples were frozen directly after centrifugation and stored frozen at −80° C. until analysis. Treated eyes of the animals of group 1 were isolated 96 hours after treatment and of the animals of group 2 168 hours after treatment. Samples were stored frozen at −80° C. until analysis.

Part 2:

All mice were injected once intravenously via the tail vein with 200 µL/animal of the appropriate solution (i.e. 21 µg compound/animal (VEGFAng2-0015 (without IHH-AAA mutation)) or 23.6 µg compound/animal (VEGFAng2-0016 (with IHH-AAA mutation)).

Mice were allocated to 2 groups with 5 animals each. Blood samples were taken from group 1 at 1, 24 and 96 hours and from group 2 at 7, 48 and 168 hours after dosing. Blood was collected via the retrobulbar venous plexus from each animal for the determination of the compound levels in serum.

Serum samples of at least 50 µL were obtained from blood after 1 hour at RT by centrifugation (9,300×g) at 4° C. for 3 min. Serum samples were frozen directly after centrifugation and stored frozen at −80° C. until analysis.

Preparation of Whole Eye Lysates (Mice)

The eye lysates were gained by physico-chemical disintegration of the whole eye from laboratory animals. For mechanical disruption, each eye was transferred into a 1.5 mL micro vial with conical bottom. After freeze and thawing, the eyes were washed with 1 mL cell washing buffer once (Bio-Rad, Bio-Plex Cell Lysis Kit, Cat. No. 171-304011). In the following step, 500 µL of freshly prepared cell lysis buffer were added and the eyes were grinded using a 1.5 mL tissue grinding pestle (Kimble Chase, 1.5 mL pestle, Art. No. 749521-1500). The mixture was then frozen and thawed five times and grinded again. To separate lysate from remaining tissue the samples were centrifuged for 4 min at 4,500 g. After centrifuging the supernatant was collected and stored at −20° C. until further analysis in the quantification ELISA.

Analysis

The concentrations of the <VEGF-ANG-2> antibodies in mice serum and eye lysates were determined with an enzyme linked immunosorbent assay (ELISA).

For quantification of <VEGF-ANG-2> antibodies in mouse serum samples and eye lysates, a standard solid-phase serial sandwich immunoassay with biotinylated and digoxigenylated monoclonal antibodies used as capture and detection antibodies was performed. To verify the integrity of the bispecificity of the analyte the biotinylated capture antibody recognizes the VEGF-binding site whereas the digoxigenylated detection antibody will bind to the ANG-2 binding site of the analyte. The bound immune complex of capture antibody, analyte and detection antibody on the solid phase of the streptavidin coated micro titer plate (SA-MTP) was then detected with a horseradish-peroxidase coupled to an anti-digoxigenin antibody. After washing unbound material from the SA-MTP and addition of ABTS-substrate, the gained signal was proportional to the amount of analyte bound on the solid phase of the SA-MTP. Quantification was then done by converting the measured signals of the samples into concentrations referring to calibrators analyzed in parallel.

In a first step the SA-MTP was coated with 100 µL/well of biotinylated capture antibody solution (anti-idiotypic antibody mAb<Id<VEGF>>M-2.45.51-IgG-Bi(DDS)) with a concentration of 1 µg/mL for one hour at 500 rpm on a MTP-shaker. Meanwhile calibrators, QC-samples and samples were prepared. Calibrators and QC-samples were diluted to 2% serum matrix; samples were diluted until the signals were within the linear range of the calibrators.

After coating the SA-MTP with capture antibody, the plate was washed three times with washing buffer and 300 µL/well. Subsequently 100 µL/well of the calibrators, QC-samples and samples were pipetted on the SA-MTP and incubated again for one hour at 500 rpm. The analyte was now bound with its anti-VEGF binding site via the capture antibody to the solid phase of the SA-MTP. After incubation and removal of unbound analyte by washing the plate 100 µL/well of the first detection antibody (anti-idiotypic antibody mAb<Id-<ANG-2>>M-2.6.81-IgG-Dig(XOSu)) with a concentration of 250 ng/mL was added to the SA-MTP. Again, the plate was incubated for one hour at 500 rpm on a shaker. After washing, 100 µL/well of the second detection antibody (pAb<Digoxigenin>S-Fab-POD (poly)) at a concentration of 50 mU/mL was added to the wells of the SA-MTP and the plate was incubated again for one hour at 500 rpm. After a final washing step to remove excess of detection antibody, 100 µL/well substrate (ABTS) was added. The antibody-enzyme conjugate catalyzes the color reaction of the ABTS® substrate. The signal was then measured by an ELISA reader at 405 nm wavelength (reference wavelength: 490 nm ([405/490] nm)).

Pharmacokinetic Evaluation

The pharmacokinetic parameters were calculated by non-compartmental analysis, using the pharmacokinetic evaluation program WinNonlin™ (Pharsight), version 5.2.1.

Results:

A) Serum Concentrations

Figure 7A:
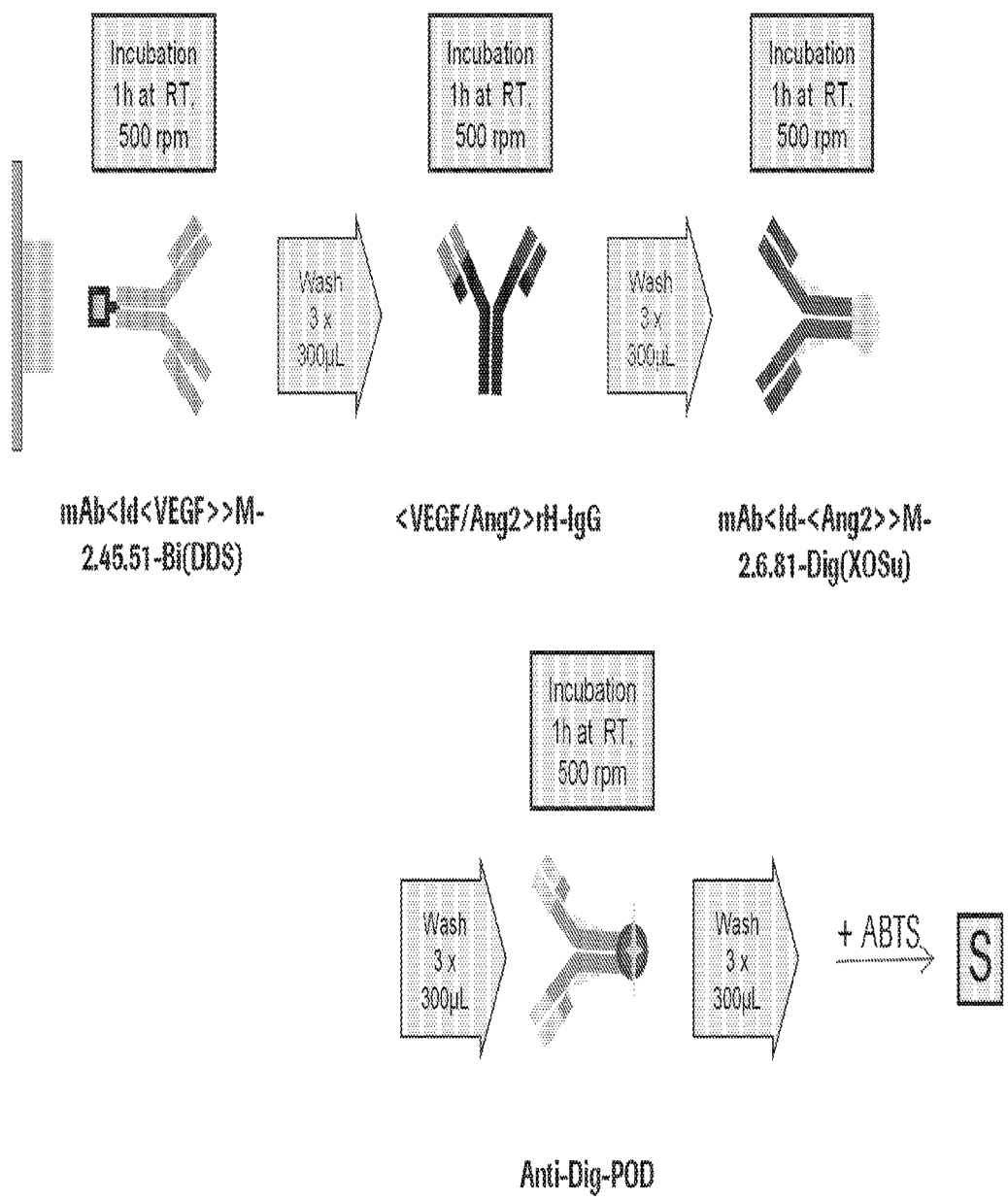
FIG. 7A Schematic pharmacokinetic (PK)-ELISA assay principle for determination of concentrations of <VEGF-ANG-2> bispecific antibodies in serum and whole eye lysates.
Figure 7C:
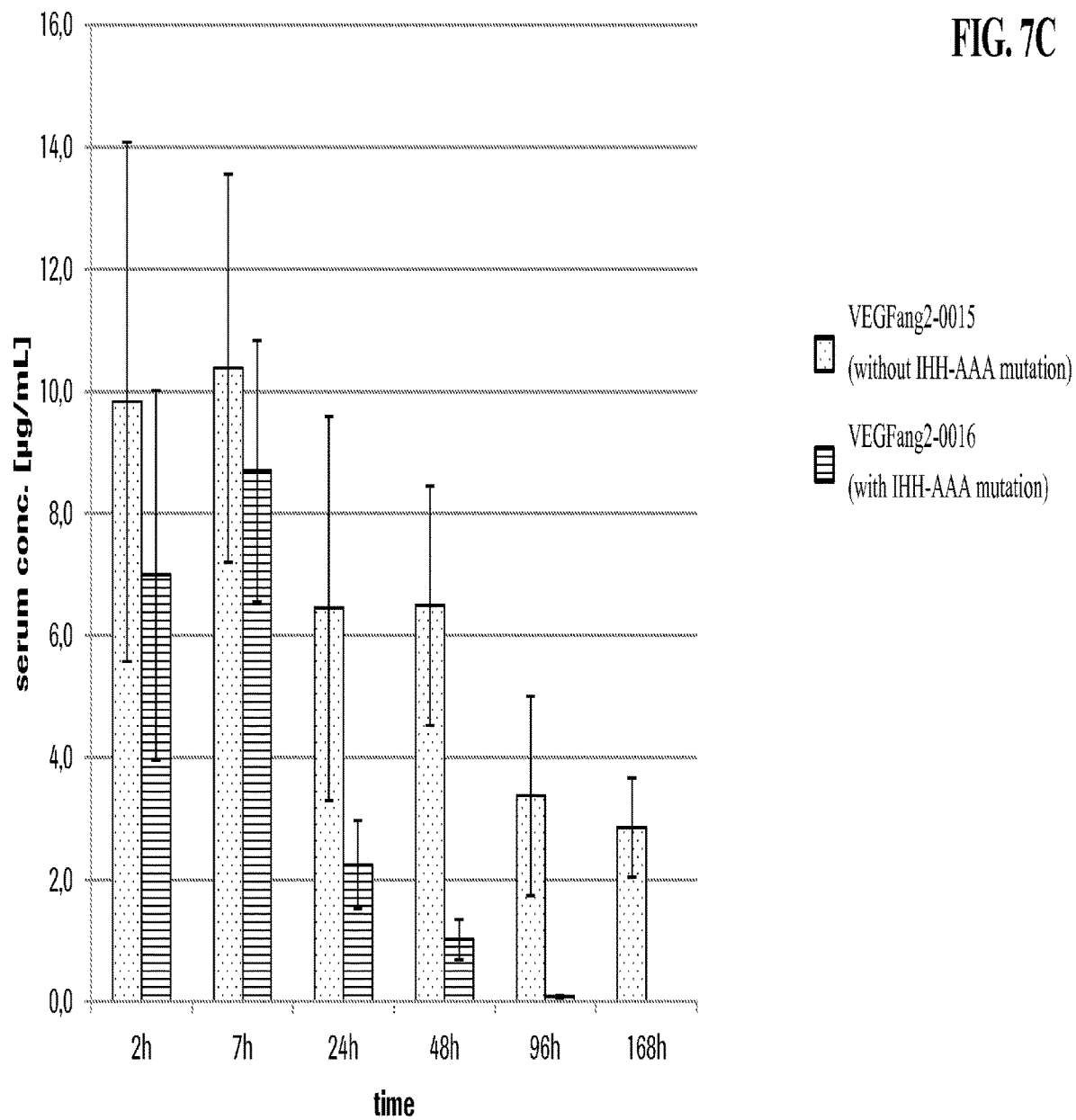
FIG. 7C Serum concentration after intravitreal application: comparison of VEGFang2-0015 without IHH-AAA mutation and VEGFang2-0016 with IHH-AAA mutation.

Results for serum concentrations are shown in the following Tables and FIGS. 7B to 7C.

TABLE

VEGFAng2-0015 (without IHH-AAA mutation): Comparison of serum concentrations after intravitreal and intravenous application

| ID | serum concentration after intravitreal application average conc. [µg/mL] | serum concentration after intravenous application average conc. [µg/mL] |
|---|---|---|
| 1 h |  | 17.7 |
| 2 h | 9.8 |  |
| 7 h | 10.4 | 12.1 |
| 24 h | 6.4 | 8.3 |
| 48 h | 6.5 | 6.9 |
| 96 h | 3.4 | 4.1 |
| 168 h | 2.9 | 2.7 |

TABLE

VEGFAng2-0016 (with IHH-AAA mutation): Comparison of serum concentrations after intravitreal and intravenous application

| ID | serum concentration after intravitreal application average conc. [µg/mL] | serum concentration after intravenous application average conc. [µg/mL] |
|---|---|---|
| 1 h |  | 18.4 |
| 2 h | 7.0 |  |
| 7 h | 8.7 | 10.0 |
| 24 h | 2.2 | 3.3 |
| 48 h | 1.0 | 1.0 |
| 96 h | 0.1 | 0.1 |
| 168 h | 0.0 | 0.0 |

TABLE

VEGFang2-0015 (without IHH-AAA mutation) and VEGFang2-0016 (with IHH-AAA mutation): Comparison of serum concentrations after intravitreal application)

| ID | VEGFang2-0015 (without IHH-AAA mutation) average conc. [µg/mL] | VEGFang2-0016 (with IHH-AAA mutation) average conc. [µg/mL] |
|---|---|---|
| 2 h | 9.8 | 7.0 |
| 7 h | 10.4 | 8.7 |
| 24 h | 6.4 | 2.2 |
| 48 h | 6.5 | 1.0 |
| 96 h | 3.4 | 0.1 |
| 168 h | 2.9 | 0.0 |

TABLE

VEGFang2-0015 (without IHH-AAA mutation) and VEGFang2-0016 (with IHH-AAA mutation): Comparison of serum concentrations after intravenous application

| ID | VEGFang2-0015 (without IHH-AAA mutation) average conc. [µg/mL] | VEGFang2-0016 (with IHH-AAA mutation) average conc. [µg/mL] |
|---|---|---|
| 1 h | 17.7 | 18.4 |
| 7 h | 12.1 | 10.0 |
| 24 h | 8.3 | 3.3 |
| 48 h | 6.9 | 1.0 |
| 96 h | 4.1 | 0.1 |
| 168 h | 2.7 | 0.0 |

Results:

b) Concentrations in Eye-Lysates of Left and Right Eyes

Figure 7D:
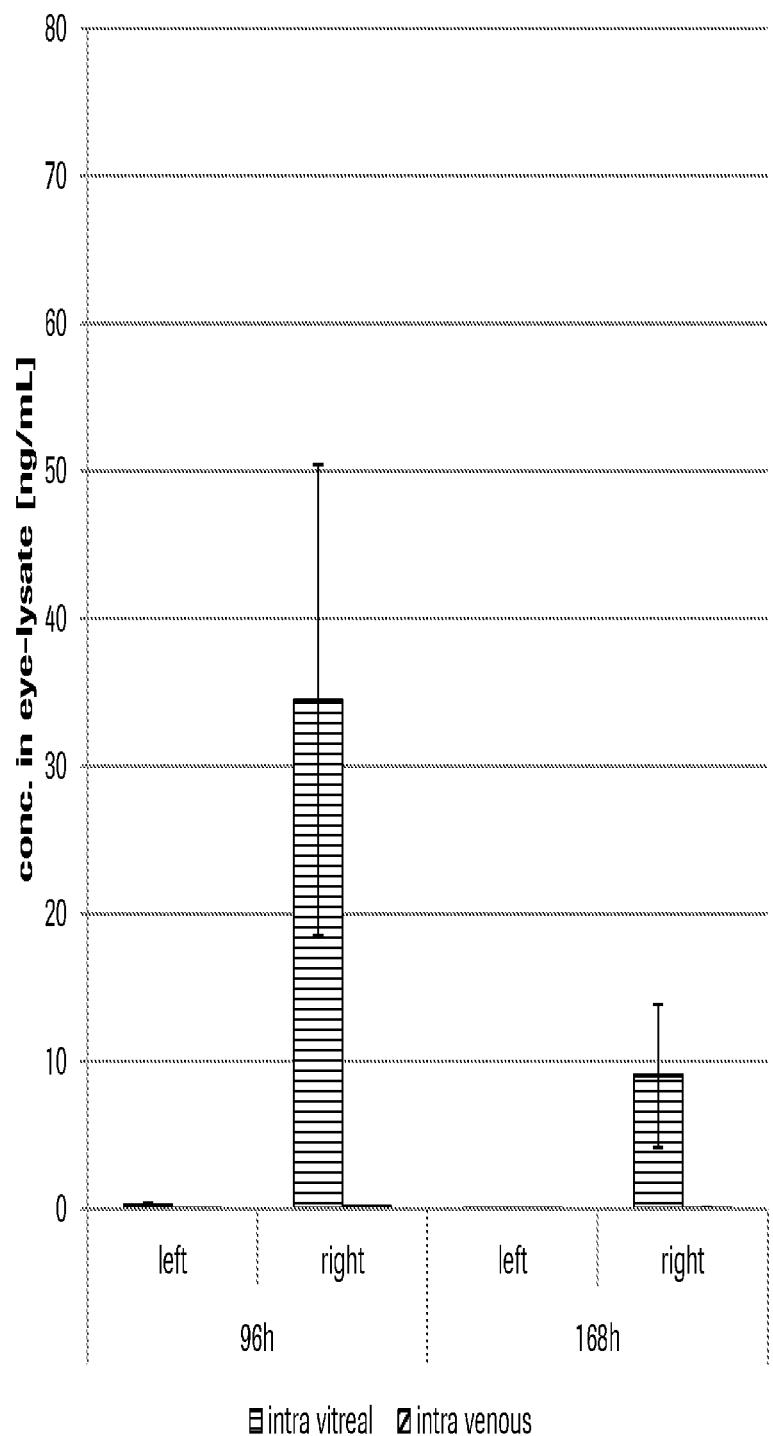
FIG. 7D Eye lysates concentration of VEGFang2-0016 (with IHH-AAA mutation) in right and left eye (after intravitreal application only into the right eye in comparison to intravenous application): significant concentrations could be detected only in the right eye after intravitreal application; after intravenous application no concentration in eye lysates could be detected due to the low serum half-life of VEGFang2-0016 (with IHH-AAA mutation).
Figure 7E:
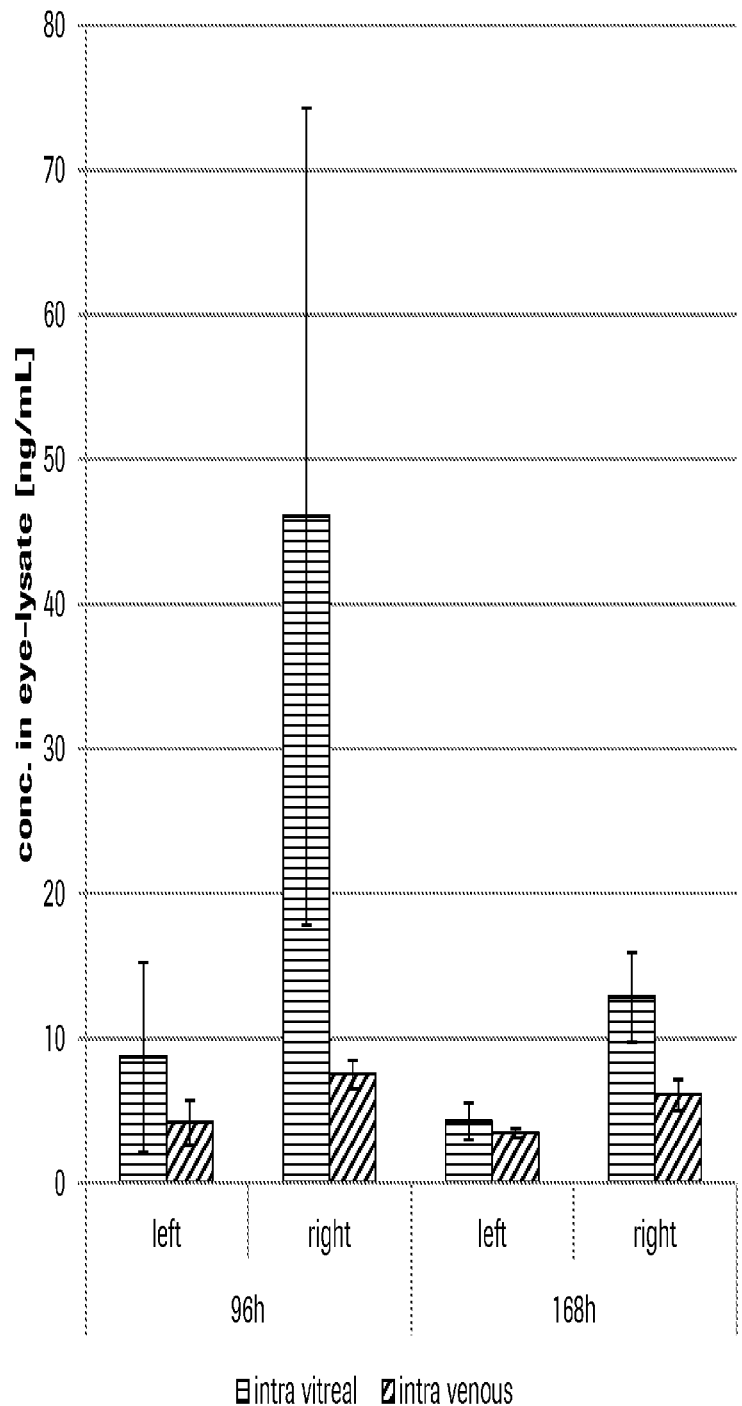
FIG. 7E Eye lysates concentration of VEGFang2-0015 (without IHH-AAA mutation) in right and left eye (after intravitreal application only into the right eye in comparison to intravenous application): in the right eye (and to some extent in the left eye) after intravitreal application concentrations of VEGFang2-0015 could be detected; this indicates the diffusion from the right eye into serum and from there into the left eye, which can be explained by the long half-life of VEGFang2-0015 (without IHH-AAA mutation); after intravenous application also significant concentrations in eye lysates of both eyes could be detected due to diffusion into the eyes of the serum-stable VEGFang2-0015 (without IHH-AAA mutation).
Figure 8A:
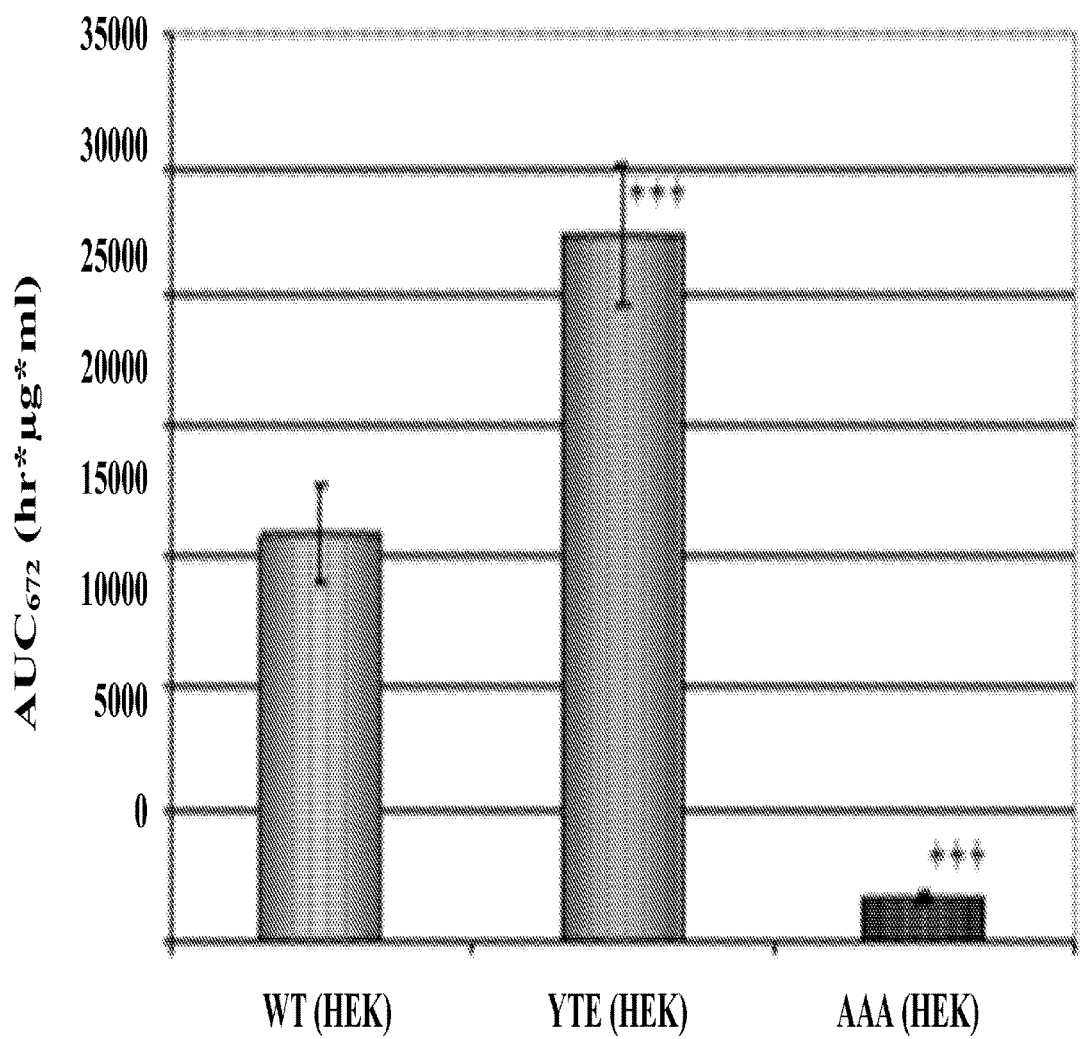
FIGS. 8A, 8B, 8C Antibodies engineered with respect to their ability to bind FcRn display prolonged (YTE mutation) or shortened (IHH-AAA mutation) in vivo half-lives, enhanced (YTE mutation) or reduced binding (IHH-AAA mutation) compared to the reference wild-type (wt) antibody in SPR analysis as well as enhanced or reduced retention time in FcRn column chromatography; 8A) PK data after single i.v. bolus application of 10 mg/kg into huFcRn transgenic male C57BL/6J mice+/−276: AUC data for wild-type IgG as well as YTE and IHH-AAA Fc-modified IgGs; 8B) BIAcore sensorgram; 8C) FcRn affinity column elution; wild-type anti-IGF-1R antibody (reference), YTE-mutant of anti-IGF-1R antibody, IHH-AAA-mutant of anti-IGF-1R antibody.
Figure 8B:
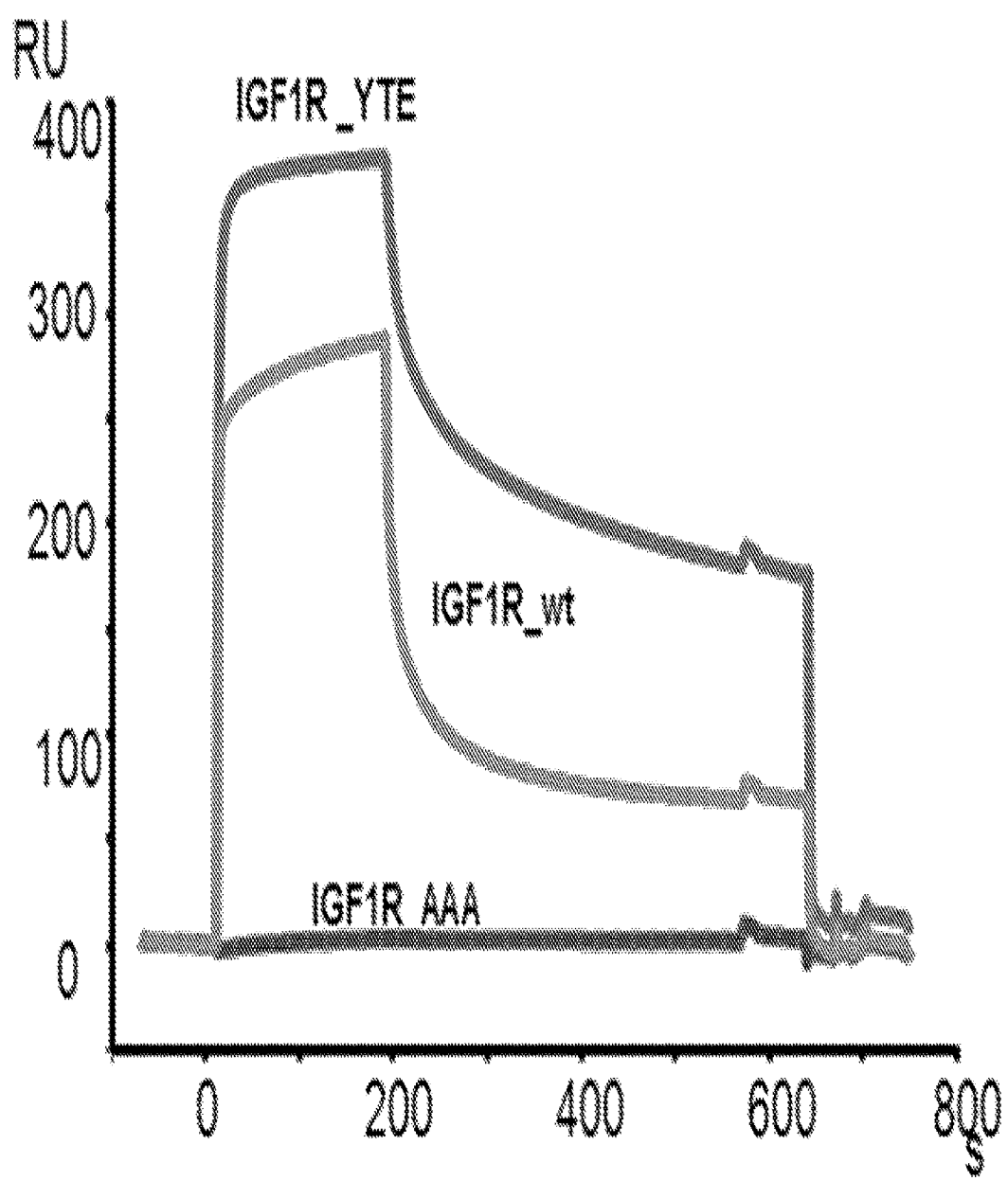
Figure 8C:
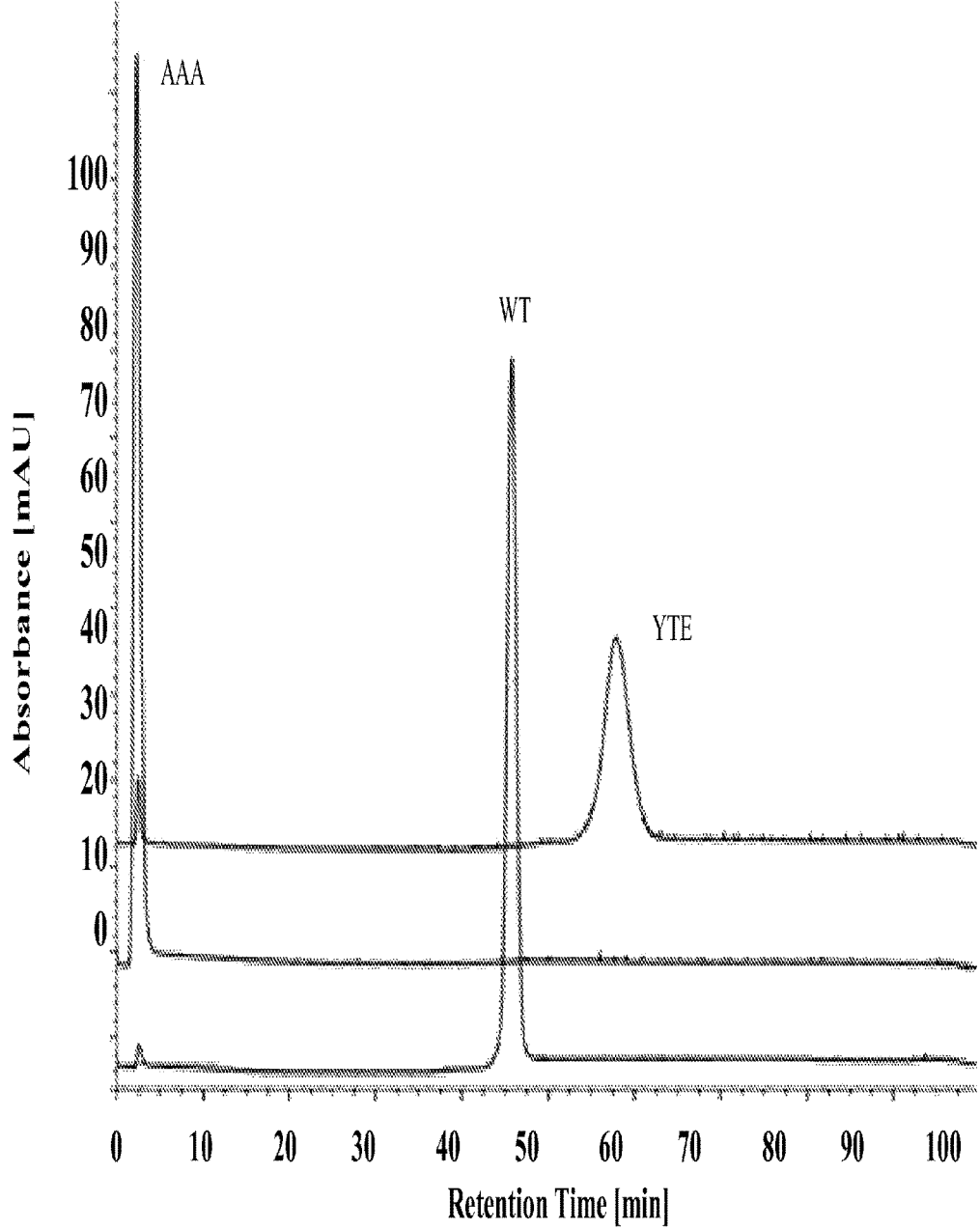
Figure 9:
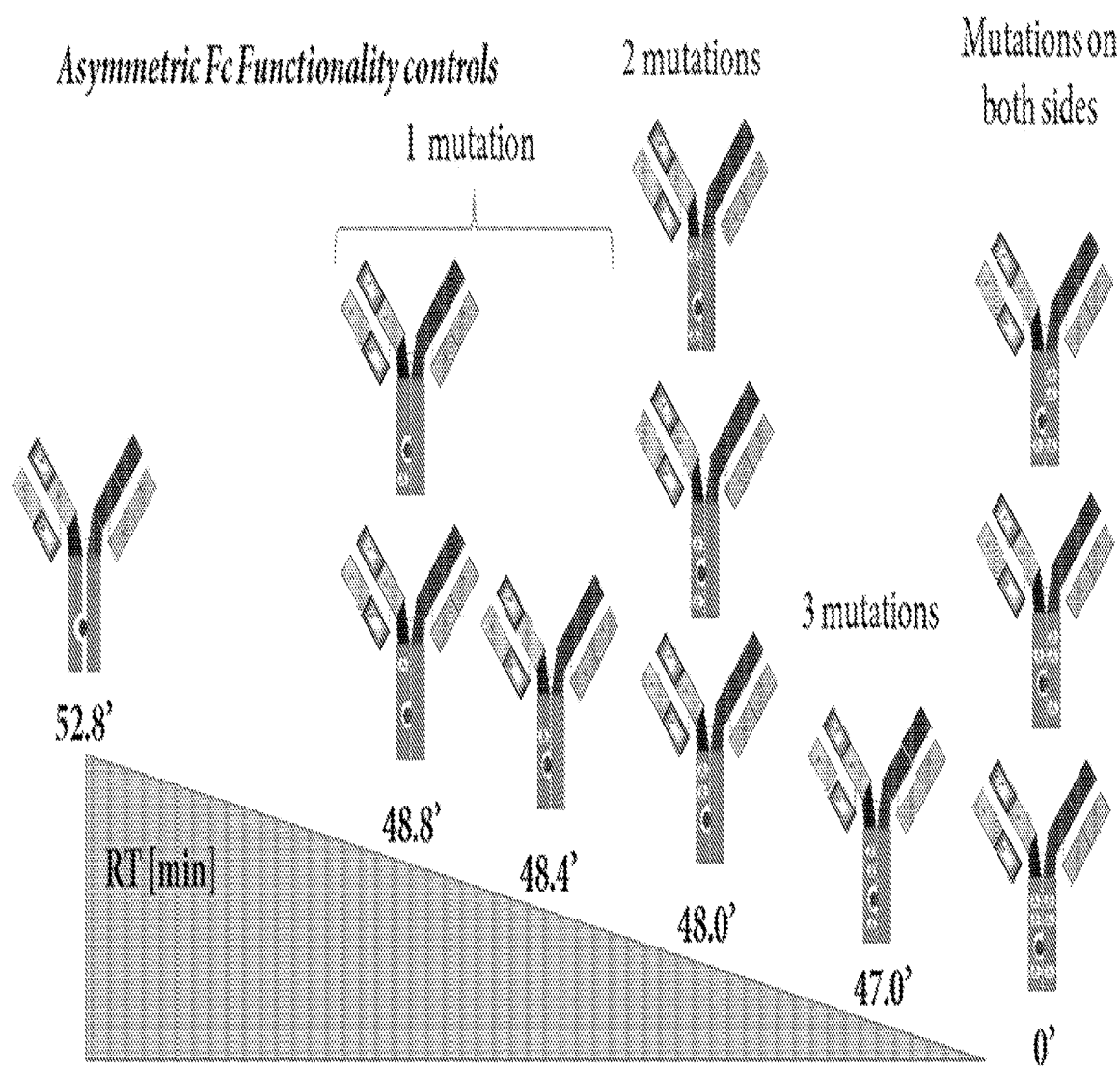
FIG. 9 Change of retention time in an FcRn affinity chromatography depending on the number of mutations introduced into the Fc-Region.
Figure 10:
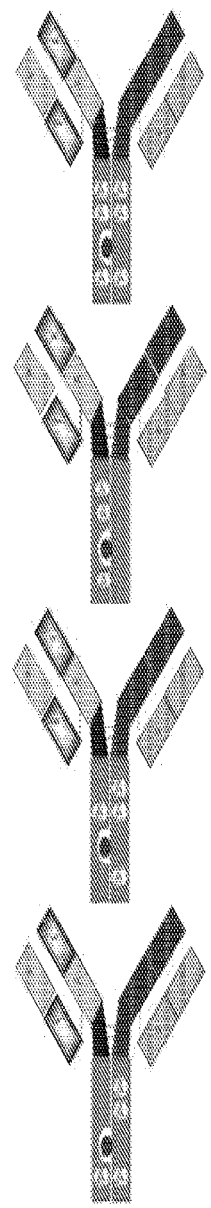
FIG. 10 Change of FcRn-binding depending on asymmetric distribution of mutations introduced into the Fc-region.
Figure 11:
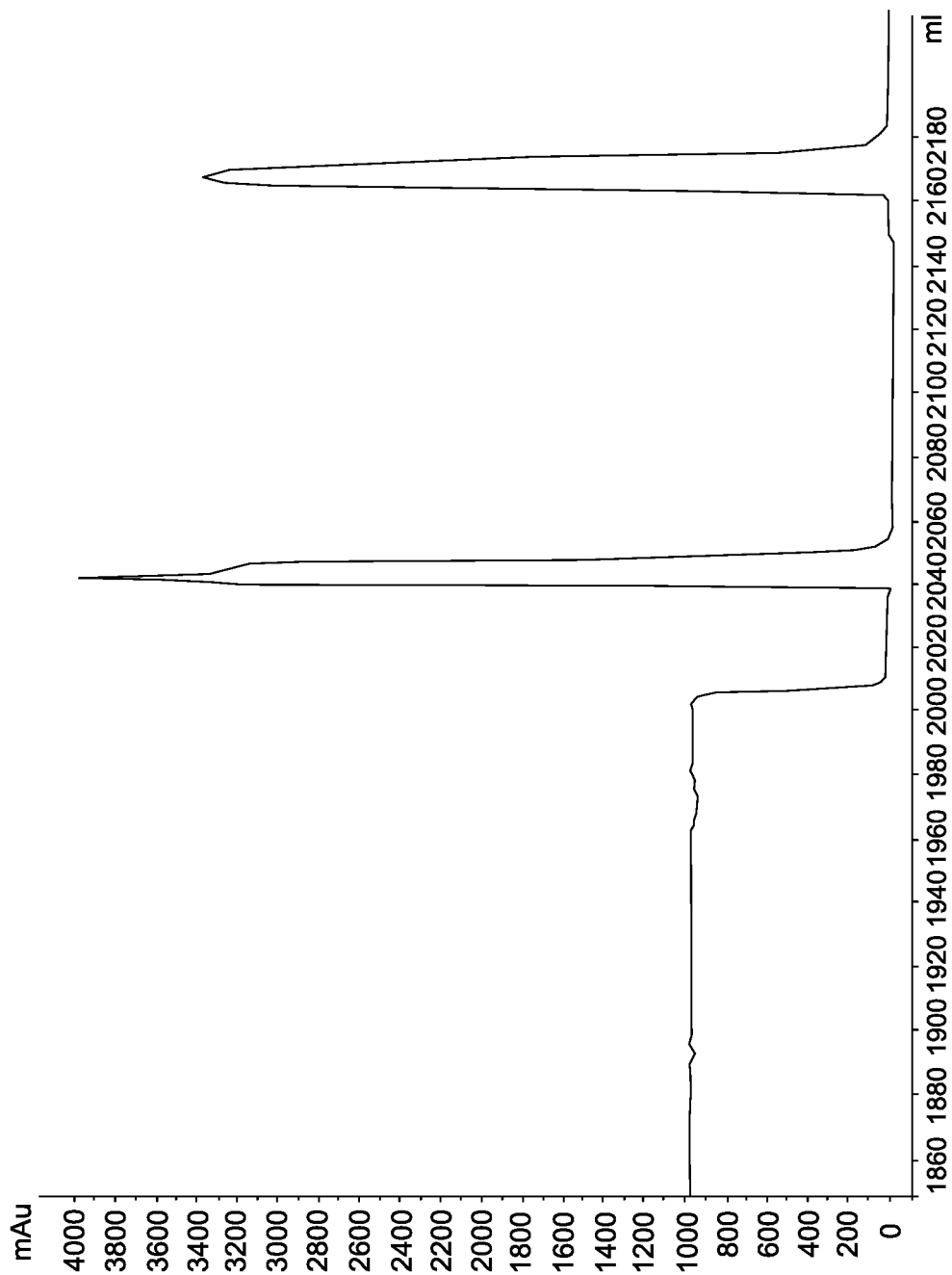
FIG. 11 Elution chromatogram of a bispecific <VEGF-ANG-2> antibody (VEGF/ANG2-0121) with the mutations H310A, H433A and Y436A in both heavy chains from two consecutive protein A affinity chromatography columns.
Figure 12:
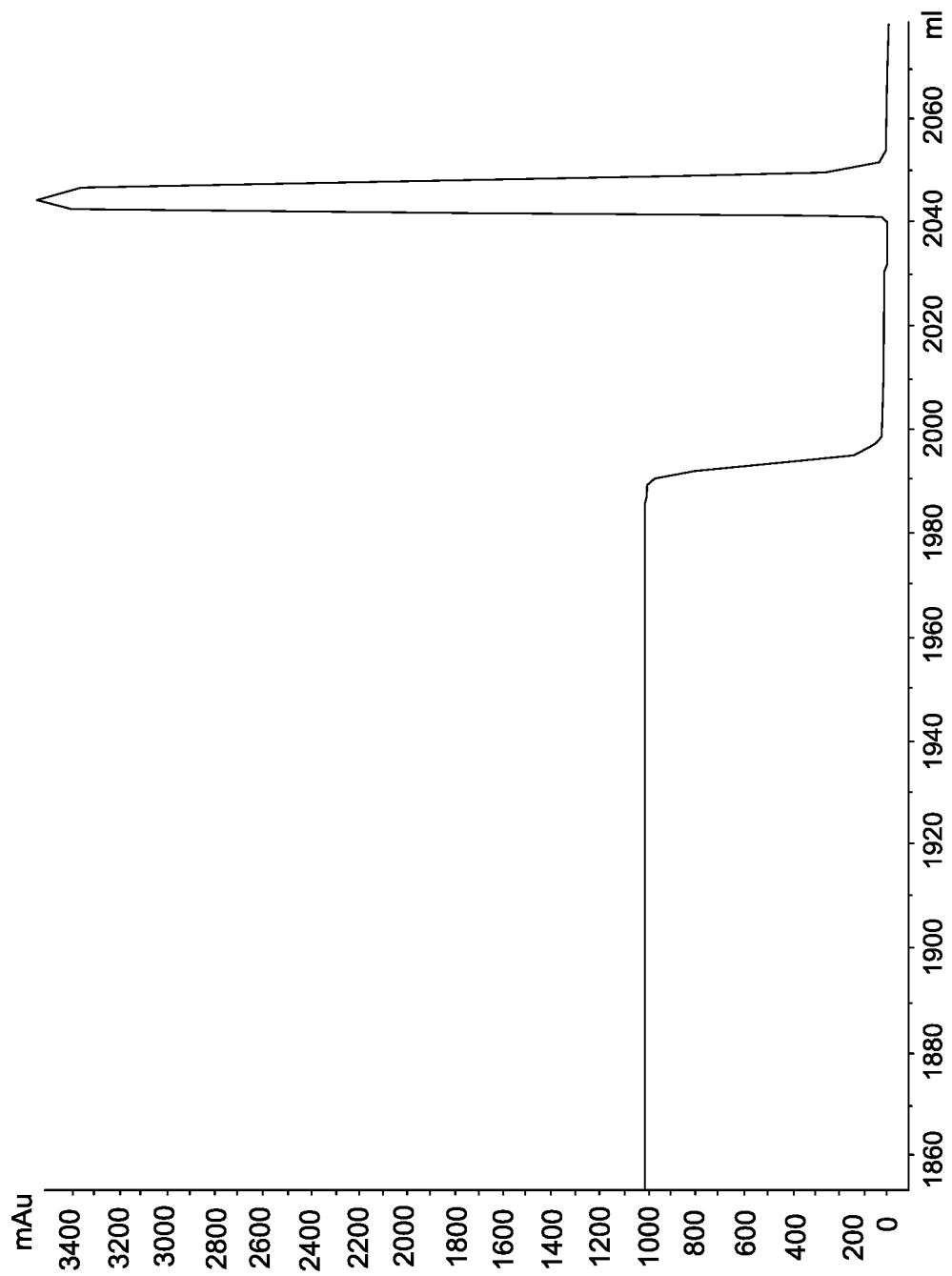
FIG. 12 Elution chromatogram of an anti-IGF-1R antibody (IGF-1R-0045) with the mutations H310A, H433A and Y436A in both heavy chains from a protein A affinity chromatography column.
Figure 13:
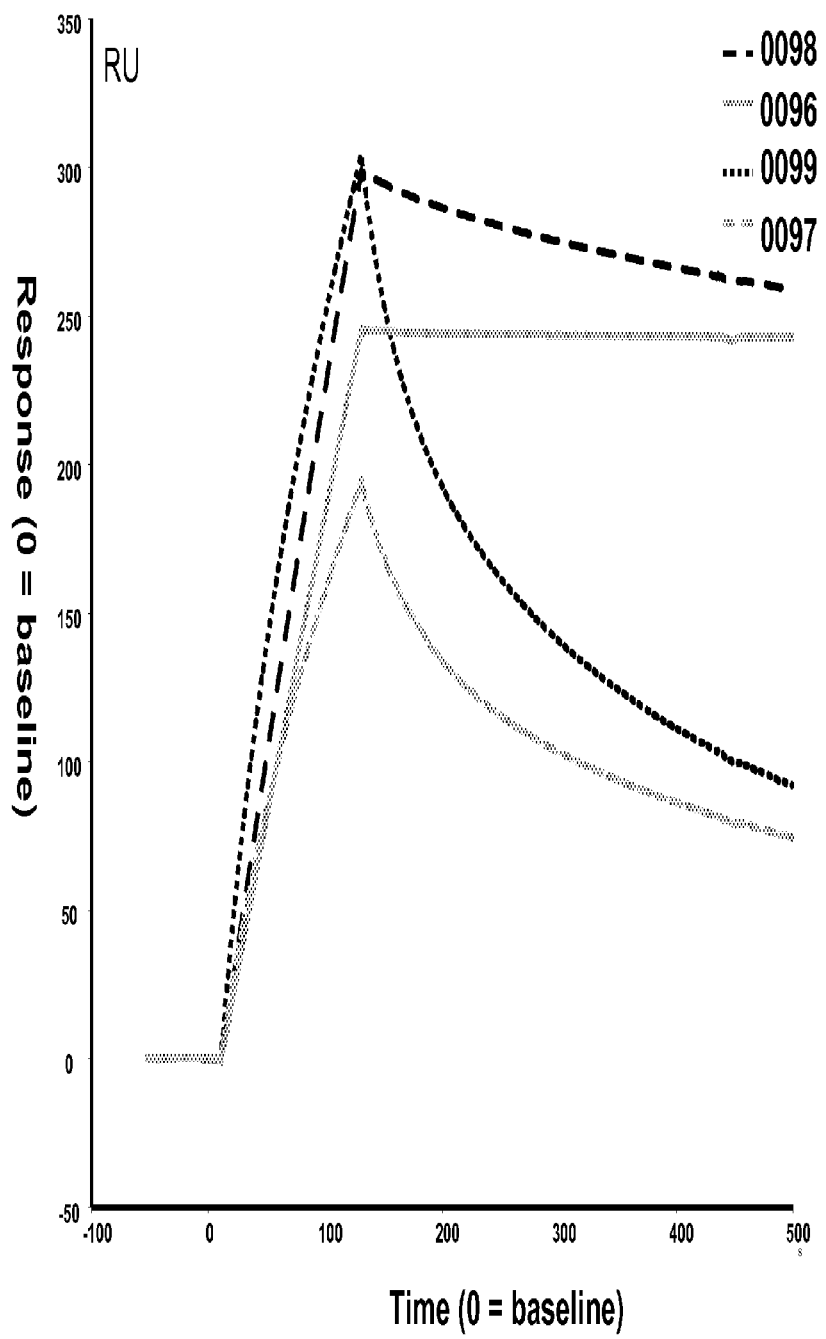
FIG. 13 Binding of IgG Fc-region modified <VEGF-ANG-2> antibodies to immobilized protein A on a CM5 chip.
Figure 14:
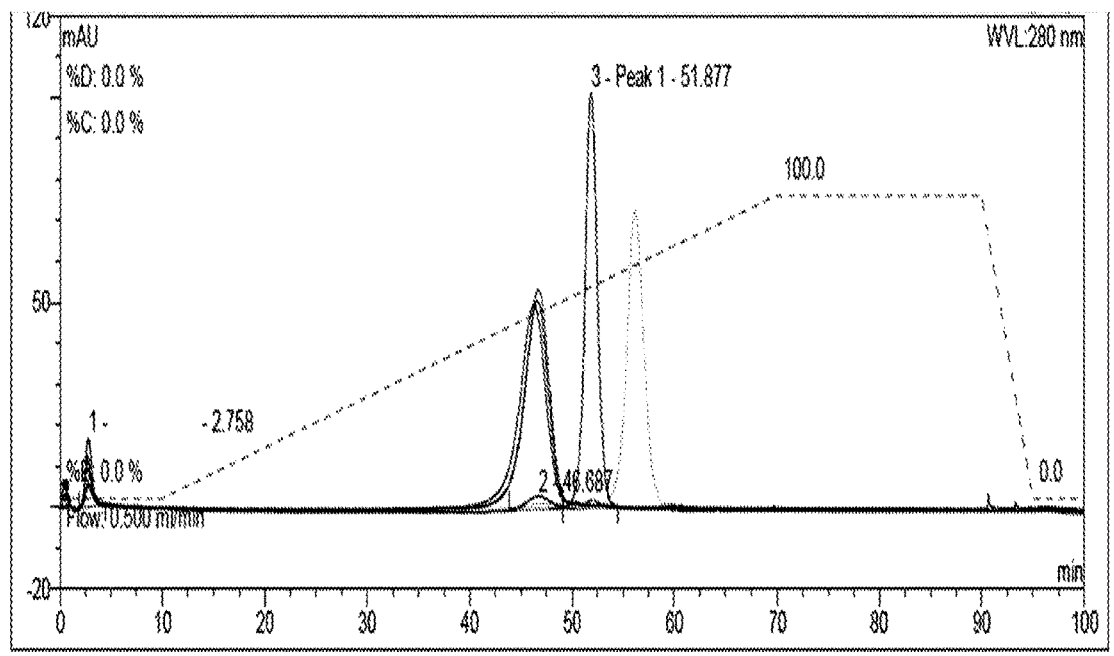
FIG. 14 Elution chromatogram of different <VEGF-ANG-2> antibodies on an FcRn affinity column.
Figure 15:
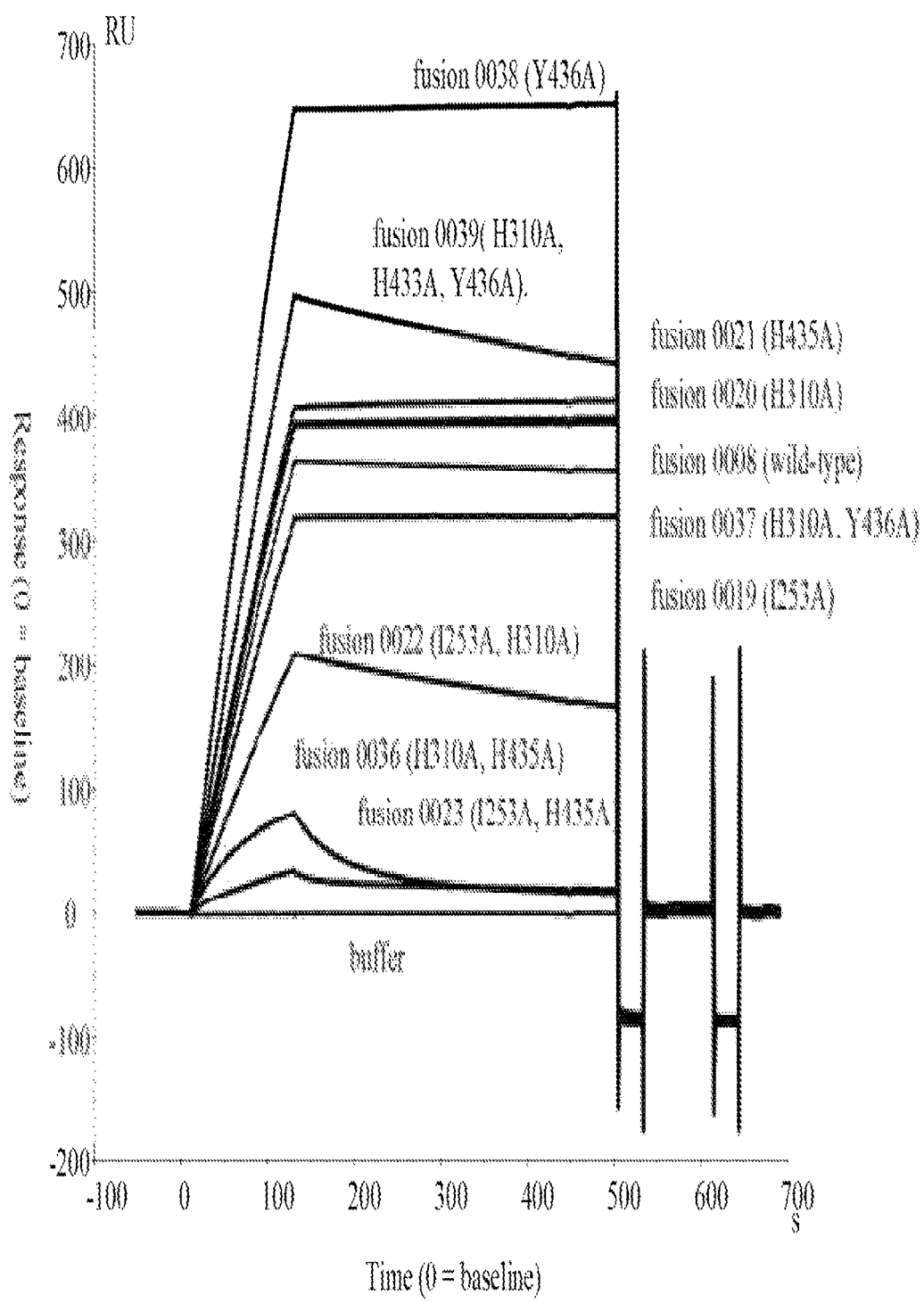
FIG. 15 Binding of different fusion polypeptides to Staphylococcal protein A (SPR).
Figure 16:
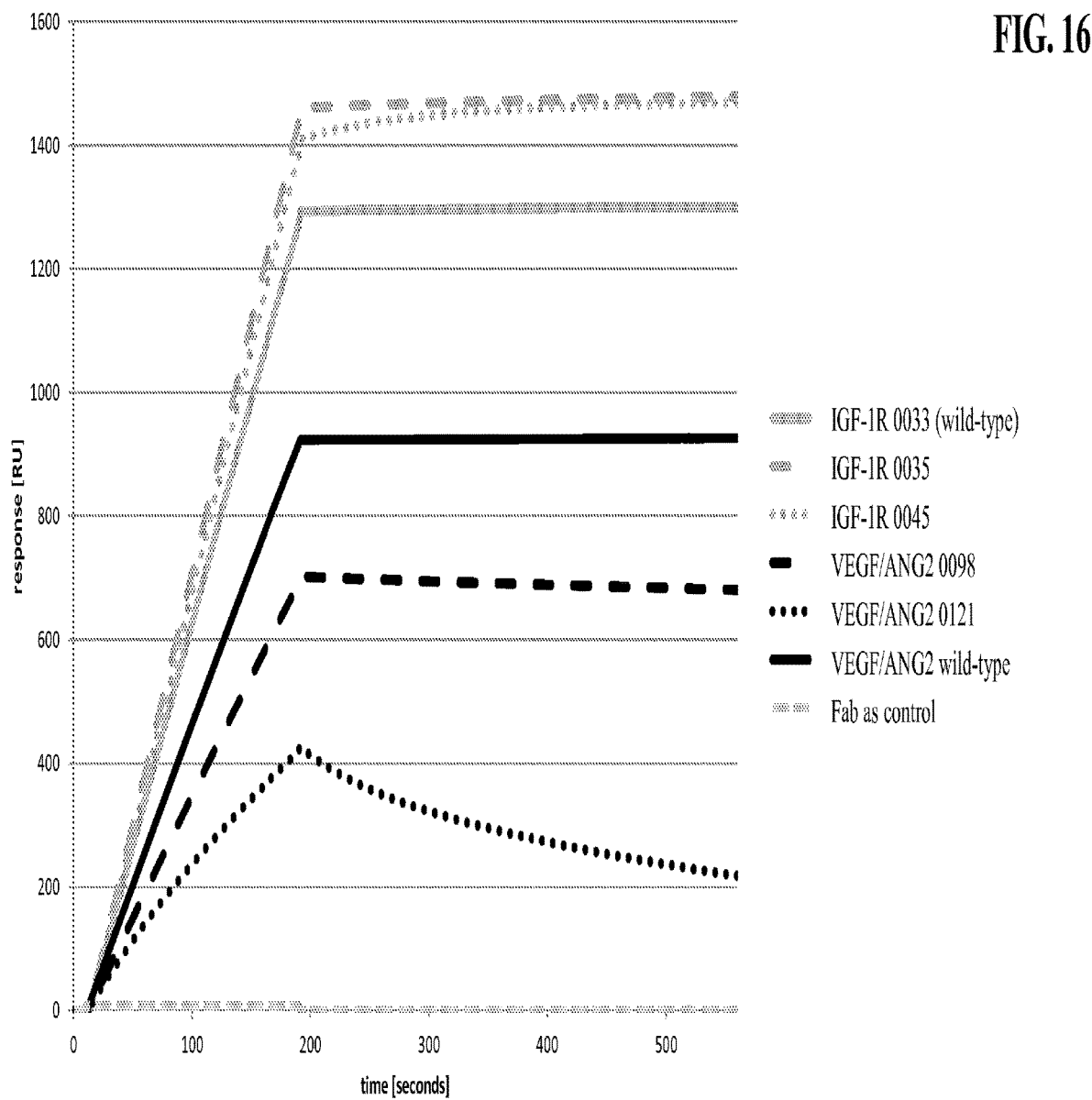
FIG. 16 Binding of different <VEGF-ANG-2> antibody and anti-IGF-1R antibody mutants to immobilized protein A (SPR).

Results for concentrations in eye lysates are shown in the following Tables and FIGS. 7D to 7E.

TABLE

Concentrations of VEGFang2-0015 (without IHH-AAA mutation) in eye lysates after intra vitreal application into right eye mean conc. values from n = 6 mice

| ID |  | mean conc. [ng/mL] |
|---|---|---|
| 96 h | left eye | 8.7 |
|  | right eye | 46.1 |
| 168 h | left eye | 4.3 |
|  | right eye t | 12.9 |

TABLE

Concentrations of VEGFang2-0015 (without IHH-AAA mutation) in eye lysates after intravenous application mean conc. values from n = 5 mice

| ID |  | mean conc. [ng/mL] |
|---|---|---|
| 96 h | left eye | 4.2 |
|  | right eye | 7.5 |
| 168 h | left eye | 3.4 |
|  | right eye | 6.1 |

TABLE

Concentrations of VEGFang2-0016 (with IHH-AAA mutation) in eye lysates after intra vitreal application into right eye mean conc. values from n = 5 mice

| ID |  | mean conc. [ng/mL] |
|---|---|---|
| 96 h | left eye | 0.3 |
|  | right eye | 34.5 |
| 168 h | left eye | 0.1 |
|  | right eye | 9.0 |

TABLE

Concentrations of VEGFang2-0016 (with IHH-AAA mutation) in eye lysates after intravenous application mean conc. values from n = 5 mice

| ID |  | mean conc. [ng/mL] |
|---|---|---|
| 96 h | left eye | 0.0 |
|  | right eye | 0.1 |

TABLE-continued

Concentrations of VEGFang2-0016 (with IHH-AAA mutation) in eye lysates after intravenous application mean conc. values from n = 5 mice

| ID | | mean conc. [ng/mL] |
|---|---|---|
| 168 h | left eye | 0.0 |
| | right eye | 0.1 |

Summary of Results:

After intravitreal application the bispecific <VEGF-ANG-2> antibody as reported herein VEGFang2-0016 (with IHH-AAA mutation) shows similar concentrations (after 96 and 168 hours) in the eye lysates as compared to the bispecific <VEGF-ANG-2> antibody without IHH-AAA mutation VEGFang2-0015.

Also after intravitreal application the bispecific <VEGF-ANG-2> antibody as reported herein VEGFang2-0016 (with IHH-AAA mutation) shows in addition a faster clearance and shorter half-life in the serum as compared to the bispecific <VEGF-ANG-2> antibody without IHH-AAA mutation VEGFang2-0015.

Example 7

Mouse Cornea Micropocket Angiogenesis Assay

To test the anti-angiogenic effect bispecific <VEGF-ANG-2> antibody with the respective VEGF binding VH and VL of SEQ ID NO: 20 and 21 and the ANG-2 binding VH and VL of SEQ ID NO: 28 and 29 on VEGF-induced angiogenesis in vivo, a mouse cornea micropocket angiogenesis assay was performed. In this assay a VEGF soaked Nylaflo disc was implanted into a pocket of the avascular cornea at a fixed distance to the limbal vessels. Vessels immediately grow into the cornea towards the developing VEGF gradient. 8 to 10 weeks old female Balb/c mice were purchased from Charles River, Sulzfeld, Germany. The protocol was modified according to the method described by Rogers, M. S., et al., Nat. Protoc. 2 (2007) 2545-2550. Briefly, micropockets with a width of about 500 μm were prepared under a microscope at approximately 1 mm from the limbus to the top of the cornea using a surgical blade and sharp tweezers in the anesthetized mouse. The disc (Nylaflo®, Pall Corporation, Michigan) with a diameter of 0.6 mm was implanted and the surface of the implantation area was smoothened. Discs were incubated in corresponding growth factor or in vehicle for at least 30 min. After 3, 5 and 7 days (or alternatively only after 3, 5 or 7 days) eyes were photographed and vascular response was measured. The assay was quantified by calculating the percentage of the area of new vessels per total area of the cornea.

The discs were loaded with 300 ng VEGF or with PBS as a control and implanted for 7 days. The outgrowth of vessels from the limbus to the disc was monitored over time on day 3, 5 and/or 7. One day prior to disc implantation the antibodies were administered intravenously at a dose of 10 mg/kg (due to the intravenous application the serum-stable VEGFang2-0015 (without IHH-AAA mutation) which only differs from VEGFang2-0016 by the IHH-AAA mutation and has the same anti-VEGF and anti-ANG-2 VHs and VLs to mediate efficacy, was used as surrogate) for testing the anti-angiogenic effect on VEGF-induced angiogenesis in vivo. Animals in the control group receive vehicle. The application volume was 10 mL/kg.

Example 8

Pharmacokinetic (PK) Properties of Antibodies with HHY-AAA Mutation
PK Data with FcRn Mice Transgenic for Human FcRn
In Life Phase:

The study includes female C57BL/6J mice (background); mouse FcRn deficient, but hemizygous transgenic for human FcRn (huFcRn, line 276-/tg)
Part 1:

All mice are injected once intravitreally into the right eye with 2 μL/animal of the appropriate solution of VEGF/ANG2-0016, VEGF/ANG2-0096, VEGF/ANG2-0098, VEGF/ANG2-0121.

Mice are allocated to 2 groups with 6 animals each. Blood samples are taken from group 1 at 2, 24 and 96 hours and from group 2 at 7, 48 and 168 hours after dosing.

Injection into the vitreous of the right mouse eye is performed by using the NanoFil Microsyringe system for nanoliter injection from World Precision Instruments, Inc., Berlin, Germany. Mice are anesthetized with 2.5% Isoflurane and for visualization of the mouse eye a Leica MZFL 3 microscope with a 40 fold magnification and a ring-light with a Leica KL 2500 LCD lightning is used. Subsequently, 2 μL of the compound are injected using a 35-gauge needle.

Blood is collected via the retrobulbar venous plexus of the contralateral eye from each animal for the determination of the compound levels in serum.

Serum samples of at least 50 μL are obtained from blood after 1 hour at RT by centrifugation (9,300×g) at 4° C. for 3 min. Serum samples are frozen directly after centrifugation and stored frozen at −80° C. until analysis. Treated eyes of the animals of group 1 are isolated 96 hours after treatment and of the animals of group 2 168 hours after treatment. Samples are stored frozen at −80° C. until analysis.
Part 2:

All mice are injected once intravenously via the tail vein with 200 μL/animal of the appropriate VEGF/ANG2-0096, VEGF/ANG2-0098, or VEGF/ANG2-0121.

Mice are allocated to 2 groups with 5 animals each. Blood samples are taken from group 1 at 1, 24 and 96 hours and from group 2 at 7, 48 and 168 hours after dosing.

Blood is collected via the retrobulbar venous plexus from each animal for the determination of the compound levels in serum.

Serum samples of at least 50 μL are obtained from blood after 1 hour at RT by centrifugation (9,300×g) at 4° C. for 3 min. Serum samples are frozen directly after centrifugation and stored frozen at −80° C. until analysis.
Preparation of Whole Eye Lysates (Mice)

The eye lysates are gained by physico-chemical disintegration of the whole eye. For mechanical disruption, each eye is transferred into a 1.5 mL micro vial with conical bottom. After freeze and thawing, the eyes are washed with 1 mL cell washing buffer once (Bio-Rad, Bio-Plex Cell Lysis Kit, Cat. No. 171-304011). In the following step, 500 μL of freshly prepared cell lysis buffer are added and the eyes are grinded using a 1.5 mL tissue grinding pestle (Kimble Chase, 1.5 mL pestle, Art. No. 749521-1500). The mixture is then frozen and thawed five times and grinded again. To separate lysate from remaining tissue the samples are centrifuged for 4 min. at 4,500 g. After centrifuging the supernatant is collected and stored at −20° C. until further analysis in the quantification ELISA.
Analysis The concentrations of the antibodies in mice serum and eye lysates are determined with an enzyme linked immunosorbent assay (ELISA).

For quantification of antibodies in mouse serum samples and eye lysates, a standard solid-phase serial sandwich immunoassay with biotinylated and digoxigenated monoclonal antibodies used as capture and detection antibodies is performed. Specifically to verify the integrity of the bispecificity of the analyte the biotinylated capture antibody recognizes the VEGF-binding site whereas the digoxigenated detection antibody binds to the ANG-2 binding site of the analyte. The bound immune complex of capture antibody, analyte and detection antibody on the solid phase of the streptavidin coated micro titer plate (SA-MTP) is then detected with a horseradish-peroxidase coupled to an anti-digoxigenin antibody. After washing unbound material from the SA-MTP and addition of ABTS-substrate, the gained signal is proportional to the amount of analyte bound on the solid phase of the SA-MTP. Quantification is then done by converting the measured signals of the samples into concentrations referring to calibrators analyzed in parallel.

In a first step the SA-MTP is coated with 100 µL/well of biotinylated capture antibody solution (anti-idiotypic antibody, e.g. mAb<Id<VEGF>>M-2.45.51-IgG-Bi(DDS)) with a concentration of 1 µg/mL for one hour at 500 rpm on a MTP-shaker. Meanwhile calibrators, QC-samples and samples are prepared. Calibrators and QC-samples are diluted to 2% serum matrix; samples are diluted until the signals are within the linear range of the calibrators.

After coating the SA-MTP with capture antibody, the plate is washed three times with washing buffer and 300 µL/well. Subsequently 100 µL/well of the calibrators, QC-samples and samples, respectively, are pipetted on the SA-MTP and incubated again for one hour at 500 rpm. The analyte is now bound with one of its binding sites via the capture antibody to the solid phase of the SA-MTP. After incubation and removal of unbound analyte by washing the plate 100 µL/well of the first detection antibody (anti-idiotypic antibody, e.g. mAb<Id-<ANG-2>>M-2.6.81-IgG-Dig(XOSu)) with a concentration of 250 ng/mL is added to the SA-MTP. Again, the plate is incubated for one hour at 500 rpm on a shaker. After washing, 100 µL/well of the second detection antibody (e.g. pAb<Digoxigenin>S-Fab-POD (poly)) at a concentration of 50 mU/mL is added to the wells of the SA-MTP and the plate is incubated again for one hour at 500 rpm. After a final washing step to remove excess of detection antibody, 100 µL/well substrate (ABTS®6) is added. The antibody-enzyme conjugate catalyzes the color reaction of the ABTS® substrate. The signal is measured by an ELISA reader at 405 nm wavelength (reference wavelength: 490 nm ([405/490] nm)).

Pharmacokinetic Evaluation

The pharmacokinetic parameters are calculated by non-compartmental analysis, using the pharmacokinetic evaluation program WinNonlin™ (Pharsight), version 5.2.1.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

What is claimed is:

1. An IgG1 Fc-region, comprising a first Fc-region polypeptide and a second Fc-region polypeptide, wherein:
   the first and the second Fc-region polypeptide are human IgG1 Fc-region polypeptide of SEQ ID NO: 60 and have the following mutations (numbering according to Kabat EU index numbering system):
   I253A in the first variant Fc-region polypeptide, and H310A and H435A in the second variant Fc-region polypeptide, or
   I253A and H310A in the first variant Fc-region polypeptide, and H435A in the second variant Fc-region polypeptide, or
   I253A and H435A in the first variant Fc-region polypeptide, and H310A in the second variant Fc-region polypeptide; and
   wherein:
   the IgG1 Fc-region has an affinity to a human Fc-receptor that is decreased in comparison to that of an IgG1 Fc-region that does not have said mutations,
   wherein
   i) the first IgG1 Fc-region polypeptide is a human IgG1 Fc-region polypeptide with the mutations L234A, L235A and the second IgG1 Fc-region polypeptide is a human IgG1 Fc-region polypeptide with the mutations L234A, L235A, or
   iii) the first IgG1 Fc-region polypeptide is a human IgG1 Fc-region polypeptide with the mutations L234A, I235A, P329G and the second IgG1 Fc-region polypeptide is a human IgG1 Fc-region polypeptide with the mutations L234A, L235A, P329G, or
   iv) the first IgG1 Fc-region polypeptide is a human IgG1 Fc-region polypeptide with the mutations L234A, L235A, S354C, T366W and the second IgG1 Fc-region polypeptide is a human IgG1 Fc-region polypeptide with the mutations L234A, L235A, Y349C, T366S, L368A, Y407V, or
   v) the first IgG1 Fc-region polypentide is a human IgG1 Fc-region polypeptide with the mutations L234A, L235A, P329G, S354C, T366W and the second IgG1 Fc-region polypeptide is a human IgG1 Fc-region polypeptide with the mutations L234A, L235A, P329G, Y349C, T366S, L368A, Y407V, or
   or
   vi) the first IgG1 Fc-region polypeptide is a human IgG1 Fc-region polypeptide with the mutation K392D and the second IgG1 Fc-region polypeptide is a human IgG1 Fc-region polypeptide with the mutations D399K, D356K, and/or E357K, and
   wherein the IgG1 Fc-region has a reduced binding to Staphylococcus protein A than an IgG1 Fc-region comprising the first IgG1 Fc-region polypeptide of a) and the second IgG1 Fc-region polypeptide of a).

2. The IgG1 Fc-region according to claim 1, wherein the affinity to the human neonatal Fc-receptor is increased or reduced by 10% or more determined by surface plasmon resonance (SPR).

3. The IgG1 Fc-region according to claim 1, characterized in comprising the mutations M252Y/S254T/T256E in the Fc-region (numbering according to Kabat EU index numbering system), whereby i) all mutations are in the first or the second Fc-region polypeptide, or ii) one or two mutations are in the first Fc-region polypeptide and one or two mutations are in the second Fc-region polypeptide so that all of the mutations M252Y/S254T/T256E are comprised in the IgG1 Fc-region.

4. An antibody comprising the IgG1 Fc-region according to claim 1.

5. The antibody according to claim 4, wherein the antibody is a monoclonal antibody.

6. The antibody according to claim 4, wherein the antibody is a human, humanized, or chimeric antibody.

7. The antibody according to claim 4, wherein the antibody is a bispecific antibody.

8. The antibody according to claim 4, wherein the antibody is a bivalent antibody.

9. The antibody according to claim 4, wherein the antibody is a bispecific, bivalent antibody with abolished FcRn binding comprising a first antigen-binding site that specifically binds to human VEGF and a second antigen-binding site that specifically binds to human ANG-2.

10. A bispecific, bivalent antibody with abolished FcRn binding comprising a first antigen-binding site that specifically binds to human VEGF and a second antigen-binding site that specifically binds to human ANG-2,
   wherein
   α) the first antigen-binding site specifically binding to VEGF comprises in the heavy chain variable domain a CDR3H region of SEQ ID NO: 14, a CDR2H region of SEQ ID NO: 15, and a CDR1H region of SEQ ID NO: 16, and in the light chain variable domain a CDR3L region of SEQ ID NO: 17, a CDR2L region of SEQ ID NO: 18, and a CDR1L region of SEQ ID NO: 19, and
   β) the second antigen-binding site specifically binding to ANG-2 comprises in the heavy chain variable domain a CDR3H region of SEQ ID NO: 22, a CDR2H region of, SEQ ID NO: 23, and a CDR1H region of SEQ ID NO: 24, and in the light chain variable domain a CDR3L region of SEQ ID NO: 25, a CDR2L region of SEQ ID NO: 26, and a CDR1L region of SEQ ID NO: 27, and γ) the bispecific antibody comprises an IgG1 Fc-region according to claim 1.

11. The bispecific antibody according to claim 10, wherein
   α) the first antigen-binding site specifically binding to VEGF comprises as heavy chain variable domain VH an amino acid sequence of SEQ ID NO: 20 and as light chain variable domain VL an amino acid sequence of SEQ ID NO: 21, and
   β) the second antigen-binding site specifically binding to ANG-2 comprises as heavy chain variable domain VH an amino acid sequence of SEQ ID NO: 28 and as light chain variable domain VL an amino acid sequence of SEQ ID NO: 29, and
   γ) the bispecific antibody comprises an IgG1 Fc-region according to claim 1.

12. An Fc-region fusion polypeptide comprising the IgG1 Fc-region according to claim 1.

13. A pharmaceutical formulation comprising the antibody according to claim 4.

14. A pharmaceutical formulation comprising the Fc region fusion polypeptide according to claim 12.

* * * * *

SEQUENCE LISTING

```
<160> NUMBER OF SEQ ID NOS: 97

<210> SEQ ID NO 1
<211> LENGTH: 448
<212> TYPE: PRT
<213> ORGANISM: Homo sapiens

<400> SEQUENCE: 1

Gln Val Glu Leu Val Glu Ser Gly Gly Gly Val Val Gln Pro Gly Arg
1               5                   10                  15

Ser Gln Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ile Ile Trp Phe Asp Gly Ser Ser Thr Tyr Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Arg Glu Leu Gly Arg Arg Tyr Phe Asp Leu Trp Gly Arg Gly Thr
            100                 105                 110

Leu Val Ser Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175
```

-continued

```
Ser Ser Gly Leu Tyr Ser Leu Ser Ser Val Val Thr Val Pro Ser Ser
                180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
        210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Gly Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 2
<211> LENGTH: 448
<212> TYPE: PRT
<213> ORGANISM: Homo sapiens

<400> SEQUENCE: 2

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Met
        35                  40                  45

Ala Ile Ile Trp Phe Asp Gly Ser Lys Tyr Tyr Gly Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Asp Asp Thr Ala Val Tyr Tyr Cys
                85                  90                  95

Ala Arg Glu Leu Gly Arg Arg Tyr Phe Asp Leu Trp Gly Arg Gly Thr
            100                 105                 110
```

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
            130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
            210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Gly Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445

<210> SEQ ID NO 3
<211> LENGTH: 215
<212> TYPE: PRT
<213> ORGANISM: Homo sapiens

<400> SEQUENCE: 3

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile

-continued

```
                35                  40                  45
Tyr Asp Ala Ser Lys Arg Ala Thr Gly Ile Pro Ala Arg Phe Ser Gly
 50                  55                  60
Ser Gly Ser Gly Thr Asp Phe Thr Leu Thr Ile Ser Ser Leu Glu Pro
 65                  70                  75                  80
Glu Asp Phe Ala Val Tyr Tyr Cys Gln Gln Arg Ser Lys Trp Pro Pro
                 85                  90                  95
Trp Thr Phe Gly Gln Gly Thr Lys Val Glu Ser Lys Arg Thr Val Ala
                100                 105                 110
Ala Pro Ser Val Phe Ile Phe Pro Pro Ser Asp Glu Gln Leu Lys Ser
                115                 120                 125
Gly Thr Ala Ser Val Val Cys Leu Leu Asn Asn Phe Tyr Pro Arg Glu
            130                 135                 140
Ala Lys Val Gln Trp Lys Val Asp Asn Ala Leu Gln Ser Gly Asn Ser
145                 150                 155                 160
Gln Glu Ser Val Thr Glu Gln Asp Ser Lys Asp Ser Thr Tyr Ser Leu
                165                 170                 175
Ser Ser Thr Leu Thr Leu Ser Lys Ala Asp Tyr Glu Lys His Lys Val
                180                 185                 190
Tyr Ala Cys Glu Val Thr His Gln Gly Leu Ser Ser Pro Val Thr Lys
                195                 200                 205
Ser Phe Asn Arg Gly Glu Cys
                210                 215

<210> SEQ ID NO 4
<211> LENGTH: 215
<212> TYPE: PRT
<213> ORGANISM: Homo sapiens

<400> SEQUENCE: 4

Glu Ile Val Leu Thr Gln Ser Pro Ala Thr Leu Ser Leu Ser Pro Gly
  1               5                  10                  15
Glu Arg Ala Thr Leu Ser Cys Arg Ala Ser Gln Ser Val Ser Ser Tyr
                 20                  25                  30
Leu Ala Trp Tyr Gln Gln Lys Pro Gly Gln Ala Pro Arg Leu Leu Ile
             35                  40                  45
Tyr Asp Ala Ser Asn Arg Ala Thr Gly Ile Pro Ala Arg Phe Ser Gly
 50                  55                  60
Ser Gly Ser Gly Thr Asp Phe Thr Leu Thr Ile Ser Ser Leu Glu Pro
 65                  70                  75                  80
Glu Asp Phe Ala Val Tyr Tyr Cys Gln Gln Arg Ser Lys Trp Pro Pro
                 85                  90                  95
Trp Thr Phe Gly Gln Gly Thr Lys Val Glu Ile Lys Arg Thr Val Ala
                100                 105                 110
Ala Pro Ser Val Phe Ile Phe Pro Pro Ser Asp Glu Gln Leu Lys Ser
                115                 120                 125
Gly Thr Ala Ser Val Val Cys Leu Leu Asn Asn Phe Tyr Pro Arg Glu
            130                 135                 140
Ala Lys Val Gln Trp Lys Val Asp Asn Ala Leu Gln Ser Gly Asn Ser
145                 150                 155                 160
Gln Glu Ser Val Thr Glu Gln Asp Ser Lys Asp Ser Thr Tyr Ser Leu
                165                 170                 175
Ser Ser Thr Leu Thr Leu Ser Lys Ala Asp Tyr Glu Lys His Lys Val
                180                 185                 190
```

```
Tyr Ala Cys Glu Val Thr His Gln Gly Leu Ser Ser Pro Val Thr Lys
            195                 200                 205

Ser Phe Asn Arg Gly Glu Cys
            210                 215
```

<210> SEQ ID NO 5
<211> LENGTH: 118
<212> TYPE: PRT
<213> ORGANISM: Homo sapiens

<400> SEQUENCE: 5

```
Gln Val Glu Leu Val Glu Ser Gly Gly Val Val Gln Pro Gly Arg
  1               5                  10                  15

Ser Gln Arg Leu Ser Cys Ala Ala Ser Gly Phe Thr Phe Ser Ser Tyr
             20                  25                  30

Gly Met His Trp Val Arg Gln Ala Pro Gly Lys Gly Leu Glu Trp Val
         35                  40                  45

Ala Ile Ile Trp Phe Asp Gly Ser Ser Thr Tyr Tyr Ala Asp Ser Val
     50                  55                  60

Arg Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Phe Cys
                 85                  90                  95

Ala Arg Glu Leu Gly Arg Arg Tyr Phe Asp Leu Trp Gly Arg Gly Thr
            100                 105                 110

Leu Val Ser Val Ser Ser
            115
```

<210> SEQ ID NO 6
<211> LENGTH: 118
<212> TYPE: PRT
<213> ORGANISM: Homo sapiens

<400> SEQUENCE: 6

```
Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Ser Ser Tyr
             20                  25                  30

Gly Met His Trp Val Arg Gln Ala Pro Gly Lys Gly Leu Glu Trp Met
         35                  40                  45

Ala Ile Ile Trp Phe Asp Gly Ser Ser Lys Tyr Tyr Gly Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Asp Asp Thr Ala Val Tyr Tyr Cys
                 85                  90                  95

Ala Arg Glu Leu Gly Arg Arg Tyr Phe Asp Leu Trp Gly Arg Gly Thr
            100                 105                 110

Leu Val Thr Val Ser Ser
            115
```

<210> SEQ ID NO 7
<211> LENGTH: 108
<212> TYPE: PRT
<213> ORGANISM: Homo sapiens

<400> SEQUENCE: 7

```
Glu Ile Val Leu Thr Gln Ser Pro Ala Thr Leu Ser Leu Ser Pro Gly
```

```
                1               5                  10                  15
            Glu Arg Ala Thr Leu Ser Cys Arg Ala Ser Gln Ser Val Ser Ser Tyr
                            20                  25                  30

Leu Ala Trp Tyr Gln Gln Lys Pro Gly Gln Ala Pro Arg Leu Leu Ile
                            35                  40                  45

Tyr Asp Ala Ser Lys Arg Ala Thr Gly Ile Pro Ala Arg Phe Ser Gly
                            50                  55                  60

Ser Gly Ser Gly Thr Asp Phe Thr Leu Thr Ile Ser Ser Leu Glu Pro
            65                  70                  75                  80

Glu Asp Phe Ala Val Tyr Tyr Cys Gln Gln Arg Ser Lys Trp Pro Pro
                                85                  90                  95

Trp Thr Phe Gly Gln Gly Thr Lys Val Glu Ser Lys
                            100                 105

<210> SEQ ID NO 8
<211> LENGTH: 108
<212> TYPE: PRT
<213> ORGANISM: Homo sapiens

<400> SEQUENCE: 8

Glu Ile Val Leu Thr Gln Ser Pro Ala Thr Leu Ser Leu Ser Pro Gly
            1               5                  10                  15

Glu Arg Ala Thr Leu Ser Cys Arg Ala Ser Gln Ser Val Ser Ser Tyr
                            20                  25                  30

Leu Ala Trp Tyr Gln Gln Lys Pro Gly Gln Ala Pro Arg Leu Leu Ile
                            35                  40                  45

Tyr Asp Ala Ser Asn Arg Ala Thr Gly Ile Pro Ala Arg Phe Ser Gly
                            50                  55                  60

Ser Gly Ser Gly Thr Asp Phe Thr Leu Thr Ile Ser Ser Leu Glu Pro
            65                  70                  75                  80

Glu Asp Phe Ala Val Tyr Tyr Cys Gln Gln Arg Ser Lys Trp Pro Pro
                                85                  90                  95

Trp Thr Phe Gly Gln Gly Thr Lys Val Glu Ile Lys
                            100                 105

<210> SEQ ID NO 9
<211> LENGTH: 107
<212> TYPE: PRT
<213> ORGANISM: Homo sapiens

<400> SEQUENCE: 9

Ala Pro Glu Leu Leu Gly Gly Pro Ser Val Phe Leu Phe Pro Pro Lys
            1               5                  10                  15

Pro Lys Asp Thr Leu Met Ile Ser Arg Thr Pro Glu Val Thr Cys Val
                            20                  25                  30

Trp Asp Val Ser His Glu Asp Pro Glu Val Lys Phe Asn Trp Tyr Val
                            35                  40                  45

Asp Gly Val Glu Val His Asn Ala Lys Thr Lys Pro Arg Glu Glu Gln
                            50                  55                  60

Glu Ser Thr Tyr Arg Trp Ser Val Leu Thr Val Leu His Gln Asp Trp
            65                  70                  75                  80

Leu Asn Gly Lys Glu Tyr Lys Cys Lys Val Ser Asn Lys Ala Leu Pro
                                85                  90                  95

Ala Pro Ile Glu Lys Thr Ile Ser Lys Ala Lys
                            100                 105
```

-continued

```
<210> SEQ ID NO 10
<211> LENGTH: 106
<212> TYPE: PRT
<213> ORGANISM: Homo sapiens

<400> SEQUENCE: 10

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly
            100                 105

<210> SEQ ID NO 11
<211> LENGTH: 1337
<212> TYPE: PRT
<213> ORGANISM: Homo sapiens

<400> SEQUENCE: 11

Glu Ile Cys Gly Pro Gly Ile Asp Ile Arg Asn Asp Tyr Gln Gln Leu
1               5                   10                  15

Lys Arg Leu Glu Asn Cys Thr Val Ile Glu Gly Tyr Leu His Ile Leu
            20                  25                  30

Leu Ile Ser Lys Ala Glu Asp Tyr Arg Ser Tyr Arg Phe Pro Lys Leu
        35                  40                  45

Thr Val Ile Thr Glu Tyr Leu Leu Leu Phe Arg Val Ala Gly Leu Glu
    50                  55                  60

Ser Leu Gly Asp Leu Phe Pro Asn Leu Thr Val Ile Arg Gly Trp Lys
65                  70                  75                  80

Leu Phe Tyr Asn Tyr Ala Leu Val Ile Phe Glu Met Thr Asn Leu Lys
                85                  90                  95

Asp Ile Gly Leu Tyr Asn Leu Arg Asn Ile Thr Arg Gly Ala Ile Arg
            100                 105                 110

Ile Glu Lys Asn Ala Asp Leu Cys Tyr Leu Ser Thr Val Asp Trp Ser
        115                 120                 125

Leu Ile Leu Asp Ala Val Ser Asn Asn Tyr Ile Val Gly Asn Lys Pro
    130                 135                 140

Pro Lys Glu Cys Gly Asp Leu Cys Pro Gly Thr Met Glu Glu Lys Pro
145                 150                 155                 160

Met Cys Glu Lys Thr Thr Ile Asn Asn Glu Tyr Asn Tyr Arg Cys Trp
                165                 170                 175

Thr Thr Asn Arg Cys Gln Lys Met Cys Pro Ser Thr Cys Gly Lys Arg
            180                 185                 190

Ala Cys Thr Glu Asn Asn Glu Cys Cys His Pro Glu Cys Leu Gly Ser
        195                 200                 205

Cys Ser Ala Pro Asp Asn Asp Thr Ala Cys Val Ala Cys Arg His Tyr
    210                 215                 220

Tyr Tyr Ala Gly Val Cys Val Pro Ala Cys Pro Pro Asn Thr Tyr Arg
```

-continued

```
                225                 230                 235                 240
        Phe Glu Gly Trp Arg Cys Val Asp Arg Asp Phe Cys Ala Asn Ile Leu
                        245                 250                 255
        Ser Ala Glu Ser Ser Asp Ser Glu Gly Phe Val Ile His Asp Gly Glu
                        260                 265                 270
        Cys Met Gln Glu Cys Pro Ser Gly Phe Ile Arg Asn Gly Ser Gln Ser
                        275                 280                 285
        Met Tyr Cys Ile Pro Cys Glu Gly Pro Cys Pro Lys Val Cys Glu Glu
                        290                 295                 300
        Glu Lys Lys Thr Lys Thr Ile Asp Ser Val Thr Ser Ala Gln Met Leu
        305                 310                 315                 320
        Gln Gly Cys Thr Ile Phe Lys Gly Asn Leu Leu Ile Asn Ile Arg Arg
                        325                 330                 335
        Gly Asn Asn Ile Ala Ser Glu Leu Glu Asn Phe Met Gly Leu Ile Glu
                        340                 345                 350
        Val Val Thr Gly Tyr Val Lys Ile Arg His Ser His Ala Leu Val Ser
                        355                 360                 365
        Leu Ser Phe Leu Lys Asn Leu Arg Leu Ile Leu Gly Glu Glu Gln Leu
        370                 375                 380
        Glu Gly Asn Tyr Ser Phe Tyr Val Leu Asp Asn Gln Asn Leu Gln Gln
        385                 390                 395                 400
        Leu Trp Asp Trp Asp His Arg Asn Leu Thr Ile Lys Ala Gly Lys Met
                        405                 410                 415
        Tyr Phe Ala Phe Asn Pro Lys Leu Cys Val Ser Glu Ile Tyr Arg Met
                        420                 425                 430
        Glu Glu Val Thr Gly Thr Lys Gly Arg Gln Ser Lys Gly Asp Ile Asn
                        435                 440                 445
        Thr Arg Asn Asn Gly Glu Arg Ala Ser Cys Glu Ser Asp Val Leu His
                        450                 455                 460
        Phe Thr Ser Thr Thr Ser Lys Asn Arg Ile Ile Ile Thr Trp His
        465                 470                 475                 480
        Arg Tyr Arg Pro Pro Asp Tyr Arg Asp Leu Ile Ser Phe Thr Val Tyr
                        485                 490                 495
        Tyr Lys Glu Ala Pro Phe Lys Asn Val Thr Glu Tyr Asp Gly Gln Asp
                        500                 505                 510
        Ala Cys Gly Ser Asn Ser Trp Asn Met Val Asp Val Asp Leu Pro Pro
                        515                 520                 525
        Asn Lys Asp Val Glu Pro Gly Ile Leu Leu His Gly Leu Lys Pro Trp
                        530                 535                 540
        Thr Gln Tyr Ala Val Tyr Val Lys Ala Val Thr Leu Thr Met Val Glu
        545                 550                 555                 560
        Asn Asp His Ile Arg Gly Ala Lys Ser Glu Ile Leu Tyr Ile Arg Thr
                        565                 570                 575
        Asn Ala Ser Val Pro Ser Ile Pro Leu Asp Val Leu Ser Ala Ser Asn
                        580                 585                 590
        Ser Ser Ser Gln Leu Ile Val Lys Trp Asn Pro Pro Ser Leu Pro Asn
                        595                 600                 605
        Gly Asn Leu Ser Tyr Tyr Ile Val Arg Trp Gln Arg Gln Pro Gln Asp
                        610                 615                 620
        Gly Tyr Leu Tyr Arg His Asn Tyr Cys Ser Lys Asp Lys Ile Pro Ile
        625                 630                 635                 640
        Arg Lys Tyr Ala Asp Gly Thr Ile Asp Ile Glu Glu Val Thr Glu Asn
                        645                 650                 655
```

-continued

Pro Lys Thr Glu Val Cys Gly Gly Glu Lys Gly Pro Cys Cys Ala Cys
            660                 665                 670

Pro Lys Thr Glu Ala Glu Lys Gln Ala Glu Lys Glu Ala Glu Tyr
        675                 680                 685

Arg Lys Val Phe Glu Asn Phe Leu His Asn Ser Ile Phe Val Pro Arg
690                 695                 700

Pro Glu Arg Lys Arg Arg Asp Val Met Gln Val Ala Asn Thr Thr Met
705                 710                 715                 720

Ser Ser Arg Ser Arg Asn Thr Thr Ala Ala Asp Thr Tyr Asn Ile Thr
                725                 730                 735

Asp Pro Glu Glu Leu Glu Thr Glu Tyr Pro Phe Phe Glu Ser Arg Val
            740                 745                 750

Asp Asn Lys Glu Arg Thr Val Ile Ser Asn Leu Arg Pro Phe Thr Leu
        755                 760                 765

Tyr Arg Ile Asp Ile His Ser Cys Asn His Glu Ala Glu Lys Leu Gly
    770                 775                 780

Cys Ser Ala Ser Asn Phe Val Phe Ala Arg Thr Met Pro Ala Glu Gly
785                 790                 795                 800

Ala Asp Asp Ile Pro Gly Pro Val Thr Trp Glu Pro Arg Pro Glu Asn
                805                 810                 815

Ser Ile Phe Leu Lys Trp Pro Glu Pro Glu Asn Pro Asn Gly Leu Ile
            820                 825                 830

Leu Met Tyr Glu Ile Lys Tyr Gly Ser Gln Val Glu Asp Gln Arg Glu
        835                 840                 845

Cys Val Ser Arg Gln Glu Tyr Arg Lys Tyr Gly Gly Ala Lys Leu Asn
    850                 855                 860

Arg Leu Asn Pro Gly Asn Tyr Thr Ala Arg Ile Gln Ala Thr Ser Leu
865                 870                 875                 880

Ser Gly Asn Gly Ser Trp Thr Asp Pro Val Phe Phe Tyr Val Gln Ala
                885                 890                 895

Lys Thr Gly Tyr Glu Asn Phe Ile His Leu Ile Ile Ala Leu Pro Val
            900                 905                 910

Ala Val Leu Leu Ile Val Gly Gly Leu Val Ile Met Leu Tyr Val Phe
        915                 920                 925

His Arg Lys Arg Asn Asn Ser Arg Leu Gly Asn Gly Val Leu Tyr Ala
    930                 935                 940

Ser Val Asn Pro Glu Tyr Phe Ser Ala Ala Asp Val Tyr Val Pro Asp
945                 950                 955                 960

Glu Trp Glu Val Ala Arg Glu Lys Ile Thr Met Ser Arg Glu Leu Gly
                965                 970                 975

Gln Gly Ser Phe Gly Met Val Tyr Glu Gly Val Ala Lys Gly Val Val
            980                 985                 990

Lys Asp Glu Pro Glu Thr Arg Val Ala Ile Lys Thr Val Asn Glu Ala
        995                 1000                1005

Ala Ser Met Arg Glu Arg Ile Glu Phe Leu Asn Glu Ala Ser Val
    1010                1015                1020

Met Lys Glu Phe Asn Cys His His Val Val Arg Leu Leu Gly Val
    1025                1030                1035

Val Ser Gln Gly Gln Pro Thr Leu Val Ile Met Glu Leu Met Thr
    1040                1045                1050

Arg Gly Asp Leu Lys Ser Tyr Leu Arg Ser Leu Arg Pro Glu Met
    1055                1060                1065

```
Glu Asn Asn Pro Val Leu Ala Pro Ser Leu Ser Lys Met Ile
    1070            1075            1080

Gln Met Ala Gly Glu Ile Ala Asp Gly Met Ala Tyr Leu Asn Ala
    1085            1090            1095

Asn Lys Phe Val His Arg Asp Leu Ala Ala Arg Asn Cys Met Val
    1100            1105            1110

Ala Glu Asp Phe Thr Val Lys Ile Gly Asp Phe Gly Met Thr Arg
    1115            1120            1125

Asp Ile Tyr Glu Thr Asp Tyr Tyr Arg Lys Gly Gly Lys Gly Leu
    1130            1135            1140

Leu Pro Val Arg Trp Met Ser Pro Glu Ser Leu Lys Asp Gly Val
    1145            1150            1155

Phe Thr Thr Tyr Ser Asp Val Trp Ser Phe Gly Val Val Leu Trp
    1160            1165            1170

Glu Ile Ala Thr Leu Ala Glu Gln Pro Tyr Gln Gly Leu Ser Asn
    1175            1180            1185

Glu Gln Val Leu Arg Phe Val Met Glu Gly Gly Leu Leu Asp Lys
    1190            1195            1200

Pro Asp Asn Cys Pro Asp Met Leu Phe Glu Leu Met Arg Met Cys
    1205            1210            1215

Trp Gln Tyr Asn Pro Lys Met Arg Pro Ser Phe Leu Glu Ile Ile
    1220            1225            1230

Ser Ser Ile Lys Glu Glu Met Glu Pro Gly Phe Arg Glu Val Ser
    1235            1240            1245

Phe Tyr Tyr Ser Glu Glu Asn Lys Leu Pro Glu Pro Glu Glu Leu
    1250            1255            1260

Asp Leu Glu Pro Glu Asn Met Glu Ser Val Pro Leu Asp Pro Ser
    1265            1270            1275

Ala Ser Ser Ser Ser Leu Pro Leu Pro Asp Arg His Ser Gly His
    1280            1285            1290

Lys Ala Glu Asn Gly Pro Gly Pro Gly Val Leu Val Leu Arg Ala
    1295            1300            1305

Ser Phe Asp Glu Arg Gln Pro Tyr Ala His Met Asn Gly Gly Arg
    1310            1315            1320

Lys Asn Glu Arg Ala Leu Pro Leu Pro Gln Ser Ser Thr Cys
    1325            1330            1335

<210> SEQ ID NO 12
<211> LENGTH: 330
<212> TYPE: PRT
<213> ORGANISM: Homo sapiens

<400> SEQUENCE: 12

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95
```

Lys Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 13
<211> LENGTH: 327
<212> TYPE: PRT
<213> ORGANISM: Homo sapiens

<400> SEQUENCE: 13

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val

```
            130                 135                 140
Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Gly Leu
                195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
                275                 280                 285

Arg Leu Thr Val Asp Lys Ser Arg Trp Gln Glu Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 14
<211> LENGTH: 14
<212> TYPE: PRT
<213> ORGANISM: Artificial
<220> FEATURE:
<223> OTHER INFORMATION: heavy chain CDR3H, <VEGF>ranibizumab

<400> SEQUENCE: 14

Tyr Pro Tyr Tyr Tyr Gly Thr Ser His Trp Tyr Phe Asp Val
1               5                   10

<210> SEQ ID NO 15
<211> LENGTH: 17
<212> TYPE: PRT
<213> ORGANISM: Artificial
<220> FEATURE:
<223> OTHER INFORMATION: heavy chain CDR2H, <VEGF>ranibizumab

<400> SEQUENCE: 15

Trp Ile Asn Thr Tyr Thr Gly Glu Pro Thr Tyr Ala Ala Asp Phe Lys
1               5                   10                  15

Arg

<210> SEQ ID NO 16
<211> LENGTH: 5
<212> TYPE: PRT
<213> ORGANISM: Artificial
<220> FEATURE:
<223> OTHER INFORMATION: heavy chain CDR1H, <VEGF>ranibizumab

<400> SEQUENCE: 16

His Tyr Gly Met Asn
1               5
```

```
<210> SEQ ID NO 17
<211> LENGTH: 9
<212> TYPE: PRT
<213> ORGANISM: Artificial
<220> FEATURE:
<223> OTHER INFORMATION: light chain CDR3L,  <VEGF>ranibizumab

<400> SEQUENCE: 17

Gln Gln Tyr Ser Thr Val Pro Trp Thr
1               5

<210> SEQ ID NO 18
<211> LENGTH: 7
<212> TYPE: PRT
<213> ORGANISM: Artificial
<220> FEATURE:
<223> OTHER INFORMATION: light chain CDR2L,  <VEGF>ranibizumab

<400> SEQUENCE: 18

Phe Thr Ser Ser Leu His Ser
1               5

<210> SEQ ID NO 19
<211> LENGTH: 11
<212> TYPE: PRT
<213> ORGANISM: Artificial
<220> FEATURE:
<223> OTHER INFORMATION: light chain CDR1L,  <VEGF>ranibizumab

<400> SEQUENCE: 19

Ser Ala Ser Gln Asp Ile Ser Asn Tyr Leu Asn
1               5                   10

<210> SEQ ID NO 20
<211> LENGTH: 123
<212> TYPE: PRT
<213> ORGANISM: Artificial
<220> FEATURE:
<223> OTHER INFORMATION: heavy chain variable domain VH,
      <VEGF>ranibizumab

<400> SEQUENCE: 20

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Asp Phe Thr His Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro Tyr Tyr Tyr Gly Thr Ser His Trp Tyr Phe Asp Val
            100                 105                 110

Trp Gly Gln Gly Thr Leu Val Thr Val Ser Ser
        115                 120

<210> SEQ ID NO 21
<211> LENGTH: 107
<212> TYPE: PRT
<213> ORGANISM: Artificial
```

-continued

```
<220> FEATURE:
<223> OTHER INFORMATION: light chain variable domain VL,
      <VEGF>ranibizumab

<400> SEQUENCE: 21

Asp Ile Gln Leu Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys
            100                 105

<210> SEQ ID NO 22
<211> LENGTH: 20
<212> TYPE: PRT
<213> ORGANISM: Artificial
<220> FEATURE:
<223> OTHER INFORMATION: heavy chain CDR3H, <ANG-2> Ang2i_LC10 variant

<400> SEQUENCE: 22

Ser Pro Asn Pro Tyr Tyr Tyr Asp Ser Ser Gly Tyr Tyr Tyr Pro Gly
1               5                   10                  15

Ala Phe Asp Ile
            20

<210> SEQ ID NO 23
<211> LENGTH: 17
<212> TYPE: PRT
<213> ORGANISM: Artificial
<220> FEATURE:
<223> OTHER INFORMATION: heavy chain CDR2H, <ANG-2> Ang2i_LC10 variant

<400> SEQUENCE: 23

Trp Ile Asn Pro Asn Ser Gly Gly Thr Asn Tyr Ala Gln Lys Phe Gln
1               5                   10                  15

Gly

<210> SEQ ID NO 24
<211> LENGTH: 5
<212> TYPE: PRT
<213> ORGANISM: Artificial
<220> FEATURE:
<223> OTHER INFORMATION: heavy chain CDR1H, <ANG-2> Ang2i_LC10 variant

<400> SEQUENCE: 24

Gly Tyr Tyr Met His
1               5

<210> SEQ ID NO 25
<211> LENGTH: 11
<212> TYPE: PRT
<213> ORGANISM: Artificial
<220> FEATURE:
<223> OTHER INFORMATION: light chain CDR3L, <ANG-2> Ang2i_LC10 variant
```

```
<400> SEQUENCE: 25

Gln Val Trp Asp Ser Ser Asp His Trp Val
1               5                   10

<210> SEQ ID NO 26
<211> LENGTH: 7
<212> TYPE: PRT
<213> ORGANISM: Artificial
<220> FEATURE:
<223> OTHER INFORMATION: light chain CDR2L, <ANG-2> Ang2i_LC10 variant

<400> SEQUENCE: 26

Asp Asp Ser Asp Arg Pro Ser
1               5

<210> SEQ ID NO 27
<211> LENGTH: 11
<212> TYPE: PRT
<213> ORGANISM: Artificial
<220> FEATURE:
<223> OTHER INFORMATION: light chain CDR1L, <ANG-2> Ang2i_LC10 variant

<400> SEQUENCE: 27

Gly Gly Asn Asn Ile Gly Ser Lys Ser Val His
1               5                   10

<210> SEQ ID NO 28
<211> LENGTH: 129
<212> TYPE: PRT
<213> ORGANISM: Artificial
<220> FEATURE:
<223> OTHER INFORMATION: heavy chain variable domain VH, <ANG-2>
      Ang2i_LC10 variant

<400> SEQUENCE: 28

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Pro Asn Pro Tyr Tyr Asp Ser Ser Gly Tyr Tyr Tyr
            100                 105                 110

Pro Gly Ala Phe Asp Ile Trp Gly Gln Gly Thr Met Val Thr Val Ser
        115                 120                 125

Ser

<210> SEQ ID NO 29
<211> LENGTH: 110
<212> TYPE: PRT
<213> ORGANISM: Artificial
<220> FEATURE:
<223> OTHER INFORMATION: light chain variable domain VL, <ANG-2>
      Ang2i_LC10 variant

<400> SEQUENCE: 29
```

```
Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
                20                  25                  30

His Trp Tyr Gln Gln Lys Pro Gly Gln Ala Pro Val Leu Val Val Tyr
                35                  40                  45

Asp Asp Ser Asp Arg Pro Ser Gly Ile Pro Glu Arg Phe Ser Gly Ser
            50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Trp Val Phe Gly Gly Gly Thr Lys Leu Thr Val Leu Gly Gln
                100                 105                 110
```

<210> SEQ ID NO 30
<211> LENGTH: 191
<212> TYPE: PRT
<213> ORGANISM: Homo sapiens

<400> SEQUENCE: 30

```
Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
                20                  25                  30

Gly Gly Gln Asn His His Glu Val Val Lys Phe Met Asp Val Tyr Gln
                35                  40                  45

Arg Ser Tyr Cys His Pro Ile Glu Thr Leu Val Asp Ile Phe Gln Glu
            50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
                100                 105                 110

Gln Gly Gln His Ile Gly Glu Met Ser Phe Leu Gln His Asn Lys Cys
                115                 120                 125

Glu Cys Arg Pro Lys Lys Asp Arg Ala Arg Gln Glu Asn Pro Cys Gly
            130                 135                 140

Pro Cys Ser Glu Arg Arg Lys His Leu Phe Val Gln Asp Pro Gln Thr
145                 150                 155                 160

Cys Lys Cys Ser Cys Lys Asn Thr Asp Ser Arg Cys Lys Ala Arg Gln
                165                 170                 175

Leu Glu Leu Asn Glu Arg Thr Cys Arg Cys Asp Lys Pro Arg Arg
                180                 185                 190
```

<210> SEQ ID NO 31
<211> LENGTH: 496
<212> TYPE: PRT
<213> ORGANISM: Homo sapiens

<400> SEQUENCE: 31

```
Met Trp Gln Ile Val Phe Phe Thr Leu Ser Cys Asp Leu Val Leu Ala
1               5                   10                  15

Ala Ala Tyr Asn Asn Phe Arg Lys Ser Met Asp Ser Ile Gly Lys Lys
                20                  25                  30
```

```
Gln Tyr Gln Val Gln His Gly Ser Cys Ser Tyr Thr Phe Leu Leu Pro
             35                  40                  45
Glu Met Asp Asn Cys Arg Ser Ser Ser Pro Tyr Val Ser Asn Ala
 50                  55                  60
Val Gln Arg Asp Ala Pro Leu Glu Tyr Asp Asp Ser Val Gln Arg Leu
 65                  70                  75                  80
Gln Val Leu Glu Asn Ile Met Glu Asn Asn Thr Gln Trp Leu Met Lys
                 85                  90                  95
Leu Glu Asn Tyr Ile Gln Asp Asn Met Lys Lys Glu Met Val Glu Ile
                100                 105                 110
Gln Gln Asn Ala Val Gln Asn Gln Thr Ala Val Met Ile Glu Ile Gly
            115                 120                 125
Thr Asn Leu Leu Asn Gln Thr Ala Glu Gln Thr Arg Lys Leu Thr Asp
130                 135                 140
Val Glu Ala Gln Val Leu Asn Gln Thr Thr Arg Leu Glu Leu Gln Leu
145                 150                 155                 160
Leu Glu His Ser Leu Ser Thr Asn Lys Leu Glu Lys Gln Ile Leu Asp
                165                 170                 175
Gln Thr Ser Glu Ile Asn Lys Leu Gln Asp Lys Asn Ser Phe Leu Glu
            180                 185                 190
Lys Lys Val Leu Ala Met Glu Asp Lys His Ile Ile Gln Leu Gln Ser
        195                 200                 205
Ile Lys Glu Glu Lys Asp Gln Leu Gln Val Leu Val Ser Lys Gln Asn
    210                 215                 220
Ser Ile Ile Glu Glu Leu Glu Lys Lys Ile Val Thr Ala Thr Val Asn
225                 230                 235                 240
Asn Ser Val Leu Gln Lys Gln Gln His Asp Leu Met Glu Thr Val Asn
                245                 250                 255
Asn Leu Leu Thr Met Met Ser Thr Ser Asn Ser Ala Lys Asp Pro Thr
            260                 265                 270
Val Ala Lys Glu Glu Gln Ile Ser Phe Arg Asp Cys Ala Glu Val Phe
        275                 280                 285
Lys Ser Gly His Thr Thr Asn Gly Ile Tyr Thr Leu Thr Phe Pro Asn
    290                 295                 300
Ser Thr Glu Glu Ile Lys Ala Tyr Cys Asp Met Glu Ala Gly Gly Gly
305                 310                 315                 320
Gly Trp Thr Ile Ile Gln Arg Arg Glu Asp Gly Ser Val Asp Phe Gln
                325                 330                 335
Arg Thr Trp Lys Glu Tyr Lys Val Gly Phe Gly Asn Pro Ser Gly Glu
            340                 345                 350
Tyr Trp Leu Gly Asn Glu Phe Val Ser Gln Leu Thr Asn Gln Gln Arg
        355                 360                 365
Tyr Val Leu Lys Ile His Leu Lys Asp Trp Glu Gly Asn Glu Ala Tyr
    370                 375                 380
Ser Leu Tyr Glu His Phe Tyr Leu Ser Ser Glu Glu Leu Asn Tyr Arg
385                 390                 395                 400
Ile His Leu Lys Gly Leu Thr Gly Thr Ala Gly Lys Ile Ser Ser Ile
                405                 410                 415
Ser Gln Pro Gly Asn Asp Phe Ser Thr Lys Asp Gly Asp Asn Asp Lys
            420                 425                 430
Cys Ile Cys Lys Cys Ser Gln Met Leu Thr Gly Gly Trp Trp Phe Asp
        435                 440                 445
Ala Cys Gly Pro Ser Asn Leu Asn Gly Met Tyr Tyr Pro Gln Arg Gln
```

```
                450            455           460
Asn Thr Asn Lys Phe Asn Gly Ile Lys Trp Tyr Tyr Trp Lys Gly Ser
465             470             475             480

Gly Tyr Ser Leu Lys Ala Thr Thr Met Met Ile Arg Pro Ala Asp Phe
            485             490             495

<210> SEQ ID NO 32
<211> LENGTH: 498
<212> TYPE: PRT
<213> ORGANISM: Homo sapiens

<400> SEQUENCE: 32

Met Thr Val Phe Leu Ser Phe Ala Phe Leu Ala Ala Ile Leu Thr His
1               5                   10                  15

Ile Gly Cys Ser Asn Gln Arg Arg Ser Pro Glu Asn Ser Gly Arg Arg
            20                  25                  30

Tyr Asn Arg Ile Gln His Gly Gln Cys Ala Tyr Thr Phe Ile Leu Pro
        35                  40                  45

Glu His Asp Gly Asn Cys Arg Glu Ser Thr Thr Asp Gln Tyr Asn Thr
    50                  55                  60

Asn Ala Leu Gln Arg Asp Ala Pro His Val Glu Pro Asp Phe Ser Ser
65              70                  75                  80

Gln Lys Leu Gln His Leu Glu His Val Met Glu Asn Tyr Thr Gln Trp
            85                  90                  95

Leu Gln Lys Leu Glu Asn Tyr Ile Val Glu Asn Met Lys Ser Glu Met
        100                 105                 110

Ala Gln Ile Gln Gln Asn Ala Val Gln Asn His Thr Ala Thr Met Leu
    115                 120                 125

Glu Ile Gly Thr Ser Leu Leu Ser Gln Thr Ala Glu Gln Thr Arg Lys
130                 135                 140

Leu Thr Asp Val Glu Thr Gln Val Leu Asn Gln Thr Ser Arg Leu Glu
145                 150                 155                 160

Ile Gln Leu Leu Glu Asn Ser Leu Ser Thr Tyr Lys Leu Glu Lys Gln
            165                 170                 175

Leu Leu Gln Gln Thr Asn Glu Ile Leu Lys Ile His Glu Lys Asn Ser
        180                 185                 190

Leu Leu Glu His Lys Ile Leu Glu Met Glu Gly Lys His Lys Glu Glu
    195                 200                 205

Leu Asp Thr Leu Lys Glu Glu Lys Glu Asn Leu Gln Gly Leu Val Thr
210                 215                 220

Arg Gln Thr Tyr Ile Ile Gln Glu Leu Glu Lys Gln Leu Asn Arg Ala
225                 230                 235                 240

Thr Thr Asn Asn Ser Val Leu Gln Lys Gln Gln Leu Glu Leu Met Asp
            245                 250                 255

Thr Val His Asn Leu Val Asn Leu Cys Thr Lys Glu Gly Val Leu Leu
        260                 265                 270

Lys Gly Gly Lys Arg Glu Glu Glu Lys Pro Phe Arg Asp Cys Ala Asp
    275                 280                 285

Val Tyr Gln Ala Gly Phe Asn Lys Ser Gly Ile Tyr Thr Ile Tyr Ile
290                 295                 300

Asn Asn Met Pro Glu Pro Lys Lys Val Phe Cys Asn Met Asp Val Asn
305                 310                 315                 320

Gly Gly Gly Trp Thr Val Ile Gln His Arg Glu Asp Gly Ser Leu Asp
            325                 330                 335
```

-continued

```
Phe Gln Arg Gly Trp Lys Glu Tyr Lys Met Gly Phe Gly Asn Pro Ser
            340                 345                 350

Gly Glu Tyr Trp Leu Gly Asn Glu Phe Ile Phe Ala Ile Thr Ser Gln
        355                 360                 365

Arg Gln Tyr Met Leu Arg Ile Glu Leu Met Asp Trp Glu Gly Asn Arg
    370                 375                 380

Ala Tyr Ser Gln Tyr Asp Arg Phe His Ile Gly Asn Glu Lys Gln Asn
385                 390                 395                 400

Tyr Arg Leu Tyr Leu Lys Gly His Thr Gly Thr Ala Gly Lys Gln Ser
                405                 410                 415

Ser Leu Ile Leu His Gly Ala Asp Phe Ser Thr Lys Asp Ala Asp Asn
            420                 425                 430

Asp Asn Cys Met Cys Lys Cys Ala Leu Met Leu Thr Gly Gly Trp Trp
        435                 440                 445

Phe Asp Ala Cys Gly Pro Ser Asn Leu Asn Gly Met Phe Tyr Thr Ala
    450                 455                 460

Gly Gln Asn His Gly Lys Leu Asn Gly Ile Lys Trp His Tyr Phe Lys
465                 470                 475                 480

Gly Pro Ser Tyr Ser Leu Arg Ser Thr Thr Met Met Ile Arg Pro Leu
                485                 490                 495

Asp Phe

<210> SEQ ID NO 33
<211> LENGTH: 1124
<212> TYPE: PRT
<213> ORGANISM: Homo sapiens

<400> SEQUENCE: 33

Met Asp Ser Leu Ala Ser Leu Val Leu Cys Gly Val Ser Leu Leu Leu
1               5                   10                  15

Ser Gly Thr Val Glu Gly Ala Met Asp Leu Ile Leu Ile Asn Ser Leu
            20                  25                  30

Pro Leu Val Ser Asp Ala Glu Thr Ser Leu Thr Cys Ile Ala Ser Gly
        35                  40                  45

Trp Arg Pro His Glu Pro Ile Thr Ile Gly Arg Asp Phe Glu Ala Leu
    50                  55                  60

Met Asn Gln His Gln Asp Pro Leu Glu Val Thr Gln Asp Val Thr Arg
65                  70                  75                  80

Glu Trp Ala Lys Lys Val Val Trp Lys Arg Glu Lys Ala Ser Lys Ile
                85                  90                  95

Asn Gly Ala Tyr Phe Cys Glu Gly Arg Val Arg Gly Glu Ala Ile Arg
            100                 105                 110

Ile Arg Thr Met Lys Met Arg Gln Gln Ala Ser Phe Leu Pro Ala Thr
        115                 120                 125

Leu Thr Met Thr Val Asp Lys Gly Asp Asn Val Asn Ile Ser Phe Lys
    130                 135                 140

Lys Val Leu Ile Lys Glu Glu Asp Ala Val Ile Tyr Lys Asn Gly Ser
145                 150                 155                 160

Phe Ile His Ser Val Pro Arg His Glu Val Pro Asp Ile Leu Glu Val
                165                 170                 175

His Leu Pro His Ala Gln Pro Gln Asp Ala Gly Val Tyr Ser Ala Arg
            180                 185                 190

Tyr Ile Gly Gly Asn Leu Phe Thr Ser Ala Phe Thr Arg Leu Ile Val
        195                 200                 205
```

```
Arg Arg Cys Glu Ala Gln Lys Trp Gly Pro Glu Cys Asn His Leu Cys
210                 215                 220

Thr Ala Cys Met Asn Asn Gly Val Cys His Glu Asp Thr Gly Glu Cys
225                 230                 235                 240

Ile Cys Pro Pro Gly Phe Met Gly Arg Thr Cys Glu Lys Ala Cys Glu
            245                 250                 255

Leu His Thr Phe Gly Arg Thr Cys Lys Glu Arg Cys Ser Gly Gln Glu
            260                 265                 270

Gly Cys Lys Ser Tyr Val Phe Cys Leu Pro Asp Pro Tyr Gly Cys Ser
        275                 280                 285

Cys Ala Thr Gly Trp Lys Gly Leu Gln Cys Asn Glu Ala Cys His Pro
290                 295                 300

Gly Phe Tyr Gly Pro Asp Cys Lys Leu Arg Cys Ser Cys Asn Asn Gly
305                 310                 315                 320

Glu Met Cys Asp Arg Phe Gln Gly Cys Leu Cys Ser Pro Gly Trp Gln
                325                 330                 335

Gly Leu Gln Cys Glu Arg Glu Gly Ile Pro Arg Met Thr Pro Lys Ile
            340                 345                 350

Val Asp Leu Pro Asp His Ile Glu Val Asn Ser Gly Lys Phe Asn Pro
            355                 360                 365

Ile Cys Lys Ala Ser Gly Trp Pro Leu Pro Thr Asn Glu Glu Met Thr
370                 375                 380

Leu Val Lys Pro Asp Gly Thr Val Leu His Pro Lys Asp Phe Asn His
385                 390                 395                 400

Thr Asp His Phe Ser Val Ala Ile Phe Thr Ile His Arg Ile Leu Pro
                405                 410                 415

Pro Asp Ser Gly Val Trp Val Cys Ser Val Asn Thr Val Ala Gly Met
            420                 425                 430

Val Glu Lys Pro Phe Asn Ile Ser Val Lys Val Leu Pro Lys Pro Leu
        435                 440                 445

Asn Ala Pro Asn Val Ile Asp Thr Gly His Asn Phe Ala Val Ile Asn
450                 455                 460

Ile Ser Ser Glu Pro Tyr Phe Gly Asp Gly Pro Ile Lys Ser Lys Lys
465                 470                 475                 480

Leu Leu Tyr Lys Pro Val Asn His Tyr Glu Ala Trp Gln His Ile Gln
                485                 490                 495

Val Thr Asn Glu Ile Val Thr Leu Asn Tyr Leu Glu Pro Arg Thr Glu
            500                 505                 510

Tyr Glu Leu Cys Val Gln Leu Val Arg Arg Gly Glu Gly Gly Glu Gly
        515                 520                 525

His Pro Gly Pro Val Arg Arg Phe Thr Thr Ala Ser Ile Gly Leu Pro
530                 535                 540

Pro Pro Arg Gly Leu Asn Leu Leu Pro Lys Ser Gln Thr Thr Leu Asn
545                 550                 555                 560

Leu Thr Trp Gln Pro Ile Phe Pro Ser Ser Glu Asp Asp Phe Tyr Val
                565                 570                 575

Glu Val Glu Arg Arg Ser Val Gln Lys Ser Asp Gln Gln Asn Ile Lys
            580                 585                 590

Val Pro Gly Asn Leu Thr Ser Val Leu Leu Asn Asn Leu His Pro Arg
        595                 600                 605

Glu Gln Tyr Val Val Arg Ala Arg Val Asn Thr Lys Ala Gln Gly Glu
610                 615                 620

Trp Ser Glu Asp Leu Thr Ala Trp Thr Leu Ser Asp Ile Leu Pro Pro
```

```
            625                 630                 635                 640
Gln Pro Glu Asn Ile Lys Ile Ser Asn Ile Thr His Ser Ser Ala Val
                    645                 650                 655

Ile Ser Trp Thr Ile Leu Asp Gly Tyr Ser Ile Ser Ser Ile Thr Ile
                660                 665                 670

Arg Tyr Lys Val Gln Gly Lys Asn Glu Asp Gln His Val Asp Val Lys
                675                 680                 685

Ile Lys Asn Ala Thr Ile Thr Gln Tyr Gln Leu Lys Gly Leu Glu Pro
            690                 695                 700

Glu Thr Ala Tyr Gln Val Asp Ile Phe Ala Glu Asn Asn Ile Gly Ser
705                 710                 715                 720

Ser Asn Pro Ala Phe Ser His Glu Leu Val Thr Leu Pro Glu Ser Gln
                    725                 730                 735

Ala Pro Ala Asp Leu Gly Gly Lys Met Leu Leu Ile Ala Ile Leu
                740                 745                 750

Gly Ser Ala Gly Met Thr Cys Leu Thr Val Leu Leu Ala Phe Leu Ile
            755                 760                 765

Ile Leu Gln Leu Lys Arg Ala Asn Val Gln Arg Arg Met Ala Gln Ala
            770                 775                 780

Phe Gln Asn Val Arg Glu Glu Pro Ala Val Gln Phe Asn Ser Gly Thr
785                 790                 795                 800

Leu Ala Leu Asn Arg Lys Val Lys Asn Pro Asp Pro Thr Ile Tyr
                805                 810                 815

Pro Val Leu Asp Trp Asn Asp Ile Lys Phe Gln Asp Val Ile Gly Glu
                820                 825                 830

Gly Asn Phe Gly Gln Val Leu Lys Ala Arg Ile Lys Lys Asp Gly Leu
            835                 840                 845

Arg Met Asp Ala Ala Ile Lys Arg Met Lys Glu Tyr Ala Ser Lys Asp
        850                 855                 860

Asp His Arg Asp Phe Ala Gly Glu Leu Glu Val Leu Cys Lys Leu Gly
865                 870                 875                 880

His His Pro Asn Ile Ile Asn Leu Leu Gly Ala Cys Glu His Arg Gly
                    885                 890                 895

Tyr Leu Tyr Leu Ala Ile Glu Tyr Ala Pro His Gly Asn Leu Leu Asp
                900                 905                 910

Phe Leu Arg Lys Ser Arg Val Leu Glu Thr Asp Pro Ala Phe Ala Ile
            915                 920                 925

Ala Asn Ser Thr Ala Ser Thr Leu Ser Ser Gln Gln Leu Leu His Phe
930                 935                 940

Ala Ala Asp Val Ala Arg Gly Met Asp Tyr Leu Ser Gln Lys Gln Phe
945                 950                 955                 960

Ile His Arg Asp Leu Ala Ala Arg Asn Ile Leu Val Gly Glu Asn Tyr
                965                 970                 975

Val Ala Lys Ile Ala Asp Phe Gly Leu Ser Arg Gly Gln Glu Val Tyr
                980                 985                 990

Val Lys Lys Thr Met Gly Arg Leu Pro Val Arg Trp Met Ala Ile Glu
            995                 1000                1005

Ser Leu Asn Tyr Ser Val Tyr Thr Thr Asn Ser Asp Val Trp Ser
    1010                1015                1020

Tyr Gly Val Leu Leu Trp Glu Ile Val Ser Leu Gly Gly Thr Pro
    1025                1030                1035

Tyr Cys Gly Met Thr Cys Ala Glu Leu Tyr Glu Lys Leu Pro Gln
    1040                1045                1050
```

-continued

Gly Tyr Arg Leu Glu Lys Pro Leu Asn Cys Asp Asp Glu Val Tyr
            1055                1060                1065

Asp Leu Met Arg Gln Cys Trp Arg Glu Lys Pro Tyr Glu Arg Pro
    1070                1075                1080

Ser Phe Ala Gln Ile Leu Val Ser Leu Asn Arg Met Leu Glu Glu
    1085                1090                1095

Arg Lys Thr Tyr Val Asn Thr Leu Tyr Glu Lys Phe Thr Tyr
    1100                1105                1110

Ala Gly Ile Asp Cys Ser Ala Glu Glu Ala Ala
    1115                1120

<210> SEQ ID NO 34
<211> LENGTH: 453
<212> TYPE: PRT
<213> ORGANISM: Artificial
<220> FEATURE:
<223> OTHER INFORMATION: Heavy chain 1 of <VEGF-ANG-2> CrossMAb IgG1
      with AAA mutations (VEGFang2-0012)

<400> SEQUENCE: 34

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Asp Phe Thr His Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro Tyr Tyr Tyr Gly Thr Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ala Ser Arg Thr Pro Glu Val Thr Cys Val Val Val Asp Val
            260                 265                 270

Ser His Glu Asp Pro Glu Val Lys Phe Asn Trp Tyr Val Asp Gly Val

```
                275                 280                 285
Glu Val His Asn Ala Lys Thr Lys Pro Arg Glu Glu Gln Tyr Asn Ser
    290                 295                 300

Thr Tyr Arg Val Val Ser Val Leu Thr Val Leu Ala Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Cys Arg Asp Glu Leu Thr Lys Asn Gln
        355                 360                 365

Val Ser Leu Trp Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn Ala Tyr Thr Gln Lys Ser Leu Ser
        435                 440                 445

Leu Ser Pro Gly Lys
    450

<210> SEQ ID NO 35
<211> LENGTH: 463
<212> TYPE: PRT
<213> ORGANISM: Artificial
<220> FEATURE:
<223> OTHER INFORMATION: Heavy chain 2 of <VEGF-ANG-2> CrossMAb IgG1
      with AAA mutations (VEGFang2-0012)

<400> SEQUENCE: 35

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Pro Asn Pro Tyr Tyr Asp Ser Ser Gly Tyr Tyr Tyr
            100                 105                 110

Pro Gly Ala Phe Asp Ile Trp Gly Gln Gly Thr Met Val Thr Val Ser
        115                 120                 125

Ser Ala Ser Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175
```

Gln Ser Gly Asn Ser Gln Glu Ser Val Thr Glu Gln Asp Ser Lys Asp
                180                 185                 190

Ser Thr Tyr Ser Leu Ser Ser Thr Leu Thr Leu Ser Lys Ala Asp Tyr
            195                 200                 205

Glu Lys His Lys Val Tyr Ala Cys Glu Val Thr His Gln Gly Leu Ser
210                 215                 220

Ser Pro Val Thr Lys Ser Phe Asn Arg Gly Glu Cys Asp Lys Thr His
225                 230                 235                 240

Thr Cys Pro Pro Cys Pro Ala Pro Glu Leu Leu Gly Gly Pro Ser Val
                245                 250                 255

Phe Leu Phe Pro Pro Lys Pro Lys Asp Thr Leu Met Ala Ser Arg Thr
            260                 265                 270

Pro Glu Val Thr Cys Val Val Val Asp Val Ser His Glu Asp Pro Glu
        275                 280                 285

Val Lys Phe Asn Trp Tyr Val Asp Gly Val Glu Val His Asn Ala Lys
    290                 295                 300

Thr Lys Pro Arg Glu Glu Gln Tyr Asn Ser Thr Tyr Arg Val Val Ser
305                 310                 315                 320

Val Leu Thr Val Leu Ala Gln Asp Trp Leu Asn Gly Lys Glu Tyr Lys
                325                 330                 335

Cys Lys Val Ser Asn Lys Ala Leu Pro Ala Pro Ile Glu Lys Thr Ile
            340                 345                 350

Ser Lys Ala Lys Gly Gln Pro Arg Glu Pro Gln Val Cys Thr Leu Pro
        355                 360                 365

Pro Ser Arg Asp Glu Leu Thr Lys Asn Gln Val Ser Leu Ser Cys Ala
    370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Val Leu Asp Ser
                405                 410                 415

Asp Gly Ser Phe Phe Leu Val Ser Lys Leu Thr Val Asp Lys Ser Arg
            420                 425                 430

Trp Gln Gln Gly Asn Val Phe Ser Cys Ser Val Met His Glu Ala Leu
        435                 440                 445

His Asn Ala Tyr Thr Gln Lys Ser Leu Ser Leu Ser Pro Gly Lys
    450                 455                 460

<210> SEQ ID NO 36
<211> LENGTH: 214
<212> TYPE: PRT
<213> ORGANISM: Artificial
<220> FEATURE:
<223> OTHER INFORMATION: Light chain 1 of <VEGF-ANG-2> CrossMAb IgG1
      with AAA mutations (VEGFang2-0012)

<400> SEQUENCE: 36

Asp Ile Gln Leu Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65              70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 37
<211> LENGTH: 213
<212> TYPE: PRT
<213> ORGANISM: Artificial
<220> FEATURE:
<223> OTHER INFORMATION: Light chain 2 of <VEGF-ANG-2> CrossMAb IgG1
      with AAA mutations (VEGF-Ang2-0012)

<400> SEQUENCE: 37

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Trp Val Phe Gly Gly Gly Thr Lys Leu Thr Val Leu Ser Ser Ala Ser
            100                 105                 110

Thr Lys Gly Pro Ser Val Phe Pro Leu Ala Pro Ser Ser Lys Ser Thr
        115                 120                 125

Ser Gly Gly Thr Ala Ala Leu Gly Cys Leu Val Lys Asp Tyr Phe Pro
    130                 135                 140

Glu Pro Val Thr Val Ser Trp Asn Ser Gly Ala Leu Thr Ser Gly Val
145                 150                 155                 160

His Thr Phe Pro Ala Val Leu Gln Ser Ser Gly Leu Tyr Ser Leu Ser
                165                 170                 175

Ser Val Val Thr Val Pro Ser Ser Ser Leu Gly Thr Gln Thr Tyr Ile
            180                 185                 190

Cys Asn Val Asn His Lys Pro Ser Asn Thr Lys Val Asp Lys Lys Val
        195                 200                 205

Glu Pro Lys Ser Cys

<210> SEQ ID NO 38
<211> LENGTH: 453
<212> TYPE: PRT
<213> ORGANISM: Artificial
<220> FEATURE:
<223> OTHER INFORMATION: Heavy chain 1 of <VEGF-ANG-2> CrossMAb IgG1 with AAA mutations and P329G LALA mutations (VEGFang2-0016)

<400> SEQUENCE: 38

| | | | | | | | | | | | | | | |
|---|---|---|---|---|---|---|---|---|---|---|---|---|---|---|
| Glu | Val | Gln | Leu | Val | Glu | Ser | Gly | Gly | Gly | Leu | Val | Gln | Pro | Gly |
| 1 | | | | 5 | | | | | 10 | | | | | 15 |
| Ser | Leu | Arg | Leu | Ser | Cys | Ala | Ala | Ser | Gly | Tyr | Asp | Phe | Thr | His | Tyr |
| | | | 20 | | | | | 25 | | | | | 30 | | |
| Gly | Met | Asn | Trp | Val | Arg | Gln | Ala | Pro | Gly | Lys | Gly | Leu | Glu | Trp | Val |
| | | | 35 | | | | | 40 | | | | | 45 | | |
| Gly | Trp | Ile | Asn | Thr | Tyr | Thr | Gly | Glu | Pro | Thr | Tyr | Ala | Ala | Asp | Phe |
| | 50 | | | | | 55 | | | | | 60 | | | | |
| Lys | Arg | Arg | Phe | Thr | Phe | Ser | Leu | Asp | Thr | Ser | Lys | Ser | Thr | Ala | Tyr |
| 65 | | | | | 70 | | | | | 75 | | | | | 80 |
| Leu | Gln | Met | Asn | Ser | Leu | Arg | Ala | Glu | Asp | Thr | Ala | Val | Tyr | Tyr | Cys |
| | | | | 85 | | | | | 90 | | | | | 95 | |
| Ala | Lys | Tyr | Pro | Tyr | Tyr | Tyr | Gly | Thr | Ser | His | Trp | Tyr | Phe | Asp | Val |
| | | | 100 | | | | | 105 | | | | | 110 | | |
| Trp | Gly | Gln | Gly | Thr | Leu | Val | Thr | Val | Ser | Ser | Ala | Ser | Thr | Lys | Gly |
| | | | 115 | | | | | 120 | | | | | 125 | | |
| Pro | Ser | Val | Phe | Pro | Leu | Ala | Pro | Ser | Ser | Lys | Ser | Thr | Ser | Gly | Gly |
| | 130 | | | | | 135 | | | | | 140 | | | | |
| Thr | Ala | Ala | Leu | Gly | Cys | Leu | Val | Lys | Asp | Tyr | Phe | Pro | Glu | Pro | Val |
| 145 | | | | | 150 | | | | | 155 | | | | | 160 |
| Thr | Val | Ser | Trp | Asn | Ser | Gly | Ala | Leu | Thr | Ser | Gly | Val | His | Thr | Phe |
| | | | | 165 | | | | | 170 | | | | | 175 | |
| Pro | Ala | Val | Leu | Gln | Ser | Ser | Gly | Leu | Tyr | Ser | Leu | Ser | Ser | Val | Val |
| | | | 180 | | | | | 185 | | | | | 190 | | |
| Thr | Val | Pro | Ser | Ser | Ser | Leu | Gly | Thr | Gln | Thr | Tyr | Ile | Cys | Asn | Val |
| | | | 195 | | | | | 200 | | | | | 205 | | |
| Asn | His | Lys | Pro | Ser | Asn | Thr | Lys | Val | Asp | Lys | Lys | Val | Glu | Pro | Lys |
| | 210 | | | | | 215 | | | | | 220 | | | | |
| Ser | Cys | Asp | Lys | Thr | His | Thr | Cys | Pro | Pro | Cys | Pro | Ala | Pro | Glu | Ala |
| 225 | | | | | 230 | | | | | 235 | | | | | 240 |
| Ala | Gly | Gly | Pro | Ser | Val | Phe | Leu | Phe | Pro | Pro | Lys | Pro | Lys | Asp | Thr |
| | | | | 245 | | | | | 250 | | | | | 255 | |
| Leu | Met | Ala | Ser | Arg | Thr | Pro | Glu | Val | Thr | Cys | Val | Val | Val | Asp | Val |
| | | | 260 | | | | | 265 | | | | | 270 | | |
| Ser | His | Glu | Asp | Pro | Glu | Val | Lys | Phe | Asn | Trp | Tyr | Val | Asp | Gly | Val |
| | | | 275 | | | | | 280 | | | | | 285 | | |
| Glu | Val | His | Asn | Ala | Lys | Thr | Lys | Pro | Arg | Glu | Glu | Gln | Tyr | Asn | Ser |
| | 290 | | | | | 295 | | | | | 300 | | | | |
| Thr | Tyr | Arg | Val | Val | Ser | Val | Leu | Thr | Val | Leu | Ala | Gln | Asp | Trp | Leu |
| 305 | | | | | 310 | | | | | 315 | | | | | 320 |
| Asn | Gly | Lys | Glu | Tyr | Lys | Cys | Lys | Val | Ser | Asn | Lys | Ala | Leu | Gly | Ala |
| | | | | 325 | | | | | 330 | | | | | 335 | |
| Pro | Ile | Glu | Lys | Thr | Ile | Ser | Lys | Ala | Lys | Gly | Gln | Pro | Arg | Glu | Pro |
| | | | 340 | | | | | 345 | | | | | 350 | | |

Gln Val Tyr Thr Leu Pro Pro Cys Arg Asp Glu Leu Thr Lys Asn Gln
            355                 360                 365

Val Ser Leu Trp Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
            405                 410                 415

Thr Val Asp Lys Ser Arg Trp Gln Gln Gly Asn Val Phe Ser Cys Ser
            420                 425                 430

Val Met His Glu Ala Leu His Asn Ala Tyr Thr Gln Lys Ser Leu Ser
            435                 440                 445

Leu Ser Pro Gly Lys
            450

<210> SEQ ID NO 39
<211> LENGTH: 463
<212> TYPE: PRT
<213> ORGANISM: Artificial
<220> FEATURE:
<223> OTHER INFORMATION: Heavy chain 2 of <VEGF-ANG-2> CrossMAb IgG1
      with AAA mutations and P329G LALA mutations (VEGFang2-0016)

<400> SEQUENCE: 39

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
            85                  90                  95

Ala Arg Ser Pro Asn Pro Tyr Tyr Asp Ser Ser Gly Tyr Tyr Tyr
            100                 105                 110

Pro Gly Ala Phe Asp Ile Trp Gly Gln Gly Thr Met Val Thr Val Ser
            115                 120                 125

Ser Ala Ser Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
            165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
            195                 200                 205

Glu Lys His Lys Val Tyr Ala Cys Glu Val Thr His Gln Gly Leu Ser
            210                 215                 220

Ser Pro Val Thr Lys Ser Phe Asn Arg Gly Glu Cys Asp Lys Thr His
225                 230                 235                 240

Thr Cys Pro Pro Cys Pro Ala Pro Glu Ala Ala Gly Gly Pro Ser Val
            245                 250                 255

```
Phe Leu Phe Pro Pro Lys Pro Lys Asp Thr Leu Met Ala Ser Arg Thr
            260                 265                 270

Pro Glu Val Thr Cys Val Val Val Asp Val Ser His Glu Asp Pro Glu
            275                 280                 285

Val Lys Phe Asn Trp Tyr Val Asp Gly Val Glu Val His Asn Ala Lys
            290                 295                 300

Thr Lys Pro Arg Glu Glu Gln Tyr Asn Ser Thr Tyr Arg Val Val Ser
305                 310                 315                 320

Val Leu Thr Val Leu Ala Gln Asp Trp Leu Asn Gly Lys Glu Tyr Lys
            325                 330                 335

Cys Lys Val Ser Asn Lys Ala Leu Gly Ala Pro Ile Glu Lys Thr Ile
            340                 345                 350

Ser Lys Ala Lys Gly Gln Pro Arg Glu Pro Gln Val Cys Thr Leu Pro
            355                 360                 365

Pro Ser Arg Asp Glu Leu Thr Lys Asn Gln Val Ser Leu Ser Cys Ala
            370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Val Leu Asp Ser
            405                 410                 415

Asp Gly Ser Phe Phe Leu Val Ser Lys Leu Thr Val Asp Lys Ser Arg
            420                 425                 430

Trp Gln Gln Gly Asn Val Phe Ser Cys Ser Val Met His Glu Ala Leu
            435                 440                 445

His Asn Ala Tyr Thr Gln Lys Ser Leu Ser Leu Ser Pro Gly Lys
            450                 455                 460

<210> SEQ ID NO 40
<211> LENGTH: 214
<212> TYPE: PRT
<213> ORGANISM: Artificial
<220> FEATURE:
<223> OTHER INFORMATION: Light chain 1 of <VEGF-ANG-2> CrossMAb IgG1
      with AAA mutations and P329G LALA mutations (VEGFang2-0016)

<400> SEQUENCE: 40

Asp Ile Gln Leu Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
            35                  40                  45

Tyr Phe Thr Ser Ser Leu His Ser Gly Val Pro Ser Arg Phe Ser Gly
            50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
            85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
```

145                 150                 155                 160
Glu Ser Val Thr Glu Gln Asp Ser Lys Asp Ser Thr Tyr Ser Leu Ser
                    165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 41
<211> LENGTH: 213
<212> TYPE: PRT
<213> ORGANISM: Artificial
<220> FEATURE:
<223> OTHER INFORMATION: Light chain 2 of <VEGF-ANG-2> CrossMAb IgG1
      with AAA mutations and P329G LALA mutations (VEGFang2-0016)

<400> SEQUENCE: 41

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Trp Val Phe Gly Gly Gly Thr Lys Leu Thr Val Leu Ser Ser Ala Ser
            100                 105                 110

Thr Lys Gly Pro Ser Val Phe Pro Leu Ala Pro Ser Ser Lys Ser Thr
        115                 120                 125

Ser Gly Gly Thr Ala Ala Leu Gly Cys Leu Val Lys Asp Tyr Phe Pro
    130                 135                 140

Glu Pro Val Thr Val Ser Trp Asn Ser Gly Ala Leu Thr Ser Gly Val
145                 150                 155                 160

His Thr Phe Pro Ala Val Leu Gln Ser Ser Gly Leu Tyr Ser Leu Ser
                165                 170                 175

Ser Val Val Thr Val Pro Ser Ser Ser Leu Gly Thr Gln Thr Tyr Ile
            180                 185                 190

Cys Asn Val Asn His Lys Pro Ser Asn Thr Lys Val Asp Lys Lys Val
        195                 200                 205

Glu Pro Lys Ser Cys
    210

<210> SEQ ID NO 42
<211> LENGTH: 450
<212> TYPE: PRT
<213> ORGANISM: Artificial
<220> FEATURE:
<223> OTHER INFORMATION: Heavy chain 1 of <VEGF-ANG-2> CrossMAb IgG4
      with AAA mutations and with SPLE mutations

<400> SEQUENCE: 42

Glu Val Gln Leu Val Glu Ser Gly Gly Gly Leu Val Gln Pro Gly Gly

-continued

```
1               5                   10                  15
Ser Leu Arg Leu Ser Cys Ala Ala Ser Gly Tyr Asp Phe Thr His Tyr
                20                  25                  30
Gly Met Asn Trp Val Arg Gln Ala Pro Gly Lys Gly Leu Glu Trp Val
                35                  40                  45
Gly Trp Ile Asn Thr Tyr Thr Gly Glu Pro Thr Tyr Ala Ala Asp Phe
            50                  55                  60
Lys Arg Arg Phe Thr Phe Ser Leu Asp Thr Ser Lys Ser Thr Ala Tyr
65                  70                  75                  80
Leu Gln Met Asn Ser Leu Arg Ala Glu Asp Thr Ala Val Tyr Tyr Cys
                85                  90                  95
Ala Lys Tyr Pro Tyr Tyr Gly Thr Ser His Trp Tyr Phe Asp Val
                100                 105                 110
Trp Gly Gln Gly Thr Leu Val Thr Val Ser Ser Ala Ser Thr Lys Gly
                115                 120                 125
Pro Ser Val Phe Pro Leu Ala Pro Cys Ser Arg Ser Thr Ser Glu Ser
            130                 135                 140
Thr Ala Leu Gly Cys Leu Val Lys Asp Tyr Phe Pro Glu Pro Val
145                 150                 155                 160
Thr Val Ser Trp Asn Ser Gly Ala Leu Thr Ser Gly Val His Thr Phe
                165                 170                 175
Pro Ala Val Leu Gln Ser Ser Gly Leu Tyr Ser Leu Ser Ser Val Val
                180                 185                 190
Thr Val Pro Ser Ser Ser Leu Gly Thr Lys Thr Tyr Thr Cys Asn Val
                195                 200                 205
Asp His Lys Pro Ser Asn Thr Lys Val Asp Lys Arg Val Glu Ser Lys
                210                 215                 220
Tyr Gly Pro Pro Cys Pro Pro Cys Pro Ala Pro Glu Phe Glu Gly Gly
225                 230                 235                 240
Pro Ser Val Phe Leu Phe Pro Pro Lys Pro Lys Asp Thr Leu Met Ala
                245                 250                 255
Ser Arg Thr Pro Glu Val Thr Cys Val Val Val Asp Val Ser Gln Glu
                260                 265                 270
Asp Pro Glu Val Gln Phe Asn Trp Tyr Val Asp Gly Val Glu Val His
                275                 280                 285
Asn Ala Lys Thr Lys Pro Arg Glu Glu Gln Phe Asn Ser Thr Tyr Arg
                290                 295                 300
Val Val Ser Val Leu Thr Val Leu Ala Gln Asp Trp Leu Asn Gly Lys
305                 310                 315                 320
Glu Tyr Lys Cys Lys Val Ser Asn Lys Gly Leu Pro Ser Ser Ile Glu
                325                 330                 335
Lys Thr Ile Ser Lys Ala Lys Gly Gln Pro Arg Glu Pro Gln Val Cys
                340                 345                 350
Thr Leu Pro Pro Ser Gln Glu Glu Met Thr Lys Asn Gln Val Ser Leu
                355                 360                 365
Ser Cys Ala Val Lys Gly Phe Tyr Pro Ser Asp Ile Ala Val Glu Trp
                370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Val Ser Arg Leu Thr Val Asp
                405                 410                 415
Lys Ser Arg Trp Gln Glu Gly Asn Val Phe Ser Cys Ser Val Met His
                420                 425                 430
```

-continued

```
Glu Ala Leu His Asn Ala Tyr Thr Gln Lys Ser Leu Ser Leu Ser Leu
        435                 440                 445
Gly Lys
    450

<210> SEQ ID NO 43
<211> LENGTH: 460
<212> TYPE: PRT
<213> ORGANISM: Artificial
<220> FEATURE:
<223> OTHER INFORMATION: Heavy chain 2 of <VEGF-ANG-2> CrossMAb IgG4
      with AAA mutations and with SPLE mutations

<400> SEQUENCE: 43

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Pro Asn Pro Tyr Tyr Tyr Asp Ser Ser Gly Tyr Tyr Tyr
            100                 105                 110

Pro Gly Ala Phe Asp Ile Trp Gly Gln Gly Thr Met Val Thr Val Ser
        115                 120                 125

Ser Ala Ser Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys Pro Pro Cys Pro
225                 230                 235                 240

Pro Cys Pro Ala Pro Glu Phe Glu Gly Gly Pro Ser Val Phe Leu Phe
                245                 250                 255

Pro Pro Lys Pro Lys Asp Thr Leu Met Ala Ser Arg Thr Pro Glu Val
            260                 265                 270

Thr Cys Val Val Val Asp Val Ser Gln Glu Asp Pro Glu Val Gln Phe
        275                 280                 285

Asn Trp Tyr Val Asp Gly Val Glu Val His Asn Ala Lys Thr Lys Pro
    290                 295                 300

Arg Glu Glu Gln Phe Asn Ser Thr Tyr Arg Val Val Ser Val Leu Thr
305                 310                 315                 320

Val Leu Ala Gln Asp Trp Leu Asn Gly Lys Glu Tyr Lys Cys Lys Val
```

```
                325                 330                 335
Ser Asn Lys Gly Leu Pro Ser Ser Ile Glu Lys Thr Ile Ser Lys Ala
            340                 345                 350
Lys Gly Gln Pro Arg Glu Pro Gln Val Tyr Thr Leu Pro Pro Cys Gln
            355                 360                 365
Glu Glu Met Thr Lys Asn Gln Val Ser Leu Trp Cys Leu Val Lys Gly
            370                 375                 380
Phe Tyr Pro Ser Asp Ile Ala Val Glu Trp Glu Ser Asn Gly Gln Pro
385                 390                 395                 400
Glu Asn Asn Tyr Lys Thr Thr Pro Pro Val Leu Asp Ser Asp Gly Ser
                405                 410                 415
Phe Phe Leu Tyr Ser Arg Leu Thr Val Asp Lys Ser Arg Trp Gln Glu
                420                 425                 430
Gly Asn Val Phe Ser Cys Ser Val Met His Glu Ala Leu His Asn Ala
                435                 440                 445
Tyr Thr Gln Lys Ser Leu Ser Leu Ser Leu Gly Lys
            450                 455                 460

<210> SEQ ID NO 44
<211> LENGTH: 214
<212> TYPE: PRT
<213> ORGANISM: Artificial
<220> FEATURE:
<223> OTHER INFORMATION: Light chain 1 of <VEGF-ANG-2> CrossMAb IgG4
      with AAA mutations and with SPLE mutations

<400> SEQUENCE: 44

Asp Ile Gln Leu Thr Gln Ser Pro Ser Ser Leu Ser Ala Ser Val Gly
1               5                   10                  15
Asp Arg Val Thr Ile Thr Cys Ser Ala Ser Gln Asp Ile Ser Asn Tyr
            20                  25                  30
Leu Asn Trp Tyr Gln Gln Lys Pro Gly Lys Ala Pro Lys Val Leu Ile
        35                  40                  45
Tyr Phe Thr Ser Ser Leu His Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Tyr Ser Thr Val Pro Trp
                85                  90                  95
Thr Phe Gly Gln Gly Thr Lys Val Glu Ile Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210
```

```
<210> SEQ ID NO 45
<211> LENGTH: 213
<212> TYPE: PRT
<213> ORGANISM: Artificial
<220> FEATURE:
<223> OTHER INFORMATION: Light chain 2 of <VEGF-ANG-2> CrossMAb IgG4
      with AAA mutations and with SPLE mutations

<400> SEQUENCE: 45

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Trp Val Phe Gly Gly Gly Thr Lys Leu Thr Val Leu Ser Ser Ala Ser
            100                 105                 110

Thr Lys Gly Pro Ser Val Phe Pro Leu Ala Pro Cys Ser Arg Ser Thr
        115                 120                 125

Ser Glu Ser Thr Ala Ala Leu Gly Cys Leu Val Lys Asp Tyr Phe Pro
    130                 135                 140

Glu Pro Val Thr Val Ser Trp Asn Ser Gly Ala Leu Thr Ser Gly Val
145                 150                 155                 160

His Thr Phe Pro Ala Val Leu Gln Ser Ser Gly Leu Tyr Ser Leu Ser
                165                 170                 175

Ser Val Val Thr Val Pro Ser Ser Ser Leu Gly Thr Lys Thr Tyr Thr
            180                 185                 190

Cys Asn Val Asp His Lys Pro Ser Asn Thr Lys Val Asp Lys Arg Val
        195                 200                 205

Glu Ser Lys Tyr Gly
    210

<210> SEQ ID NO 46
<211> LENGTH: 453
<212> TYPE: PRT
<213> ORGANISM: Artificial
<220> FEATURE:
<223> OTHER INFORMATION: Heavy chain 1 of <VEGF-ANG-2> OAscFab IgG1 with
      AAA mutations

<400> SEQUENCE: 46

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Asp Phe Thr His Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80
```

```
Leu Gln Met Asn Ser Leu Arg Ala Glu Asp Thr Ala Val Tyr Tyr Cys
                85                  90                  95

Ala Lys Tyr Pro Tyr Tyr Gly Thr Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ala Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu Ala Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Cys Thr Leu Pro Pro Ser Arg Asp Glu Leu Thr Lys Asn Gln
        355                 360                 365

Val Ser Leu Ser Cys Ala Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Val Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn Ala Tyr Thr Gln Lys Ser Leu Ser
        435                 440                 445

Leu Ser Pro Gly Lys
    450

<210> SEQ ID NO 47
<211> LENGTH: 705
<212> TYPE: PRT
<213> ORGANISM: Artificial
<220> FEATURE:
<223> OTHER INFORMATION: Heavy chain 2 of <VEGF-ANG-2> OAscFab IgG1 with
```

AAA mutations

<400> SEQUENCE: 47

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Trp Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser Gly Gly Gly Ser Gly Gly Gly Gly Ser
    210                 215                 220

Gly Gly Gly Gly Ser Gly Gly Gly Ser Gly Gly Gly Ser Gly
225                 230                 235                 240

Gly Gly Gly Ser Gly Gly Gln Val Gln Leu Val Glu Ser Gly Ala Glu
            245                 250                 255

Val Lys Lys Pro Gly Ala Ser Val Lys Val Ser Cys Lys Ala Ser Gly
        260                 265                 270

Tyr Thr Phe Thr Gly Tyr Tyr Met His Trp Val Arg Gln Ala Pro Gly
    275                 280                 285

Gln Gly Leu Glu Trp Met Gly Trp Ile Asn Pro Asn Ser Gly Gly Thr
290                 295                 300

Asn Tyr Ala Gln Lys Phe Gln Gly Arg Val Thr Met Thr Arg Asp Thr
305                 310                 315                 320

Ser Ile Ser Thr Ala Tyr Met Glu Leu Ser Arg Leu Arg Ser Asp Asp
                325                 330                 335

Thr Ala Val Tyr Tyr Cys Ala Arg Ser Pro Asn Pro Tyr Tyr Tyr Asp
            340                 345                 350

Ser Ser Gly Tyr Tyr Tyr Pro Gly Ala Phe Asp Ile Trp Gly Gln Gly
        355                 360                 365

Thr Met Val Thr Val Ser Ser Ala Ser Thr Lys Gly Pro Ser Val Phe
    370                 375                 380

Pro Leu Ala Pro Ser Ser Lys Ser Thr Ser Gly Gly Thr Ala Ala Leu
385                 390                 395                 400

```
Gly Cys Leu Val Lys Asp Tyr Phe Pro Glu Pro Val Thr Val Ser Trp
            405                 410                 415

Asn Ser Gly Ala Leu Thr Ser Gly Val His Thr Phe Pro Ala Val Leu
            420                 425                 430

Gln Ser Ser Gly Leu Tyr Ser Leu Ser Ser Val Val Thr Val Pro Ser
            435                 440                 445

Ser Ser Leu Gly Thr Gln Thr Tyr Ile Cys Asn Val Asn His Lys Pro
            450                 455                 460

Ser Asn Thr Lys Val Asp Lys Lys Val Glu Pro Lys Ser Cys Asp Lys
465                 470                 475                 480

Thr His Thr Cys Pro Pro Cys Pro Ala Pro Glu Leu Leu Gly Gly Pro
            485                 490                 495

Ser Val Phe Leu Phe Pro Pro Lys Pro Lys Asp Thr Leu Met Ala Ser
            500                 505                 510

Arg Thr Pro Glu Val Thr Cys Val Val Val Asp Val Ser His Glu Asp
            515                 520                 525

Pro Glu Val Lys Phe Asn Trp Tyr Val Asp Gly Val Glu Val His Asn
            530                 535                 540

Ala Lys Thr Lys Pro Arg Glu Glu Gln Tyr Asn Ser Thr Tyr Arg Val
545                 550                 555                 560

Val Ser Val Leu Thr Val Leu Ala Gln Asp Trp Leu Asn Gly Lys Glu
            565                 570                 575

Tyr Lys Cys Lys Val Ser Asn Lys Ala Leu Pro Ala Pro Ile Glu Lys
            580                 585                 590

Thr Ile Ser Lys Ala Lys Gly Gln Pro Arg Glu Pro Gln Val Tyr Thr
            595                 600                 605

Leu Pro Pro Cys Arg Asp Glu Leu Thr Lys Asn Gln Val Ser Leu Trp
            610                 615                 620

Cys Leu Val Lys Gly Phe Tyr Pro Ser Asp Ile Ala Val Glu Trp Glu
625                 630                 635                 640

Ser Asn Gly Gln Pro Glu Asn Asn Tyr Lys Thr Thr Pro Pro Val Leu
            645                 650                 655

Asp Ser Asp Gly Ser Phe Phe Leu Tyr Ser Lys Leu Thr Val Asp Lys
            660                 665                 670

Ser Arg Trp Gln Gln Gly Asn Val Phe Ser Cys Ser Val Met His Glu
            675                 680                 685

Ala Leu His Asn Ala Tyr Thr Gln Lys Ser Leu Ser Leu Ser Pro Gly
            690                 695                 700

Lys
705

<210> SEQ ID NO 48
<211> LENGTH: 214
<212> TYPE: PRT
<213> ORGANISM: Artificial
<220> FEATURE:
<223> OTHER INFORMATION: Light chain 1 of <VEGF-ANG-2> OAscFab IgG1 with
      AAA mutations

<400> SEQUENCE: 48

Asp Ile Gln Leu Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
            35                  40                  45
```

Tyr Phe Thr Ser Ser Leu His Ser Gly Val Pro Ser Arg Phe Ser Gly
            50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 49
<211> LENGTH: 450
<212> TYPE: PRT
<213> ORGANISM: Artificial
<220> FEATURE:
<223> OTHER INFORMATION: Heavy chain 1 of <VEGF-ANG-2> OAscFab IgG4 with
      AAA mutations and with SPLE mutations

<400> SEQUENCE: 49

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Asp Phe Thr His Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro Tyr Tyr Gly Thr Ser His Trp Tyr Phe Asp Val
            100                 105                 110

Trp Gly Gln Gly Thr Leu Val Thr Val Ser Ser Ala Ser Thr Lys Gly
            115                 120                 125

Pro Ser Val Phe Pro Leu Ala Pro Cys Ser Arg Ser Thr Ser Glu Ser
130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val

-continued

```
                180                 185                 190
Thr Val Pro Ser Ser Leu Gly Thr Lys Thr Tyr Thr Cys Asn Val
            195                 200                 205
Asp His Lys Pro Ser Asn Thr Lys Val Asp Lys Arg Val Glu Ser Lys
        210                 215                 220
Tyr Gly Pro Pro Cys Pro Cys Pro Ala Pro Glu Phe Glu Gly Gly
225                 230                 235                 240
Pro Ser Val Phe Leu Phe Pro Pro Lys Pro Lys Asp Thr Leu Met Ala
            245                 250                 255
Ser Arg Thr Pro Glu Val Thr Cys Val Val Val Asp Val Ser Gln Glu
            260                 265                 270
Asp Pro Glu Val Gln Phe Asn Trp Tyr Val Asp Gly Val Glu Val His
            275                 280                 285
Asn Ala Lys Thr Lys Pro Arg Glu Glu Gln Phe Asn Ser Thr Tyr Arg
            290                 295                 300
Val Val Ser Val Leu Thr Val Leu Ala Gln Asp Trp Leu Asn Gly Lys
305                 310                 315                 320
Glu Tyr Lys Cys Lys Val Ser Asn Lys Gly Leu Pro Ser Ser Ile Glu
                325                 330                 335
Lys Thr Ile Ser Lys Ala Lys Gly Gln Pro Arg Glu Pro Gln Val Cys
            340                 345                 350
Thr Leu Pro Pro Ser Gln Glu Glu Met Thr Lys Asn Gln Val Ser Leu
            355                 360                 365
Ser Cys Ala Val Lys Gly Phe Tyr Pro Ser Asp Ile Ala Val Glu Trp
370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Val Ser Arg Leu Thr Val Asp
                405                 410                 415
Lys Ser Arg Trp Gln Glu Gly Asn Val Phe Ser Cys Ser Val Met His
                420                 425                 430
Glu Ala Leu His Asn Ala Tyr Thr Gln Lys Ser Leu Ser Leu Ser Leu
            435                 440                 445
Gly Lys
    450

<210> SEQ ID NO 50
<211> LENGTH: 702
<212> TYPE: PRT
<213> ORGANISM: Artificial
<220> FEATURE:
<223> OTHER INFORMATION: Heavy chain 2 of <VEGF-ANG-2> OAscFab IgG4 with
      AAA mutations and with SPLE mutations

<400> SEQUENCE: 50

Ser Tyr Val Leu Thr Gln Pro Pro Ser Val Ser Val Ala Pro Gly Gln
1               5                   10                  15
Thr Ala Arg Ile Thr Cys Gly Gly Asn Asn Ile Gly Ser Lys Ser Val
            20                  25                  30
His Trp Tyr Gln Gln Lys Pro Gly Gln Ala Pro Val Leu Val Val Tyr
        35                  40                  45
Asp Asp Ser Asp Arg Pro Ser Gly Ile Pro Glu Arg Phe Ser Gly Ser
    50                  55                  60
Asn Ser Gly Asn Thr Ala Thr Leu Thr Ile Ser Arg Val Glu Ala Gly
65                  70                  75                  80
```

-continued

```
Asp Glu Ala Asp Tyr Tyr Cys Gln Val Trp Asp Ser Ser Ser Asp His
                 85                  90                  95
Trp Val Phe Gly Gly Gly Thr Lys Leu Thr Val Leu Gly Gln Pro Lys
            100                 105                 110
Ala Ala Pro Ser Val Thr Leu Phe Pro Pro Ser Ser Glu Glu Leu Gln
        115                 120                 125
Ala Asn Lys Ala Thr Leu Val Cys Leu Ile Ser Asp Phe Tyr Pro Gly
    130                 135                 140
Ala Val Thr Val Ala Trp Lys Ala Asp Ser Ser Pro Val Lys Ala Gly
145                 150                 155                 160
Val Glu Thr Thr Thr Pro Ser Lys Gln Ser Asn Asn Lys Tyr Ala Ala
                165                 170                 175
Ser Ser Tyr Leu Ser Leu Thr Pro Glu Gln Trp Lys Ser His Arg Ser
            180                 185                 190
Tyr Ser Cys Gln Val Thr His Glu Gly Ser Thr Val Glu Lys Thr Val
        195                 200                 205
Ala Pro Thr Glu Cys Ser Gly Gly Gly Ser Gly Gly Gly Gly Gly Ser
    210                 215                 220
Gly Gly Gly Gly Ser Gly Gly Gly Ser Gly Gly Gly Gly Ser Gly
225                 230                 235                 240
Gly Gly Gly Ser Gly Gly Gln Val Gln Leu Val Glu Ser Gly Ala Glu
                245                 250                 255
Val Lys Lys Pro Gly Ala Ser Val Lys Val Ser Cys Lys Ala Ser Gly
            260                 265                 270
Tyr Thr Phe Thr Gly Tyr Tyr Met His Trp Val Arg Gln Ala Pro Gly
        275                 280                 285
Gln Gly Leu Glu Trp Met Gly Trp Ile Asn Pro Asn Ser Gly Gly Thr
    290                 295                 300
Asn Tyr Ala Gln Lys Phe Gln Gly Arg Val Thr Met Thr Arg Asp Thr
305                 310                 315                 320
Ser Ile Ser Thr Ala Tyr Met Glu Leu Ser Arg Leu Arg Ser Asp Asp
                325                 330                 335
Thr Ala Val Tyr Tyr Cys Ala Arg Ser Pro Asn Pro Tyr Tyr Tyr Asp
            340                 345                 350
Ser Ser Gly Tyr Tyr Tyr Pro Gly Ala Phe Asp Ile Trp Gly Gln Gly
        355                 360                 365
Thr Met Val Thr Val Ser Ser Ala Ser Thr Lys Gly Pro Ser Val Phe
    370                 375                 380
Pro Leu Ala Pro Cys Ser Arg Ser Thr Ser Glu Ser Thr Ala Ala Leu
385                 390                 395                 400
Gly Cys Leu Val Lys Asp Tyr Phe Pro Glu Pro Val Thr Val Ser Trp
                405                 410                 415
Asn Ser Gly Ala Leu Thr Ser Gly Val His Thr Phe Pro Ala Val Leu
            420                 425                 430
Gln Ser Ser Gly Leu Tyr Ser Leu Ser Ser Val Val Thr Val Pro Ser
        435                 440                 445
Ser Ser Leu Gly Thr Lys Thr Tyr Thr Cys Asn Val Asp His Lys Pro
    450                 455                 460
Ser Asn Thr Lys Val Asp Lys Arg Val Glu Ser Lys Tyr Gly Pro Pro
465                 470                 475                 480
Cys Pro Pro Cys Pro Ala Pro Glu Phe Glu Gly Gly Pro Ser Val Phe
                485                 490                 495
Leu Phe Pro Pro Lys Pro Lys Asp Thr Leu Met Ala Ser Arg Thr Pro
```

```
                500               505               510
Glu Val Thr Cys Val Val Val Asp Val Ser Gln Glu Asp Pro Glu Val
            515                   520                   525

Gln Phe Asn Trp Tyr Val Asp Gly Val Glu Val His Asn Ala Lys Thr
            530                   535                   540

Lys Pro Arg Glu Glu Gln Phe Asn Ser Thr Tyr Arg Val Val Ser Val
545                   550                   555                   560

Leu Thr Val Leu Ala Gln Asp Trp Leu Asn Gly Lys Glu Tyr Lys Cys
            565                   570                   575

Lys Val Ser Asn Lys Gly Leu Pro Ser Ser Ile Glu Lys Thr Ile Ser
            580                   585                   590

Lys Ala Lys Gly Gln Pro Arg Glu Pro Gln Val Tyr Thr Leu Pro Pro
            595                   600                   605

Cys Gln Glu Glu Met Thr Lys Asn Gln Val Ser Leu Trp Cys Leu Val
            610                   615                   620

Lys Gly Phe Tyr Pro Ser Asp Ile Ala Val Glu Trp Glu Ser Asn Gly
625                   630                   635                   640

Gln Pro Glu Asn Asn Tyr Lys Thr Thr Pro Pro Val Leu Asp Ser Asp
            645                   650                   655

Gly Ser Phe Phe Leu Tyr Ser Arg Leu Thr Val Asp Lys Ser Arg Trp
            660                   665                   670

Gln Glu Gly Asn Val Phe Ser Cys Ser Val Met His Glu Ala Leu His
            675                   680                   685

Asn Ala Tyr Thr Gln Lys Ser Leu Ser Leu Ser Leu Gly Lys
            690                   695                   700

<210> SEQ ID NO 51
<211> LENGTH: 214
<212> TYPE: PRT
<213> ORGANISM: Artificial
<220> FEATURE:
<223> OTHER INFORMATION: Light chain 1 of <VEGF-ANG-2> OAscFab IgG4 with
      AAA mutations and with SPLE mutations

<400> SEQUENCE: 51

Asp Ile Gln Leu Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160
```

-continued

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
        180                 185                 190

Ala Cys Glu Val Thr His Gln Gly Leu Ser Ser Pro Val Thr Lys Ser
    195                 200                 205

Phe Asn Arg Gly Glu Cys
    210

<210> SEQ ID NO 52
<211> LENGTH: 453
<212> TYPE: PRT
<213> ORGANISM: Artificial
<220> FEATURE:
<223> OTHER INFORMATION: Heavy chain 1 of <VEGF-ANG-2> CrossMAb IgG1
      wild type (without AAA mutations) (VEGFang2-0201)

<400> SEQUENCE: 52

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Asp Phe Thr His Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro Tyr Tyr Tyr Gly Thr Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

```
Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Cys Arg Asp Glu Leu Thr Lys Asn Gln
            355                 360                 365

Val Ser Leu Trp Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
            435                 440                 445

Leu Ser Pro Gly Lys
    450

<210> SEQ ID NO 53
<211> LENGTH: 463
<212> TYPE: PRT
<213> ORGANISM: Artificial
<220> FEATURE:
<223> OTHER INFORMATION: Heavy chain 2 of <VEGF-ANG-2> CrossMAb IgG1
      wild type (without AAA mutations) (VEGFang2-0201)

<400> SEQUENCE: 53

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Pro Asn Pro Tyr Tyr Tyr Asp Ser Ser Gly Tyr Tyr Tyr
            100                 105                 110

Pro Gly Ala Phe Asp Ile Trp Gly Gln Gly Thr Met Val Thr Val Ser
        115                 120                 125

Ser Ala Ser Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
```

```
            195                 200                 205
Glu Lys His Lys Val Tyr Ala Cys Glu Val Thr His Gln Gly Leu Ser
    210                 215                 220

Ser Pro Val Thr Lys Ser Phe Asn Arg Gly Glu Cys Asp Lys Thr His
225                 230                 235                 240

Thr Cys Pro Pro Cys Pro Ala Pro Glu Leu Leu Gly Gly Pro Ser Val
                245                 250                 255

Phe Leu Phe Pro Pro Lys Pro Lys Asp Thr Leu Met Ile Ser Arg Thr
                260                 265                 270

Pro Glu Val Thr Cys Val Val Val Asp Val Ser His Glu Asp Pro Glu
            275                 280                 285

Val Lys Phe Asn Trp Tyr Val Asp Gly Val Glu Val His Asn Ala Lys
        290                 295                 300

Thr Lys Pro Arg Glu Glu Gln Tyr Asn Ser Thr Tyr Arg Val Val Ser
305                 310                 315                 320

Val Leu Thr Val Leu His Gln Asp Trp Leu Asn Gly Lys Glu Tyr Lys
                325                 330                 335

Cys Lys Val Ser Asn Lys Ala Leu Pro Ala Pro Ile Glu Lys Thr Ile
                340                 345                 350

Ser Lys Ala Lys Gly Gln Pro Arg Glu Pro Gln Val Cys Thr Leu Pro
            355                 360                 365

Pro Ser Arg Asp Glu Leu Thr Lys Asn Gln Val Ser Leu Ser Cys Ala
        370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Val Leu Asp Ser
                405                 410                 415

Asp Gly Ser Phe Phe Leu Val Ser Lys Leu Thr Val Asp Lys Ser Arg
                420                 425                 430

Trp Gln Gln Gly Asn Val Phe Ser Cys Ser Val Met His Glu Ala Leu
            435                 440                 445

His Asn His Tyr Thr Gln Lys Ser Leu Ser Leu Ser Pro Gly Lys
        450                 455                 460

<210> SEQ ID NO 54
<211> LENGTH: 214
<212> TYPE: PRT
<213> ORGANISM: Artificial
<220> FEATURE:
<223> OTHER INFORMATION: Light chain 1 of <VEGF-ANG-2> CrossMAb IgG1
      wild type ( without AAA mutations) (VEGFang2-0201)

<400> SEQUENCE: 54

Asp Ile Gln Leu Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95
```

-continued

```
Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 55
<211> LENGTH: 213
<212> TYPE: PRT
<213> ORGANISM: Artificial
<220> FEATURE:
<223> OTHER INFORMATION: Light chain 2 of <VEGF-ANG-2> CrossMAb IgG1
      wild type (without AAA mutations) (VEGFang2-0201)

<400> SEQUENCE: 55

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Trp Val Phe Gly Gly Gly Thr Lys Leu Thr Val Leu Ser Ser Ala Ser
            100                 105                 110

Thr Lys Gly Pro Ser Val Phe Pro Leu Ala Pro Ser Ser Lys Ser Thr
        115                 120                 125

Ser Gly Gly Thr Ala Ala Leu Gly Cys Leu Val Lys Asp Tyr Phe Pro
    130                 135                 140

Glu Pro Val Thr Val Ser Trp Asn Ser Gly Ala Leu Thr Ser Gly Val
145                 150                 155                 160

His Thr Phe Pro Ala Val Leu Gln Ser Ser Gly Leu Tyr Ser Leu Ser
                165                 170                 175

Ser Val Val Thr Val Pro Ser Ser Ser Leu Gly Thr Gln Thr Tyr Ile
            180                 185                 190

Cys Asn Val Asn His Lys Pro Ser Asn Thr Lys Val Asp Lys Lys Val
        195                 200                 205

Glu Pro Lys Ser Cys
    210

<210> SEQ ID NO 56
```

```
<211> LENGTH: 453
<212> TYPE: PRT
<213> ORGANISM: Artificial
<220> FEATURE:
<223> OTHER INFORMATION: Heavy chain 1 of <VEGF-ANG-2> CrossMAb IgG1
      with P329G LALA mutations only (without AAA mutations)
      (VEGFang2-0015)

<400> SEQUENCE: 56
```

| | | | | | | | | | | | | | | |
|---|---|---|---|---|---|---|---|---|---|---|---|---|---|---|
| Glu | Val | Gln | Leu | Val | Glu | Ser | Gly | Gly | Gly | Leu | Val | Gln | Pro | Gly |
| 1 | | | | 5 | | | | | 10 | | | | | 15 |
| Gly | | | | | | | | | | | | | | |
| Ser | Leu | Arg | Leu | Ser | Cys | Ala | Ala | Ser | Gly | Tyr | Asp | Phe | Thr | His |
| | | | 20 | | | | | 25 | | | | | 30 | |
| Tyr | | | | | | | | | | | | | | |
| Gly | Met | Asn | Trp | Val | Arg | Gln | Ala | Pro | Gly | Lys | Gly | Leu | Glu | Trp |
| | | 35 | | | | | 40 | | | | | 45 | | |
| Val | | | | | | | | | | | | | | |
| Gly | Trp | Ile | Asn | Thr | Tyr | Thr | Gly | Glu | Pro | Thr | Tyr | Ala | Ala | Asp |
| | 50 | | | | | 55 | | | | | 60 | | | |
| Phe | | | | | | | | | | | | | | |
| Lys | Arg | Arg | Phe | Thr | Phe | Ser | Leu | Asp | Thr | Ser | Lys | Ser | Thr | Ala |
| 65 | | | | | 70 | | | | | 75 | | | | | 
| Tyr | | | | | | | | | | | | | | |
| Leu | Gln | Met | Asn | Ser | Leu | Arg | Ala | Glu | Asp | Thr | Ala | Val | Tyr | Tyr |
| | | | | 85 | | | | | 90 | | | | | 95 |
| Cys | | | | | | | | | | | | | | |
| Ala | Lys | Tyr | Pro | Tyr | Tyr | Gly | Thr | Ser | His | Trp | Tyr | Phe | Asp | Val |
| | | | 100 | | | | | 105 | | | | | 110 | |
| Trp | Gly | Gln | Gly | Thr | Leu | Val | Thr | Val | Ser | Ser | Ala | Ser | Thr | Lys |
| | | 115 | | | | | 120 | | | | | 125 | | |
| Gly | | | | | | | | | | | | | | |
| Pro | Ser | Val | Phe | Pro | Leu | Ala | Pro | Ser | Ser | Lys | Ser | Thr | Ser | Gly |
| | 130 | | | | | 135 | | | | | 140 | | | |
| Gly | | | | | | | | | | | | | | |
| Thr | Ala | Ala | Leu | Gly | Cys | Leu | Val | Lys | Asp | Tyr | Phe | Pro | Glu | Pro |
| 145 | | | | | 150 | | | | | 155 | | | | | 
| Val | | | | | | | | | | | | | | |
| Thr | Val | Ser | Trp | Asn | Ser | Gly | Ala | Leu | Thr | Ser | Gly | Val | His | Thr |
| | | | | 165 | | | | | 170 | | | | | 175 |
| Phe | | | | | | | | | | | | | | |
| Pro | Ala | Val | Leu | Gln | Ser | Ser | Gly | Leu | Tyr | Ser | Leu | Ser | Ser | Val |
| | | | 180 | | | | | 185 | | | | | 190 | |
| Val | | | | | | | | | | | | | | |
| Thr | Val | Pro | Ser | Ser | Ser | Leu | Gly | Thr | Gln | Thr | Tyr | Ile | Cys | Asn |
| | | 195 | | | | | 200 | | | | | 205 | | |
| Val | | | | | | | | | | | | | | |
| Asn | His | Lys | Pro | Ser | Asn | Thr | Lys | Val | Asp | Lys | Val | Glu | Pro | Lys |
| | 210 | | | | | 215 | | | | | 220 | | | |
| Ser | Cys | Asp | Lys | Thr | His | Thr | Cys | Pro | Pro | Cys | Pro | Ala | Pro | Glu |
| 225 | | | | | 230 | | | | | 235 | | | | | 
| Ala | | | | | | | | | | | | | | |
| Ala | Gly | Gly | Pro | Ser | Val | Phe | Leu | Phe | Pro | Pro | Lys | Pro | Lys | Asp |
| | | | | 245 | | | | | 250 | | | | | 255 |
| Thr | | | | | | | | | | | | | | |
| Leu | Met | Ile | Ser | Arg | Thr | Pro | Glu | Val | Thr | Cys | Val | Val | Val | Asp |
| | | | 260 | | | | | 265 | | | | | 270 | |
| Val | | | | | | | | | | | | | | |
| Ser | His | Glu | Asp | Pro | Glu | Val | Lys | Phe | Asn | Trp | Tyr | Val | Asp | Gly |
| | | 275 | | | | | 280 | | | | | 285 | | |
| Val | | | | | | | | | | | | | | |
| Glu | Val | His | Asn | Ala | Lys | Thr | Lys | Pro | Arg | Glu | Glu | Gln | Tyr | Asn |
| | 290 | | | | | 295 | | | | | 300 | | | |
| Ser | | | | | | | | | | | | | | |
| Thr | Tyr | Arg | Val | Val | Ser | Val | Leu | Thr | Val | Leu | His | Gln | Asp | Trp |
| 305 | | | | | 310 | | | | | 315 | | | | | 
| Leu | | | | | | | | | | | | | | |
| | | | | | | | | | | | | | | 320 |
| Asn | Gly | Lys | Glu | Tyr | Lys | Cys | Lys | Val | Ser | Asn | Lys | Ala | Leu | Gly |
| | | | | 325 | | | | | 330 | | | | | 335 |
| Ala | | | | | | | | | | | | | | |
| Pro | Ile | Glu | Lys | Thr | Ile | Ser | Lys | Ala | Lys | Gly | Gln | Pro | Arg | Glu |
| | | | 340 | | | | | 345 | | | | | 350 | |
| Pro | | | | | | | | | | | | | | |
| Gln | Val | Tyr | Thr | Leu | Pro | Pro | Cys | Arg | Asp | Glu | Leu | Thr | Lys | Asn |
| | | 355 | | | | | 360 | | | | | 365 | | |
| Gln | | | | | | | | | | | | | | |

```
Val Ser Leu Trp Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
            405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 57
<211> LENGTH: 463
<212> TYPE: PRT
<213> ORGANISM: Artificial
<220> FEATURE:
<223> OTHER INFORMATION: Heavy chain 2 of <VEGF-ANG-2> CrossMAb IgG1
      with P329G LALA mutations only (without AAA mutations)
      (VEGFang2-0015)

<400> SEQUENCE: 57

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Pro Asn Pro Tyr Tyr Tyr Asp Ser Ser Gly Tyr Tyr Tyr
            100                 105                 110

Pro Gly Ala Phe Asp Ile Trp Gly Gln Gly Thr Met Val Thr Val Ser
        115                 120                 125

Ser Ala Ser Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys Asp Lys Thr His
225                 230                 235                 240

Thr Cys Pro Pro Cys Pro Ala Pro Glu Ala Ala Gly Gly Pro Ser Val
                245                 250                 255

Phe Leu Phe Pro Pro Lys Pro Lys Asp Thr Leu Met Ile Ser Arg Thr
```

```
                260                 265                 270
Pro Glu Val Thr Cys Val Val Asp Val Ser His Glu Asp Pro Glu
            275                 280                 285

Val Lys Phe Asn Trp Tyr Val Asp Gly Val Glu Val His Asn Ala Lys
            290                 295                 300

Thr Lys Pro Arg Glu Glu Gln Tyr Asn Ser Thr Tyr Arg Val Val Ser
305                 310                 315                 320

Val Leu Thr Val Leu His Gln Asp Trp Leu Asn Gly Lys Glu Tyr Lys
                    325                 330                 335

Cys Lys Val Ser Asn Lys Ala Leu Gly Ala Pro Ile Glu Lys Thr Ile
                340                 345                 350

Ser Lys Ala Lys Gly Gln Pro Arg Glu Pro Gln Val Cys Thr Leu Pro
            355                 360                 365

Pro Ser Arg Asp Glu Leu Thr Lys Asn Gln Val Ser Leu Ser Cys Ala
        370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Val Leu Asp Ser
                405                 410                 415

Asp Gly Ser Phe Phe Leu Val Ser Lys Leu Thr Val Asp Lys Ser Arg
                420                 425                 430

Trp Gln Gln Gly Asn Val Phe Ser Cys Ser Val Met His Glu Ala Leu
            435                 440                 445

His Asn His Tyr Thr Gln Lys Ser Leu Ser Leu Ser Pro Gly Lys
        450                 455                 460

<210> SEQ ID NO 58
<211> LENGTH: 214
<212> TYPE: PRT
<213> ORGANISM: Artificial
<220> FEATURE:
<223> OTHER INFORMATION: Light chain 1 of <VEGF-ANG-2> CrossMAb IgG1
      with P329G LALA mutations only (without AAA mutations)
      (VEGFang2-0015)

<400> SEQUENCE: 58

Asp Ile Gln Leu Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160
```

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
            210

<210> SEQ ID NO 59
<211> LENGTH: 213
<212> TYPE: PRT
<213> ORGANISM: Artificial
<220> FEATURE:
<223> OTHER INFORMATION: Light chain 2 of <VEGF-ANG-2> CrossMAb IgG1
      with P329G LALA mutations only (without AAA mutations)
      (VEGFang2-0015)

<400> SEQUENCE: 59

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Trp Val Phe Gly Gly Gly Thr Lys Leu Thr Val Leu Ser Ser Ala Ser
            100                 105                 110

Thr Lys Gly Pro Ser Val Phe Pro Leu Ala Pro Ser Ser Lys Ser Thr
        115                 120                 125

Ser Gly Gly Thr Ala Ala Leu Gly Cys Leu Val Lys Asp Tyr Phe Pro
    130                 135                 140

Glu Pro Val Thr Val Ser Trp Asn Ser Gly Ala Leu Thr Ser Gly Val
145                 150                 155                 160

His Thr Phe Pro Ala Val Leu Gln Ser Ser Gly Leu Tyr Ser Leu Ser
                165                 170                 175

Ser Val Val Thr Val Pro Ser Ser Ser Leu Gly Thr Gln Thr Tyr Ile
            180                 185                 190

Cys Asn Val Asn His Lys Pro Ser Asn Thr Lys Val Asp Lys Lys Val
        195                 200                 205

Glu Pro Lys Ser Cys
    210

<210> SEQ ID NO 60
<211> LENGTH: 227
<212> TYPE: PRT
<213> ORGANISM: Homo sapiens

<400> SEQUENCE: 60

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met

```
            20                  25                  30
Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
 50                  55                  60

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Pro Ala Pro Ile
             100                 105                 110

Glu Lys Thr Ile Ser Lys Ala Lys Gly Gln Pro Arg Glu Pro Gln Val
         115                 120                 125

Tyr Thr Leu Pro Pro Ser Arg Asp Glu Leu Thr Lys Asn Gln Val Ser
     130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                 165                 170                 175

Val Leu Asp Ser Asp Gly Ser Phe Phe Leu Tyr Ser Lys Leu Thr Val
             180                 185                 190

Asp Lys Ser Arg Trp Gln Gln Gly Asn Val Phe Ser Cys Ser Val Met
         195                 200                 205

His Glu Ala Leu His Asn His Tyr Thr Gln Lys Ser Leu Ser Leu Ser
     210                 215                 220

Pro Gly Lys
225

<210> SEQ ID NO 61
<211> LENGTH: 223
<212> TYPE: PRT
<213> ORGANISM: Homo sapiens

<400> SEQUENCE: 61

Val Glu Cys Pro Pro Cys Pro Ala Pro Pro Val Ala Gly Pro Ser Val
 1               5                   10                  15

Phe Leu Phe Pro Pro Lys Pro Lys Asp Thr Leu Met Ile Ser Arg Thr
             20                  25                  30

Pro Glu Val Thr Cys Val Val Val Asp Val Ser His Glu Asp Pro Glu
         35                  40                  45

Val Gln Phe Asn Trp Tyr Val Asp Gly Val Glu Val His Asn Ala Lys
     50                  55                  60

Thr Lys Pro Arg Glu Glu Gln Phe Asn Ser Thr Phe Arg Val Val Ser
65                  70                  75                  80

Val Leu Thr Val Val His Gln Asp Trp Leu Asn Gly Lys Glu Tyr Lys
                 85                  90                  95

Cys Lys Val Ser Asn Lys Gly Leu Pro Ala Pro Ile Glu Lys Thr Ile
             100                 105                 110

Ser Lys Thr Lys Gly Gln Pro Arg Glu Pro Gln Val Tyr Thr Leu Pro
         115                 120                 125

Pro Ser Arg Glu Glu Met Thr Lys Asn Gln Val Ser Leu Thr Cys Leu
     130                 135                 140

Val Lys Gly Phe Tyr Pro Ser Asp Ile Ser Val Glu Trp Glu Ser Asn
145                 150                 155                 160
```

Gly Gln Pro Glu Asn Asn Tyr Lys Thr Thr Pro Pro Met Leu Asp Ser
                165                 170                 175

Asp Gly Ser Phe Phe Leu Tyr Ser Lys Leu Thr Val Asp Lys Ser Arg
            180                 185                 190

Trp Gln Gln Gly Asn Val Phe Ser Cys Ser Val Met His Glu Ala Leu
        195                 200                 205

His Asn His Tyr Thr Gln Lys Ser Leu Ser Leu Ser Pro Gly Lys
    210                 215                 220

<210> SEQ ID NO 62
<211> LENGTH: 227
<212> TYPE: PRT
<213> ORGANISM: Homo sapiens

<400> SEQUENCE: 62

Asp Thr Pro Pro Pro Cys Pro Arg Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
            35                  40                  45

Glu Asp Pro Glu Val Gln Phe Lys Trp Tyr Val Asp Gly Val Glu Val
50                  55                  60

His Asn Ala Lys Thr Lys Pro Arg Glu Glu Gln Tyr Asn Ser Thr Phe
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Thr Lys Gly Gln Pro Arg Glu Pro Gln Val
        115                 120                 125

Tyr Thr Leu Pro Pro Ser Arg Glu Glu Met Thr Lys Asn Gln Val Ser
130                 135                 140

Leu Thr Cys Leu Val Lys Gly Phe Tyr Pro Ser Asp Ile Ala Val Glu
145                 150                 155                 160

Trp Glu Ser Ser Gly Gln Pro Glu Asn Asn Tyr Asn Thr Thr Pro Pro
                165                 170                 175

Met Leu Asp Ser Asp Gly Ser Phe Phe Leu Tyr Ser Lys Leu Thr Val
            180                 185                 190

Asp Lys Ser Arg Trp Gln Gln Gly Asn Ile Phe Ser Cys Ser Val Met
        195                 200                 205

His Glu Ala Leu His Asn Arg Phe Thr Gln Lys Ser Leu Ser Leu Ser
210                 215                 220

Pro Gly Lys
225

<210> SEQ ID NO 63
<211> LENGTH: 229
<212> TYPE: PRT
<213> ORGANISM: Homo sapiens

<400> SEQUENCE: 63

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

```
Leu Met Ile Ser Arg Thr Pro Glu Val Thr Cys Val Val Asp Val
         35                  40                  45

Ser Gln Glu Asp Pro Glu Val Gln Phe Asn Trp Tyr Val Asp Gly Val
 50                  55                  60

Glu Val His Asn Ala Lys Thr Lys Pro Arg Glu Glu Gln Phe Asn Ser
 65                  70                  75                  80

Thr Tyr Arg Val Val Ser Val Leu Thr Val Leu His Gln Asp Trp Leu
                 85                  90                  95

Asn Gly Lys Glu Tyr Lys Cys Lys Val Ser Asn Lys Gly Leu Pro Ser
             100                 105                 110

Ser Ile Glu Lys Thr Ile Ser Lys Ala Lys Gly Gln Pro Arg Glu Pro
         115                 120                 125

Gln Val Tyr Thr Leu Pro Pro Ser Gln Glu Glu Met Thr Lys Asn Gln
130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225

<210> SEQ ID NO 64
<211> LENGTH: 227
<212> TYPE: PRT
<213> ORGANISM: Artificial Sequence
<220> FEATURE:
<223> OTHER INFORMATION: human IgG1 Fc-region derived Fc-region
      polypeptide with the mutations L234A, L235A

<400> SEQUENCE: 64

Asp Lys Thr His Thr Cys Pro Pro Cys Pro Ala Pro Glu Ala Ala Gly
 1               5                  10                  15

Gly Pro Ser Val Phe Leu Phe Pro Pro Lys Pro Lys Asp Thr Leu Met
             20                  25                  30

Ile Ser Arg Thr Pro Glu Val Thr Cys Val Val Val Asp Val Ser His
         35                  40                  45

Glu Asp Pro Glu Val Lys Phe Asn Trp Tyr Val Asp Gly Val Glu Val
 50                  55                  60

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Pro Ala Pro Ile
             100                 105                 110

Glu Lys Thr Ile Ser Lys Ala Lys Gly Gln Pro Arg Glu Pro Gln Val
         115                 120                 125

Tyr Thr Leu Pro Pro Ser Arg Asp Glu Leu Thr Lys Asn Gln Val Ser
130                 135                 140

Leu Thr Cys Leu Val Lys Gly Phe Tyr Pro Ser Asp Ile Ala Val Glu
145                 150                 155                 160
```

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 65
<211> LENGTH: 227
<212> TYPE: PRT
<213> ORGANISM: Artificial Sequence
<220> FEATURE:
<223> OTHER INFORMATION: human IgG1 Fc-region derived Fc-region
      polypeptide with Y349C, T366S, L368A and Y407V mutations

<400> SEQUENCE: 65

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Asp Glu Leu Thr Lys Asn Gln Val Ser
130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 66
<211> LENGTH: 227
<212> TYPE: PRT
<213> ORGANISM: Artificial Sequence
<220> FEATURE:
<223> OTHER INFORMATION: human IgG1 Fc-region derived Fc-region polypeptide with S354C, T366W mutations

<400> SEQUENCE: 66

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Asp Glu Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225
```

<210> SEQ ID NO 67
<211> LENGTH: 227
<212> TYPE: PRT
<213> ORGANISM: Artificial Sequence
<220> FEATURE:
<223> OTHER INFORMATION: human IgG1 Fc-region derived Fc-region
      polypeptide with L234A, L235A mutations and Y349C, T366S, L368A,
      Y407V mutations

<400> SEQUENCE: 67

```
Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95
```

```
Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Asp Glu Leu Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 68
<211> LENGTH: 227
<212> TYPE: PRT
<213> ORGANISM: Artificial Sequence
<220> FEATURE:
<223> OTHER INFORMATION: human IgG1 Fc-region derived Fc-region
      polypeptide with a L234A, L235A and S354C, T366W mutations

<400> SEQUENCE: 68

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Asp Glu Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220
```

Pro Gly Lys
225

<210> SEQ ID NO 69
<211> LENGTH: 227
<212> TYPE: PRT
<213> ORGANISM: Artificial Sequence
<220> FEATURE:
<223> OTHER INFORMATION: human IgG1 Fc-region derived Fc-region
      polypeptide with a P329G mutation

<400> SEQUENCE: 69

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Gly Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 70
<211> LENGTH: 227
<212> TYPE: PRT
<213> ORGANISM: Artificial Sequence
<220> FEATURE:
<223> OTHER INFORMATION: human IgG1 Fc-region derived Fc-region
      polypeptide with L234A, L235A mutations and P329G mutation

<400> SEQUENCE: 70

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Gly Ala Pro Ile
                100                 105                 110

Glu Lys Thr Ile Ser Lys Ala Lys Gly Gln Pro Arg Glu Pro Gln Val
                115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
                180                 185                 190

Asp Lys Ser Arg Trp Gln Gln Gly Asn Val Phe Ser Cys Ser Val Met
                195                 200                 205

His Glu Ala Leu His Asn His Tyr Thr Gln Lys Ser Leu Ser Leu Ser
    210                 215                 220

Pro Gly Lys
225

<210> SEQ ID NO 71
<211> LENGTH: 227
<212> TYPE: PRT
<213> ORGANISM: Artificial Sequence
<220> FEATURE:
<223> OTHER INFORMATION: human IgG1 Fc-region derived Fc-region
      polypeptide with a P239G mutation and Y349C, T366S, L368A, Y407V
      mutations

<400> SEQUENCE: 71

Asp Lys Thr His Thr Cys Pro Pro Cys Pro Ala Pro Glu Leu Leu Gly
 1               5                  10                  15

Gly Pro Ser Val Phe Leu Phe Pro Pro Lys Pro Lys Asp Thr Leu Met
                 20                  25                  30

Ile Ser Arg Thr Pro Glu Val Thr Cys Val Val Val Asp Val Ser His
             35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Gly Ala Pro Ile
                100                 105                 110

Glu Lys Thr Ile Ser Lys Ala Lys Gly Gln Pro Arg Glu Pro Gln Val
                115                 120                 125

Cys Thr Leu Pro Pro Ser Arg Asp Glu Leu Thr Lys Asn Gln Val Ser
    130                 135                 140

Leu Ser Cys Ala Val Lys Gly Phe Tyr Pro Ser Asp Ile Ala Val Glu
145                 150                 155                 160

```
Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 72
<211> LENGTH: 227
<212> TYPE: PRT
<213> ORGANISM: Artificial Sequence
<220> FEATURE:
<223> OTHER INFORMATION: human IgG1 Fc-region derived Fc-region
      polypeptide with a P329G mutation and S354C, T366W mutation

<400> SEQUENCE: 72

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Gly Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Asp Glu Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 73
<211> LENGTH: 227
<212> TYPE: PRT
<213> ORGANISM: Artificial Sequence
<220> FEATURE:
<223> OTHER INFORMATION: human IgG1 Fc-region derived Fc-region
      polypeptide with L234A, L235A, P329G and Y349C, T366S, L368A,
```

Y407V mutations

<400> SEQUENCE: 73

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
 50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Gly Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Asp Glu Leu Thr Lys Asn Gln Val Ser
130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
210                 215                 220

Pro Gly Lys
225

<210> SEQ ID NO 74
<211> LENGTH: 227
<212> TYPE: PRT
<213> ORGANISM: Artificial Sequence
<220> FEATURE:
<223> OTHER INFORMATION: human IgG1 Fc-region derived Fc-region
      polypeptide with L234A, L235A, P329G mutations and S354C, T366W
      mutations

<400> SEQUENCE: 74

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
 50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Gly Ala Pro Ile
            100                 105                 110

Glu Lys Thr Ile Ser Lys Ala Lys Gly Gln Pro Arg Glu Pro Gln Val
            115                 120                 125

Tyr Thr Leu Pro Pro Cys Arg Asp Glu Leu Thr Lys Asn Gln Val Ser
            130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
            210                 215                 220

Pro Gly Lys
225

<210> SEQ ID NO 75
<211> LENGTH: 229
<212> TYPE: PRT
<213> ORGANISM: Artificial Sequence
<220> FEATURE:
<223> OTHER INFORMATION: human IgG4 Fc-region derived Fc-region
      polypeptide with S228P and L235E mutations

<400> SEQUENCE: 75

Glu Ser Lys Tyr Gly Pro Pro Cys Pro Pro Cys Pro Ala Pro Glu Phe
1               5                   10                  15

Glu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
            35                  40                  45

Ser Gln Glu Asp Pro Glu Val Gln Phe Asn Trp Tyr Val Asp Gly Val
50                  55                  60

Glu Val His Asn Ala Lys Thr Lys Pro Arg Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
            115                 120                 125

Gln Val Tyr Thr Leu Pro Pro Ser Gln Glu Glu Met Thr Lys Asn Gln
            130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
            195                 200                 205

Val Met His Glu Ala Leu His Asn His Tyr Thr Gln Lys Ser Leu Ser
210                 215                 220

Leu Ser Leu Gly Lys
225

<210> SEQ ID NO 76
<211> LENGTH: 229
<212> TYPE: PRT
<213> ORGANISM: Artificial Sequence
<220> FEATURE:
<223> OTHER INFORMATION: human IgG4 Fc-region derived Fc-region
      polypeptide with S228P, L235E mutations and P329G mutation

<400> SEQUENCE: 76

Glu Ser Lys Tyr Gly Pro Pro Cys Pro Pro Cys Pro Ala Pro Glu Phe
1               5                   10                  15

Glu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Gly Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225

<210> SEQ ID NO 77
<211> LENGTH: 229
<212> TYPE: PRT
<213> ORGANISM: Artificial Sequence
<220> FEATURE:
<223> OTHER INFORMATION: human IgG4 Fc-region derived Fc-region
      polypeptide with S354C, T366W mutations

<400> SEQUENCE: 77

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
            115                 120                 125

Gln Val Tyr Thr Leu Pro Pro Cys Gln Glu Met Thr Lys Asn Gln
    130                 135                 140

Val Ser Leu Trp Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
            195                 200                 205

Val Met His Glu Ala Leu His Asn His Tyr Thr Gln Lys Ser Leu Ser
210                 215                 220

Leu Ser Leu Gly Lys
225

<210> SEQ ID NO 78
<211> LENGTH: 229
<212> TYPE: PRT
<213> ORGANISM: Artificial Sequence
<220> FEATURE:
<223> OTHER INFORMATION: human IgG4 Fc-region derived Fc-region
      polypeptide with Y349C, T366S, L368A, Y407V mutations

<400> SEQUENCE: 78

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Cys Thr Leu Pro Pro Ser Gln Glu Met Thr Lys Asn Gln
    130                 135                 140

Val Ser Leu Ser Cys Ala Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr

```
                    165                 170                 175
Pro Pro Val Leu Asp Ser Asp Gly Ser Phe Phe Leu Val Ser Arg Leu
                180                 185                 190

Thr Val Asp Lys Ser Arg Trp Gln Glu Gly Asn Val Phe Ser Cys Ser
            195                 200                 205

Val Met His Glu Ala Leu His Asn His Tyr Thr Gln Lys Ser Leu Ser
        210                 215                 220

Leu Ser Leu Gly Lys
225

<210> SEQ ID NO 79
<211> LENGTH: 229
<212> TYPE: PRT
<213> ORGANISM: Artificial Sequence
<220> FEATURE:
<223> OTHER INFORMATION: human IgG4 Fc-region derived Fc-region
      polypeptide with a S228P, L235E and S354C, T366W mutations

<400> SEQUENCE: 79

Glu Ser Lys Tyr Gly Pro Pro Cys Pro Pro Cys Pro Ala Pro Glu Phe
1               5                   10                  15

Glu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Cys Gln Glu Glu Met Thr Lys Asn Gln
    130                 135                 140

Val Ser Leu Trp Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225

<210> SEQ ID NO 80
<211> LENGTH: 229
<212> TYPE: PRT
<213> ORGANISM: Artificial Sequence
<220> FEATURE:
<223> OTHER INFORMATION: human IgG4 Fc-region derived Fc-region
      polypeptide with a S228P, L235E and Y349C, T366S, L368A, Y407V
      mutations
```

```
<400> SEQUENCE: 80

Glu Ser Lys Tyr Gly Pro Pro Cys Pro Pro Cys Pro Ala Pro Glu Phe
1               5                   10                  15

Glu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Cys Thr Leu Pro Pro Ser Gln Glu Glu Met Thr Lys Asn Gln
    130                 135                 140

Val Ser Leu Ser Cys Ala Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Val Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225

<210> SEQ ID NO 81
<211> LENGTH: 229
<212> TYPE: PRT
<213> ORGANISM: Artificial Sequence
<220> FEATURE:
<223> OTHER INFORMATION: human IgG4 Fc-region derived Fc-region
      polypeptide with a P329G mutation

<400> SEQUENCE: 81

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Gly Ser
            100                 105                 110
```

Ser Ile Glu Lys Thr Ile Ser Lys Ala Lys Gly Gln Pro Arg Glu Pro
            115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
            195                 200                 205

Val Met His Glu Ala Leu His Asn His Tyr Thr Gln Lys Ser Leu Ser
210                 215                 220

Leu Ser Leu Gly Lys
225

<210> SEQ ID NO 82
<211> LENGTH: 229
<212> TYPE: PRT
<213> ORGANISM: Artificial Sequence
<220> FEATURE:
<223> OTHER INFORMATION: human IgG4 Fc-region derived Fc-region
      polypeptide with a P239G and Y349C, T366S, L368A, Y407V mutations

<400> SEQUENCE: 82

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
            35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Gly Ser
            100                 105                 110

Ser Ile Glu Lys Thr Ile Ser Lys Ala Lys Gly Gln Pro Arg Glu Pro
            115                 120                 125

Gln Val Cys Thr Leu Pro Pro Ser Gln Glu Glu Met Thr Lys Asn Gln
    130                 135                 140

Val Ser Leu Ser Cys Ala Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Val Ser Arg Leu
            180                 185                 190

Thr Val Asp Lys Ser Arg Trp Gln Glu Gly Asn Val Phe Ser Cys Ser
            195                 200                 205

Val Met His Glu Ala Leu His Asn His Tyr Thr Gln Lys Ser Leu Ser
210                 215                 220

Leu Ser Leu Gly Lys

<210> SEQ ID NO 83
<211> LENGTH: 229
<212> TYPE: PRT
<213> ORGANISM: Artificial Sequence
<220> FEATURE:
<223> OTHER INFORMATION: human IgG4 Fc-region derived Fc-region
      polypeptide with a P329G and S354C, T366W mutations

<400> SEQUENCE: 83

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Gly Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Cys Gln Glu Glu Met Thr Lys Asn Gln
    130                 135                 140

Val Ser Leu Trp Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225

<210> SEQ ID NO 84
<211> LENGTH: 229
<212> TYPE: PRT
<213> ORGANISM: Artificial Sequence
<220> FEATURE:
<223> OTHER INFORMATION: human IgG4 Fc-region derived Fc-region
      polypeptide with a S228P, L235E, P329G and Y349C, T366S, L368A,
      Y407V mutations

<400> SEQUENCE: 84

Glu Ser Lys Tyr Gly Pro Pro Cys Pro Pro Cys Pro Ala Pro Glu Phe
1               5                   10                  15

Glu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

```
Ser Gln Glu Asp Pro Glu Val Gln Phe Asn Trp Tyr Val Asp Gly Val
 50                  55                  60

Glu Val His Asn Ala Lys Thr Lys Pro Arg Glu Glu Gln Phe Asn Ser
 65                  70                  75                  80

Thr Tyr Arg Val Val Ser Val Leu Thr Val Leu His Gln Asp Trp Leu
                 85                  90                  95

Asn Gly Lys Glu Tyr Lys Cys Lys Val Ser Asn Lys Gly Leu Gly Ser
                100                 105                 110

Ser Ile Glu Lys Thr Ile Ser Lys Ala Lys Gly Gln Pro Arg Glu Pro
            115                 120                 125

Gln Val Cys Thr Leu Pro Pro Ser Gln Glu Glu Met Thr Lys Asn Gln
130                 135                 140

Val Ser Leu Ser Cys Ala Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Val Ser Arg Leu
            180                 185                 190

Thr Val Asp Lys Ser Arg Trp Gln Glu Gly Asn Val Phe Ser Cys Ser
            195                 200                 205

Val Met His Glu Ala Leu His Asn His Tyr Thr Gln Lys Ser Leu Ser
210                 215                 220

Leu Ser Leu Gly Lys
225

<210> SEQ ID NO 85
<211> LENGTH: 229
<212> TYPE: PRT
<213> ORGANISM: Artificial Sequence
<220> FEATURE:
<223> OTHER INFORMATION: human IgG4 Fc-region derived Fc-region
      polypeptide with a S228P, L235E, P329G and S354C, T366W mutations

<400> SEQUENCE: 85

Glu Ser Lys Tyr Gly Pro Pro Cys Pro Pro Cys Pro Ala Pro Glu Phe
 1               5                  10                  15

Glu Gly Gly Pro Ser Val Phe Leu Phe Pro Pro Lys Pro Lys Asp Thr
                 20                  25                  30

Leu Met Ile Ser Arg Thr Pro Glu Val Thr Cys Val Val Val Asp Val
             35                  40                  45

Ser Gln Glu Asp Pro Glu Val Gln Phe Asn Trp Tyr Val Asp Gly Val
 50                  55                  60

Glu Val His Asn Ala Lys Thr Lys Pro Arg Glu Glu Gln Phe Asn Ser
 65                  70                  75                  80

Thr Tyr Arg Val Val Ser Val Leu Thr Val Leu His Gln Asp Trp Leu
                 85                  90                  95

Asn Gly Lys Glu Tyr Lys Cys Lys Val Ser Asn Lys Gly Leu Gly Ser
                100                 105                 110

Ser Ile Glu Lys Thr Ile Ser Lys Ala Lys Gly Gln Pro Arg Glu Pro
            115                 120                 125

Gln Val Tyr Thr Leu Pro Pro Cys Gln Glu Glu Met Thr Lys Asn Gln
130                 135                 140

Val Ser Leu Trp Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175
```

-continued

```
Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
            195                 200                 205

Val Met His Glu Ala Leu His Asn His Tyr Thr Gln Lys Ser Leu Ser
    210                 215                 220

Leu Ser Leu Gly Lys
225

<210> SEQ ID NO 86
<211> LENGTH: 105
<212> TYPE: PRT
<213> ORGANISM: homo sapiens

<400> SEQUENCE: 86

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val
        35                  40                  45

Lys Ala Gly Val Glu Thr Thr Thr Pro Ser Lys Gln Ser Asn Asn Lys
    50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Cys Ser
            100                 105

<210> SEQ ID NO 87
<211> LENGTH: 107
<212> TYPE: PRT
<213> ORGANISM: Homo sapiens

<400> SEQUENCE: 87

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 88
<211> LENGTH: 453
<212> TYPE: PRT
<213> ORGANISM: Artificial
<220> FEATURE:
<223> OTHER INFORMATION: Heavy chain 1 of <VEGF-ANG-2> CrossMAb IgG1
      wild type (without AAA mutations) (VEGFang2-0201)
```

<400> SEQUENCE: 88

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Asp Phe Thr His Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro Tyr Tyr Gly Thr Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu Ala Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Cys Arg Asp Glu Leu Thr Lys Asn Gln
        355                 360                 365

Val Ser Leu Trp Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu

-continued

```
                    405                 410                 415
Thr Val Asp Lys Ser Arg Trp Gln Gln Gly Asn Val Phe Ser Cys Ser
            420                 425                 430

Val Met His Glu Ala Leu Ala Asn His Ala Thr Gln Lys Ser Leu Ser
        435                 440                 445

Leu Ser Pro Gly Lys
    450

<210> SEQ ID NO 89
<211> LENGTH: 463
<212> TYPE: PRT
<213> ORGANISM: Artificial
<220> FEATURE:
<223> OTHER INFORMATION: Heavy chain 2 of <VEGF-ANG-2> CrossMAb IgG1
      wild type (without AAA mutations) (VEGFang2-0201)

<400> SEQUENCE: 89

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Pro Asn Pro Tyr Tyr Tyr Asp Ser Ser Gly Tyr Tyr Tyr
            100                 105                 110

Pro Gly Ala Phe Asp Ile Trp Gly Gln Gly Thr Met Val Thr Val Ser
        115                 120                 125

Ser Ala Ser Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys Asp Lys Thr His
225                 230                 235                 240

Thr Cys Pro Pro Cys Pro Ala Pro Glu Leu Leu Gly Gly Pro Ser Val
                245                 250                 255

Phe Leu Phe Pro Pro Lys Pro Lys Asp Thr Leu Met Ile Ser Arg Thr
            260                 265                 270

Pro Glu Val Thr Cys Val Val Val Asp Val Ser His Glu Asp Pro Glu
        275                 280                 285

Val Lys Phe Asn Trp Tyr Val Asp Gly Val Glu Val His Asn Ala Lys
    290                 295                 300
```

Thr Lys Pro Arg Glu Glu Gln Tyr Asn Ser Thr Tyr Arg Val Val Ser
305                 310                 315                 320

Val Leu Thr Val Leu Ala Gln Asp Trp Leu Asn Gly Lys Glu Tyr Lys
            325                 330                 335

Cys Lys Val Ser Asn Lys Ala Leu Pro Ala Pro Ile Glu Lys Thr Ile
            340                 345                 350

Ser Lys Ala Lys Gly Gln Pro Arg Glu Pro Gln Val Cys Thr Leu Pro
            355                 360                 365

Pro Ser Arg Asp Glu Leu Thr Lys Asn Gln Val Ser Leu Ser Cys Ala
            370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Val Leu Asp Ser
            405                 410                 415

Asp Gly Ser Phe Phe Leu Val Ser Lys Leu Thr Val Asp Lys Ser Arg
            420                 425                 430

Trp Gln Gln Gly Asn Val Phe Ser Cys Ser Val Met His Glu Ala Leu
            435                 440                 445

Ala Asn His Ala Thr Gln Lys Ser Leu Ser Leu Ser Pro Gly Lys
            450                 455                 460

<210> SEQ ID NO 90
<211> LENGTH: 453
<212> TYPE: PRT
<213> ORGANISM: Artificial
<220> FEATURE:
<223> OTHER INFORMATION: Heavy chain 1 of <VEGF-ANG-2> CrossMAb IgG1
      wild type (without AAA mutations) (VEGFang2-0201)

<400> SEQUENCE: 90

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Asp Phe Thr His Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
            85                  90                  95

Ala Lys Tyr Pro Tyr Tyr Tyr Gly Thr Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
            165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

```
Asn His Lys Pro Ser Asn Thr Lys Val Asp Lys Lys Val Glu Pro Lys
            210                 215                 220

Ser Cys Asp Lys Thr His Thr Cys Pro Pro Cys Pro Ala Pro Glu Ala
225                 230                 235                 240

Ala Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu Ala Gln Asp Trp Leu
305                 310                 315                 320

Asn Gly Lys Glu Tyr Lys Cys Lys Val Ser Asn Lys Ala Leu Gly Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Cys Arg Asp Glu Leu Thr Lys Asn Gln
        355                 360                 365

Val Ser Leu Trp Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu Ala Asn His Ala Thr Gln Lys Ser Leu Ser
        435                 440                 445

Leu Ser Pro Gly Lys
    450

<210> SEQ ID NO 91
<211> LENGTH: 463
<212> TYPE: PRT
<213> ORGANISM: Artificial
<220> FEATURE:
<223> OTHER INFORMATION: Heavy chain 2 of <VEGF-ANG-2> CrossMAb IgG1
      wild type (without AAA mutations) (VEGFang2-0201)

<400> SEQUENCE: 91

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Pro Asn Pro Tyr Tyr Tyr Asp Ser Ser Gly Tyr Tyr Tyr
```

```
            100                 105                 110
Pro Gly Ala Phe Asp Ile Trp Gly Gln Gly Thr Met Val Thr Val Ser
            115                 120                 125

Ser Ala Ser Val Ala Ala Pro Ser Val Phe Ile Phe Pro Pro Ser Asp
            130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                    165                 170                 175

Gln Ser Gly Asn Ser Gln Glu Ser Val Thr Glu Gln Asp Ser Lys Asp
                180                 185                 190

Ser Thr Tyr Ser Leu Ser Ser Thr Leu Thr Leu Ser Lys Ala Asp Tyr
            195                 200                 205

Glu Lys His Lys Val Tyr Ala Cys Glu Val Thr His Gln Gly Leu Ser
            210                 215                 220

Ser Pro Val Thr Lys Ser Phe Asn Arg Gly Glu Cys Asp Lys Thr His
225                 230                 235                 240

Thr Cys Pro Pro Cys Pro Ala Pro Glu Ala Ala Gly Gly Pro Ser Val
                    245                 250                 255

Phe Leu Phe Pro Pro Lys Pro Lys Asp Thr Leu Met Ile Ser Arg Thr
                260                 265                 270

Pro Glu Val Thr Cys Val Val Val Asp Val Ser His Glu Asp Pro Glu
            275                 280                 285

Val Lys Phe Asn Trp Tyr Val Asp Gly Val Glu Val His Asn Ala Lys
            290                 295                 300

Thr Lys Pro Arg Glu Glu Gln Tyr Asn Ser Thr Tyr Arg Val Val Ser
305                 310                 315                 320

Val Leu Thr Val Leu Ala Gln Asp Trp Leu Asn Gly Lys Glu Tyr Lys
                    325                 330                 335

Cys Lys Val Ser Asn Lys Ala Leu Gly Ala Pro Ile Glu Lys Thr Ile
                340                 345                 350

Ser Lys Ala Lys Gly Gln Pro Arg Glu Pro Gln Val Cys Thr Leu Pro
            355                 360                 365

Pro Ser Arg Asp Glu Leu Thr Lys Asn Gln Val Ser Leu Ser Cys Ala
            370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Val Leu Asp Ser
                    405                 410                 415

Asp Gly Ser Phe Phe Leu Val Ser Lys Leu Thr Val Asp Lys Ser Arg
                420                 425                 430

Trp Gln Gln Gly Asn Val Phe Ser Cys Ser Val Met His Glu Ala Leu
            435                 440                 445

Ala Asn His Ala Thr Gln Lys Ser Leu Ser Leu Ser Pro Gly Lys
            450                 455                 460

<210> SEQ ID NO 92
<211> LENGTH: 450
<212> TYPE: PRT
<213> ORGANISM: Artificial
<220> FEATURE:
<223> OTHER INFORMATION: Heavy chain 1 of <VEGF-ANG-2> CrossMAb IgG4
      with AAA mutations and with SPLE mutations

<400> SEQUENCE: 92
```

```
Glu Val Gln Leu Val Glu Ser Gly Gly Leu Val Gln Pro Gly Gly
1               5                   10                  15

Ser Leu Arg Leu Ser Cys Ala Ala Ser Gly Tyr Asp Phe Thr His Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro Tyr Tyr Gly Thr Ser His Trp Tyr Phe Asp Val
            100                 105                 110

Trp Gly Gln Gly Thr Leu Val Thr Val Ser Ser Ala Ser Thr Lys Gly
            115                 120                 125

Pro Ser Val Phe Pro Leu Ala Pro Cys Ser Arg Ser Thr Ser Glu Ser
            130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
            195                 200                 205

Asp His Lys Pro Ser Asn Thr Lys Val Asp Lys Arg Val Glu Ser Lys
            210                 215                 220

Tyr Gly Pro Pro Cys Pro Pro Cys Pro Ala Pro Glu Phe Glu Gly Gly
225                 230                 235                 240

Pro Ser Val Phe Leu Phe Pro Pro Lys Pro Lys Asp Thr Leu Met Ala
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
            275                 280                 285

Asn Ala Lys Thr Lys Pro Arg Glu Glu Gln Phe Asn Ser Thr Tyr Arg
290                 295                 300

Val Val Ser Val Leu Thr Val Leu Ala Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Cys
            340                 345                 350

Thr Leu Pro Pro Ser Gln Glu Glu Met Thr Lys Asn Gln Val Ser Leu
            355                 360                 365

Ser Cys Ala Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Val Ser Arg Leu Thr Val Asp
                405                 410                 415

Lys Ser Arg Trp Gln Glu Gly Asn Val Phe Ser Cys Ser Val Met His
```

-continued

```
                420             425             430

Glu Ala Leu Ala Asn His Ala Thr Gln Lys Ser Leu Ser Leu
            435             440             445

Gly Lys
    450

<210> SEQ ID NO 93
<211> LENGTH: 460
<212> TYPE: PRT
<213> ORGANISM: Artificial
<220> FEATURE:
<223> OTHER INFORMATION: Heavy chain 2 of <VEGF-ANG-2> CrossMAb IgG4
      with AAA mutations and with SPLE mutations

<400> SEQUENCE: 93

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Pro Asn Pro Tyr Tyr Tyr Asp Ser Ser Gly Tyr Tyr Tyr
            100                 105                 110

Pro Gly Ala Phe Asp Ile Trp Gly Gln Gly Thr Met Val Thr Val Ser
        115                 120                 125

Ser Ala Ser Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys Pro Pro Cys Pro
225                 230                 235                 240

Pro Cys Pro Ala Pro Glu Phe Glu Gly Gly Pro Ser Val Phe Leu Phe
                245                 250                 255

Pro Pro Lys Pro Lys Asp Thr Leu Met Ile Ser Arg Thr Pro Glu Val
            260                 265                 270

Thr Cys Val Val Val Asp Val Ser Gln Glu Asp Pro Glu Val Gln Phe
        275                 280                 285

Asn Trp Tyr Val Asp Gly Val Glu Val His Asn Ala Lys Thr Lys Pro
    290                 295                 300

Arg Glu Glu Gln Phe Asn Ser Thr Tyr Arg Val Val Ser Val Leu Thr
305                 310                 315                 320
```

Val Leu Ala Gln Asp Trp Leu Asn Gly Lys Glu Tyr Lys Cys Lys Val
            325                 330                 335

Ser Asn Lys Gly Leu Pro Ser Ser Ile Glu Lys Thr Ile Ser Lys Ala
            340                 345                 350

Lys Gly Gln Pro Arg Glu Pro Gln Val Tyr Thr Leu Pro Pro Cys Gln
            355                 360                 365

Glu Glu Met Thr Lys Asn Gln Val Ser Leu Trp Cys Leu Val Lys Gly
            370                 375                 380

Phe Tyr Pro Ser Asp Ile Ala Val Glu Trp Glu Ser Asn Gly Gln Pro
385                 390                 395                 400

Glu Asn Asn Tyr Lys Thr Thr Pro Pro Val Leu Asp Ser Asp Gly Ser
            405                 410                 415

Phe Phe Leu Tyr Ser Arg Leu Thr Val Asp Lys Ser Arg Trp Gln Glu
            420                 425                 430

Gly Asn Val Phe Ser Cys Ser Val Met His Glu Ala Leu Ala Asn His
            435                 440                 445

Ala Thr Gln Lys Ser Leu Ser Leu Ser Leu Gly Lys
            450                 455                 460

<210> SEQ ID NO 94
<211> LENGTH: 453
<212> TYPE: PRT
<213> ORGANISM: Artificial
<220> FEATURE:
<223> OTHER INFORMATION: Heavy chain 1 of <VEGF-ANG-2> OAscFab IgG1 with
      AAA mutations

<400> SEQUENCE: 94

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Asp Phe Thr His Tyr
            20                  25                  30

Gly Met Asn Trp Val Arg Gln Ala Pro Gly Lys Gly Leu Glu Trp Val
            35                  40                  45

Gly Trp Ile Asn Thr Tyr Thr Gly Glu Pro Thr Tyr Ala Ala Asp Phe
        50                  55                  60

Lys Arg Arg Phe Thr Phe Ser Leu Asp Thr Ser Lys Ser Thr Ala Tyr
65              70                  75                  80

Leu Gln Met Asn Ser Leu Arg Ala Glu Asp Thr Ala Val Tyr Tyr Cys
            85                  90                  95

Ala Lys Tyr Pro Tyr Tyr Tyr Gly Thr Ser His Trp Tyr Phe Asp Val
            100                 105                 110

Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
            130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
            165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Lys Val Glu Pro Lys
            210                 215                 220

-continued

```
Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Ile Ala Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu Ala Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Cys Thr Leu Pro Pro Ser Arg Asp Glu Leu Thr Lys Asn Gln
        355                 360                 365

Val Ser Leu Ser Cys Ala Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Val Ser Lys Leu
                405                 410                 415

Thr Val Asp Lys Ser Arg Trp Gln Gln Gly Asn Val Phe Ser Cys Ser
            420                 425                 430

Val Met His Glu Ala Leu Ala Asn His Ala Thr Gln Lys Ser Leu Ser
        435                 440                 445

Leu Ser Pro Gly Lys
    450

<210> SEQ ID NO 95
<211> LENGTH: 705
<212> TYPE: PRT
<213> ORGANISM: Artificial
<220> FEATURE:
<223> OTHER INFORMATION: Heavy chain 2 of <VEGF-ANG-2> OAscFab IgG1 with
      AAA mutations

<400> SEQUENCE: 95

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Trp Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
```

-continued

```
            115                 120                 125
Ala Asn Lys Ala Thr Leu Val Cys Leu Ile Ser Asp Phe Tyr Pro Gly
        130                 135                 140
Ala Val Thr Val Ala Trp Lys Ala Asp Ser Ser Pro Val Lys Ala Gly
145                 150                 155                 160
Val Glu Thr Thr Thr Pro Ser Lys Gln Ser Asn Asn Lys Tyr Ala Ala
                165                 170                 175
Ser Ser Tyr Leu Ser Leu Thr Pro Glu Gln Trp Lys Ser His Arg Ser
            180                 185                 190
Tyr Ser Cys Gln Val Thr His Glu Gly Ser Thr Val Glu Lys Thr Val
        195                 200                 205
Ala Pro Thr Glu Cys Ser Gly Gly Gly Ser Gly Gly Gly Gly Ser
    210                 215                 220
Gly Gly Gly Gly Ser Gly Gly Gly Ser Gly Gly Gly Ser Gly
225                 230                 235                 240
Gly Gly Gly Ser Gly Gly Gln Val Gln Leu Val Glu Ser Gly Ala Glu
                245                 250                 255
Val Lys Lys Pro Gly Ala Ser Val Lys Val Ser Cys Lys Ala Ser Gly
            260                 265                 270
Tyr Thr Phe Thr Gly Tyr Tyr Met His Trp Val Arg Gln Ala Pro Gly
        275                 280                 285
Gln Gly Leu Glu Trp Met Gly Trp Ile Asn Pro Asn Ser Gly Gly Thr
    290                 295                 300
Asn Tyr Ala Gln Lys Phe Gln Gly Arg Val Thr Met Thr Arg Asp Thr
305                 310                 315                 320
Ser Ile Ser Thr Ala Tyr Met Glu Leu Ser Arg Leu Arg Ser Asp Asp
                325                 330                 335
Thr Ala Val Tyr Tyr Cys Ala Arg Ser Pro Asn Pro Tyr Tyr Tyr Asp
            340                 345                 350
Ser Ser Gly Tyr Tyr Tyr Pro Gly Ala Phe Asp Ile Trp Gly Gln Gly
        355                 360                 365
Thr Met Val Thr Val Ser Ser Ala Ser Thr Lys Gly Pro Ser Val Phe
    370                 375                 380
Pro Leu Ala Pro Ser Ser Lys Ser Thr Ser Gly Gly Thr Ala Ala Leu
385                 390                 395                 400
Gly Cys Leu Val Lys Asp Tyr Phe Pro Glu Pro Val Thr Val Ser Trp
                405                 410                 415
Asn Ser Gly Ala Leu Thr Ser Gly Val His Thr Phe Pro Ala Val Leu
            420                 425                 430
Gln Ser Ser Gly Leu Tyr Ser Leu Ser Ser Val Val Thr Val Pro Ser
        435                 440                 445
Ser Ser Leu Gly Thr Gln Thr Tyr Ile Cys Asn Val Asn His Lys Pro
    450                 455                 460
Ser Asn Thr Lys Val Asp Lys Lys Val Glu Pro Lys Ser Cys Asp Lys
465                 470                 475                 480
Thr His Thr Cys Pro Pro Cys Pro Ala Pro Glu Leu Leu Gly Gly Pro
                485                 490                 495
Ser Val Phe Leu Phe Pro Pro Lys Pro Lys Asp Thr Leu Met Ile Ser
            500                 505                 510
Arg Thr Pro Glu Val Thr Cys Val Val Val Asp Val Ser His Glu Asp
        515                 520                 525
Pro Glu Val Lys Phe Asn Trp Tyr Val Asp Gly Val Glu Val His Asn
    530                 535                 540
```

Ala Lys Thr Lys Pro Arg Glu Glu Gln Tyr Asn Ser Thr Tyr Arg Val
545                 550                 555                 560

Val Ser Val Leu Thr Val Leu Ala Gln Asp Trp Leu Asn Gly Lys Glu
                565                 570                 575

Tyr Lys Cys Lys Val Ser Asn Lys Ala Leu Pro Ala Pro Ile Glu Lys
            580                 585                 590

Thr Ile Ser Lys Ala Lys Gly Gln Pro Arg Glu Pro Gln Val Tyr Thr
                595                 600                 605

Leu Pro Pro Cys Arg Asp Glu Leu Thr Lys Asn Gln Val Ser Leu Trp
            610                 615                 620

Cys Leu Val Lys Gly Phe Tyr Pro Ser Asp Ile Ala Val Glu Trp Glu
625                 630                 635                 640

Ser Asn Gly Gln Pro Glu Asn Asn Tyr Lys Thr Thr Pro Pro Val Leu
                645                 650                 655

Asp Ser Asp Gly Ser Phe Phe Leu Tyr Ser Lys Leu Thr Val Asp Lys
            660                 665                 670

Ser Arg Trp Gln Gln Gly Asn Val Phe Ser Cys Ser Val Met His Glu
            675                 680                 685

Ala Leu Ala Asn His Ala Thr Gln Lys Ser Leu Ser Leu Ser Pro Gly
            690                 695                 700

Lys
705

<210> SEQ ID NO 96
<211> LENGTH: 450
<212> TYPE: PRT
<213> ORGANISM: Artificial
<220> FEATURE:
<223> OTHER INFORMATION: Heavy chain 1 of <VEGF-ANG-2> OAscFab IgG4 with
      AAA mutations and with SPLE mutations

<400> SEQUENCE: 96

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Asp Phe Thr His Tyr
                20                  25                  30

Gly Met Asn Trp Val Arg Gln Ala Pro Gly Lys Gly Leu Glu Trp Val
            35                  40                  45

Gly Trp Ile Asn Thr Tyr Thr Gly Glu Pro Thr Tyr Ala Ala Asp Phe
        50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro Tyr Tyr Gly Thr Ser His Trp Tyr Phe Asp Val
                100                 105                 110

Trp Gly Gln Gly Thr Leu Val Thr Val Ser Ser Ala Ser Thr Lys Gly
            115                 120                 125

Pro Ser Val Phe Pro Leu Ala Pro Cys Ser Arg Ser Thr Ser Glu Ser
        130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val

-continued

```
                180             185                 190
Thr Val Pro Ser Ser Leu Gly Thr Lys Thr Tyr Thr Cys Asn Val
            195                 200                 205
Asp His Lys Pro Ser Asn Thr Lys Val Asp Lys Arg Val Glu Ser Lys
        210                 215                 220
Tyr Gly Pro Pro Cys Pro Cys Pro Ala Pro Glu Phe Glu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser Gln Glu
            260                 265                 270
Asp Pro Glu Val Gln Phe Asn Trp Tyr Val Asp Gly Val Glu Val His
        275                 280                 285
Asn Ala Lys Thr Lys Pro Arg Glu Glu Gln Phe Asn Ser Thr Tyr Arg
    290                 295                 300
Val Val Ser Val Leu Thr Val Leu Ala Gln Asp Trp Leu Asn Gly Lys
305                 310                 315                 320
Glu Tyr Lys Cys Lys Val Ser Asn Lys Gly Leu Pro Ser Ser Ile Glu
                325                 330                 335
Lys Thr Ile Ser Lys Ala Lys Gly Gln Pro Arg Glu Pro Gln Val Cys
            340                 345                 350
Thr Leu Pro Pro Ser Gln Glu Glu Met Thr Lys Asn Gln Val Ser Leu
        355                 360                 365
Ser Cys Ala Val Lys Gly Phe Tyr Pro Ser Asp Ile Ala Val Glu Trp
    370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Val Ser Arg Leu Thr Val Asp
                405                 410                 415
Lys Ser Arg Trp Gln Glu Gly Asn Val Phe Ser Cys Ser Val Met His
            420                 425                 430
Glu Ala Leu Ala Asn His Ala Thr Gln Lys Ser Leu Ser Leu Ser Leu
        435                 440                 445
Gly Lys
    450
```

```
<210> SEQ ID NO 97
<211> LENGTH: 702
<212> TYPE: PRT
<213> ORGANISM: Artificial
<220> FEATURE:
<223> OTHER INFORMATION: Heavy chain 2 of <VEGF-ANG-2> OAscFab IgG4 with
      AAA mutations and with SPLE mutations

<400> SEQUENCE: 97

Ser Tyr Val Leu Thr Gln Pro Pro Ser Val Ser Val Ala Pro Gly Gln
1               5                   10                  15
Thr Ala Arg Ile Thr Cys Gly Gly Asn Asn Ile Gly Ser Lys Ser Val
            20                  25                  30
His Trp Tyr Gln Gln Lys Pro Gly Gln Ala Pro Val Leu Val Val Tyr
        35                  40                  45
Asp Asp Ser Asp Arg Pro Ser Gly Ile Pro Glu Arg Phe Ser Gly Ser
    50                  55                  60
Asn Ser Gly Asn Thr Ala Thr Leu Thr Ile Ser Arg Val Glu Ala Gly
65                  70                  75                  80
```

-continued

```
Asp Glu Ala Asp Tyr Tyr Cys Gln Val Trp Asp Ser Ser Ser Asp His
                85                  90                  95
Trp Val Phe Gly Gly Gly Thr Lys Leu Thr Val Leu Gly Gln Pro Lys
            100                 105                 110
Ala Ala Pro Ser Val Thr Leu Phe Pro Pro Ser Ser Glu Glu Leu Gln
        115                 120                 125
Ala Asn Lys Ala Thr Leu Val Cys Leu Ile Ser Asp Phe Tyr Pro Gly
    130                 135                 140
Ala Val Thr Val Ala Trp Lys Ala Asp Ser Ser Pro Val Lys Ala Gly
145                 150                 155                 160
Val Glu Thr Thr Thr Pro Ser Lys Gln Ser Asn Asn Lys Tyr Ala Ala
                165                 170                 175
Ser Ser Tyr Leu Ser Leu Thr Pro Glu Gln Trp Lys Ser His Arg Ser
            180                 185                 190
Tyr Ser Cys Gln Val Thr His Glu Gly Ser Thr Val Glu Lys Thr Val
        195                 200                 205
Ala Pro Thr Glu Cys Ser Gly Gly Gly Ser Gly Gly Gly Gly Gly Ser
    210                 215                 220
Gly Gly Gly Gly Ser Gly Gly Gly Ser Gly Gly Gly Gly Ser Gly
225                 230                 235                 240
Gly Gly Gly Ser Gly Gly Gln Val Gln Leu Val Glu Ser Gly Ala Glu
                245                 250                 255
Val Lys Lys Pro Gly Ala Ser Val Lys Val Ser Cys Lys Ala Ser Gly
            260                 265                 270
Tyr Thr Phe Thr Gly Tyr Tyr Met His Trp Val Arg Gln Ala Pro Gly
        275                 280                 285
Gln Gly Leu Glu Trp Met Gly Trp Ile Asn Pro Asn Ser Gly Gly Thr
    290                 295                 300
Asn Tyr Ala Gln Lys Phe Gln Gly Arg Val Thr Met Thr Arg Asp Thr
305                 310                 315                 320
Ser Ile Ser Thr Ala Tyr Met Glu Leu Ser Arg Leu Arg Ser Asp Asp
                325                 330                 335
Thr Ala Val Tyr Tyr Cys Ala Arg Ser Pro Asn Pro Tyr Tyr Tyr Asp
            340                 345                 350
Ser Ser Gly Tyr Tyr Tyr Pro Gly Ala Phe Asp Ile Trp Gly Gln Gly
        355                 360                 365
Thr Met Val Thr Val Ser Ser Ala Ser Thr Lys Gly Pro Ser Val Phe
    370                 375                 380
Pro Leu Ala Pro Cys Ser Arg Ser Thr Ser Glu Ser Thr Ala Ala Leu
385                 390                 395                 400
Gly Cys Leu Val Lys Asp Tyr Phe Pro Glu Pro Val Thr Val Ser Trp
                405                 410                 415
Asn Ser Gly Ala Leu Thr Ser Gly Val His Thr Phe Pro Ala Val Leu
            420                 425                 430
Gln Ser Ser Gly Leu Tyr Ser Leu Ser Ser Val Val Thr Val Pro Ser
        435                 440                 445
Ser Ser Leu Gly Thr Lys Thr Tyr Thr Cys Asn Val Asp His Lys Pro
    450                 455                 460
Ser Asn Thr Lys Val Asp Lys Arg Val Glu Ser Lys Tyr Gly Pro Pro
465                 470                 475                 480
Cys Pro Pro Cys Pro Ala Pro Glu Phe Glu Gly Gly Pro Ser Val Phe
                485                 490                 495
Leu Phe Pro Pro Lys Pro Lys Asp Thr Leu Met Ile Ser Arg Thr Pro
```

-continued

```
                500                   505                   510
Glu Val Thr Cys Val Val Val Asp Val Ser Gln Glu Asp Pro Glu Val
            515                 520                 525

Gln Phe Asn Trp Tyr Val Asp Gly Val Glu Val His Asn Ala Lys Thr
        530                 535                 540

Lys Pro Arg Glu Glu Gln Phe Asn Ser Thr Tyr Arg Val Val Ser Val
545                 550                 555                 560

Leu Thr Val Leu Ala Gln Asp Trp Leu Asn Gly Lys Glu Tyr Lys Cys
                565                 570                 575

Lys Val Ser Asn Lys Gly Leu Pro Ser Ser Ile Glu Lys Thr Ile Ser
            580                 585                 590

Lys Ala Lys Gly Gln Pro Arg Glu Pro Gln Val Tyr Thr Leu Pro Pro
        595                 600                 605

Cys Gln Glu Glu Met Thr Lys Asn Gln Val Ser Leu Trp Cys Leu Val
            610                 615                 620

Lys Gly Phe Tyr Pro Ser Asp Ile Ala Val Glu Trp Glu Ser Asn Gly
625                 630                 635                 640

Gln Pro Glu Asn Asn Tyr Lys Thr Thr Pro Pro Val Leu Asp Ser Asp
                645                 650                 655

Gly Ser Phe Phe Leu Tyr Ser Arg Leu Thr Val Asp Lys Ser Arg Trp
                660                 665                 670

Gln Glu Gly Asn Val Phe Ser Cys Ser Val Met His Glu Ala Leu Ala
            675                 680                 685

Asn His Ala Thr Gln Lys Ser Leu Ser Leu Ser Leu Gly Lys
            690                 695                 700
```